United States Patent
Gu et al.

(10) Patent No.: US 11,248,054 B2
(45) Date of Patent: Feb. 15, 2022

(54) ANTI-IL1RAP ANTIBODIES AND ANTIBODY DRUG CONJUGATES

(71) Applicant: Bluefin BioMedicine, Inc., Beverly, MA (US)

(72) Inventors: Tinglei Gu, Andover, MA (US); Scott Michael Lonning, Westford, MA (US); Jason G. Beaudet, Beverly, MA (US); Sean A. Beausoleil, Essex, MA (US); Nels Eric Pederson, Mansfield, MA (US); Daniel Mulhern, Somerville, MA (US)

(73) Assignee: BLUEFIN BIOMEDICINE, INC., Beverly, MA (US)

( * ) Notice: Subject to any disclaimer, the term of this patent is extended or adjusted under 35 U.S.C. 154(b) by 0 days.

(21) Appl. No.: 16/620,386

(22) PCT Filed: Jun. 12, 2018

(86) PCT No.: PCT/US2018/037101
§ 371 (c)(1),
(2) Date: Dec. 6, 2019

(87) PCT Pub. No.: WO2018/231827
PCT Pub. Date: Dec. 20, 2018

(65) Prior Publication Data
US 2020/0140561 A1   May 7, 2020

Related U.S. Application Data

(60) Provisional application No. 62/518,069, filed on Jun. 12, 2017.

(51) Int. Cl.
| | | |
|---|---|---|
| *C07K 16/28* | (2006.01) | |
| *A61K 47/68* | (2017.01) | |
| *A61P 35/00* | (2006.01) | |
| *A61K 9/00* | (2006.01) | |
| *A61K 45/06* | (2006.01) | |

(52) U.S. Cl.
CPC ...... *C07K 16/2866* (2013.01); *A61K 47/6803* (2017.08); *A61K 47/6867* (2017.08); *A61P 35/00* (2018.01); *A61K 9/0019* (2013.01); *A61K 45/06* (2013.01)

(58) Field of Classification Search
None
See application file for complete search history.

(56) References Cited

U.S. PATENT DOCUMENTS

| | | |
|---|---|---|
| 6,280,955 B1 | 8/2001 | Cao |
| 8,114,394 B2 | 2/2012 | Vicary et al. |
| 8,187,596 B1 | 5/2012 | Chackerian et al. |
| 8,618,054 B2 | 12/2013 | Chemtob et al. |
| 8,658,133 B2 | 2/2014 | Ward et al. |
| 9,200,074 B2 | 12/2015 | Campbell et al. |
| 9,371,390 B2 | 6/2016 | Karsunky |
| 9,534,053 B2 | 1/2017 | Varnum et al. |
| 9,534,058 B2 | 1/2017 | Stull et al. |
| 9,873,918 B2 | 1/2018 | Steidl et al. |
| 9,932,409 B2 | 4/2018 | Tavernier et al. |
| 10,105,441 B2 | 10/2018 | Dana et al. |
| 10,117,906 B2 | 11/2018 | Dana et al. |
| 10,118,971 B2 | 11/2018 | Kim |
| 10,222,376 B2 | 3/2019 | Gerber |
| 10,344,085 B2 | 7/2019 | Dengl et al. |
| 10,471,086 B2 | 11/2019 | Merali et al. |
| 10,519,230 B2 | 12/2019 | Murphy et al. |
| 10,544,212 B2 | 1/2020 | Bloom et al. |
| 10,562,971 B2 | 2/2020 | Ågerstam et al. |
| 10,588,298 B2 | 3/2020 | Wang et al. |
| 10,668,150 B2 | 6/2020 | Cohen et al. |
| 10,669,594 B2 | 6/2020 | Monpoeho et al. |
| 10,723,795 B2 | 7/2020 | Hass et al. |
| 10,752,692 B2 | 8/2020 | Ågerstam et al. |
| 10,752,703 B2 | 8/2020 | Chen et al. |
| 10,774,128 B2 | 9/2020 | Murphy et al. |
| 10,815,305 B2 | 10/2020 | Orengo et al. |
| 10,851,158 B2 | 12/2020 | Orengo et al. |
| 10,877,049 B2 | 12/2020 | Bielekova et al. |
| 10,878,703 B2 | 12/2020 | Fioretos et al. |
| 10,898,580 B2 | 1/2021 | Junutula et al. |
| 10,906,971 B2 | 2/2021 | Fischer et al. |
| 10,966,997 B2 | 4/2021 | Slaby et al. |
| 10,995,144 B2 | 5/2021 | Fioretos et al. |
| 2003/0049255 A1 | 3/2003 | Sims et al. |
| 2003/0138803 A1 | 7/2003 | Brooksbank et al. |

(Continued)

FOREIGN PATENT DOCUMENTS

| | | |
|---|---|---|
| AU | 2013203432 A1 | 5/2013 |
| AU | 2014203217 B2 | 3/2017 |

(Continued)

OTHER PUBLICATIONS

Lloyd et al., Protein Eng. Design & Select., 22, 159-168,2009. (Year: 2009).*
International Search Report and Written Opinion for Application No. PCT/US2018/037101, dated Oct. 26, 2018, 14 pages.
International Preliminary Report on Patentability for Application No. PCT/US2018/037101, dated Dec. 26, 2019, 10 pages.
Agerstam et al., Antibodies targeting human IL1RAP (IL1R3) show therapeutic effects in xenograft models of acute myeloid leukemia., Aug. 10, 2015.

(Continued)

*Primary Examiner* — Elly-Gerald Stoica
(74) *Attorney, Agent, or Firm* — Procopio, Cory, Hargreaves & Savitch LLP

(57) ABSTRACT

Disclosed herein are Interleukin 1 Receptor Accessory Protein (IL1RAP) antibodies and antibody drug conjugates (ADCs), including compositions and methods of using said antibodies and ADCs.

8 Claims, 28 Drawing Sheets
Specification includes a Sequence Listing.

(56) References Cited

U.S. PATENT DOCUMENTS

| | | |
|---|---|---|
| 2005/0084493 A1 | 4/2005 | Witte et al. |
| 2005/0129685 A1 | 6/2005 | Cao et al. |
| 2007/0248597 A1 | 10/2007 | Henley et al. |
| 2008/0219979 A1 | 9/2008 | Tocker et al. |
| 2008/0292590 A1 | 11/2008 | Becher et al. |
| 2009/0191187 A1 | 7/2009 | Bartke et al. |
| 2009/0234106 A1 | 9/2009 | Han et al. |
| 2010/0004584 A1 | 1/2010 | Sen |
| 2010/0190652 A1 | 7/2010 | Nagalla et al. |
| 2012/0045764 A1 | 2/2012 | Grompe et al. |
| 2012/0195900 A1 | 8/2012 | Ghayur et al. |
| 2012/0201746 A1 | 8/2012 | Liu et al. |
| 2012/0302737 A1 | 11/2012 | Christensen et al. |
| 2013/0195868 A1 | 8/2013 | Adelman |
| 2014/0044738 A1 | 2/2014 | Langermann et al. |
| 2014/0212412 A1 | 7/2014 | Rankin et al. |
| 2014/0308294 A1 | 10/2014 | Seshire et al. |
| 2015/0030586 A1 | 1/2015 | Warren et al. |
| 2015/0315279 A1 | 11/2015 | Jiang et al. |
| 2016/0068591 A1 | 3/2016 | Anderson et al. |
| 2016/0120941 A1 | 5/2016 | Croll et al. |
| 2016/0208019 A1 | 7/2016 | Bacac et al. |
| 2017/0129961 A1 | 5/2017 | Raum et al. |
| 2017/0218091 A1 | 8/2017 | Ambrosi |
| 2018/0168490 A1 | 6/2018 | Jones et al. |
| 2018/0171405 A1 | 6/2018 | Khosla et al. |
| 2018/0275123 A1 | 9/2018 | Steidl et al. |
| 2018/0312592 A1 | 11/2018 | Junutula et al. |
| 2018/0346605 A1 | 12/2018 | Chiu et al. |
| 2018/0355044 A1 | 12/2018 | Jiang et al. |
| 2018/0369230 A1 | 12/2018 | Shair et al. |
| 2019/0194336 A1 | 6/2019 | Fischer et al. |
| 2019/0225682 A1 | 7/2019 | Nanchahal et al. |
| 2019/0241668 A1 | 8/2019 | Van Rompaey |
| 2019/0270826 A1 | 9/2019 | Heidrich et al. |
| 2020/0048349 A1 | 2/2020 | Gaudet et al. |
| 2020/0140559 A1 | 5/2020 | Fischer et al. |
| 2020/0140561 A1 | 5/2020 | Gu et al. |
| 2020/0149081 A1 | 5/2020 | Oshodi et al. |
| 2020/0247893 A1 | 8/2020 | Meng et al. |
| 2020/0255880 A1 | 8/2020 | Chen et al. |
| 2020/0315540 A1 | 10/2020 | Jones et al. |
| 2020/0325220 A1 | 10/2020 | Lanzavecchia et al. |
| 2021/0008047 A1 | 1/2021 | Marine et al. |
| 2021/0008070 A1 | 1/2021 | Marine et al. |
| 2021/0008108 A1 | 1/2021 | Ferrand et al. |

FOREIGN PATENT DOCUMENTS

| | | |
|---|---|---|
| CN | 101348526 A | 1/2009 |
| CN | 106831998 B | 9/2020 |
| EP | 0908365 A1 | 11/1997 |
| EP | 1751175 B1 | 7/2012 |
| EP | 3294418 A1 | 3/2018 |
| EP | 3522932 A1 | 8/2019 |
| EP | 3610041 A1 | 2/2020 |
| EP | 3623814 A2 | 3/2020 |
| EP | 3710016 A1 | 9/2020 |
| EP | 3717666 A1 | 10/2020 |
| EP | 3749362 A1 | 12/2020 |
| EP | 3802831 A1 | 4/2021 |
| JP | 2016044126 A | 4/2016 |
| JP | 684824 B2 | 7/2016 |
| JP | 6405549 A | 10/2018 |
| JP | 6519913 B2 | 5/2019 |
| KR | 20190140756 A | 12/2019 |
| WO | 2011017294 A1 | 2/2011 |
| WO | 2014135655 A1 | 9/2014 |
| WO | 2016179319 A1 | 11/2016 |
| WO | 2017024062 A1 | 2/2017 |
| WO | 2017/079121 A2 | 5/2017 |
| WO | 2018053552 A2 | 3/2018 |

OTHER PUBLICATIONS

Agerstam et al., IL1RAP antibodies block IL-1-induced expansion of candidate CML stem cells and mediate cell killing in xenograft models., Dec, 8, 2016.

Agerstam et al., Strong Therapeutic Effect of Anti-IL1RAP Immunotherapy in a Xenograft Model of Acute Myeloid Leukemia, Nov. 15, 2013.

Askmyr et al., Selective killing of candidate AML stem cells by antibody targeting of IL1RAP., Mar. 11, 2013.

Barreyro et al., Abstract C225: IL1RAP as functionally relevant target for stem-cell directed therapy in acute myeloid leukemia (AML) and myelodysplastic syndromes (MDS)., Nov. 2013.

Jaras et al., Isolation and killing of candidate chronic myeloid leukemia stem cells by antibody targeting of IL-1 receptor accessory protein, Agusut 30, 2010.

Jiang et al., Targeting acute myeloid leukemia via anti-IL1RAP antibodies, Jul. 2016.

Mansur et al., Engagement of IL-1 receptor accessory protein (IL-1RAcP) with the monoclonal antibody AY19 provides co-activating signals and prolongs the CD2-induced proliferation of peripheral blood lymphocytes, May 11, 2011.

Yin et al., Construction of hybridoma cells with IL1RAP as a new marker for leukemia stem cells and detection of its monoclonal antibody., Dec. 21, 2013.

Yoon et al., Antibodies to domains II and III of the IL-1 receptor accessory protein inhibit IL-1 beta activity but not binding: regulation of IL-1 responses is via type I receptor, not the accessory protein, Apr. 1, 1998.

Zhao et al., microRNA-4331 Promotes Transmissible Gastroenteritis Virus (TGEV)-induced Mitochondrial Damage Via Targeting RB1, Upregulating Interleukin-1 Receptor Accessory Protein (IL1RAP), and Activating p38 MAPK Pathway In Vitro, Dec. 7, 2017.

\* cited by examiner

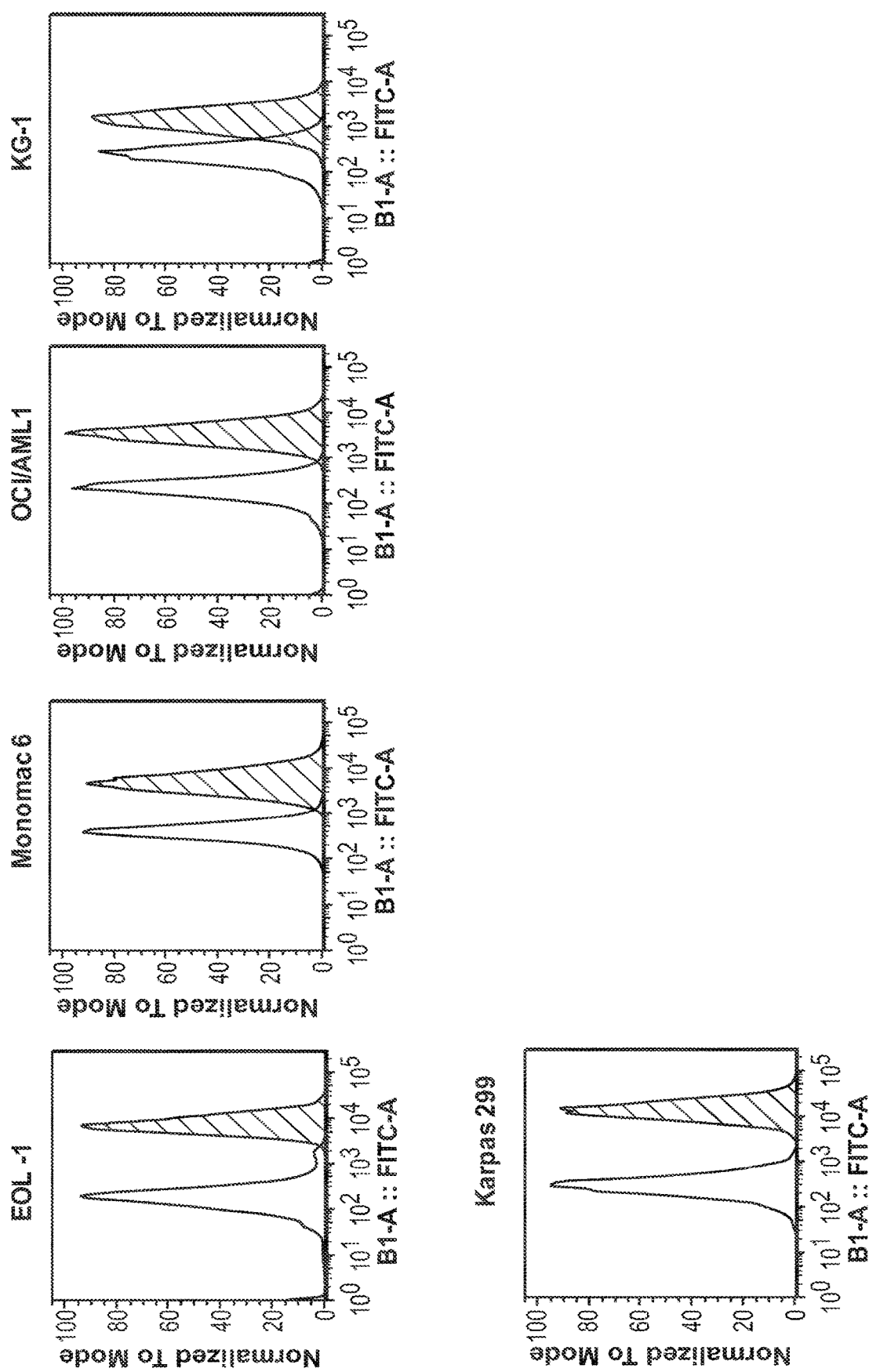
Figure 1. Surface expression of IL1RAP in leukemia cell lines.

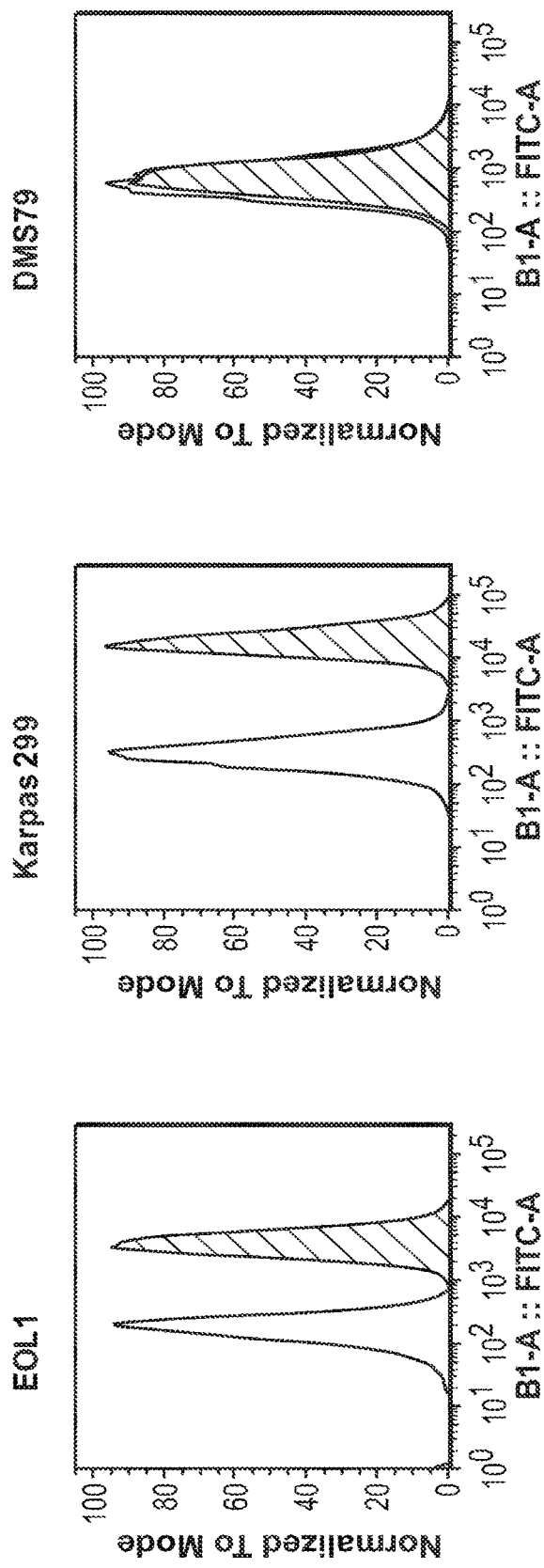
Figure 2. Anti-IL1RAP antibody (44E5) binds specifically to IL1RAP positive cell lines.
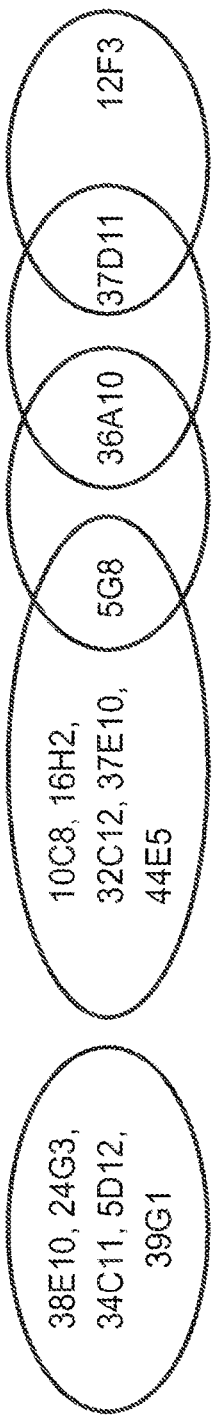
Figure 3

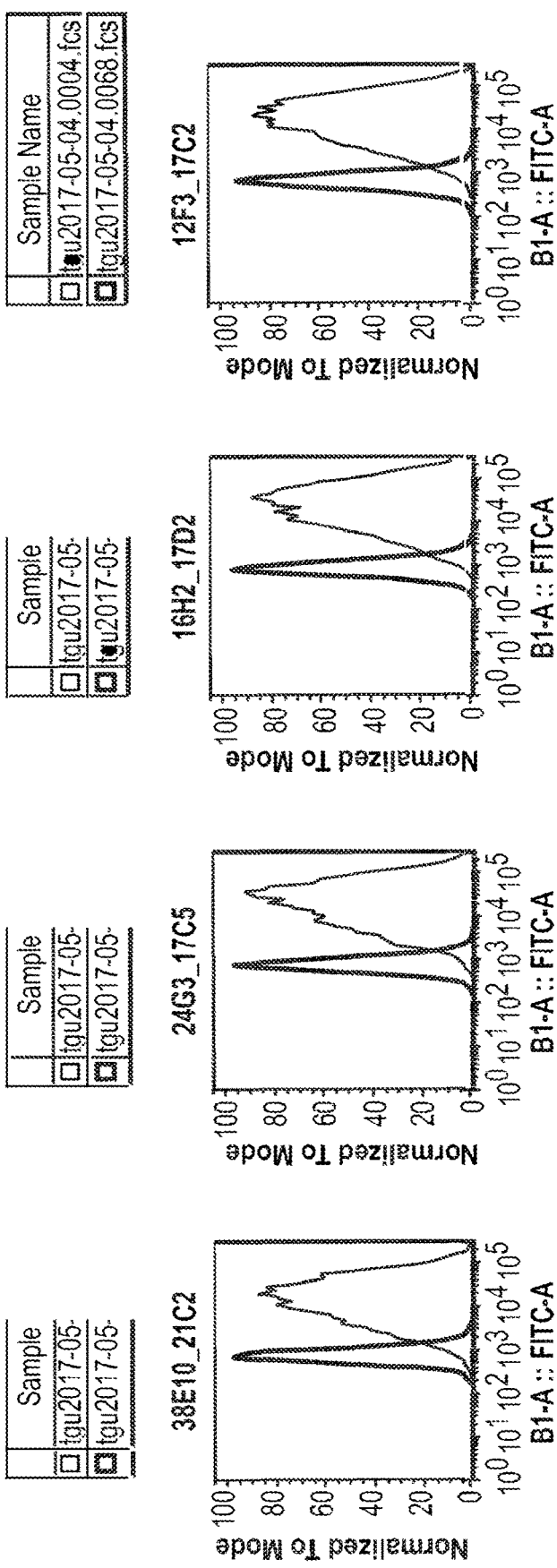
Figure 4A Binding of anti-IL1RAP antibodies to IL1RAP orthologs.
Binding of anti-IL 1 RAP antibodies to human IL 1 RAP.

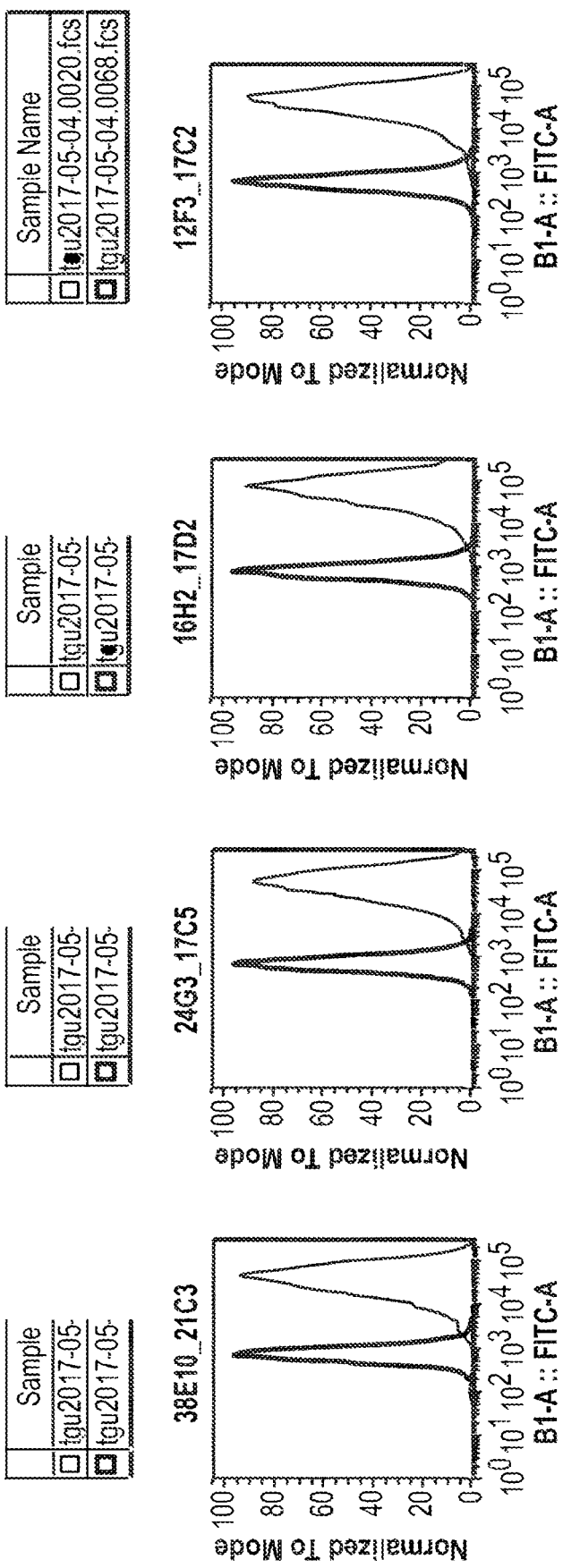
Figure 4B. Binding of anti-IL1RAP antibodies to macaca fascicularis IL1RAP.

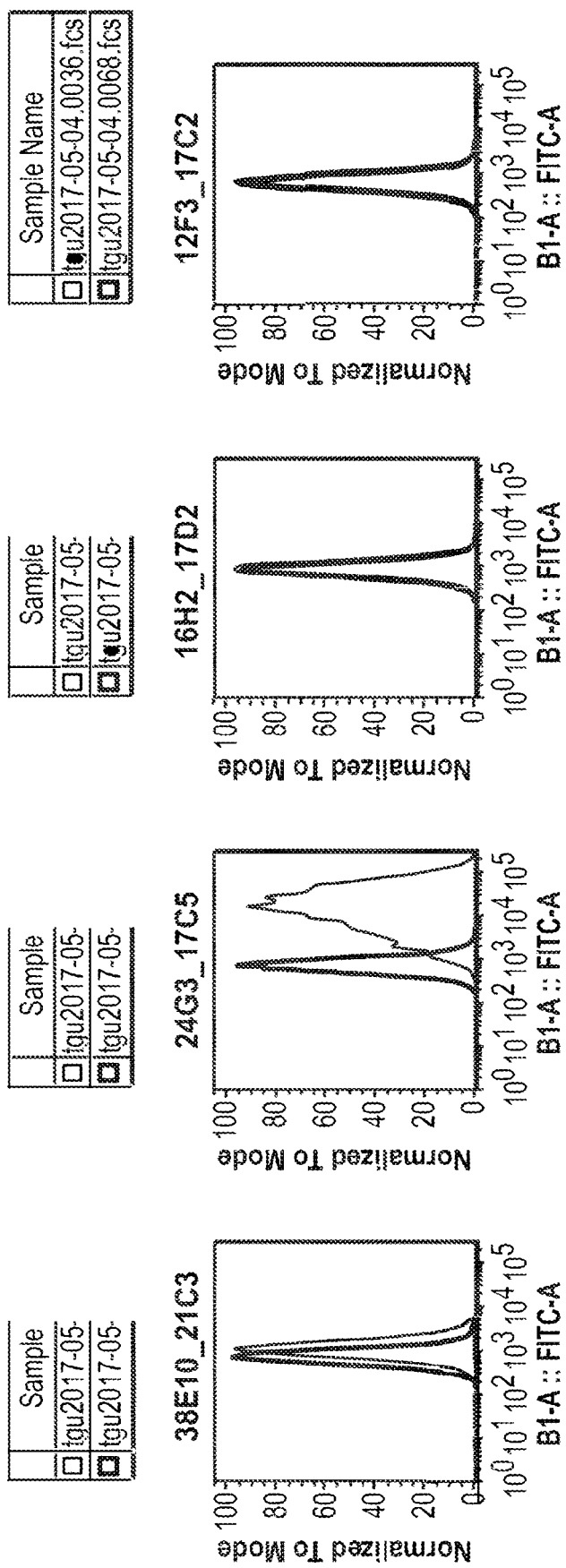
Figure 4C Binding of anti-IL1RAP antibodies to rat IL1RAP.

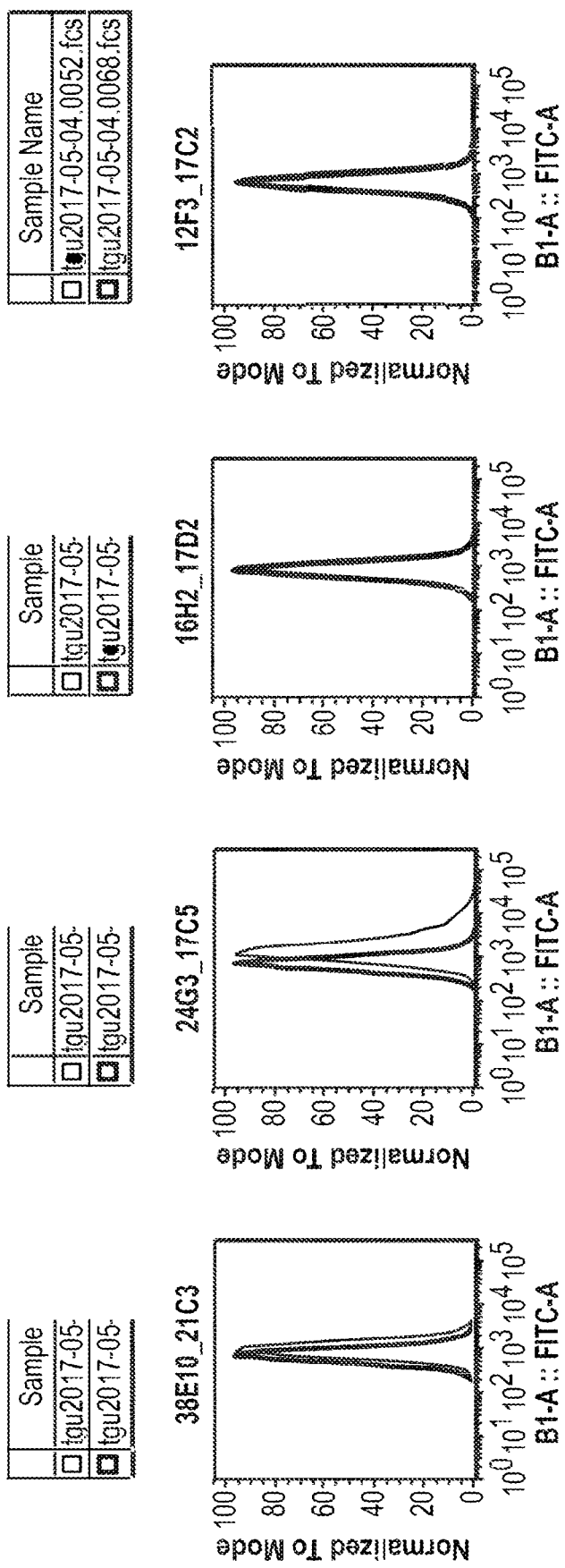
Figure 4D. Binding of anti-IL1RAP antibodies to mouse IL1RAP.

Figure 5. Internalization of 44E5 into EOL1 cells.
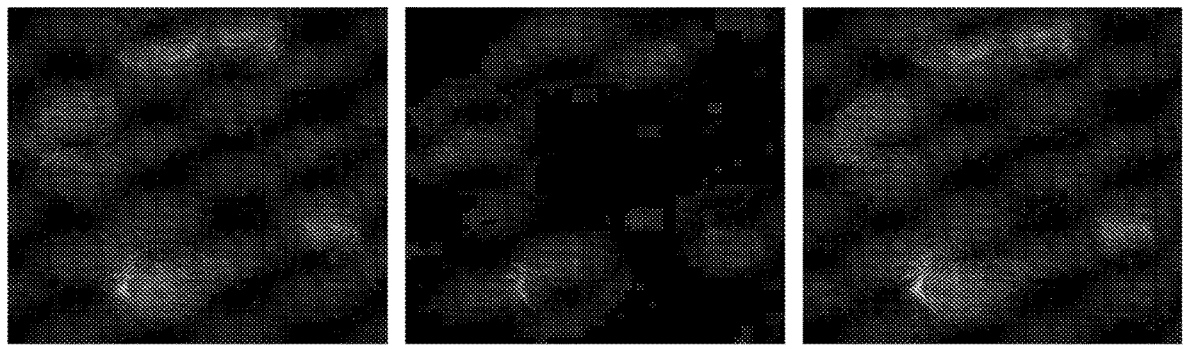

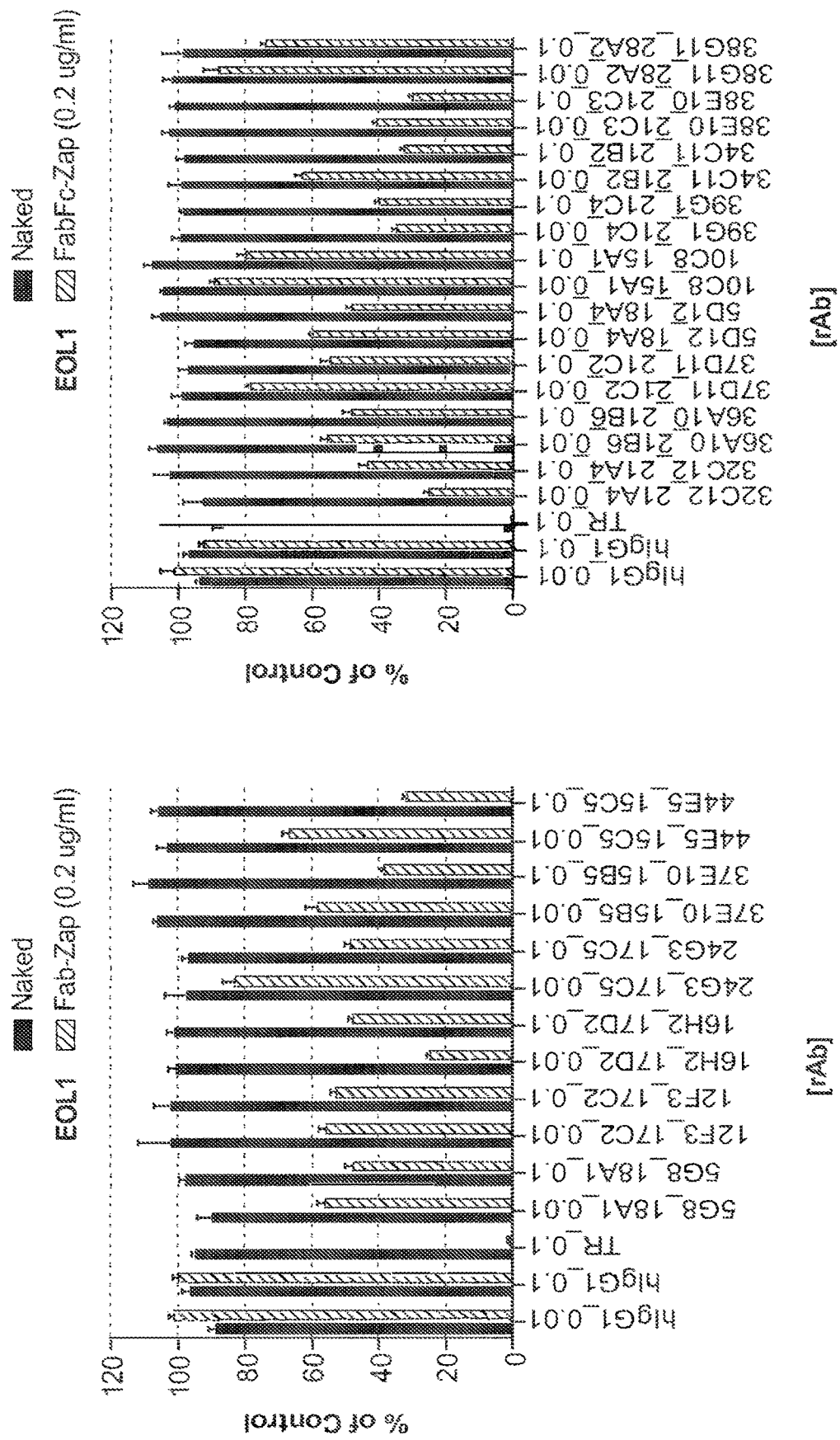
Figure 6A Anti-IL1RAP antibodies internalization and in vitro efficacy.

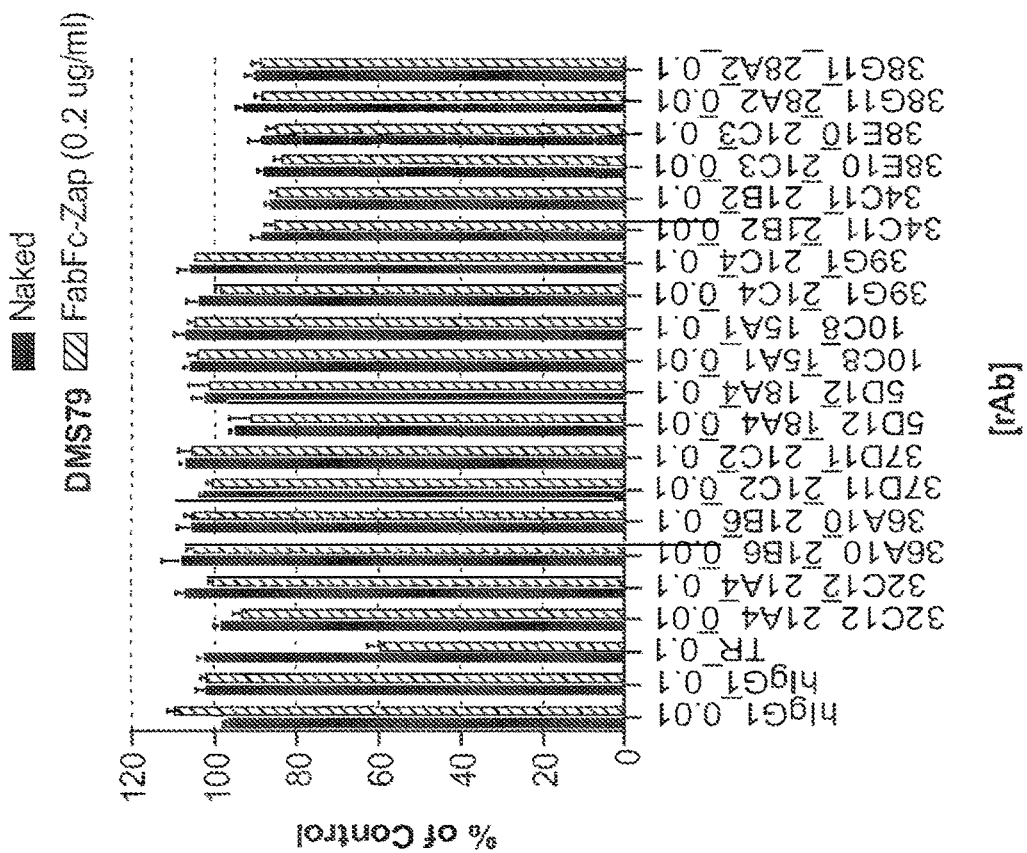
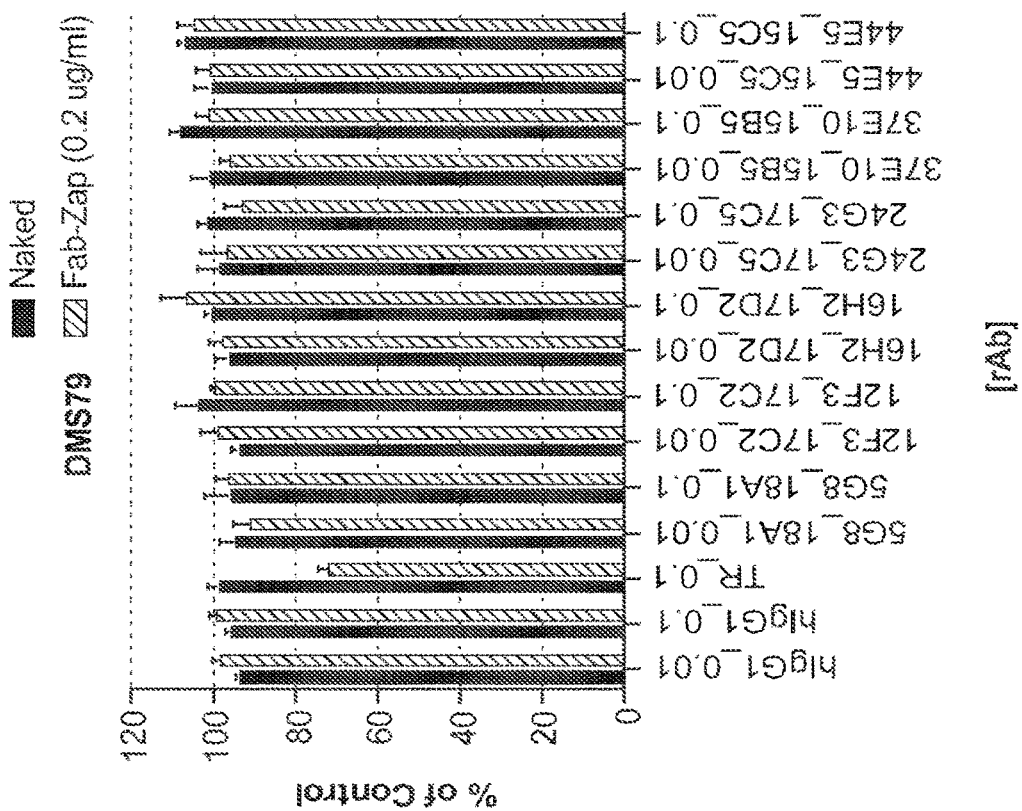
Figure 6C

In vitro efficacy of Anti-IL1RAP ADC in AML cell lines.

Blockage of IL1α/β signaling by anti-IL1RAP antibodies.

Figure 9A  Blockage of IL-33 signaling by anti-IL1RAP antibodies.
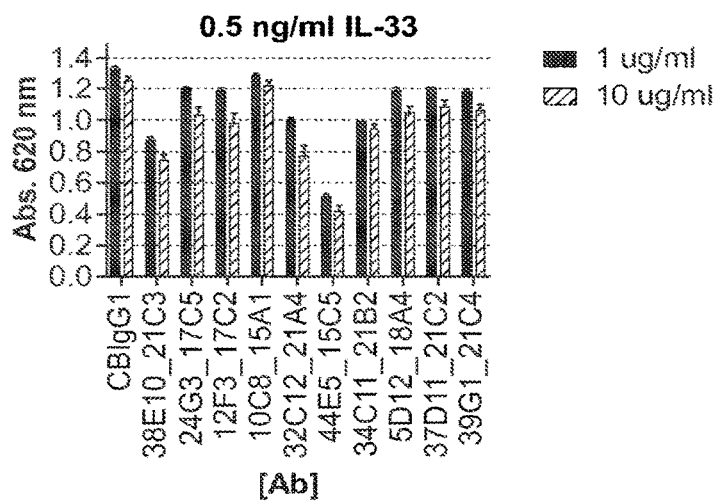
Figure 9B
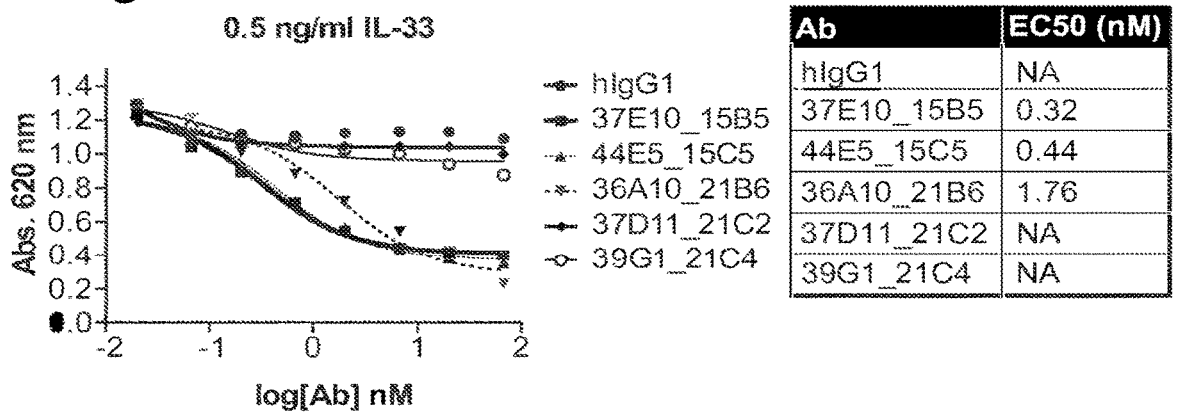

ANTI-IL1RAP ANTIBODIES AND ANTIBODY DRUG CONJUGATES

RELATED APPLICATIONS

The instant application is a 35 U.S.C. § 371 national stage filing of International Application No. PCT/US2018/037101, filed on Jun. 12, 2018, which in turn claims priority to U.S. Provisional Application No. 62/518,069, filed on Jun. 12, 2017, the entire contents of each of which are expressly incorporated by reference herein in their entirety.

SEQUENCE LISTING

The instant application contains a Sequence Listing which has been filed electronically in ASCII format and is hereby incorporated by reference in its entirety. Said ASCII copy, created on Jun. 12, 2018, is named 127913-00820_SL.txt and is 163,057 bytes in size.

BACKGROUND

IL1RAP, also known as "Interleukin 1 Receptor Accessory Protein," "IL-1R Accessory Protein", "IL-1 Receptor Accessory Protein," "Interleukin-1 Receptor 3," "IL-1RAcP," "C3orf13," "IL-1R3," "IL1R3," "Interleukin-1 Receptor Accessory Protein Beta," "Interleukin-1 Receptor Accessory Protein," and "IL-1R-3," (Wesche, H., J. Biol. Chem. 272: 7727-7731, 1997) is a necessary part of the interleukin 1 (IL-1) receptor complex which initiates signaling events that result in the activation of interleukin 1-responsive genes. In addition to IL 1-signaling, IL1RAP is critical for mediating the effects of IL33, through the ST2/IL1RAP complex, and IL36, through the IL 1Rrp2/IL1RAP complex (Garlanda et al, Immunity. 2013 Dec. 12; 39(6): 1003-18).

Two IL-1 receptors, IL-1R type I and IL-1R type II, have been identified. Both receptors can interact with all three forms of the IL-1 family molecules. IL-1 RI is responsible for mediating IL-1-induced cellular activation. However, the IL-1/IL-1 RI complex cannot signal by itself, but is dependent on association with IL1RAP (Dinarello, C A, Blood 30 1996, 87(6): 2095-147) (see, e.g., WO 2015/132602).

Alternative splicing of IL1RAP results in two transcript variants encoding two different isoforms, one membrane-bound and one soluble. The ratio of soluble to membrane-bound forms increases during acute-phase induction or stress. IL1RAP is expressed on candidate leukemic stem cells in the majority of AML patients, but not on normal hematopoietic stem cells (Ågerstam, et al. *PNAS USA* (2015) vol. 112:34, 10786-10791).

Interleukin-1

Interleukin 1 (IL-1) is a potent pro-inflammatory cytokine that induces synthesis of acute phase and proinflammatory proteins during infection, tissue damage, or stress, by forming a complex at the cell membrane with an interleukin 1 receptor and an accessory protein. IL-1 can be produced by a variety of cell types, including mononuclear phagocytes, in response to infection and inflammation. The IL-1 family consists of seven agonists, including IL-1α and IL-1β, and three naturally occurring receptor antagonists, including the IL-1 receptor antagonist (IL-25 1Ra) (Dinarello, C A, Blood 1996, 87(6): 2095-147).

IL-1 is capable of activating several cell types including leukocytes and endothelial cells. IL-1 induces and amplifies immunological responses by promoting the production and expression of adhesion molecules, cytokines, chemokines and other inflammatory mediators such as prostaglandin E2 and nitric oxide (NO). As a consequence, local inflammation is amplified and sustained. In addition, the IL-1 induced production of inflammatory mediators results in fever, headache, hypotension and weight loss. Furthermore, IL-1 is a hematopoietic growth factor and has been shown to reduce the nadir of leukocytes and platelets in patients during bone marrow transplantation. IL-1 has also been shown to promote angiogenesis by inducing the production of vascular endothelial growth factor, thereby promoting pannus formation and blood supply in rheumatic joints. Finally, IL-1 has been shown to promote the bone and cartilage degradation in rheumatic diseases.

IL-1 is implicated in a wide range of diseases and conditions ranging from gout to cancer (for reviews, see Dinarello et al., 2012, *Nature Reviews* 11:633-652 and Dinarello, 2014, *Mol. Med.* 20 (suppl. 1):S43-S58; the disclosures of which are incorporated herein by reference), including joint, bone and muscle diseases, such as rheumatoid arthritis and osteoarthritis; hereditary systemic autoinflammatory diseases, such as familial Mediterranean fever; systemic autoinflammatory diseases, such as systemic juvenile idiopathic arthritis and adult-onset Still's disease; common inflammatory diseases, such as gout and type 2 diabetes; acute-onset ischemic diseases, such as myocardial infarction; and cancer.

A number of therapies for blocking IL-1 activity are approved and in development. Targeting IL-1 began in 1993 with the introduction of anakinra (Kineret™; Amgen), a recombinant form of the naturally occurring IL-1 receptor antagonist (IL-1 Ra), which blocks the activity of both IL-1α and IL-1β. This therapeutic has since been used to demonstrate a role for IL-1 in numerous diseases. Neutralizing IL-1 with antibodies or soluble receptors has also proved to be effective, and the soluble decoy receptor rilonacept (Arcalyst™; Regeneron) and the anti-IL-1 (3 neutralizing monoclonal antibody canakinumab (Ilaris™; Novartis) have now been approved. Other therapeutic approaches, including IL-1α neutralisation, a therapeutic vaccine targeting IL-1β and a chimeric IL-1 Ra, are in clinical trials. In addition, orally active small-molecule inhibitors of IL-1 production, such as caspase 1 inhibitors, have been developed.

Antibody drug conjugates (ADC) represent a new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen.

Accordingly, there remains a need in the art for anti-IL1RAP antibodies and ADCs that can be used for therapeutic purposes in the treatment of cancer.

SUMMARY

In certain aspects, the present invention provides for anti-IL1RAP antibodies, antigen-binding portions thereof, and antibody drug conjugates (ADCs). In certain embodiments of the invention, the antibodies, or antigen binding portions thereof, bind to IL1RAP (SEQ ID NO: 286) or the extracellular domain of IL1RAP.

In one embodiment, the antibodies, or antigen binding portions thereof, of the invention, bind to IL1RAP with a $K_d$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less.

In yet other embodiments of the invention, anti-IL1RAP antibody drug conjugates (ADCs) of the invention (e.g., the IL1RAP antibodies of the invention conjugated to a toxin) capable of being internalized. In another embodiment, the anti-IL1RAP antibody drug conjugates (ADCs) of the invention are capable of inducing cell death of cells endogenously expressing IL1RAP.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 4 and a light chain variable region comprising a CDR3 having the amino acid sequence of SEQ ID NO: 8.

In some embodiments, the antibody, or antigen binding portion thereof, further comprises a heavy chain variable region comprising a CDR2 having the amino acid sequence of SEQ ID NO: 3 and a light chain variable region comprising a CDR2 having the amino acid sequence of SEQ ID NO: 7. In other embodiments, the antibody, or antigen binding portion thereof, comprises a heavy chain variable region comprising a CDR1 having the amino acid sequence of SEQ ID NO: 2 and a light chain variable region comprising a CDR1 having the amino acid sequence of either SEQ ID NO: 6.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 12 and a light chain variable region comprising a CDR3 having the amino acid sequence of SEQ ID NO: 16.

In some embodiments, the antibody, or antigen binding portion thereof, further comprises a heavy chain variable region comprising a CDR2 having the amino acid sequence of SEQ ID NO: 11 and a light chain variable region comprising a CDR2 having the amino acid sequence of SEQ ID NO: 15. In other embodiments, the antibody, or antigen binding portion thereof, comprises a heavy chain variable region comprising a CDR1 having the amino acid sequence of SEQ ID NO: 10 and a light chain variable region comprising a CDR1 having the amino acid sequence of either SEQ ID NO: 14.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 20 and a light chain variable region comprising a CDR3 having the amino acid sequence of SEQ ID NO: 24.

In some embodiments, the antibody, or antigen binding portion thereof, comprises a heavy chain variable region comprising a CDR2 having the amino acid sequence of SEQ ID NO: 19 and a light chain variable region comprising a CDR2 having the amino acid sequence of SEQ ID NO: 23. In other embodiments, the antibody, or antigen binding portion thereof, comprises a heavy chain variable region comprising a CDR1 having the amino acid sequence of SEQ ID NO: 18 and a light chain variable region comprising a CDR1 having the amino acid sequence of either SEQ ID NO: 22.

In yet another aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 28 and a light chain variable region comprising a CDR3 having the amino acid sequence of SEQ ID NO: 31.

In some embodiments, the antibody, or antigen binding portion thereof, comprises a heavy chain variable region comprising a CDR2 having the amino acid sequence of SEQ ID NO: 27 and a light chain variable region comprising a CDR2 having the amino acid sequence of SEQ ID NO: 23. In other embodiments, the antibody, or antigen binding portion thereof, comprises a heavy chain variable region comprising a CDR1 having the amino acid sequence of SEQ ID NO: 26 and a light chain variable region comprising a CDR1 having the amino acid sequence of either SEQ ID NO: 30.

In another aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 35 and a light chain variable region comprising a CDR3 having the amino acid sequence of SEQ ID NO: 39.

In some embodiments, the antibody, or antigen binding portion thereof, comprises a heavy chain variable region comprising a CDR2 having the amino acid sequence of SEQ ID NO: 34 and a light chain variable region comprising a CDR2 having the amino acid sequence of SEQ ID NO: 38. In other embodiments, the antibody, or antigen binding portion thereof, comprises a heavy chain variable region comprising a CDR1 having the amino acid sequence of SEQ ID NO: 33 and a light chain variable region comprising a CDR1 having the amino acid sequence of either SEQ ID NO: 37.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 43 and a light chain variable region comprising a CDR3 having the amino acid sequence of SEQ ID NO: 47.

In some embodiments, the antibody, or antigen binding portion thereof, comprises a heavy chain variable region comprising a CDR2 having the amino acid sequence of SEQ ID NO: 42 and a light chain variable region comprising a CDR2 having the amino acid sequence of SEQ ID NO: 46. In other embodiments, the antibody, or antigen binding portion thereof, comprises a heavy chain variable region comprising a CDR1 having the amino acid sequence of SEQ ID NO: 41 and a light chain variable region comprising a CDR1 having the amino acid sequence of either SEQ ID NO: 45.

In another aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 51 and a light chain variable region comprising a CDR3 having the amino acid sequence of SEQ ID NO: 55.

In some embodiments, the antibody, or antigen binding portion thereof, comprises a heavy chain variable region comprising a CDR2 having the amino acid sequence of SEQ ID NO: 50 and a light chain variable region comprising a CDR2 having the amino acid sequence of SEQ ID NO: 54. In other embodiments, the antibody, or antigen binding portion thereof, comprises a heavy chain variable region comprising a CDR1 having the amino acid sequence of SEQ ID NO: 49 and a light chain variable region comprising a CDR1 having the amino acid sequence of either SEQ ID NO: 53.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 59 and a light chain variable region comprising a CDR3 having the amino acid sequence of SEQ ID NO: 63.

In some embodiments, the antibody, or antigen binding portion thereof, comprises a heavy chain variable region comprising a CDR2 having the amino acid sequence of SEQ ID NO: 58 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 57 and a light chain variable region comprising a CDR1 having the amino acid sequence of either SEQ ID NO: 61.

In another aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 67 and a light chain variable region comprising a CDR3 having the amino acid sequence of SEQ ID NO: 70.

In some embodiments, the antibody, or antigen binding portion thereof, comprises a heavy chain variable region comprising a CDR2 having the amino acid sequence of SEQ ID NO: 66 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 65 and a light chain variable region comprising a CDR1 having the amino acid sequence of either SEQ ID NO: 69.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 67 and a light chain variable region comprising a CDR3 having the amino acid sequence of SEQ ID NO: 70.

In some embodiments, the antibody, or antigen binding portion thereof, comprises a heavy chain variable region comprising a CDR2 having the amino acid sequence of SEQ ID NO: 72 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 65 and a light chain variable region comprising a CDR1 having the amino acid sequence of either SEQ ID NO: 69.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 77 and a light chain variable region comprising a CDR3 having the amino acid sequence of SEQ ID NO: 81.

In some embodiments, the antibody, or antigen binding portion thereof, comprises a heavy chain variable region comprising a CDR2 having the amino acid sequence of SEQ ID NO: 76 and a light chain variable region comprising a CDR2 having the amino acid sequence of SEQ ID NO: 80. In other embodiments, the antibody, or antigen binding portion thereof, comprises a heavy chain variable region comprising a CDR1 having the amino acid sequence of SEQ ID NO: 75 and a light chain variable region comprising a CDR1 having the amino acid sequence of either SEQ ID NO: 79.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 12 and a light chain variable region comprising a CDR3 having the amino acid sequence of SEQ ID NO: 16.

In some embodiments, the antibody, or antigen binding portion thereof, comprises a heavy chain variable region comprising a CDR2 having the amino acid sequence of SEQ ID NO: 11 and a light chain variable region comprising a CDR2 having the amino acid sequence of SEQ ID NO: 15. In other embodiments, the antibody, or antigen binding portion thereof, comprises a heavy chain variable region comprising a CDR1 having the amino acid sequence of SEQ ID NO: 10 and a light chain variable region comprising a CDR1 having the amino acid sequence of either SEQ ID NO: 14.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 86 and a light chain variable region comprising a CDR3 having the amino acid sequence of SEQ ID NO: 89.

In some embodiments, the antibody, or antigen binding portion thereof, comprises a heavy chain variable region comprising a CDR2 having the amino acid sequence of SEQ ID NO: 85 and a light chain variable region comprising a CDR2 having the amino acid sequence of SEQ ID NO: 80. In other embodiments, the antibody, or antigen binding portion thereof, comprises a heavy chain variable region comprising a CDR1 having the amino acid sequence of SEQ ID NO: 84 and a light chain variable region comprising a CDR1 having the amino acid sequence of either SEQ ID NO: 88.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 92 and a light chain variable region comprising a CDR3 having the amino acid sequence of SEQ ID NO: 95.

In some embodiments, the antibody, or antigen binding portion thereof, comprises a heavy chain variable region comprising a CDR2 having the amino acid sequence of SEQ ID NO: 91 and a light chain variable region comprising a CDR2 having the amino acid sequence of SEQ ID NO: 80. In other embodiments, the antibody, or antigen binding portion thereof, comprises a heavy chain variable region comprising a CDR1 having the amino acid sequence of SEQ ID NO: 84 and a light chain variable region comprising a CDR1 having the amino acid sequence of either SEQ ID NO: 94.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 92 and a light chain variable region comprising a CDR3 having the amino acid sequence of SEQ ID NO: 99.

In some embodiments, the antibody, or antigen binding portion thereof, comprises a heavy chain variable region comprising a CDR2 having the amino acid sequence of SEQ ID NO: 97 and a light chain variable region comprising a CDR2 having the amino acid sequence of SEQ ID NO: 80. In other embodiments, the antibody, or antigen binding portion thereof, comprises a heavy chain variable region comprising a CDR1 having the amino acid sequence of SEQ ID NO: 84 and a light chain variable region comprising a CDR1 having the amino acid sequence of either SEQ ID NO: 79.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 20 and a light chain variable region comprising a CDR3 having the amino acid sequence of SEQ ID NO: 24.

In some embodiments, the antibody, or antigen binding portion thereof, comprises a heavy chain variable region comprising a CDR2 having the amino acid sequence of SEQ ID NO: 102 and a light chain variable region comprising a CDR2 having the amino acid sequence of SEQ ID NO: 105. In other embodiments, the antibody, or antigen binding portion thereof, comprises a heavy chain variable region comprising a CDR1 having the amino acid sequence of SEQ ID NO: 101 and a light chain variable region comprising a CDR1 having the amino acid sequence of either SEQ ID NO: 104.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 86 and a light chain variable region comprising a CDR3 having the amino acid sequence of SEQ ID NO: 89.

In some embodiments, the antibody, or antigen binding portion thereof, comprises a heavy chain variable region comprising a CDR2 having the amino acid sequence of SEQ ID NO: 107 and a light chain variable region comprising a CDR2 having the amino acid sequence of SEQ ID NO: 80. In other embodiments, the antibody, or antigen binding portion thereof, comprises a heavy chain variable region comprising a CDR1 having the amino acid sequence of SEQ ID NO: 84 and a light chain variable region comprising a CDR1 having the amino acid sequence of either SEQ ID NO: 88.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 112 and a light chain variable region comprising a CDR3 having the amino acid sequence of SEQ ID NO: 39.

In some embodiments, the antibody, or antigen binding portion thereof, comprises a heavy chain variable region comprising a CDR2 having the amino acid sequence of SEQ ID NO: 111 and a light chain variable region comprising a CDR2 having the amino acid sequence of SEQ ID NO: 38. In other embodiments, the antibody, or antigen binding portion thereof, comprises a heavy chain variable region comprising a CDR1 having the amino acid sequence of SEQ ID NO: 110 and a light chain variable region comprising a CDR1 having the amino acid sequence of either SEQ ID NO: 37.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 35 and a light chain variable region comprising a CDR3 having the amino acid sequence of SEQ ID NO: 39.

In some embodiments, the antibody, or antigen binding portion thereof, comprises a heavy chain variable region comprising a CDR2 having the amino acid sequence of SEQ ID NO: 34 and a light chain variable region comprising a CDR2 having the amino acid sequence of SEQ ID NO: 38. In other embodiments, the antibody, or antigen binding portion thereof, comprises a heavy chain variable region comprising a CDR1 having the amino acid sequence of SEQ ID NO: 33 and a light chain variable region comprising a CDR1 having the amino acid sequence of either SEQ ID NO: 115.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 35 and a light chain variable region comprising a CDR3 having the amino acid sequence of SEQ ID NO: 39.

In some embodiments, the antibody, or antigen binding portion thereof, comprises a heavy chain variable region comprising a CDR2 having the amino acid sequence of SEQ ID NO: 34 and a light chain variable region comprising a CDR2 having the amino acid sequence of SEQ ID NO: 38. In other embodiments, the antibody, or antigen binding portion thereof, comprises a heavy chain variable region comprising a CDR1 having the amino acid sequence of SEQ ID NO: 117 and a light chain variable region comprising a CDR1 having the amino acid sequence of either SEQ ID NO: 37.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 67 and a light chain variable region comprising a CDR3 having the amino acid sequence of SEQ ID NO: 70.

In some embodiments, the antibody, or antigen binding portion thereof, comprises a heavy chain variable region comprising a CDR2 having the amino acid sequence of SEQ ID NO: 119 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 26 and a light chain variable region comprising a CDR1 having the amino acid sequence of either SEQ ID NO: 69.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 67 and a light chain variable region comprising a CDR3 having the amino acid sequence of SEQ ID NO: 70.

In some embodiments, the antibody, or antigen binding portion thereof, comprises a heavy chain variable region comprising a CDR2 having the amino acid sequence of SEQ ID NO: 66 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 101 and a light chain variable region comprising a CDR1 having the amino acid sequence of either SEQ ID NO: 69.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 67 and a light chain variable region comprising a CDR3 having the amino acid sequence of SEQ ID NO: 70.

In some embodiments, the antibody, or antigen binding portion thereof, comprises a heavy chain variable region comprising a CDR2 having the amino acid sequence of SEQ ID NO: 66 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 26 and a light chain variable region comprising a CDR1 having the amino acid sequence of either SEQ ID NO: 69.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 67 and a light chain variable region comprising a CDR3 having the amino acid sequence of SEQ ID NO: 129.

In some embodiments, the antibody, or antigen binding portion thereof, comprises a heavy chain variable region comprising a CDR2 having the amino acid sequence of SEQ ID NO: 66 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 101 and a light chain variable region comprising a CDR1 having the amino acid sequence of either SEQ ID NO: 69.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 133 and a light chain variable region comprising a CDR3 having the amino acid sequence of SEQ ID NO: 70.

In some embodiments, the antibody, or antigen binding portion thereof, comprises a heavy chain variable region comprising a CDR2 having the amino acid sequence of SEQ ID NO: 132 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 131 and a light chain variable region comprising a CDR1 having the amino acid sequence of either SEQ ID NO: 135.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 51 and a light chain variable region comprising a CDR3 having the amino acid sequence of SEQ ID NO: 55.

In some embodiments, the antibody, or antigen binding portion thereof, comprises a heavy chain variable region comprising a CDR2 having the amino acid sequence of SEQ ID NO: 50 and a light chain variable region comprising a CDR2 having the amino acid sequence of SEQ ID NO: 139. In other embodiments, the antibody, or antigen binding portion thereof, comprises a heavy chain variable region comprising a CDR1 having the amino acid sequence of SEQ ID NO: 49 and a light chain variable region comprising a CDR1 having the amino acid sequence of either SEQ ID NO: 138.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 142 and a light chain variable region comprising a CDR3 having the amino acid sequence of SEQ ID NO: 47.

In some embodiments, the antibody, or antigen binding portion thereof, comprises a heavy chain variable region comprising a CDR2 having the amino acid sequence of SEQ ID NO: 42 and a light chain variable region comprising a CDR2 having the amino acid sequence of SEQ ID NO: 46. In other embodiments, the antibody, or antigen binding portion thereof, comprises a heavy chain variable region comprising a CDR1 having the amino acid sequence of SEQ ID NO: 141 and a light chain variable region comprising a CDR1 having the amino acid sequence of either SEQ ID NO: 45.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 43 and a light chain variable region comprising a CDR3 having the amino acid sequence of SEQ ID NO: 150.

In some embodiments, the antibody, or antigen binding portion thereof, comprises a heavy chain variable region comprising a CDR2 having the amino acid sequence of SEQ ID NO: 146 and a light chain variable region comprising a CDR2 having the amino acid sequence of SEQ ID NO: 149. In other embodiments, the antibody, or antigen binding portion thereof, comprises a heavy chain variable region comprising a CDR1 having the amino acid sequence of SEQ ID NO: 145 and a light chain variable region comprising a CDR1 having the amino acid sequence of either SEQ ID NO: 148.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 43 and a light chain variable region comprising a CDR3 having the amino acid sequence of SEQ ID NO: 157.

In some embodiments, the antibody, or antigen binding portion thereof, comprises a heavy chain variable region comprising a CDR2 having the amino acid sequence of SEQ ID NO: 153 and a light chain variable region comprising a CDR2 having the amino acid sequence of SEQ ID NO: 156. In other embodiments, the antibody, or antigen binding portion thereof, comprises a heavy chain variable region comprising a CDR1 having the amino acid sequence of SEQ ID NO: 152 and a light chain variable region comprising a CDR1 having the amino acid sequence of either SEQ ID NO: 155.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 43 and a light chain variable region comprising a CDR3 having the amino acid sequence of SEQ ID NO: 162.

In some embodiments, the antibody, or antigen binding portion thereof, comprises a heavy chain variable region comprising a CDR2 having the amino acid sequence of SEQ ID NO: 159 and a light chain variable region comprising a CDR2 having the amino acid sequence of SEQ ID NO: 161. In other embodiments, the antibody, or antigen binding portion thereof, comprises a heavy chain variable region comprising a CDR1 having the amino acid sequence of SEQ ID NO: 145 and a light chain variable region comprising a CDR1 having the amino acid sequence of either SEQ ID NO: 148.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 166 and a light chain variable region comprising a CDR3 having the amino acid sequence of SEQ ID NO: 169.

In some embodiments, the antibody, or antigen binding portion thereof, comprises a heavy chain variable region comprising a CDR2 having the amino acid sequence of SEQ ID NO: 165 and a light chain variable region comprising a CDR2 having the amino acid sequence of SEQ ID NO: 168. In other embodiments, the antibody, or antigen binding portion thereof, comprises a heavy chain variable region comprising a CDR1 having the amino acid sequence of SEQ ID NO: 164 and a light chain variable region comprising a CDR1 having the amino acid sequence of either SEQ ID NO: 155.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 171 and a light chain variable region comprising a CDR3 having the amino acid sequence of SEQ ID NO: 169.

In some embodiments, the antibody, or antigen binding portion thereof, comprises a heavy chain variable region comprising a CDR2 having the amino acid sequence of SEQ ID NO: 165 and a light chain variable region comprising a CDR2 having the amino acid sequence of SEQ ID NO: 168. In other embodiments, the antibody, or antigen binding portion thereof, comprises a heavy chain variable region comprising a CDR1 having the amino acid sequence of SEQ ID NO: 164 and a light chain variable region comprising a CDR1 having the amino acid sequence of either SEQ ID NO: 155.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 176 and a light chain variable region comprising a CDR3 having the amino acid sequence of SEQ ID NO: 179.

In some embodiments, the antibody, or antigen binding portion thereof, comprises a heavy chain variable region comprising a CDR2 having the amino acid sequence of SEQ ID NO: 175 and a light chain variable region comprising a CDR2 having the amino acid sequence of SEQ ID NO: 178. In other embodiments, the antibody, or antigen binding portion thereof, comprises a heavy chain variable region comprising a CDR1 having the amino acid sequence of SEQ ID NO: 174 and a light chain variable region comprising a CDR1 having the amino acid sequence of either SEQ ID NO: 79.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 183 and a light chain variable region comprising a CDR3 having the amino acid sequence of SEQ ID NO: 179.

In some embodiments, the antibody, or antigen binding portion thereof, comprises a heavy chain variable region comprising a CDR2 having the amino acid sequence of SEQ ID NO: 182 and a light chain variable region comprising a CDR2 having the amino acid sequence of SEQ ID NO: 80. In other embodiments, the antibody, or antigen binding portion thereof, comprises a heavy chain variable region comprising a CDR1 having the amino acid sequence of SEQ ID NO: 101 and a light chain variable region comprising a CDR1 having the amino acid sequence of either SEQ ID NO: 79.

In one aspect of the invention, the present disclosure provides an isolated antibody, or antigen binding portion thereof, that binds to human IL1RAP, wherein the antibody, or antigen binding portion thereof, comprises a heavy chain variable region comprising a CDR3 having the amino acid sequence of SEQ ID NO: 188 and a light chain variable region comprising a CDR3 having the amino acid sequence of SEQ ID NO: 63.

In some embodiments, the antibody, or antigen binding portion thereof, comprises a heavy chain variable region comprising a CDR2 having the amino acid sequence of SEQ ID NO: 187 and a light chain variable region comprising a CDR2 having the amino acid sequence of SEQ ID NO: 62. In other embodiments, the antibody, or antigen binding portion thereof, comprises a heavy chain variable region comprising a CDR1 having the amino acid sequence of SEQ ID NO: 186 and a light chain variable region comprising a CDR1 having the amino acid sequence of either SEQ ID NO: 190.

In some aspects, the antibody, or antigen binding portion thereof, a human or humanized antibody. In one embodiments, the antibody or antigen binding portion thereof is an IgG isotype. In some embodiments, the antibody, or antigen binding portion thereof, is an $IgG_1$ isotype. In another embodiment, the antibody, or antigen-binding portion thereof, is an $IgG_4$ isotype. In another embodiment, the antibody, or antigen-binding portion thereof, is an $IgG_2$ isotype. In another embodiment, the antibody, or antigen-binding portion thereof, is an $IgG_3$ isotype.

In one embodiment, the antibody, or antigen-binding portion thereof, is capable of inducing antibody dependent cellular cytotoxicity (ADCC). In one embodiment, the antibody, or antigen-binding portion thereof, is not capable of inducing ADCC.

In one embodiment, the antibody, or antigen-binding portion thereof, is capable of inducing complement-dependent cytotoxicity (CDC). In one embodiment, the antibody, or antigen-binding portion thereof, is not capable of inducing CDC.

In one embodiment, the antibody, or antigen-binding portion thereof, is capable of inducing ADCC and CDC. In one embodiment, the antibody, or antigen-binding portion thereof, is not capable of inducing ADCC or CDC.

In certain embodiments, the anti-IL1RAP antibody, or antigen binding portion thereof, is a multispecific antibody, e.g., a bispecific antibody.

In some aspects, the antibody, or antigen binding portion thereof, has a $K_D$ of 200 nM or less.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 31, a CDR2 domain comprising the amino acid sequence of SEQ ID NO: 23, and a CDR1 domain comprising the amino acid sequence of SEQ ID NO: 30.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37.

In one aspect of the invention, the present disclosure provides an anti-IL1RAP antibody, or antigen-binding portion thereof, comprising a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 51, a CDR2 domain comprising the amino acid sequence of SEQ ID NO: 50, and a CDR1 domain comprising the amino acid sequence of SEQ ID NO: 49, and a light chain variable region comprising a CDR3 domain comprising the amino acid sequence of SEQ ID NO: 55, a CDR2 domain comprising the amino acid sequence of SEQ ID NO: 54, and a CDR1 domain comprising the amino acid sequence of SEQ ID NO: 53.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO:

57, and a light chain variable region comprising a CDR3 domain comprising the amino acid sequence of SEQ ID NO: 63, a CDR2 domain comprising the amino acid sequence of SEQ ID NO: 62, and a CDR1 domain comprising the amino acid sequence of SEQ ID NO: 61.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 65, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 67, a CDR2 domain comprising the amino acid sequence of SEQ ID NO: 72, and a CDR1 domain comprising the amino acid sequence of SEQ ID NO: 65, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 81, a CDR2 domain comprising the amino acid sequence of SEQ ID NO: 80, and a CDR1 domain comprising the amino acid sequence of SEQ ID NO: 79.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 86, a CDR2 domain comprising the amino acid sequence of SEQ ID NO: 85, and a CDR1 domain comprising the amino acid sequence of SEQ ID NO: 84, and a light chain variable region comprising a CDR3 domain comprising the amino acid sequence of SEQ ID NO: 89, a CDR2 domain comprising the amino acid sequence of SEQ ID NO: 80, and a CDR1 domain comprising the amino acid sequence of SEQ ID NO: 88.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 84, and a light chain variable region comprising a CDR3 domain comprising the amino acid sequence of SEQ ID NO: 95, a CDR2 domain comprising the amino acid sequence of SEQ ID NO: 80, and a CDR1 domain comprising the amino acid sequence of SEQ ID NO: 94.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 92, a CDR2 domain comprising the amino acid sequence of SEQ ID NO: 97, and a CDR1 domain comprising the amino acid sequence of SEQ ID NO: 84, and a light chain variable region comprising a CDR3 domain comprising the amino acid sequence of SEQ ID NO: 99, a CDR2 domain comprising the amino acid sequence of SEQ ID NO: 80, and a CDR1 domain comprising the amino acid sequence of SEQ ID NO: 79.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 20, a CDR2 domain comprising the amino acid sequence of SEQ ID NO: 102, and a CDR1 domain comprising the amino acid sequence of SEQ ID NO: 101, and a light chain variable region comprising a CDR3 domain comprising the amino acid sequence of SEQ ID NO: 24, a CDR2 domain comprising the amino acid sequence of SEQ ID NO: 105, and a CDR1 domain comprising the amino acid sequence of SEQ ID NO: 104.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 86, a CDR2 domain comprising the amino acid sequence of SEQ ID NO: 107, and a CDR1 domain comprising the amino acid sequence of SEQ ID NO: 84, and a light chain variable region comprising a CDR3 domain comprising the amino acid sequence of SEQ ID NO: 89, a CDR2 domain comprising the amino acid sequence of SEQ ID NO: 80, and a CDR1 domain comprising the amino acid sequence of SEQ ID NO: 88.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 115.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 117, and a light chain variable region comprising a CDR3 domain comprising the amino acid sequence of SEQ ID NO:

39, a CDR2 domain comprising the amino acid sequence of SEQ ID NO: 38, and a CDR1 domain comprising the amino acid sequence of SEQ ID NO: 37.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 67, a CDR2 domain comprising the amino acid sequence of SEQ ID NO: 119, and a CDR1 domain comprising the amino acid sequence of SEQ ID NO: 26, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 101, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 26, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 101, and a light chain variable region comprising a CDR3 domain comprising the amino acid sequence of SEQ ID NO: 129, a CDR2 domain comprising the amino acid sequence of SEQ ID NO: 62, and a CDR1 domain comprising the amino acid sequence of SEQ ID NO: 69.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 133, a CDR2 domain comprising the amino acid sequence of SEQ ID NO: 132, and a CDR1 domain comprising the amino acid sequence of SEQ ID NO: 131, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 135.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 51, a CDR2 domain comprising the amino acid sequence of SEQ ID NO: 50, and a CDR1 domain comprising the amino acid sequence of SEQ ID NO: 49, and a light chain variable region comprising a CDR3 domain comprising the amino acid sequence of SEQ ID NO: 55, a CDR2 domain comprising the amino acid sequence of SEQ ID NO: 139, and a CDR1 domain comprising the amino acid sequence of SEQ ID NO: 138.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 142, a CDR2 domain comprising the amino acid sequence of SEQ ID NO: 42, and a CDR1 domain comprising the amino acid sequence of SEQ ID NO: 141, and a light chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 43, a CDR2 domain comprising the amino acid sequence of SEQ ID NO: 146, and a CDR1 domain comprising the amino acid sequence of SEQ ID NO: 145, and a light chain variable region comprising a CDR3 domain comprising the amino acid sequence of SEQ ID NO: 150, a CDR2 domain comprising the amino acid sequence of SEQ ID NO: 149, and a CDR1 domain comprising the amino acid sequence of SEQ ID NO: 148.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 43, a CDR2 domain comprising the amino acid sequence of SEQ ID NO: 153, and a CDR1 domain comprising the amino acid sequence of SEQ ID NO: 152, and a light chain variable region comprising a CDR3 domain comprising the amino acid sequence of SEQ ID NO: 157, a CDR2 domain comprising the amino acid sequence of SEQ ID NO: 156, and a CDR1 domain comprising the amino acid sequence of SEQ ID NO: 155.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 43, a CDR2 domain comprising the amino acid sequence of SEQ ID NO: 159, and a CDR1 domain comprising the amino acid sequence of SEQ ID NO: 145, and a light chain variable region comprising a CDR3 domain comprising the amino acid sequence of SEQ ID NO: 162, a CDR2 domain comprising the amino acid sequence of SEQ ID NO: 161, and a CDR1 domain comprising the amino acid sequence of SEQ ID NO: 148.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 166, a CDR2 domain comprising the amino acid sequence of SEQ ID NO: 165, and a CDR1 domain comprising the amino acid sequence of SEQ ID NO: 164, and a light chain variable region comprising a CDR3 domain comprising the amino acid sequence of SEQ ID NO: 169, a CDR2 domain comprising the amino acid sequence of SEQ ID NO: 168, and a CDR1 domain comprising the amino acid sequence of SEQ ID NO: 155.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 171, a CDR2 domain comprising the amino acid sequence of SEQ ID NO: 165, and a CDR1 domain comprising the amino acid sequence of SEQ ID NO: 164, and a light chain variable region comprising a CDR3 domain comprising the amino acid sequence of SEQ ID NO: 169, a CDR2 domain comprising the amino acid sequence of SEQ ID NO: 168, and a CDR1 domain comprising the amino acid sequence of SEQ ID NO: 155.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 176, a CDR2 domain comprising the amino acid sequence of SEQ ID NO: 175, and a CDR1 domain comprising the amino acid sequence of SEQ ID NO: 174, and a light chain variable region comprising a CDR3 domain comprising the amino acid sequence of SEQ ID NO: 179, a CDR2 domain comprising the amino acid sequence of SEQ ID NO: 178, and a CDR1 domain comprising the amino acid sequence of SEQ ID NO: 79.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 183, a CDR2 domain comprising the amino acid sequence of SEQ ID NO: 182, and a CDR1 domain comprising the amino acid sequence of SEQ ID NO: 181, and a light chain variable region comprising a CDR3 domain comprising the amino acid sequence of SEQ ID NO: 179, a CDR2 domain comprising the amino acid sequence of SEQ ID NO: 80, and a CDR1 domain comprising the amino acid sequence of SEQ ID NO: 79.

In another aspect of the invention, the present disclosure provides an anti-IL1RAP antibody, or antigen-binding portion thereof, comprising a heavy chain variable region comprising a CDR3 domain comprising the amino acid sequence of SEQ ID NO: 188, a CDR2 domain comprising the amino acid sequence of SEQ ID NO: 187, and a CDR1 domain comprising the amino acid sequence of SEQ ID NO: 186, and a light chain variable region comprising a CDR3 domain comprising the amino acid sequence of SEQ ID NO: 63, a CDR2 domain comprising the amino acid sequence of SEQ ID NO: 62, and a CDR1 domain comprising the amino acid sequence of SEQ ID NO: 190.

In another aspect of the invention, the present disclosure provides an anti-IL1RAP antibody, or antigen-binding portion thereof, comprising a heavy chain variable domain comprising an amino acid sequence set forth in SEQ ID NO: 1 and a light chain variable domain comprising an amino acid sequence set forth in SEQ ID NO: 5.

In another aspect of the invention, the present disclosure provides an anti-IL1RAP antibody, or antigen-binding portion thereof, comprising a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In another aspect of the invention, the present disclosure provides an anti-IL1RAP antibody, or antigen-binding portion thereof, comprising a heavy chain variable region comprising the amino acid sequence of SEQ ID NO: 9 and a light chain variable region comprising the amino acid sequence of SEQ ID NO: 13.

In another aspect of the invention, the present disclosure provides an anti-IL1RAP antibody, or antigen-binding portion thereof, comprising a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In another aspect of the invention, the present disclosure provides an anti-IL1RAP antibody, or antigen-binding portion thereof, comprising a heavy chain variable region comprising the amino acid sequence of SEQ ID NO: 17 and a light chain variable region comprising the amino acid sequence of SEQ ID NO: 21.

In another aspect of the invention, the present disclosure provides an anti-IL1RAP antibody, or antigen-binding portion thereof, comprising a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 21, or a sequence having at least 90%, 95%, 96%, 97%, 98%, or 99% identity to SEQ ID NO: 21.

In another aspect of the invention, the present disclosure provides an anti-IL1RAP antibody, or antigen-binding portion thereof, comprising a heavy chain variable region comprising the amino acid sequence of SEQ ID NO: 25 and a light chain variable region comprising the amino acid sequence of SEQ ID NO: 29.

In another aspect of the invention, the present disclosure provides an anti-IL1RAP antibody, or antigen-binding portion thereof, comprising a heavy chain comprising an amino acid sequence set forth in SEQ ID NO: 25, or a sequence having at least 90%, 95%, 96%, 97%, 98%, or 99% identity to SEQ ID NO: 25, and/or a light chain comprising an amino acid sequence set forth in SEQ ID NO: 29, or a sequence having at least 90%, 95%, 96%, 97%, 98%, or 99% identity to SEQ ID NO: 29.

In another aspect of the invention, the present disclosure provides an anti-IL1RAP antibody, or antigen-binding portion thereof, comprising a heavy chain variable region comprising the amino acid sequence of SEQ ID NO: 32 and a light chain variable region comprising the amino acid sequence of SEQ ID NO: 36.

In another aspect of the invention, the present disclosure provides an anti-IL1RAP antibody, or antigen-binding portion thereof, comprising a heavy chain comprising an amino acid sequence set forth in SEQ ID NO: 32, or a sequence having at least 90%, 95%, 96%, 97%, 98%, or 99% identity to SEQ ID NO: 32, and/or a light chain comprising an amino acid sequence set forth in SEQ ID NO: 36, or a sequence having at least 90%, 95%, 96%, 97%, 98%, or 99% identity to SEQ ID NO: 36.

In another aspect of the invention, the present disclosure provides an anti-IL1RAP antibody, or antigen-binding portion thereof, comprising a heavy chain variable region comprising the amino acid sequence of SEQ ID NO: 40 and a light chain variable region comprising the amino acid sequence of SEQ ID NO: 44.

In another aspect of the invention, the present disclosure provides an anti-IL1RAP antibody, or antigen-binding portion thereof, comprising a heavy chain comprising an amino acid sequence set forth in SEQ ID NO: 40, or a sequence having at least 90%, 95%, 96%, 97%, 98%, or 99% identity to SEQ ID NO: 40, and/or a light chain comprising an amino acid sequence set forth in SEQ ID NO: 44, or a sequence having at least 90%, 95%, 96%, 97%, 98%, or 99% identity to SEQ ID NO: 44.

In another aspect of the invention, the present disclosure provides an anti-IL1RAP antibody, or antigen-binding portion thereof, comprising a heavy chain variable region comprising the amino acid sequence of SEQ ID NO: 48 and a light chain variable region comprising the amino acid sequence of SEQ ID NO: 52.

In another aspect of the invention, the present disclosure provides an anti-IL1RAP antibody, or antigen-binding portion thereof, comprising a heavy chain comprising an amino acid sequence set forth in SEQ ID NO: 48, or a sequence having at least 90%, 95%, 96%, 97%, 98%, or 99% identity to SEQ ID NO: 48, and/or a light chain comprising an amino acid sequence set forth in SEQ ID NO: 52, or a sequence having at least 90%, 95%, 96%, 97%, 98%, or 99% identity to SEQ ID NO: 52.

In another aspect of the invention, the present disclosure provides an anti-IL1RAP antibody, or antigen-binding portion thereof, comprising a heavy chain variable region comprising the amino acid sequence of SEQ ID NO: 56 and a light chain variable region comprising the amino acid sequence of SEQ ID NO: 60.

In another aspect of the invention, the present disclosure provides an anti-IL1RAP antibody, or antigen-binding portion thereof, comprising a heavy chain comprising an amino acid sequence set forth in SEQ ID NO: 56, or a sequence having at least 90%, 95%, 96%, 97%, 98%, or 99% identity to SEQ ID NO: 56, and/or a light chain comprising an amino acid sequence set forth in SEQ ID NO: 60, or a sequence having at least 90%, 95%, 96%, 97%, 98%, or 99% identity to SEQ ID NO: 60.

In another aspect of the invention, the present disclosure provides an anti-IL1RAP antibody, or antigen-binding portion thereof, comprising a heavy chain variable region comprising the amino acid sequence of SEQ ID NO: 64 and a light chain variable region comprising the amino acid sequence of SEQ ID NO: 68.

In another aspect of the invention, the present disclosure provides an anti-IL1RAP antibody, or antigen-binding portion thereof, comprising a heavy chain comprising an amino acid sequence set forth in SEQ ID NO: 64, or a sequence having at least 90%, 95%, 96%, 97%, 98%, or 99% identity to SEQ ID NO: 64, and/or a light chain comprising an amino acid sequence set forth in SEQ ID NO: 68, or a sequence having at least 90%, 95%, 96%, 97%, 98%, or 99% identity to SEQ ID NO: 68.

In another aspect of the invention, the present disclosure provides an anti-IL1RAP antibody, or antigen-binding portion thereof, comprising a heavy chain variable region comprising the amino acid sequence of SEQ ID NO: 71 and a light chain variable region comprising the amino acid sequence of SEQ ID NO: 73.

In another aspect of the invention, the present disclosure provides an anti-IL1RAP antibody, or antigen-binding portion thereof, comprising a heavy chain comprising an amino acid sequence set forth in SEQ ID NO: 71, or a sequence having at least 90%, 95%, 96%, 97%, 98%, or 99% identity to SEQ ID NO: 71, and/or a light chain comprising an amino acid sequence set forth in SEQ ID NO: 73, or a sequence having at least 90%, 95%, 96%, 97%, 98%, or 99% identity to SEQ ID NO: 73.

In another aspect of the invention, the present disclosure provides an anti-IL1RAP antibody, or antigen-binding portion thereof, comprising a heavy chain variable region comprising the amino acid sequence of SEQ ID NO: 74 and a light chain variable region comprising the amino acid sequence of SEQ ID NO: 78.

In another aspect of the invention, the present disclosure provides an anti-IL1RAP antibody, or antigen-binding portion thereof, comprising a heavy chain comprising an amino acid sequence set forth in SEQ ID NO: 74, or a sequence having at least 90%, 95%, 96%, 97%, 98%, or 99% identity to SEQ ID NO: 74, and/or a light chain comprising an amino acid sequence set forth in SEQ ID NO: 78, or a sequence having at least 90%, 95%, 96%, 97%, 98%, or 99% identity to SEQ ID NO: 78.

In another aspect of the invention, the present disclosure provides an anti-IL1RAP antibody, or antigen-binding portion thereof, comprising a heavy chain variable region comprising the amino acid sequence of SEQ ID NO: 9 and a light chain variable region comprising the amino acid sequence of SEQ ID NO: 82.

In another aspect of the invention, the present disclosure provides an anti-IL1RAP antibody, or antigen-binding portion thereof, comprising a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 82, or a sequence having at least 90%, 95%, 96%, 97%, 98%, or 99% identity to SEQ ID NO: 82.

In another aspect of the invention, the present disclosure provides an anti-IL1RAP antibody, or antigen-binding portion thereof, comprising a heavy chain variable region comprising the amino acid sequence of SEQ ID NO: 83 and a light chain variable region comprising the amino acid sequence of SEQ ID NO: 87.

In another aspect of the invention, the present disclosure provides an anti-IL1RAP antibody, or antigen-binding portion thereof, comprising a heavy chain comprising an amino acid sequence set forth in SEQ ID NO: 83, or a sequence having at least 90%, 95%, 96%, 97%, 98%, or 99% identity to SEQ ID NO: 83, and/or a light chain comprising an amino acid sequence set forth in SEQ ID NO: 87, or a sequence having at least 90%, 95%, 96%, 97%, 98%, or 99% identity to SEQ ID NO: 87.

In another aspect of the invention, the present disclosure provides an anti-IL1RAP antibody, or antigen-binding portion thereof, comprising a heavy chain variable region comprising the amino acid sequence of SEQ ID NO: 90 and a light chain variable region comprising the amino acid sequence of SEQ ID NO: 93.

In another aspect of the invention, the present disclosure provides an anti-IL1RAP antibody, or antigen-binding portion thereof, comprising a heavy chain comprising an amino acid sequence set forth in SEQ ID NO: 90, or a sequence having at least 90%, 95%, 96%, 97%, 98%, or 99% identity to SEQ ID NO: 90, and/or a light chain comprising an amino acid sequence set forth in SEQ ID NO: 93, or a sequence having at least 90%, 95%, 96%, 97%, 98%, or 99% identity to SEQ ID NO: 93.

In another aspect of the invention, the present disclosure provides an anti-IL1RAP antibody, or antigen-binding portion thereof, comprising a heavy chain variable region comprising the amino acid sequence of SEQ ID NO: 96 and a light chain variable region comprising the amino acid sequence of SEQ ID NO: 98.

In another aspect of the invention, the present disclosure provides an anti-IL1RAP antibody, or antigen-binding portion thereof, comprising a heavy chain comprising an amino acid sequence set forth in SEQ ID NO: 96, or a sequence having at least 90%, 95%, 96%, 97%, 98%, or 99% identity to SEQ ID NO: 96, and/or a light chain comprising an amino acid sequence set forth in SEQ ID NO: 98, or a sequence having at least 90%, 95%, 96%, 97%, 98%, or 99% identity to SEQ ID NO: 98.

In another aspect of the invention, the present disclosure provides an anti-IL1RAP antibody, or antigen-binding portion thereof, comprising a heavy chain variable region comprising the amino acid sequence of SEQ ID NO: 100 and a light chain variable region comprising the amino acid sequence of SEQ ID NO: 103.

In another aspect of the invention, the present disclosure provides an anti-IL1RAP antibody, or antigen-binding portion thereof, comprising a heavy chain comprising an amino acid sequence set forth in SEQ ID NO: 100, or a sequence having at least 90%, 95%, 96%, 97%, 98%, or 99% identity to SEQ ID NO: 100, and/or a light chain comprising an amino acid sequence set forth in SEQ ID NO: 103, or a sequence having at least 90%, 95%, 96%, 97%, 98%, or 99% identity to SEQ ID NO: 103.

In another aspect of the invention, the present disclosure provides an anti-IL1RAP antibody, or antigen-binding portion thereof, comprising a heavy chain variable region comprising the amino acid sequence of SEQ ID NO: 106 and a light chain variable region comprising the amino acid sequence of SEQ ID NO: 108.

In another aspect of the invention, the present disclosure provides an anti-IL1RAP antibody, or antigen-binding portion thereof, comprising a heavy chain comprising an amino acid sequence set forth in SEQ ID NO: 106, or a sequence having at least 90%, 95%, 96%, 97%, 98%, or 99% identity to SEQ ID NO: 106, and/or a light chain comprising an amino acid sequence set forth in SEQ ID NO: 108, or a sequence having at least 90%, 95%, 96%, 97%, 98%, or 99% identity to SEQ ID NO: 108.

In another aspect of the invention, the present disclosure provides an anti-IL1RAP antibody, or antigen-binding portion thereof, comprising a heavy chain variable region comprising the amino acid sequence of SEQ ID NO: 109 and a light chain variable region comprising the amino acid sequence of SEQ ID NO: 113.

In another aspect of the invention, the present disclosure provides an anti-IL1RAP antibody, or antigen-binding portion thereof, comprising a heavy chain comprising an amino acid sequence set forth in SEQ ID NO: 109, or a sequence having at least 90%, 95%, 96%, 97%, 98%, or 99% identity to SEQ ID NO: 109, and/or a light chain comprising an amino acid sequence set forth in SEQ ID NO: 113, or a sequence having at least 90%, 95%, 96%, 97%, 98%, or 99% identity to SEQ ID NO: 113.

In another aspect of the invention, the present disclosure provides an anti-IL1RAP antibody, or antigen-binding portion thereof, comprising a heavy chain variable region comprising the amino acid sequence of SEQ ID NO: 32 and a light chain variable region comprising the amino acid sequence of SEQ ID NO: 114.

In another aspect of the invention, the present disclosure provides an anti-IL1RAP antibody, or antigen-binding portion thereof, comprising a heavy chain comprising an amino acid sequence set forth in SEQ ID NO: 32, or a sequence having at least 90%, 95%, 96%, 97%, 98%, or 99% identity to SEQ ID NO: 32, and/or a light chain comprising an amino acid sequence set forth in SEQ ID NO: 114, or a sequence having at least 90%, 95%, 96%, 97%, 98%, or 99% identity to SEQ ID NO: 114.

In another aspect of the invention, the present disclosure provides an anti-IL1RAP antibody, or antigen-binding portion thereof, comprising a heavy chain variable region comprising the amino acid sequence of SEQ ID NO: 116 and a light chain variable region comprising the amino acid sequence of SEQ ID NO: 36.

In another aspect of the invention, the present disclosure provides an anti-IL1RAP antibody, or antigen-binding portion thereof, comprising a heavy chain comprising an amino acid sequence set forth in SEQ ID NO: 116, or a sequence having at least 90%, 95%, 96%, 97%, 98%, or 99% identity to SEQ ID NO: 116, and/or a light chain comprising an amino acid sequence set forth in SEQ ID NO: 36, or a sequence having at least 90%, 95%, 96%, 97%, 98%, or 99% identity to SEQ ID NO: 36.

In another aspect of the invention, the present disclosure provides an anti-IL1RAP antibody, or antigen-binding portion thereof, comprising a heavy chain variable region comprising the amino acid sequence of SEQ ID NO: 118 and a light chain variable region comprising the amino acid sequence of SEQ ID NO: 120.

In another aspect of the invention, the present disclosure provides an anti-IL1RAP antibody, or antigen-binding portion thereof, comprising a heavy chain comprising an amino acid sequence set forth in SEQ ID NO: 118, or a sequence having at least 90%, 95%, 96%, 97%, 98%, or 99% identity to SEQ ID NO: 118, and/or a light chain comprising an amino acid sequence set forth in SEQ ID NO: 120, or a sequence having at least 90%, 95%, 96%, 97%, 98%, or 99% identity to SEQ ID NO: 120.

In another aspect of the invention, the present disclosure provides an anti-IL1RAP antibody, or antigen-binding portion thereof, comprising a heavy chain variable region comprising the amino acid sequence of SEQ ID NO: 121 and a light chain variable region comprising the amino acid sequence of SEQ ID NO: 122.

In another aspect of the invention, the present disclosure provides an anti-IL1RAP antibody, or antigen-binding portion thereof, comprising a heavy chain comprising an amino acid sequence set forth in SEQ ID NO: 121, or a sequence having at least 90%, 95%, 96%, 97%, 98%, or 99% identity to SEQ ID NO: 121, and/or a light chain comprising an amino acid sequence set forth in SEQ ID NO: 122, or a sequence having at least 90%, 95%, 96%, 97%, 98%, or 99% identity to SEQ ID NO: 122.

In another aspect of the invention, the present disclosure provides an anti-IL1RAP antibody, or antigen-binding portion thereof, comprising a heavy chain variable region comprising the amino acid sequence of SEQ ID NO: 123 and a light chain variable region comprising the amino acid sequence of SEQ ID NO: 124.

In another aspect of the invention, the present disclosure provides an anti-IL1RAP antibody, or antigen-binding portion thereof, comprising a heavy chain comprising an amino acid sequence set forth in SEQ ID NO: 123, or a sequence having at least 90%, 95%, 96%, 97%, 98%, or 99% identity to SEQ ID NO: 123, and/or a light chain comprising an amino acid sequence set forth in SEQ ID NO: 124, or a sequence having at least 90%, 95%, 96%, 97%, 98%, or 99% identity to SEQ ID NO: 124.

In another aspect of the invention, the present disclosure provides an anti-IL1RAP antibody, or antigen-binding portion thereof, comprising a heavy chain variable region comprising the amino acid sequence of SEQ ID NO: 125 and a light chain variable region comprising the amino acid sequence of SEQ ID NO: 126.

In another aspect of the invention, the present disclosure provides an anti-IL1RAP antibody, or antigen-binding portion thereof, comprising a heavy chain comprising an amino acid sequence set forth in SEQ ID NO: 125, or a sequence having at least 90%, 95%, 96%, 97%, 98%, or 99% identity to SEQ ID NO: 125, and/or a light chain comprising an amino acid sequence set forth in SEQ ID NO: 126, or a sequence having at least 90%, 95%, 96%, 97%, 98%, or 99% identity to SEQ ID NO: 126.

In another aspect of the invention, the present disclosure provides an anti-IL1RAP antibody, or antigen-binding portion thereof, comprising a heavy chain variable region comprising the amino acid sequence of SEQ ID NO: 127 and a light chain variable region comprising the amino acid sequence of SEQ ID NO: 128.

In another aspect of the invention, the present disclosure provides an anti-IL1RAP antibody, or antigen-binding portion thereof, comprising a heavy chain comprising an amino acid sequence set forth in SEQ ID NO: 127, or a sequence having at least 90%, 95%, 96%, 97%, 98%, or 99% identity to SEQ ID NO: 127, and/or a light chain comprising an amino acid sequence set forth in SEQ ID NO: 128, or a sequence having at least 90%, 95%, 96%, 97%, 98%, or 99% identity to SEQ ID NO: 128.

In another aspect of the invention, the present disclosure provides an anti-IL1RAP antibody, or antigen-binding portion thereof, comprising a heavy chain variable region comprising the amino acid sequence of SEQ ID NO: 130 and a light chain variable region comprising the amino acid sequence of SEQ ID NO: 134.

In another aspect of the invention, the present disclosure provides an anti-IL1RAP antibody, or antigen-binding portion thereof, comprising a heavy chain comprising an amino acid sequence set forth in SEQ ID NO: 130, or a sequence having at least 90%, 95%, 96%, 97%, 98%, or 99% identity to SEQ ID NO: 130, and/or a light chain comprising an amino acid sequence set forth in SEQ ID NO: 134, or a sequence having at least 90%, 95%, 96%, 97%, 98%, or 99% identity to SEQ ID NO: 134.

In another aspect of the invention, the present disclosure provides an anti-IL1RAP antibody, or antigen-binding portion thereof, comprising a heavy chain variable region comprising the amino acid sequence of SEQ ID NO: 136 and a light chain variable region comprising the amino acid sequence of SEQ ID NO: 137.

In another aspect of the invention, the present disclosure provides an anti-IL1RAP antibody, or antigen-binding portion thereof, comprising a heavy chain comprising an amino acid sequence set forth in SEQ ID NO: 136, or a sequence having at least 90%, 95%, 96%, 97%, 98%, or 99% identity to SEQ ID NO: 136, and/or a light chain comprising an amino acid sequence set forth in SEQ ID NO: 137, or a sequence having at least 90%, 95%, 96%, 97%, 98%, or 99% identity to SEQ ID NO: 137.

In another aspect of the invention, the present disclosure provides an anti-IL1RAP antibody, or antigen-binding portion thereof, comprising a heavy chain variable region comprising the amino acid sequence of SEQ ID NO: 140 and a light chain variable region comprising the amino acid sequence of SEQ ID NO: 143.

In another aspect of the invention, the present disclosure provides an anti-IL1RAP antibody, or antigen-binding portion thereof, comprising a heavy chain comprising an amino acid sequence set forth in SEQ ID NO: 140, or a sequence having at least 90%, 95%, 96%, 97%, 98%, or 99% identity to SEQ ID NO: 140, and/or a light chain comprising an amino acid sequence set forth in SEQ ID NO: 143, or a sequence having at least 90%, 95%, 96%, 97%, 98%, or 99% identity to SEQ ID NO: 143.

In another aspect of the invention, the present disclosure provides an anti-IL1RAP antibody, or antigen-binding portion thereof, comprising a heavy chain variable region comprising the amino acid sequence of SEQ ID NO: 144 and a light chain variable region comprising the amino acid sequence of SEQ ID NO: 147.

In another aspect of the invention, the present disclosure provides an anti-IL1RAP antibody, or antigen-binding portion thereof, comprising a heavy chain comprising an amino acid sequence set forth in SEQ ID NO: 144, or a sequence having at least 90%, 95%, 96%, 97%, 98%, or 99% identity to SEQ ID NO: 144, and/or a light chain comprising an amino acid sequence set forth in SEQ ID NO: 147, or a sequence having at least 90%, 95%, 96%, 97%, 98%, or 99% identity to SEQ ID NO: 147.

In another aspect of the invention, the present disclosure provides an anti-IL1RAP antibody, or antigen-binding portion thereof, comprising a heavy chain variable region comprising the amino acid sequence of SEQ ID NO: 151 and a light chain variable region comprising the amino acid sequence of SEQ ID NO: 154.

In another aspect of the invention, the present disclosure provides an anti-IL1RAP antibody, or antigen-binding portion thereof, comprising a heavy chain comprising an amino acid sequence set forth in SEQ ID NO: 151, or a sequence having at least 90%, 95%, 96%, 97%, 98%, or 99% identity to SEQ ID NO: 151, and/or a light chain comprising an amino acid sequence set forth in SEQ ID NO: 154, or a sequence having at least 90%, 95%, 96%, 97%, 98%, or 99% identity to SEQ ID NO: 154.

In another aspect of the invention, the present disclosure provides an anti-IL1RAP antibody, or antigen-binding portion thereof, comprising a heavy chain variable region comprising the amino acid sequence of SEQ ID NO: 158 and a light chain variable region comprising the amino acid sequence of SEQ ID NO: 160.

In another aspect of the invention, the present disclosure provides an anti-IL1RAP antibody, or antigen-binding portion thereof, comprising a heavy chain comprising an amino acid sequence set forth in SEQ ID NO: 158, or a sequence having at least 90%, 95%, 96%, 97%, 98%, or 99% identity to SEQ ID NO: 158, and/or a light chain comprising an amino acid sequence set forth in SEQ ID NO: 160, or a sequence having at least 90%, 95%, 96%, 97%, 98%, or 99% identity to SEQ ID NO: 160.

In another aspect of the invention, the present disclosure provides an anti-IL1RAP antibody, or antigen-binding portion thereof, comprising a heavy chain variable region comprising the amino acid sequence of SEQ ID NO: 163 and a light chain variable region comprising the amino acid sequence of SEQ ID NO: 167.

In another aspect of the invention, the present disclosure provides an anti-IL1RAP antibody, or antigen-binding portion thereof, comprising a heavy chain comprising an amino acid sequence set forth in SEQ ID NO: 163, or a sequence having at least 90%, 95%, 96%, 97%, 98%, or 99% identity to SEQ ID NO: 163, and/or a light chain comprising an amino acid sequence set forth in SEQ ID NO: 167, or a sequence having at least 90%, 95%, 96%, 97%, 98%, or 99% identity to SEQ ID NO: 167.

In another aspect of the invention, the present disclosure provides an anti-IL1RAP antibody, or antigen-binding portion thereof, comprising a heavy chain variable region comprising the amino acid sequence of SEQ ID NO: 170 and a light chain variable region comprising the amino acid sequence of SEQ ID NO: 172.

In another aspect of the invention, the present disclosure provides an anti-IL1RAP antibody, or antigen-binding portion thereof, comprising a heavy chain comprising an amino acid sequence set forth in SEQ ID NO: 170, or a sequence having at least 90%, 95%, 96%, 97%, 98%, or 99% identity to SEQ ID NO: 170, and/or a light chain comprising an amino acid sequence set forth in SEQ ID NO: 172, or a sequence having at least 90%, 95%, 96%, 97%, 98%, or 99% identity to SEQ ID NO: 172.

In another aspect of the invention, the present disclosure provides an anti-IL1RAP antibody, or antigen-binding portion thereof, comprising a heavy chain variable region comprising the amino acid sequence of SEQ ID NO: 173 and a light chain variable region comprising the amino acid sequence of SEQ ID NO: 177.

In another aspect of the invention, the present disclosure provides an anti-IL1RAP antibody, or antigen-binding portion thereof, comprising a heavy chain comprising an amino acid sequence set forth in SEQ ID NO: 173, or a sequence having at least 90%, 95%, 96%, 97%, 98%, or 99% identity to SEQ ID NO: 173, and/or a light chain comprising an amino acid sequence set forth in SEQ ID NO: 177, or a sequence having at least 90%, 95%, 96%, 97%, 98%, or 99% identity to SEQ ID NO: 177.

In another aspect of the invention, the present disclosure provides an anti-IL1RAP antibody, or antigen-binding portion thereof, comprising a heavy chain variable region comprising the amino acid sequence of SEQ ID NO: 180 and a light chain variable region comprising the amino acid sequence of SEQ ID NO: 184.

In another aspect of the invention, the present disclosure provides an anti-IL1RAP antibody, or antigen-binding portion thereof, comprising a heavy chain comprising an amino acid sequence set forth in SEQ ID NO: 180, or a sequence having at least 90%, 95%, 96%, 97%, 98%, or 99% identity to SEQ ID NO: 180, and/or a light chain comprising an amino acid sequence set forth in SEQ ID NO: 184, or a sequence having at least 90%, 95%, 96%, 97%, 98%, or 99% identity to SEQ ID NO: 184

In another aspect of the invention, the present disclosure provides an anti-IL1RAP antibody, or antigen-binding portion thereof, comprising a heavy chain variable region comprising the amino acid sequence of SEQ ID NO: 185 and a light chain variable region comprising the amino acid sequence of SEQ ID NO: 189.

In another aspect of the invention, the present disclosure provides an anti-IL1RAP antibody, or antigen-binding portion thereof, comprising a heavy chain comprising an amino acid sequence set forth in SEQ ID NO: 185, or a sequence having at least 90%, 95%, 96%, 97%, 98%, or 99% identity to SEQ ID NO: 185, and/or a light chain comprising an amino acid sequence set forth in SEQ ID NO: 189, or a sequence having at least 90%, 95%, 96%, 97%, 98%, or 99% identity to SEQ ID NO: 189.

In another aspect of the invention, the present disclosure provides an antibody, or antigen-binding portion thereof, that binds to the same epitope as an antibody, or antigen-binding portion thereof, as described herein.

In another aspect of the invention, the present disclosure provides an isolated nucleic acid encoding an antibody, or antigen binding portion thereof, as described herein.

In another aspect of the invention, the present disclosure provides a pharmaceutical composition comprising the antibody, or antigen binding portion thereof, as described herein, and a pharmaceutically acceptable carrier.

In another aspect of the invention, the present disclosure provides an antibody, or antigen binding portion thereof, as described herein, conjugated to at least one drug.

In some aspects, the at least one drug is selected from the group consisting of a DNA damaging agent, an anti-apoptotic agent, a mitotic inhibitor, an anti-tumor antibiotic, an immunomodulating agent, a nucleic acid for gene therapy, an anti-angiogenic agent, an antimetabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In one embodiment, the drug is a DNA damaging agent. In one embodiment, the DNA damaging agent is a PBD.

In other embodiments, the at least one drug is conjugated to the antibody, or antigen-binding portion thereof, via a linker. In another embodiment, the linker is a cleavable linker. In yet other embodiments, the linker is a non-cleavable linker.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 31, a CDR2 domain comprising the amino acid sequence of SEQ ID NO: 23, and a CDR1 domain comprising the amino acid sequence of SEQ ID NO: 30.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 51, a CDR2 domain comprising the amino acid sequence of SEQ ID NO: 50, and a CDR1 domain comprising the amino acid sequence of SEQ ID NO: 49, and a light chain variable region comprising a CDR3 domain comprising the amino acid sequence of SEQ ID NO: 55, a CDR2 domain comprising the amino acid sequence of SEQ ID NO: 54, and a CDR1 domain comprising the amino acid sequence of SEQ ID NO: 53.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO: 57, and a light chain variable region comprising a CDR3 domain comprising the amino acid sequence of SEQ ID NO: 63, a CDR2 domain comprising the amino acid sequence of SEQ ID NO: 62, and a CDR1 domain comprising the amino acid sequence of SEQ ID NO: 61.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 65, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 67, a CDR2 domain comprising the amino acid sequence of SEQ ID NO: 72, and a CDR1 domain comprising the amino acid sequence of SEQ ID NO: 65, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 81, a CDR2 domain comprising the amino acid sequence of SEQ ID NO: 80, and a CDR1 domain comprising the amino acid sequence of SEQ ID NO: 79.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 86, a CDR2 domain comprising the amino acid sequence of SEQ ID NO: 85, and a CDR1 domain comprising the amino acid sequence of SEQ ID NO: 84, and a light chain variable region comprising a CDR3 domain comprising the amino acid sequence of SEQ ID NO: 89, a CDR2 domain comprising the amino acid sequence of SEQ ID NO: 80, and a CDR1 domain comprising the amino acid sequence of SEQ ID NO: 88.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 84, and a light chain variable region comprising a CDR3 domain comprising the amino acid sequence of SEQ ID NO:

95, a CDR2 domain comprising the amino acid sequence of SEQ ID NO: 80, and a CDR1 domain comprising the amino acid sequence of SEQ ID NO: 94.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 92, a CDR2 domain comprising the amino acid sequence of SEQ ID NO: 97, and a CDR1 domain comprising the amino acid sequence of SEQ ID NO: 84, and a light chain variable region comprising a CDR3 domain comprising the amino acid sequence of SEQ ID NO: 99, a CDR2 domain comprising the amino acid sequence of SEQ ID NO: 80, and a CDR1 domain comprising the amino acid sequence of SEQ ID NO: 79.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 20, a CDR2 domain comprising the amino acid sequence of SEQ ID NO: 102, and a CDR1 domain comprising the amino acid sequence of SEQ ID NO: 101, and a light chain variable region comprising a CDR3 domain comprising the amino acid sequence of SEQ ID NO: 24, a CDR2 domain comprising the amino acid sequence of SEQ ID NO: 105, and a CDR1 domain comprising the amino acid sequence of SEQ ID NO: 104.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 86, a CDR2 domain comprising the amino acid sequence of SEQ ID NO: 107, and a CDR1 domain comprising the amino acid sequence of SEQ ID NO: 84, and a light chain variable region comprising a CDR3 domain comprising the amino acid sequence of SEQ ID NO: 89, a CDR2 domain comprising the amino acid sequence of SEQ ID NO: 80, and a CDR1 domain comprising the amino acid sequence of SEQ ID NO: 88.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 115.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 117, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 67, a CDR2 domain comprising the amino acid sequence of SEQ ID NO: 119, and a CDR1 domain comprising the amino acid sequence of SEQ ID NO: 26, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 101, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 26, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 101, and a light chain variable region comprising a CDR3 domain comprising the amino acid sequence of SEQ ID NO: 129, a CDR2 domain comprising the amino acid sequence of SEQ ID NO: 62, and a CDR1 domain comprising the amino acid sequence of SEQ ID NO: 69.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 133, a CDR2 domain comprising the amino acid sequence of SEQ ID NO: 132, and a CDR1 domain comprising the amino acid sequence of SEQ ID NO: 131, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 135.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 51, a CDR2 domain comprising the amino acid sequence of SEQ ID NO: 50, and a CDR1 domain comprising the amino acid sequence of SEQ ID NO: 49, and a light chain variable region comprising a CDR3 domain comprising the amino acid sequence of SEQ ID NO: 55, a CDR2 domain comprising the amino acid sequence of SEQ ID NO: 139, and a CDR1 domain comprising the amino acid sequence of SEQ ID NO: 138.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 142, a CDR2 domain comprising the amino acid sequence of SEQ ID NO: 42, and a CDR1 domain comprising the amino acid sequence of SEQ ID NO: 141, and a light chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 43, a CDR2 domain comprising the amino acid sequence of SEQ ID NO: 146, and a CDR1 domain comprising the amino acid sequence of SEQ ID NO: 145, and a light chain variable region comprising a CDR3 domain comprising the amino acid sequence of SEQ ID NO: 150, a CDR2 domain comprising the amino acid sequence of SEQ ID NO: 149, and a CDR1 domain comprising the amino acid sequence of SEQ ID NO: 148.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 43, a CDR2 domain comprising the amino acid sequence of SEQ ID NO: 153, and a CDR1 domain comprising the amino acid sequence of SEQ ID NO: 152, and a light chain variable region comprising a CDR3 domain comprising the amino acid sequence of SEQ ID NO: 157, a CDR2 domain comprising the amino acid sequence of SEQ ID NO: 156, and a CDR1 domain comprising the amino acid sequence of SEQ ID NO: 155.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 43, a CDR2 domain comprising the amino acid sequence of SEQ ID NO: 159, and a CDR1 domain comprising the amino acid sequence of SEQ ID NO: 145, and a light chain variable region comprising a CDR3 domain comprising the amino acid sequence of SEQ ID NO: 162, a CDR2 domain comprising the amino acid sequence of SEQ ID NO: 161, and a CDR1 domain comprising the amino acid sequence of SEQ ID NO: 148.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 166, a CDR2 domain comprising the amino acid sequence of SEQ ID NO: 165, and a CDR1 domain comprising the amino acid sequence of SEQ ID NO: 164, and a light chain variable region comprising a CDR3 domain comprising the amino acid sequence of SEQ ID NO: 169, a CDR2 domain comprising the amino acid sequence of SEQ ID NO: 168, and a CDR1 domain comprising the amino acid sequence of SEQ ID NO: 155.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 171, a CDR2 domain comprising the amino acid sequence of SEQ ID NO: 165, and a CDR1 domain comprising the amino acid sequence of SEQ ID NO: 164, and a light chain variable region comprising a CDR3 domain comprising the amino acid sequence of SEQ ID NO: 169, a CDR2 domain comprising the amino acid sequence of SEQ ID NO: 168, and a CDR1 domain comprising the amino acid sequence of SEQ ID NO: 155.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 176, a CDR2 domain comprising the amino acid sequence of SEQ ID NO: 175, and a CDR1 domain comprising the amino acid sequence of SEQ ID NO: 174, and a light chain variable region comprising a CDR3 domain comprising the amino acid sequence of SEQ ID NO: 179, a CDR2 domain comprising the amino acid sequence of SEQ ID NO: 178, and a CDR1 domain comprising the amino acid sequence of SEQ ID NO: 79.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 183, a CDR2 domain comprising the amino acid sequence of SEQ ID NO: 182, and a CDR1 domain comprising the amino acid sequence of SEQ ID NO: 181, and a light chain variable region comprising a CDR3 domain comprising the amino acid sequence of SEQ ID NO: 179, a CDR2 domain comprising the amino acid sequence of SEQ ID NO: 80, and a CDR1 domain comprising the amino acid sequence of SEQ ID NO: 79.

In another aspect of the invention, the present disclosure provides an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 188, a CDR2 domain comprising the amino acid sequence of SEQ ID NO: 187, and a CDR1 domain comprising the amino acid sequence of SEQ ID NO: 186, and a light chain variable region comprising a CDR3 domain comprising the amino acid sequence of SEQ ID NO: 63, a CDR2 domain comprising the amino acid sequence of SEQ ID NO: 62, and a CDR1 domain comprising the amino acid sequence of SEQ ID NO: 190.

In another aspect of the invention, the present disclosure provides an antibody, or antigen binding portion thereof, as described herein, conjugated to at least one drug.

In some embodiments, the at least one drug is selected from the group consisting of a DNA damaging agent, an anti-apoptotic agent, a mitotic inhibitor, an anti-tumor antibiotic, an immunomodulating agent, a nucleic acid for gene therapy, an anti-angiogenic agent, an antimetabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In one embodiment, the drug is a DNA damaging agent. In one embodiment, the DNA damaging agent is a PBD.

In other embodiments, the at least one drug is conjugated to the antibody, or antigen-binding portion thereof, via a linker. In yet other embodiments, the linker is a cleavable linker. In another embodiment, the linker is a non-cleavable linker.

In some embodiments, the antibody, or antigen binding portion thereof, is an IgG1 isotype. In other embodiment, the antibody, or antigen binding portion thereof, is an IgG$_4$ isotype. In another embodiment, the antibody, or antigen-binding portion thereof, is an IgG$_2$ isotype. In another embodiment, the antibody, or antigen-binding portion thereof, is an IgG$_3$ isotype.

In another aspect of the invention, the present disclosure provides a pharmaceutical composition comprising an ADC mixture comprising a plurality of the ADC as described herein, and a pharmaceutically acceptable carrier.

In some embodiments, the ADC mixture has an average drug to antibody ratio (DAR) of 0 to 8.

In another aspect of the invention, the present disclosure provides a method for treating cancer, comprising administering a therapeutically effective amount of an antibody or antigen binding portion thereof, as described herein, or an ADC as described herein, to a subject in need thereof.

In some embodiments, cancer is acute myeloid leukemia (AML). In other embodiments, the cancer is myelodysplastic syndrome (MDS). In other embodiments, the cancer is NSCLC. In other embodiments, the cancer is ovarian cancer.

In some embodiments, the present disclosure provides a method for inhibiting or decreasing solid tumor growth in a subject having a solid tumor, said method comprising administering an effective amount of the antibody or antigen binding portion thereof, as described herein, or the ADC, as described herein, to the subject having the solid tumor, such that the solid tumor growth is inhibited or decreased.

In some embodiments, the antibody or antigen binding portion thereof or the ADC is administered in combination with an additional agent or an additional therapy. In other embodiments, the additional agent is an immune checkpoint inhibitor. In yet another embodiment, the immune checkpoint inhibitor is an antibody. In another embodiment, the antibody is selected from the group consisting of an anti-PD1 antibody, an anti-PD-L1 antibody or an anti-CTLA-4 antibody. In other embodiments, the additional therapy is radiation. In yet another embodiment, the additional agent is a chemotherapeutic agent. In some embodiments, the cancer or tumor is characterized as having IL1RAP expression or overexpression.

BRIEF DESCRIPTION OF THE DRAWINGS

FIG. 1 shows surface expression of IL1RAP in human acute myeloid leukemia cell lines EOL1, Monomac 6, OCI/AML1, and KG-1, as well as T cell leukemia cell line, Karpas 299, as determined by flow cytometry analysis.

FIG. 2 shows specific binding of IL1RAP antibody 44E5_15C5 to IL1RAP positive cell lines EOL1, and Karpas 299. DMS79 cell line, which is IL1RAP negative, shows lack of binding by IL1RAP antibody 44E5_15C5.

FIG. 3 is a diagram representing the arrangement of competing bins of antibodies.

FIG. 5 shows internalization of IL1RAP antibody 44E5_15C5 into EOL1 cells. Live EOL1 cells were incubated with IL1RAP antibody 44E5_15C5 for 0.5 hours at 37° C. After cytospin, cells were then fixed, permeablized and co-stained with LAMP1 antibody.

FIGS. 6A, 6B, and 6C show internalization and in vitro efficacy of IL1RAP antibodies in human leukemia cell lines EOL1 (FIG. 6A) and Karpas 299 (FIG. 6B). There was no cytotoxicity in IL1RAP negative cell line DMS79 (FIG. 6C).

FIGS. 9A and 9B show blockage of IL-33 signaling by anti-IL1RAP antibodies. HEK-Blue IL-33 cells (Invivogen, CA) were harvested and plated in technical duplicates at a density of 50,000 cells per well in a 96-well plate. Antibodies, or a corresponding human IgG1 control antibody, was added to the wells in a serial dilution starting at 10 µg/ml (FIG. 9A), or a concentration of 1 and 10 µg/ml (FIG. 9B). After incubating cells with antibodies for 30 minutes, IL-33 was added to a final concentration of 0.5 ng/ml, and the plate was incubated overnight. 24 hours later, substrate was added to the supernatants, and samples were analyzed for absorbance at 620 nm. CBIgG1 (anti-hen egg lysozyme antibody, CrownBio™) was included as a negative control.

DETAILED DESCRIPTION

Figure 4A:
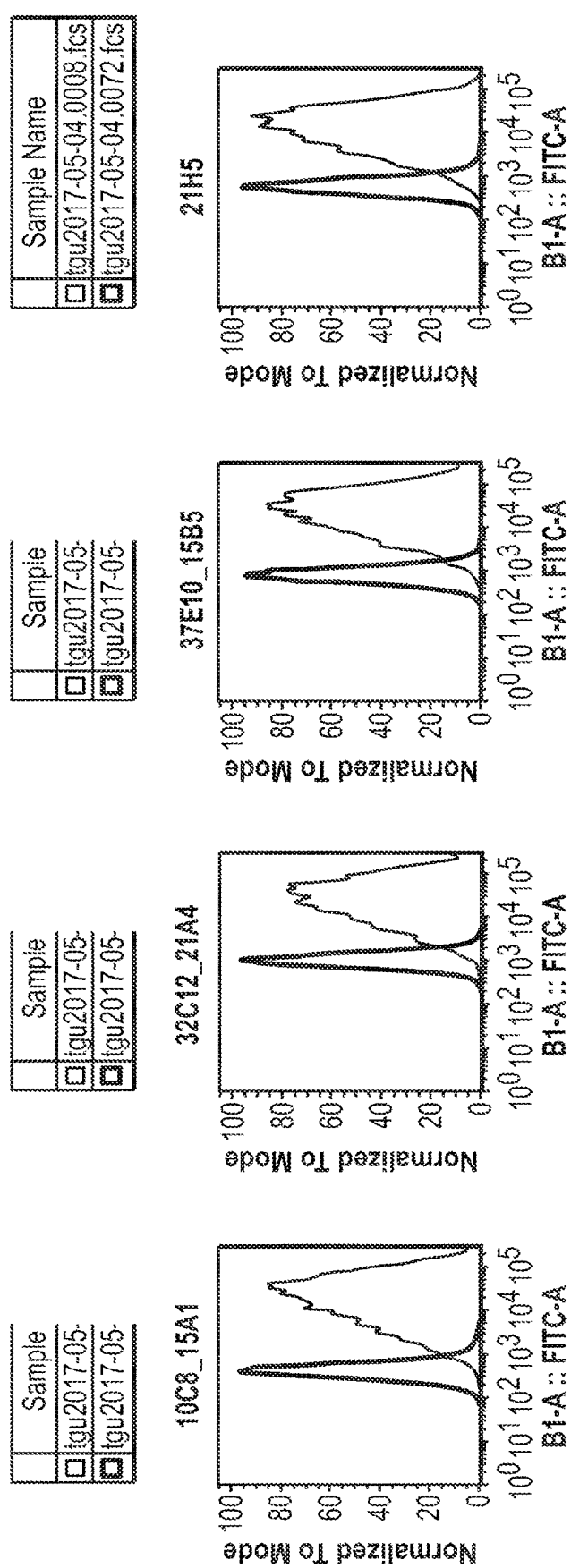
FIGS. 4A, 4B, 4C and 4D show binding of anti-IL1RAP antibodies to IL1RAP orthologs. Anti-IL1RAP antibodies were evaluated for cell surface binding to 293 cells expressing human (FIG. 4A), *Macaca fascicularis* (FIG. 4B), rat IL1RAP (FIG. 4C), and mouse IL1RAP (FIG. 4D) by flow cytometry. 21H5 was the mouse antibody against human IL1RAP. CB1gG1 (anti-hen egg lysozyme antibody, CrownBio™), was included as a negative control.
Figure 4A:
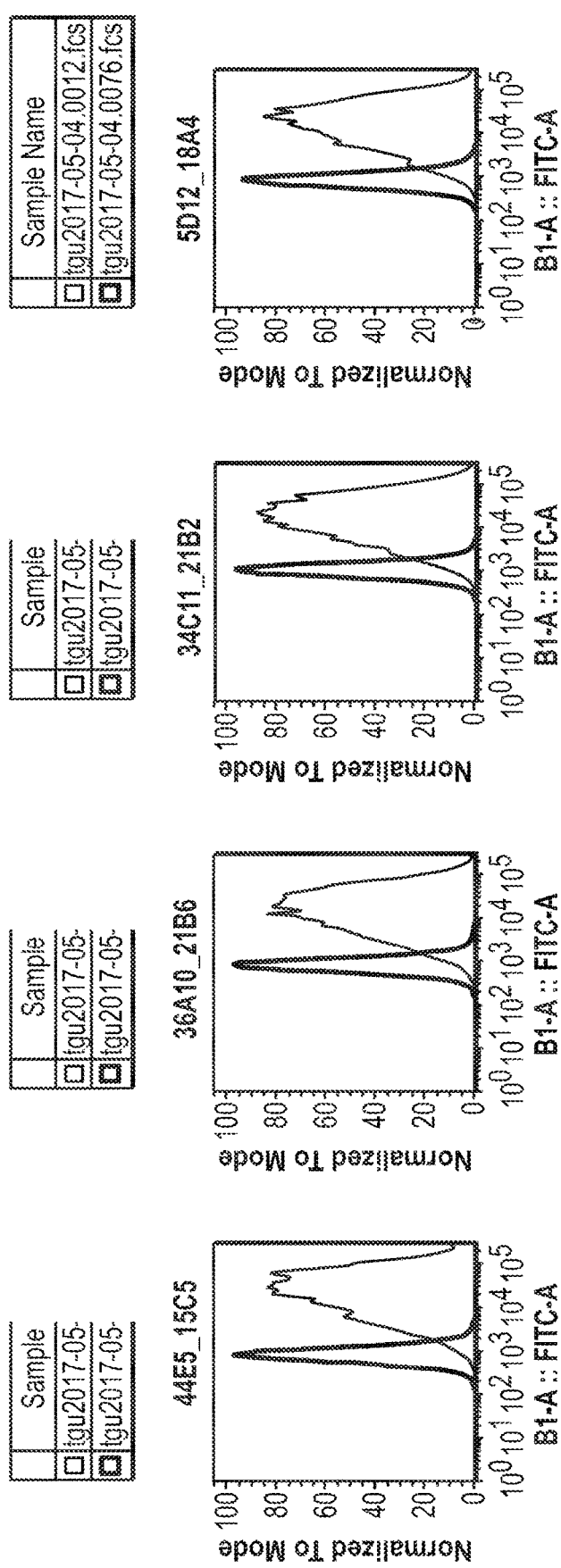
Figure 4A:
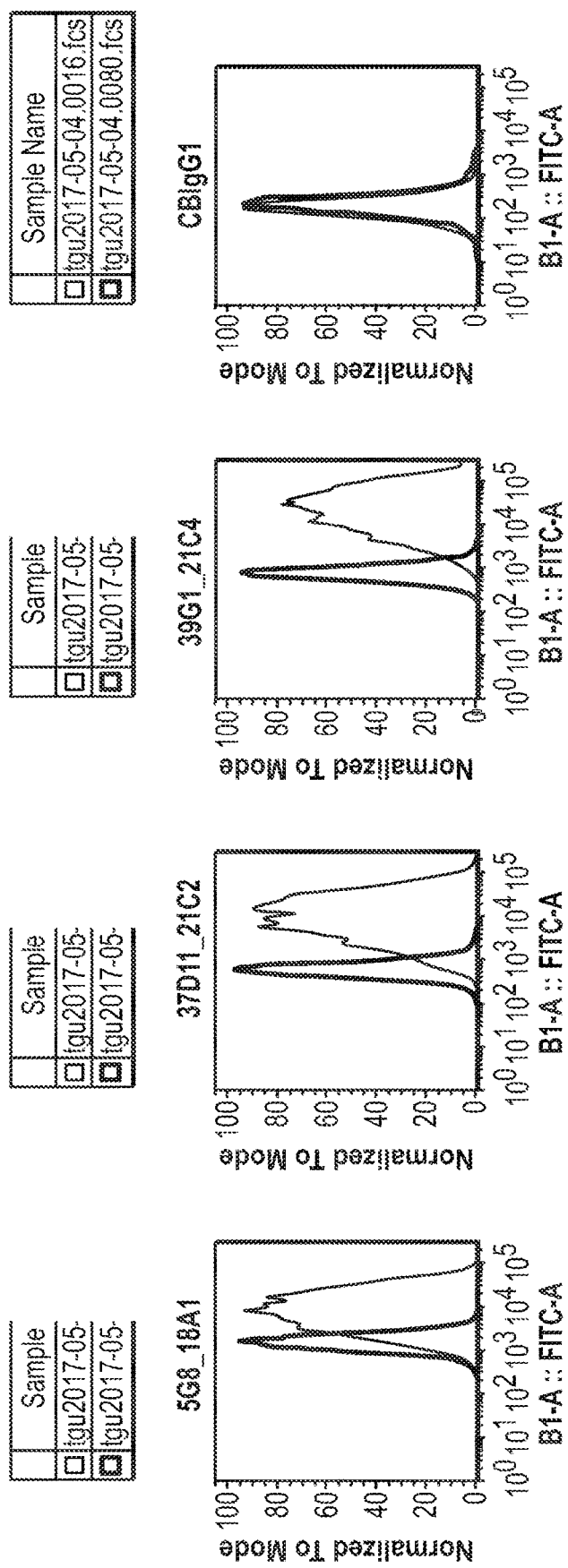
Figure 4B:
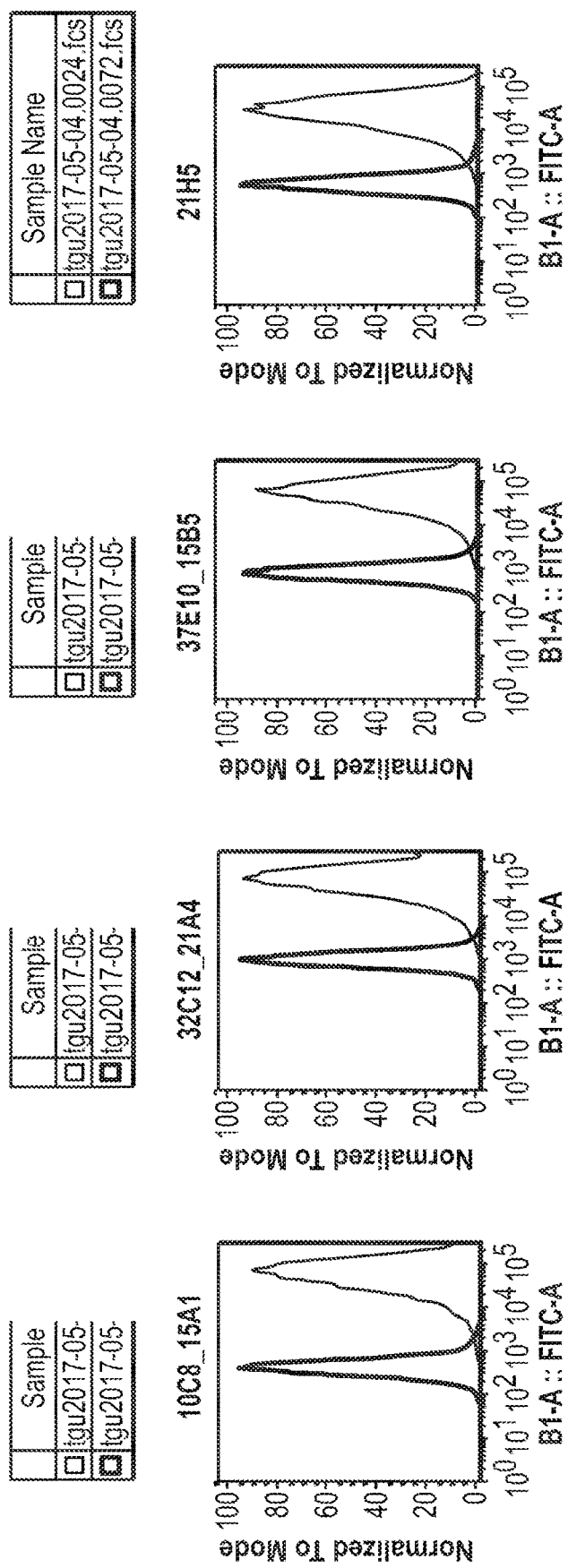
Figure 4B:
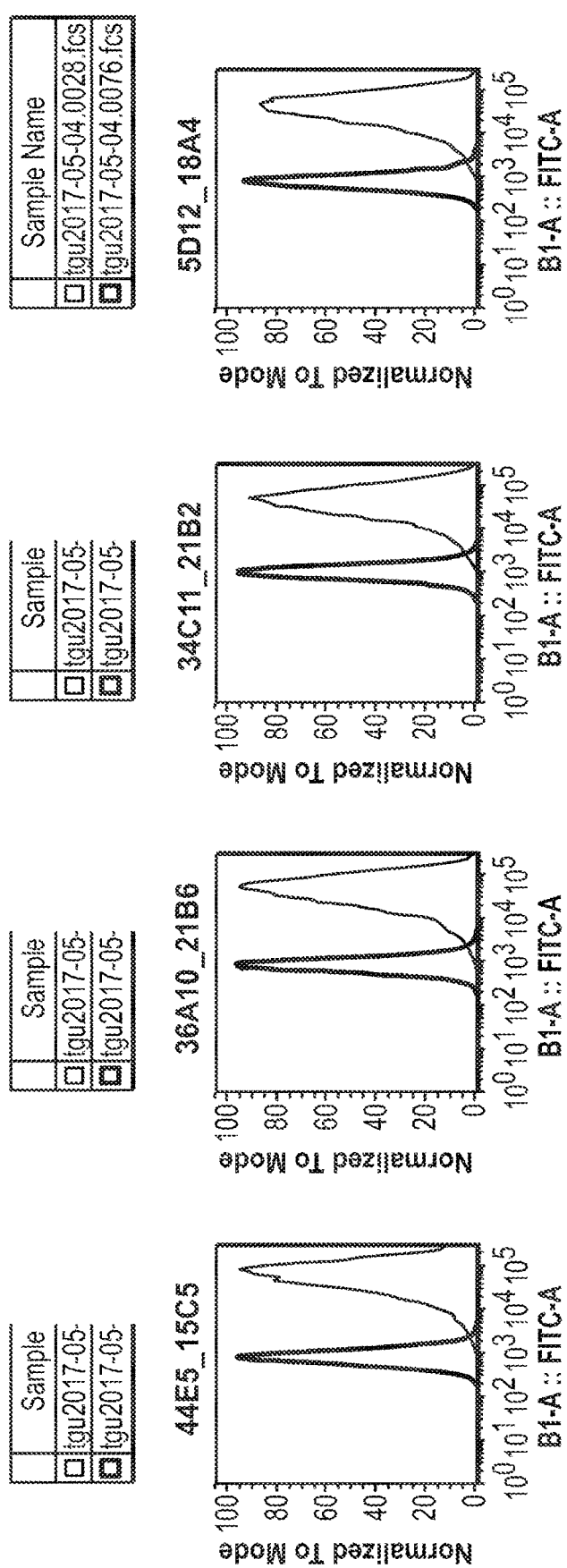
Figure 4B:
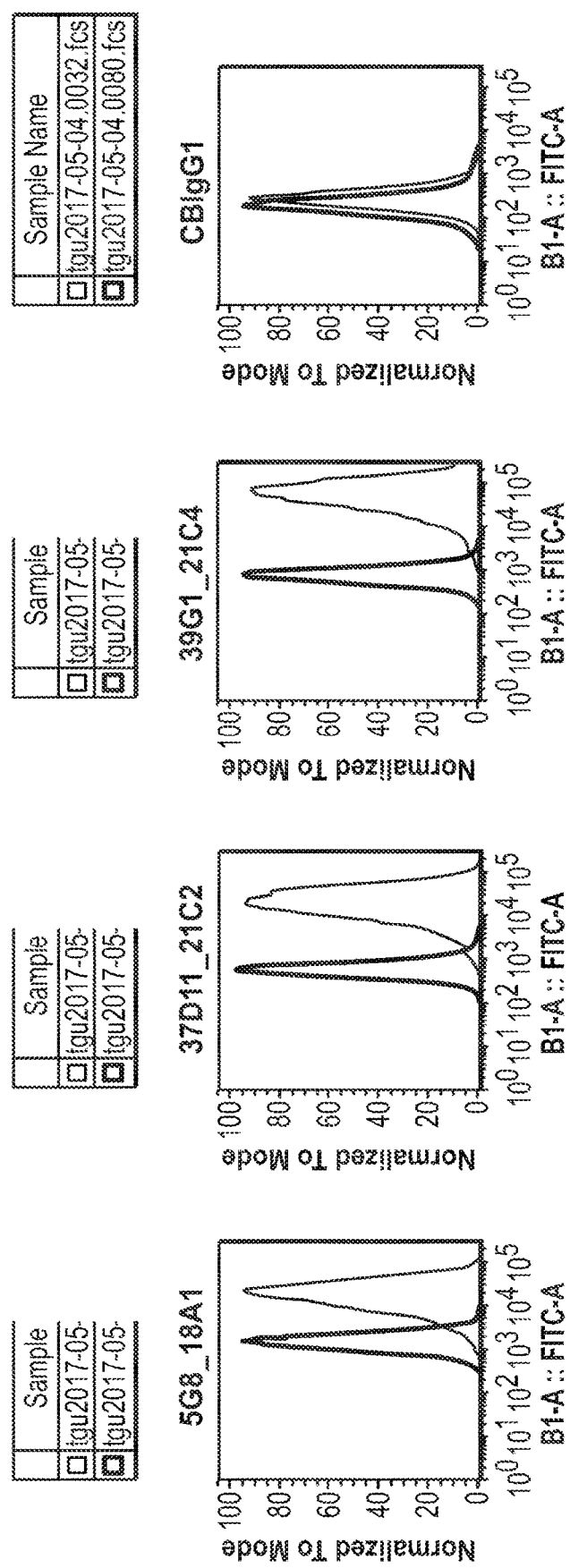

Various aspects of the disclosure relate to anti-IL1RAP antibodies and antibody fragments, anti-IL1RAP ADCs, and pharmaceutical compositions thereof, as well as nucleic acids, recombinant expression vectors and host cells for making such antibodies and fragments. Methods of using the antibodies and ADCs described herein to detect human IL1RAP, to bind to and inhibit human IL1RAP on IL1RAP expressing cells, to inhibit IL-1, e.g., IL-1β and/or IL-1α signaling, in vivo, and/or to treat IL1RAP-associated disorders, e.g., cancer, including, but not limited to, acute myeloid leukemia (AML), myelodysplastic syndrome (MDS), lung cancer, including non-small cell lung cancer (NSCLC) and ovarian cancer.

The terms "Interleukin 1 Receptor Accessory Protein antibody" or "anti-IL1RAP antibody", used interchangeably herein, refer to an antibody that specifically binds to IL1RAP, e.g., human IL1RAP. An antibody "which binds" an antigen of interest, i.e., IL1RAP, is one capable of binding that antigen with sufficient affinity such that the antibody is useful in targeting a cell expressing the antigen. In a preferred embodiment, the antibody specifically binds to human IL1RAP (hIL1RAP). Examples of anti-IL1RAP antibodies are disclosed in the Examples, below. Unless otherwise indicated, the term "anti-IL1RAP antibody" is meant to refer to an antibody which binds to wild type IL1RAP, a variant, or an isoform of IL1RAP.

Several different isoforms of IL1RAP have been identified. An exemplary amino acid sequence of wild type human IL1RAP, which contains 570 amino acids, is provided below as SEQ ID NO: 286. The extracellular domain (ECD) of IL1-RAP comprises amino acids 21-367 of SEQ ID NO:286.

```
         10         20         30         40         50
     MTLLWCVVSL YFYGILQSDA SERCDDWGLD TMRQIQVFED EPARIKCPLF 60         70         80         90        100
     EHFLKFNYST AHSAGLTLIW YWTRQDRDLE EPINFRLPEN RISKEKDVLW 110        120        130        140        150
     FRPTLLNDTG NYTCMLRNTT YCSKVAFPLE VVQKDSCFNS PMKLPVHKLY 160        170        180        190        200
     IEYGIQRITC PNVDGYFPSS VKPTITWYMG CYKIQNFNNV IPEGMNLSFL 210        220        230        240        250
     IALISNNGNY TCVVTYPENG RTFHLTRTLT VKVVGSPKNA VPPVIHSPND 260        270        280        290        300
     HVVYEKEPGE ELLIPCTVYF SFLMDSRNEV WWTIDGKKPD DITIDVTINE 310        320        330        340        350
     SISHSRTEDE TRTQILSIKK VTSEDLKRSY VCHARSAKGE VAKAAKVKQK 360        370        380        390        400
     VPAPRYTVEL ACGFGATVLL VVILIVVYHV YWLEMVLFYR AHFGTDETIL 410        420        430        440        450
     DGKEYDIYVS YARNAEEEEF VLLTLRGVLE NEFGYKLCIF DRDSLPGGIV 460        470        480        490        500
     TDETLSFIQK SRRLLVVLSP NYVLQGTQAL LELKAGLENM ASRGNINVIL 510        520        530        540        550
     VQYKAVKETK VKELKRAKTV LTVIKWKGEK SKYPQGRFWK QLQVAMPVKK 560        570
     SPRRSSSDEQ GLSYSSLKNV
```

In one embodiment, the anti-IL1RAP antibodies or ADCs of the invention are administered in combination with one or more immune checkpoint inhibitors (e.g., antibody or small molecule immune checkpoint inhibitors) for the treatment of a cancer. In another embodiment of the invention, anti-IL1RAP antibody drug conjugates (ADCs) of the invention (e.g., the IL1RAP antibodies of the invention conjugated to a toxin) are internalized and induce cell death of cells endogenously expressing IL1RAP.

I. Definitions

In order that the invention may be more readily understood, certain terms are first defined. In addition, it should be noted that whenever a value or range of values of a parameter are recited, it is intended that values and ranges intermediate to the recited values are also intended to be part of this invention.

The terms "specific binding" or "specifically binding", as used herein, in reference to the interaction of a IL1RAP antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

In one embodiment, the phrase "specifically binds to hIL1RAP" or "specific binding to hIL1RAP", as used herein, refers to the ability of an anti-IL1RAP antibody or ADC to interact with IL1RAP (human or cynomolgus monkey IL1RAP) with a dissociation constant ($K_D$) of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less. In another embodiment, the phrase "specifically binds to hIL1RAP" or "specific binding to hIL1RAP", as used herein, refers to the ability of an anti-IL1RAP antibody or ADC to interact with hIL1RAP with a dissociation constant ($K_D$) of between about 1 pM (0.001 nM) to 2,000 nM, between about 500 pM (0.5 nM) to 1,000 nM, between about 500 pM (0.5 nM) to 500 nM, between about 1 nM) to 200 nM, between about 1 nM to 100 nM, between about 1 nM to 50 nM, between about 1 nM to 20 nM, or between about 1 nM to 5 nM. In one embodiment, $K_D$ is determined by surface plasmon resonance or Bio-Layer Interferometry, or by any other method known in the art. Bio-Layer Interferometry refers to an optical phenomenon that allows for the analysis of real-time biospecific interactions by measuring the interference patterns of reflected white light, for example using the Octet™ system (ForteBio, Pall Corp. Fremont, Calif.). For further description of the Octet™ system, see Li, B et al. (2011) *J. Pharm. Biomed. Anal.* 54(2):286-294 and Abdiche, Y. N., et al. (2009) *Anal. Biochem.* 386(2):172-180, the contents of which are incorporated herein by reference.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 Immunoglobulin molecules can be of any type (e.g., IgG, IgE, IgM, IgD, IgA and IgY) and class (e.g., IgG1, IgG2, IgG3, IgG4, IgA1 and IgA2) or subclass.

The term "antigen binding portion" of an antibody (or simply "antibody portion"), as used herein, refers to one or more fragments of an antibody that retain the ability to specifically bind to an antigen (e.g., hIL1RAP). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen binding portion" of an antibody. In certain embodiments, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions disclosed herein linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds IL1RAP is substantially free of antibodies that specifically bind antigens other than IL1RAP). An isolated antibody that specifically binds IL1RAP may, however, have cross-reactivity to other antigens, such as IL1RAP molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In one embodiment, the disclosure includes an amino acid sequence having at least 80%, at least 85%, at least 90%, at least 95%, at least 96%, at least 97%, at least 98%, or at least 99% identity to an amino acid sequence set forth in any one of SEQ ID NOs: 1 to 190.

In one embodiment, the antibody, or antigen-binding portion thereof, is capable of inducing antibody dependent cellular cytotoxicity (ADCC). In one embodiment, the antibody, or antigen-binding portion thereof, is not capable of inducing ADCC.

In one embodiment, the antibody, or antigen-binding portion thereof, is capable of inducing complement-dependent cytotoxicity (CDC). In one embodiment, the antibody, or antigen-binding portion thereof, is not capable of inducing CDC.

In one embodiment, the antibody, or antigen-binding portion thereof, is capable of inducing ADCC and CDC. In one embodiment, the antibody, or antigen-binding portion thereof, is not capable of inducing ADCC or CDC.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-IL1RAP DVD.

The term "activity" includes activities such as the binding specificity/affinity of an antibody or ADC for an antigen, for example, an anti-hIL1RAP antibody or ADC that binds to a IL1RAP antigen. In one embodiment, an anti-IL1RAP antibody or anti-IL1RAP ADC activity includes, but it not limited to, binding to IL1RAP in vitro; binding to IL1RAP on cells expressing IL1RAP in vivo; modulating (e.g., inhibiting) IL-1, e.g., IL-1β and/or IL-1α, signaling; inducing cell death in cells expressing IL1RAP, including leukemia cells; inhibiting cancer cell invasion and metastasis; decreasing or inhibiting cancer, e.g., acute myeloid leukemia (AML), myelodysplastic syndrome (MDS), lung cancer, including non-small cell lung cancer (NSCLC) and ovarian cancer; and decreasing or inhibiting tumor cellular proliferation or tumor growth in vivo. In one embodiment, an anti-IL1RAP antibody or ADC is capable of being internalized into a cell expressing IL1RAP and/or inducing cytotoxicity.

In one embodiment, the antibody, or antigen-binding portion thereof, is capable of inducing antibody dependent cellular cytotoxicity (ADCC). In one embodiment, the antibody, or antigen-binding portion thereof, is not capable of inducing ADCC.

In one embodiment, the antibody, or antigen-binding portion thereof, is capable of inducing complement-dependent cytotoxicity (CDC). In one embodiment, the antibody, or antigen-binding portion thereof, is not capable of inducing CDC.

In one embodiment, the antibody, or antigen-binding portion thereof, is capable of inducing ADCC and CDC. In one embodiment, the antibody, or antigen-binding portion thereof, is not capable of inducing ADCC or CDC.

The term "epitope" refers to a region of an antigen that is bound by an antibody, antibody fragment, or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$k_{on}$" or "$k_a$", as used herein, is intended to refer to the on rate constant for association of an antibody to the antigen to form the antibody/antigen complex.

The term "$k_{off}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction. $K_D$ is calculated by $k_a/k_d$. In one embodiment, the antibodies of the invention have a $K_D$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}TC$, $^{111}In$, $^{125}I$, $^{131}I$, $^{177}Lu$ $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The terms "V-set domain containing T cell activation inhibitor 1 antibody drug conjugate," "anti-IL1RAP antibody drug conjugate," or "anti-IL1RAP ADC", used interchangeably herein, refer to an ADC comprising an antibody that specifically binds to IL1RAP, whereby the antibody is conjugated to one or more chemical agent(s) or payloads. In one embodiment, the chemical agent is linked to the antibody via a linker.

The term "drug-to-antibody ratio" or "DAR" refers to the number of drugs, e.g., IGN, auristatin, or maytansinoid, attached to the antibody of the ADC. The DAR of an ADC can range from 1 to 8, although higher loads, e.g., 10, are also possible depending on the number of linkage site on an antibody. The term DAR may be used in reference to the number of drugs loaded onto an individual antibody, or, alternatively, may be used in reference to the average or mean DAR of a group of ADCs.

The term "IL1RAP associated disorder," as used herein, includes any disorder or disease (including proliferative disorders, e.g., cancer) that is marked, diagnosed, detected or identified by a phenotypic or genotypic aberration of IL1RAP genetic components or expression during the course or etiology of the disease or disorder. In this regard a IL1RAP phenotypic aberration or determinant may, for example, comprise increased or decreased levels of IL1RAP protein expression on one cell population, e.g., a cancer cell population, as compared to another cell population, e.g., a normal cell population, or increased or decreased IL1RAP protein expression on certain definable cell populations, or increased or decreased IL1RAP protein expression at an inappropriate phase or stage of a cell lifecycle. It will be appreciated that similar expression patterns of genotypic determinants (e.g., mRNA transcription levels) of IL1RAP may also be used to classify or detect IL1RAP associated disorders. In one embodiment, an IL1RAP associated disorder is leukemia, e.g., acute myeloid leukemia (AML). In another embodiment, an IL1RAP associated disorder is myelodysplastic syndrome (MDS). In another embodiment, an IL1RAP associated disorder is lung cancer. In another embodiment, an IL1RAP associated disorder is non-small cell lung cancer (NSCLC). In another embodiment, an IL1RAP associated disorder is ovarian cancer.

The term "cancer," as used herein, is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include, but are not limited to, breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid leukemia (AML), myelodysplastic syndrome (MDS), acute lymphoblastic leukemia (ALL), chronic myelogenous leukemia (CML), myeloproliferative disorders (MPD), chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, PVNS, acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma, and any combinations of said cancers. The present invention is also applicable to treatment of metastatic cancers.

In one embodiment, the antibodies or ADCs of the invention are administered to a patient having a solid tumor, including an advanced solid tumor. In one embodiment, the antibodies or ADCs of the invention are administered to a patient having a leukemia. In another embodiment, administration of antibodies or ADCs of the invention induce cell death of IL1RAP expressing cells.

The term "IL1RAP expressing tumor," as used herein, refers to a tumor which expresses IL1RAP protein (including a tumor comprising tumor infiltrating cells that express IL1RAP protein).

In one embodiment, IL1RAP expression in a tumor is determined using immunohistochemical staining of tumor cell membranes, where any immunohistochemical staining above background level in a tumor sample indicates that the tumor is a IL1RAP expressing tumor. In another embodiment, a IL1RAP expressing tumor is identified in a patient when greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a tumor sample are positive for IL1RAP expression. In another embodiment, IL1RAP positive expression is determined based on membrane staining as determined by, e.g., immunohistochemistry (IHC) analysis.

A IL1RAP expressing tumor is identified as having an "elevated level of IL1RAP" or "expressing IL1RAP at an elevated level" when the level of IL1RAP is higher than in tissue surrounding the cancer. In some embodiments, an "elevated level of IL1RAP" is one in which 5% or more of the cells in a tumor sample have membrane staining. In some embodiments a "high level" in regard to IL1RAP is 5% or more staining, for example, 5, 10, 20, 30, 40, 50, 60, 70, 80, 90, or 100% of the cells in the tumor sample are stained. In some embodiments, the protein expression levels can be measured by IHC analysis.

A IL1RAP expressing tumor is identified as having a "low level of IL1RAP" or "expressing IL1RAP at a low level" is one in which 5% or less of the cells in a tumor sample have membrane staining. In some embodiments a "low level" in regard to IL1RAP is 5% or less staining, for example, 4.9, 4.5, 4, 3, 2, 1, 0.9, 0.8, 0.7, 0.6, 0.5, 0.4, 0.3, 0.2, 0.1% or less of the cells in the tumor sample are stained. In some embodiments, the protein expression levels can be measured by IHC analysis.

A cell that expresses no IL1RAP can also be described as expressing a "low level of IL1RAP". Thus, the phrase "expresses a low level of IL1RAP" encompasses no IL1RAP expression. In some embodiments, a low level of IL1RAP is within the background staining levels. In some embodiments, a sample that is IL1RAP "negative" has no IL1RAP expression or a low level of IL1RAP. In some embodiments, IL1RAP staining is negative when no or less than 5%, 4%, 3%, 2%, or 1% of the cells have membrane staining for IL1RAP.

As used herein, the term "tumor sample" refers to a tumor tissue or cell sample obtained from a solid tumor. The sample can include both tumor cells and tumor infiltrating cells, e.g., tumor infiltrating immune cells.

As used herein, the term "non-cancer sample" or "normal sample" refers to a sample from a normal tissue (e.g., a lung or ovarian tissue sample or a normal cell sample). In some embodiments, the non-cancer sample comes from the same subject, but is from a different part of the subject than that being tested. In some embodiments, the non-cancer sample is from a tissue area surrounding or adjacent to the cancer. In some embodiments, the non-cancer sample is not from the subject being tested, but is a sample from a subject known to have, or not to have, a disorder in question (for example, a particular cancer such an IL1RAP related disorder). In some embodiments, the non-cancer sample is from the same subject, but from a point in time before the subject developed cancer. In some embodiments, the reference sample is from a benign cancer sample (for example, benign ovarian cancer sample), from the same or a different subject.

Methods for detecting expression of IL1RAP in a tumor are known in the art.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 5%, 10%, 20%, 30%, 40%, 50%, 60%, 70%, 80%, 90% or more in comparison to a normal cell or comparison cell. In certain embodiments, the anti-IL1RAP antibodies or ADCs are used to treat solid tumors likely to overexpress IL1RAP.

The term "administering" as used herein is meant to refer to the delivery of a substance (e.g., an anti-IL1RAP antibody or ADC) to achieve a therapeutic objective (e.g., the treatment of an IL1RAP-associated disorder or the inhibition or reduction of a tumor). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy", as used herein, refers to the administration of two or more therapeutic substances, e.g., an anti-IL1RAP antibody or ADC and an additional therapeutic agent. The additional therapeutic agent may be administered concomitant with, prior to, or following the administration of the anti-IL1RAP antibody or ADC. In one embodiment, the anti-IL1RAP antibodies or ADCs of the invention are administered in combination with one or more immune checkpoint inhibitors (e.g., one or more antibody or small molecule immune checkpoint inhibitors) for the treatment of a cancer.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

Various aspects of the invention are described in further detail in the following subsections.

II. Anti-IL1RAP Antibodies

One aspect disclosed herein provides humanized anti-IL1RAP antibodies, or antigen binding portions thereof. Another aspect disclosed herein provides human anti-IL1RAP antibodies, or antigen binding portions thereof. In one embodiment, the antibodies disclosed herein bind human IL1RAP. In another embodiment, the antibodies disclosed herein bind cynomolgus monkey IL1RAP. In another embodiment, the antibodies disclosed herein bind human IL1RAP expressed on tumor cells.

Another aspect disclosed herein features antibody drug conjugates (ADCs) comprising an anti-IL1RAP antibody described herein and at least one drug(s). The antibodies or ADCs disclosed herein have characteristics including, but not limited to, binding to human IL1RAP in vitro, modulating, e.g., inhibiting IL-1 signaling, inducing cell death in cells expressing IL1RAP, including, but not limited to, leukemia cells, and decreasing or inhibiting cancer, tumor cellular proliferation or tumor growth, or tumor invasion and metastasis. ADCs disclosed herein, in particular, have characteristics including, but not limited to, inducing cell death in cells expressing IL1RAP, e.g., leukemia cells expressing IL1RAP. In one embodiment, an anti-IL1RAP antibody or ADC disclosed herein is capable of being internalized into a cell expressing IL1RAP.

In one embodiment, anti-IL1RAP antibodies are disclosed which have the ability to bind to IL1RAP, as described in the Examples below. Collectively, the novel antibodies are referred to herein as "IL1RAP antibodies." The anti-IL1RAP antibodies, ADCs, or antigen binding fragments thereof, are able to inhibit or decrease tumor growth in vivo. The tumor can be a IL1RAP negative tumor or an IL1RAP expressing tumor. In various embodiments, anti-IL1RAP antibodies, ADCs, or antigen binding fragments thereof, are capable of modulating a biological function of IL1RAP. In other embodiments of the foregoing aspects, the anti-IL1RAP antibodies, ADCs, or antigen binding fragments thereof, bind IL1RAP on cells expressing IL1RAP. Thus, the disclosure includes anti-IL1RAP antibodies, ADCs, or antigen binding fragments thereof, that are effective at inhibiting or decreasing tumor growth. Without wishing to be bound by any particular theory, in one embodiment, the anti-IL1RAP antibodies, antigen-binding portions thereof, and ADCs are capable of inhibiting multiple IL1RAP activities including, but not limited to, IL-1β signaling through IL1RAP; IL-1α, IL-1β, and IL-38 signaling through the IL-1R; IL-33 signaling through the IL-33R, and IL-36Ra, IL-36β, and IL-36γ signaling through the IL-36R. It is known in the art that blocking IL-1β signaling is effective for treating lung cancer (see, for example, Ridker et al., Antiinflammatory Therapy with Canakinumab for Atherosclerotic Disease, New England J. Med., 2017; and Ridker et al., The Lancet, 390:1833-1842, 2017, the entire contents of each of which are expressly incorporated herein by reference). Therefore, in one embodiment, the anti-IL1RAP antibodies, antigen-binding portions thereof, and ADCs described herein are useful for downstream inhibition of IL-1β pathways for the treatment of cancers, e.g., lung cancer.

In addition, the present inventors have further shown that IL1RAP is expressed by leukemia cells (see Example 1). Accordingly, the anti-IL1RAP antibodies, ADCs, and antigen-binding portions thereof, can be used for the treatment of leukemia in a subject, e.g., acute myeloid leukemia. The anti-IL1RAP antibodies, ADCs, and antigen-binding portions thereof, can be used for the treatment of bone marrow disorders such as myelodysplastic syndrome (MDS), acute myeloid leukemia (AML), ovarian cancer, lung cancer, and non-small cell lung cancer. In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a leukemia sample are positive for IL1RAP expression. In another embodiment, a leukemia or tumor sample has a high level of IL1RAP expression. For example, in one embodiment, at least 5% or more of the cells in a leukemia or tumor sample have membrane staining. In another embodiment, a tumor sample obtained from the subject displays a low level of expression of IL1RAP. The expression level of IL1RAP can be determined by any method known in the art. For example, the expression level of IL1RAP can be determined via immunohistochemical analysis. In another embodiment, the cancer has been previously treated with another anti-cancer agent or anti-cancer therapy, e.g., a chemotherapy. In one embodiment, the cancer is resistant to chemotherapy.

Antibodies having combinations of any of the aforementioned characteristics are contemplated as aspects of the disclosure. ADCs, described in more detail below, may also have any of the foregoing characteristics.

One aspect of the disclosure features an anti-human IL1RAP (anti-hIL1RAP) Antibody Drug Conjugate (ADC) comprising an anti-hIL1RAP antibody conjugated to a drug via a linker. Exemplary anti-IL1RAP antibodies (and sequences thereof) that can be used in the ADCs are described herein.

The anti-IL1RAP antibodies described herein provide the ADCs with the ability to bind to IL1RAP such that the cytotoxic molecule attached to the antibody may be delivered to the IL1RAP-expressing cell, particularly a IL1RAP expressing cancer cell.

While the term "antibody" is used throughout, it should be noted that antibody fragments (i.e., antigen-binding portions of an anti-IL1RAP antibody) are also included in the disclosure and may be included in the embodiments (methods and compositions) described throughout. For example, an anti-IL1RAP antibody fragment may be conjugated to the drugs, as described herein. In certain embodiments, an anti-IL1RAP antibody binding portion is a Fab, a Fab', a F(ab')2, a Fv, a disulfide linked Fv, an scFv, a single domain antibody, or a diabody.

Example 2 describes the generation of fully human IL1RAP antibodies against the extracellular domain of human IL1RAP. The heavy and light chain variable region amino acid sequences for these human antibodies are set forth in Table 5. The heavy and light chain variable region nucleotide sequences for these human antibodies are set forth in Table 6.

Thus, in one embodiment, the disclosure includes human anti-IL1RAP antibodies, or antigen binding portions thereof, comprising a heavy chain variable region comprising an amino acid sequence selected from the group consisting of SEQ ID NOs: 1, 9, 17, 25, 32, 40, 48, 56, 64, 71, 74, 83, 90, 96, 100, 106, 109, 116, 118, 121, 123, 125, 127, 130, 136, 140, 144, 151, 158, 163, 170, 173, 180, and 185; and a light chain variable region comprising an amino acid sequence selected from the group consisting of 5, 13, 21, 29, 36, 44, 52, 60, 68, 73, 78, 82, 87, 93, 98, 103, 108, 113, 114, 120, 122, 124, 126, 128, 134, 137, 143, 147, 154, 160, 167, 172, 177, 184, and 189.

In one embodiment, the disclosure includes a human anti-IL1RAP antibody, or antigen binding portion thereof, comprising an HC CDR set (CDR1, CDR2, and CDR3) selected from those set forth in Table 5; and an LC CDR set (CDR1, CDR2, and CDR3) selected from those set forth in Table 5.

In one embodiment, an anti-IL1RAP antibody, or antigen binding portion thereof, is the human antibody 5G8_18A1. The 5G8_18A1 antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 1 and a light chain variable region comprising the amino acid sequence of SEQ ID NO: 5.

In some embodiments, an anti-IL1RAP antibody, or antigen-binding portion thereof, comprises a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In one embodiment, the disclosure features an anti-IL1RAP antibody, or antigen binding portion thereof, which is the human antibody 1008_15A1. The 1008_15A1 antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 9 and a light chain variable region comprising the amino acid sequence of SEQ ID NO: 13.

In some embodiments, an anti-IL1RAP antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In one embodiment, the disclosure features an anti-IL1RAP antibody, or antigen binding portion thereof, which is the human antibody 12F3_17C2. The 12F3_17C2 antibody comprises a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22. In further embodiments, the disclosure provides an antibody having a heavy chain variable region comprising the amino acid sequence of SEQ ID NO: 17 and a light chain variable region comprising the amino acid sequence of SEQ ID NO: 21.

In some embodiments, an anti-IL1RAP antibody, or antigen-binding portion thereof, comprises a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 21, or a sequence having at least 90%, 95%, 96%, 97%, 98%, or 99% identity to SEQ ID NO: 21.

In one embodiment, the disclosure features an anti-IL1RAP antibody, or antigen binding portion thereof, which is the human antibody 16H2_17D2. The 16H2_17D2 antibody comprises a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 32, a CDR2 domain comprising the amino acid sequence of SEQ ID NO: 23, and a CDR1 domain comprising the amino acid sequence of SEQ ID NO: 31. In further embodiments, the disclosure provides an antibody having a heavy chain variable region comprising the amino acid sequence of SEQ ID NO: 25 and a light chain variable region comprising the amino acid sequence of SEQ ID NO: 29.

In some embodiments, an anti-IL1RAP antibody, or antigen-binding portion thereof, comprises a heavy chain comprising an amino acid sequence set forth in SEQ ID NO: 25, or a sequence having at least 90%, 95%, 96%, 97%, 98%, or 99% identity to SEQ ID NO: 25, and/or a light chain comprising an amino acid sequence set forth in SEQ ID NO: 29, or a sequence having at least 90%, 95%, 96%, 97%, 98%, or 99% identity to SEQ ID NO: 29.

In one embodiment, an anti-IL1RAP antibody, or antigen binding portion thereof, is the human antibody 32C12_21A4. The 32C12_21A4 antibody comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37. In further embodiments, disclosed herein is an antibody having a heavy chain variable region comprising the amino acid sequence of SEQ ID NO: 32 and a light chain variable region comprising the amino acid sequence of SEQ ID NO: 36.

In some embodiments, an anti-IL1RAP antibody, or antigen-binding portion thereof, comprises a heavy chain comprising an amino acid sequence set forth in SEQ ID NO: 32, or a sequence having at least 90%, 95%, 96%, 97%, 98%, or 99% identity to SEQ ID NO: 32, and/or a light chain comprising an amino acid sequence set forth in SEQ ID NO: 36, or a sequence having at least 90%, 95%, 96%, 97%, 98%, or 99% identity to SEQ ID NO: 36.

In one embodiment, an anti-IL1RAP antibody, or antigen binding portion thereof, is the human antibody 34C11_21B2. The 34C11_21B2 antibody comprises a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45. In further embodiments, disclosed herein is an antibody having a heavy chain variable region comprising the amino acid sequence of SEQ ID NO: 40 and a light chain variable region comprising the amino acid sequence of SEQ ID NO: 44.

In some embodiments, an anti-IL1RAP antibody, or antigen-binding portion thereof, comprises a heavy chain comprising an amino acid sequence set forth in SEQ ID NO: 40 or a sequence having at least 90%, 95%, 96%, 97%, 98%, or 99% identity to SEQ ID NO: 40, and/or a light chain comprising an amino acid sequence set forth in SEQ ID NO: 44, or a sequence having at least 90%, 95%, 96%, 97%, 98%, or 99% identity to SEQ ID NO: 44.

In one embodiment, an anti-IL1RAP antibody, or antigen binding portion thereof, is the human antibody 36A10_21B6. The 36A10_21B6 antibody comprises a heavy chain variable region comprising a CDR3 domain comprising the amino acid sequence of SEQ ID NO: 51, a CDR2 domain comprising the amino acid sequence of SEQ ID NO: 50, and a CDR1 domain comprising the amino acid sequence of SEQ ID NO: 49, and a light chain variable region comprising a CDR3 domain comprising the amino acid sequence of SEQ ID NO: 55, a CDR2 domain comprising the amino acid sequence of SEQ ID NO: 54, and a CDR1 domain comprising the amino acid sequence of SEQ ID NO: 53. In further embodiments, disclosed herein is an antibody having a heavy chain variable region comprising the amino acid sequence of SEQ ID NO: 48 and a light chain variable region comprising the amino acid sequence of SEQ ID NO: 52.

In some embodiments, an anti-IL1RAP antibody, or antigen-binding portion thereof, comprises a heavy chain comprising an amino acid sequence set forth in SEQ ID NO: 48, or a sequence having at least 90%, 95%, 96%, 97%, 98%, or 99% identity to SEQ ID NO: 48, and/or a light chain comprising an amino acid sequence set forth in SEQ ID NO: 52, or a sequence having at least 90%, 95%, 96%, 97%, 98%, or 99% identity to SEQ ID NO: 52.

In one embodiment, an anti-IL1RAP antibody, or antigen binding portion thereof, is the human antibody 39G1_21C4. The 39G1_21C4 antibody comprises a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO: 57, and a light chain variable region comprising a CDR3 domain comprising the amino acid sequence of SEQ ID NO: 63, a CDR2 domain comprising the amino acid sequence of SEQ ID NO: 62, and a CDR1 domain comprising the amino acid sequence of SEQ ID NO: 61. In further embodiments, disclosed herein is an antibody having a heavy chain variable region comprising the amino acid sequence of SEQ ID NO: 56 and a light chain variable region comprising the amino acid sequence of SEQ ID NO: 60.

In some embodiments, an anti-IL1RAP antibody, or antigen-binding portion thereof, comprises a heavy chain comprising an amino acid sequence set forth in SEQ ID NO: 56, or a sequence having at least 90%, 95%, 96%, 97%, 98%, or 99% identity to SEQ ID NO: 56, and/or a light chain comprising an amino acid sequence set forth in SEQ ID NO: 60, or a sequence having at least 90%, 95%, 96%, 97%, 98%, or 99% identity to SEQ ID NO: 60.

In one embodiment, an anti-IL1RAP antibody, or antigen binding portion thereof, is the human antibody 37E10_15B5. The 37E10_15B5 antibody comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 65, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69. In further embodiments, disclosed herein is an antibody having a heavy chain variable region comprising the amino acid sequence of SEQ ID NO: 64 and a light chain variable region comprising the amino acid sequence of SEQ ID NO: 68.

In some embodiments, an anti-IL1RAP antibody, or antigen-binding portion thereof, comprises a heavy chain comprising an amino acid sequence set forth in SEQ ID NO: 64, or a sequence having at least 90%, 95%, 96%, 97%, 98%, or 99% identity to SEQ ID NO: 64, and/or a light chain comprising an amino acid sequence set forth in SEQ ID NO: 68, or a sequence having at least 90%, 95%, 96%, 97%, 98%, or 99% identity to SEQ ID NO: 68.

In one embodiment, an anti-IL1RAP antibody, or antigen binding portion thereof, is the human antibody 44E5_15C5. The 44E5_15C5 antibody comprises a heavy chain variable region comprising a CDR3 domain comprising the amino acid sequence of SEQ ID NO: 67, a CDR2 domain comprising the amino acid sequence of SEQ ID NO: 72, and a CDR1 domain comprising the amino acid sequence of SEQ ID NO: 65, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69. In further embodiments, disclosed herein is an antibody having a heavy chain variable region comprising the amino acid sequence of SEQ ID NO: 71 and a light chain variable region comprising the amino acid sequence of SEQ ID NO: 73.

In some embodiments, an anti-IL1RAP antibody, or antigen-binding portion thereof, comprises a heavy chain comprising an amino acid sequence set forth in SEQ ID NO: 71, or a sequence having at least 90%, 95%, 96%, 97%, 98%, or 99% identity to SEQ ID NO: 71, and/or a light chain comprising an amino acid sequence set forth in SEQ ID NO: 73, or a sequence having at least 90%, 95%, 96%, 97%, 98%, or 99% identity to SEQ ID NO: 73.

In one embodiment, an anti-IL1RAP antibody, or antigen binding portion thereof, is the human antibody 38E10_21C3. The 38E10_21C3 antibody comprises a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 81, a CDR2 domain comprising the amino acid sequence of SEQ ID NO: 80, and a CDR1 domain comprising the amino acid sequence of SEQ ID NO: 79. In further embodiments, disclosed herein is an antibody having a heavy chain variable region comprising the amino acid sequence of SEQ ID NO: 74 and a light chain variable region comprising the amino acid sequence of SEQ ID NO: 78.

In some embodiments, an anti-IL1RAP antibody, or antigen-binding portion thereof, comprises a heavy chain comprising an amino acid sequence set forth in SEQ ID NO: 74, or a sequence having at least 90%, 95%, 96%, 97%, 98%, or 99% identity to SEQ ID NO: 74, and/or a light chain comprising an amino acid sequence set forth in SEQ ID NO: 78, or a sequence having at least 90%, 95%, 96%, 97%, 98%, or 99% identity to SEQ ID NO: 78.

In one embodiment, an anti-IL1RAP antibody, or antigen binding portion thereof, is the human antibody 1008_C43A. The 1008_C43A antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, disclosed herein is an antibody having a heavy chain variable region comprising the amino acid sequence of SEQ ID NO: 9 and a light chain variable region comprising the amino acid sequence of SEQ ID NO: 82.

In some embodiments, an anti-IL1RAP antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 82, or a sequence having at least 90%, 95%, 96%, 97%, 98%, or 99% identity to SEQ ID NO: 82.

In one embodiment, an anti-IL1RAP antibody, or antigen binding portion thereof, is the human antibody 16H2_17D1. The 16H2_17D1 antibody comprises a heavy chain variable region comprising a CDR3 domain comprising the amino acid sequence of SEQ ID NO: 86, a CDR2 domain comprising the amino acid sequence of SEQ ID NO: 85, and a CDR1 domain comprising the amino acid sequence of SEQ ID NO: 84, and a light chain variable region comprising a CDR3 domain comprising the amino acid sequence of SEQ ID NO: 89, a CDR2 domain comprising the amino acid sequence of SEQ ID NO: 80, and a CDR1 domain comprising the amino acid sequence of SEQ ID NO: 88, In further embodiments, disclosed herein is an antibody having a heavy chain variable region comprising the amino acid sequence of SEQ ID NO: 83 and a light chain variable region comprising the amino acid sequence of SEQ ID NO: 87.

In some embodiments, an anti-IL1RAP antibody, or antigen-binding portion thereof, comprises a heavy chain comprising an amino acid sequence set forth in SEQ ID NO: 83, or a sequence having at least 90%, 95%, 96%, 97%, 98%, or 99% identity to SEQ ID NO: 83, and/or a light chain comprising an amino acid sequence set forth in SEQ ID NO: 87, or a sequence having at least 90%, 95%, 96%, 97%, 98%, or 99% identity to SEQ ID NO: 87.

In one embodiment, an anti-IL1RAP antibody, or antigen binding portion thereof, is the human antibody 24G3_17C5. The 24G3_17C5 antibody comprises a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 84, and a light chain variable region comprising a CDR3 domain comprising the amino acid sequence of SEQ ID NO: 95, a CDR2 domain comprising the amino acid sequence of SEQ ID NO: 80, and a CDR1 domain comprising the amino acid sequence of SEQ ID NO: 94. In further embodiments, disclosed herein is an antibody having a heavy chain variable region comprising the amino acid sequence of SEQ ID NO: 90 and a light chain variable region comprising the amino acid sequence of SEQ ID NO: 93.

In some embodiments, an anti-IL1RAP antibody, or antigen-binding portion thereof, comprises a heavy chain comprising an amino acid sequence set forth in SEQ ID NO: 90, or a sequence having at least 90%, 95%, 96%, 97%, 98%, or 99% identity to SEQ ID NO: 90, and/or a light chain comprising an amino acid sequence set forth in SEQ ID NO: 93, or a sequence having at least 90%, 95%, 96%, 97%, 98%, or 99% identity to SEQ ID NO: 93.

In one embodiment, an anti-IL1RAP antibody, or antigen binding portion thereof, is the human antibody 26C5_15B4. The 26C5_15B4 antibody comprises a heavy chain variable region comprising a CDR3 domain comprising the amino acid sequence of SEQ ID NO: 92, a CDR2 domain comprising the amino acid sequence of SEQ ID NO: 97, and a CDR1 domain comprising the amino acid sequence of SEQ ID NO: 84, and a light chain variable region comprising a CDR3 domain comprising the amino acid sequence of SEQ ID NO: 99, a CDR2 domain comprising the amino acid sequence of SEQ ID NO: 80, and a CDR1 domain comprising the amino acid sequence of SEQ ID NO: 79. In further embodiments, disclosed herein is an antibody having a heavy chain variable region comprising the amino acid sequence of SEQ ID NO: 96 and a light chain variable region comprising the amino acid sequence of SEQ ID NO: 98.

In some embodiments, an anti-IL1RAP antibody, or antigen-binding portion thereof, comprises a heavy chain comprising an amino acid sequence set forth in SEQ ID NO: 96, or a sequence having at least 90%, 95%, 96%, 97%, 98%, or 99% identity to SEQ ID NO: 96, and/or a light chain comprising an amino acid sequence set forth in SEQ ID NO:

98, or a sequence having at least 90%, 95%, 96%, 97%, 98%, or 99% identity to SEQ ID NO: 98.

In one embodiment, an anti-IL1RAP antibody, or antigen binding portion thereof, is the human antibody 17E9_15B1. The 17E9_15B1 antibody comprises a heavy chain variable region comprising a CDR3 domain comprising the amino acid sequence of SEQ ID NO: 20, a CDR2 domain comprising the amino acid sequence of SEQ ID NO: 102, and a CDR1 domain comprising the amino acid sequence of SEQ ID NO: 101, and a light chain variable region comprising a CDR3 domain comprising the amino acid sequence of SEQ ID NO: 24, a CDR2 domain comprising the amino acid sequence of SEQ ID NO: 105, and a CDR1 domain comprising the amino acid sequence of SEQ ID NO: 104. In further embodiments, disclosed herein is an antibody having a heavy chain variable region comprising the amino acid sequence of SEQ ID NO: 100 and a light chain variable region comprising the amino acid sequence of SEQ ID NO: 103.

In some embodiments, an anti-IL1RAP antibody, or antigen-binding portion thereof, comprises a heavy chain comprising an amino acid sequence set forth in SEQ ID NO: 100, or a sequence having at least 90%, 95%, 96%, 97%, 98%, or 99% identity to SEQ ID NO: 100, and/or a light chain comprising an amino acid sequence set forth in SEQ ID NO: 103, or a sequence having at least 90%, 95%, 96%, 97%, 98%, or 99% identity to SEQ ID NO: 103.

In one embodiment, an anti-IL1RAP antibody, or antigen binding portion thereof, is the human antibody 1008_15A4. The 1008_15A4 antibody comprises a heavy chain variable region comprising a CDR3 domain comprising the amino acid sequence of SEQ ID NO: 86, a CDR2 domain comprising the amino acid sequence of SEQ ID NO: 107, and a CDR1 domain comprising the amino acid sequence of SEQ ID NO: 84, and a light chain variable region comprising a CDR3 domain comprising the amino acid sequence of SEQ ID NO: 89, a CDR2 domain comprising the amino acid sequence of SEQ ID NO: 80, and a CDR1 domain comprising the amino acid sequence of SEQ ID NO: 88. In further embodiments, disclosed herein is an antibody having a heavy chain variable region comprising the amino acid sequence of SEQ ID NO: 106 and a light chain variable region comprising the amino acid sequence of SEQ ID NO: 108.

In some embodiments, an anti-IL1RAP antibody, or antigen-binding portion thereof, comprises a heavy chain comprising an amino acid sequence set forth in SEQ ID NO: 106, or a sequence having at least 90%, 95%, 96%, 97%, 98%, or 99% identity to SEQ ID NO: 106, and/or a light chain comprising an amino acid sequence set forth in SEQ ID NO: 108, or a sequence having at least 90%, 95%, 96%, 97%, 98%, or 99% identity to SEQ ID NO: 108.

In one embodiment, an anti-IL1RAP antibody, or antigen binding portion thereof, is the human antibody 32A2_21A3. The 32A2_21A3 antibody comprises a heavy chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37. In further embodiments, disclosed herein is an antibody having a heavy chain variable region comprising the amino acid sequence of SEQ ID NO: 109 and a light chain variable region comprising the amino acid sequence of SEQ ID NO: 113.

In some embodiments, an anti-IL1RAP antibody, or antigen-binding portion thereof, comprises a heavy chain comprising an amino acid sequence set forth in SEQ ID NO: 109, or a sequence having at least 90%, 95%, 96%, 97%, 98%, or 99% identity to SEQ ID NO: 109, and/or a light chain comprising an amino acid sequence set forth in SEQ ID NO: 113, or a sequence having at least 90%, 95%, 96%, 97%, 98%, or 99% identity to SEQ ID NO: 113.

In one embodiment, an anti-IL1RAP antibody, or antigen binding portion thereof, is the human antibody 32C12_N26S. The 32C12_N26S antibody comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 115. In further embodiments, disclosed herein is an antibody having a heavy chain variable region comprising the amino acid sequence of SEQ ID NO: 32 and a light chain variable region comprising the amino acid sequence of SEQ ID NO: 114.

In some embodiments, an anti-IL1RAP antibody, or antigen-binding portion thereof, comprises a heavy chain comprising an amino acid sequence set forth in SEQ ID NO: 32, or a sequence having at least 90%, 95%, 96%, 97%, 98%, or 99% identity to SEQ ID NO: 32, and/or a light chain comprising an amino acid sequence set forth in SEQ ID NO: 114, or a sequence having at least 90%, 95%, 96%, 97%, 98%, or 99% identity to SEQ ID NO: 114.

In one embodiment, an anti-IL1RAP antibody, or antigen binding portion thereof, is the human antibody 41G4_15B6. The 41G4_15B6 antibody comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 117, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37. In further embodiments, disclosed herein is an antibody having a heavy chain variable region comprising the amino acid sequence of SEQ ID NO: 116 and a light chain variable region comprising the amino acid sequence of SEQ ID NO: 36.

In some embodiments, an anti-IL1RAP antibody, or antigen-binding portion thereof, comprises a heavy chain comprising an amino acid sequence set forth in SEQ ID NO: 116, or a sequence having at least 90%, 95%, 96%, 97%, 98%, or 99% identity to SEQ ID NO: 116, and/or a light chain comprising an amino acid sequence set forth in SEQ ID NO: 36, or a sequence having at least 90%, 95%, 96%, 97%, 98%, or 99% identity to SEQ ID NO: 36.

In one embodiment, an anti-IL1RAP antibody, or antigen binding portion thereof, is the human antibody 31F9_21A1. The 31F9_21A1 antibody comprises a heavy chain variable region comprising a CDR3 domain comprising the amino acid sequence of SEQ ID NO: 67, a CDR2 domain comprising the amino acid sequence of SEQ ID NO: 119, and a CDR1 domain comprising the amino acid sequence of SEQ ID NO: 26, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69. In further embodiments, disclosed herein is an antibody having a heavy chain variable region comprising the amino acid sequence of SEQ ID NO: 118 and a light chain variable region comprising the amino acid sequence of SEQ ID NO: 120.

In some embodiments, an anti-IL1RAP antibody, or antigen-binding portion thereof, comprises a heavy chain comprising an amino acid sequence set forth in SEQ ID NO: 118, or a sequence having at least 90%, 95%, 96%, 97%, 98%, or 99% identity to SEQ ID NO: 118, and/or a light chain comprising an amino acid sequence set forth in SEQ ID NO: 120, or a sequence having at least 90%, 95%, 96%, 97%, 98%, or 99% identity to SEQ ID NO: 120.

In one embodiment, an anti-IL1RAP antibody, or antigen binding portion thereof, is the human antibody 32D4_21D6. The 32D4_21D6 antibody comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 101, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69. In further embodiments, disclosed herein is an antibody having a heavy chain variable region comprising the amino acid sequence of SEQ ID NO: 121 and a light chain variable region comprising the amino acid sequence of SEQ ID NO: 122.

In some embodiments, an anti-IL1RAP antibody, or antigen-binding portion thereof, comprises a heavy chain comprising an amino acid sequence set forth in SEQ ID NO: 121, or a sequence having at least 90%, 95%, 96%, 97%, 98%, or 99% identity to SEQ ID NO: 121, and/or a light chain comprising an amino acid sequence set forth in SEQ ID NO: 122, or a sequence having at least 90%, 95%, 96%, 97%, 98%, or 99% identity to SEQ ID NO: 122.

In one embodiment, an anti-IL1RAP antibody, or antigen binding portion thereof, is the human antibody 32F9_21A5. The 32F9_21A5 antibody comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 26, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69. In further embodiments, disclosed herein is an antibody having a heavy chain variable region comprising the amino acid sequence of SEQ ID NO: 123 and a light chain variable region comprising the amino acid sequence of SEQ ID NO: 124.

In some embodiments, an anti-IL1RAP antibody, or antigen-binding portion thereof, comprises a heavy chain comprising an amino acid sequence set forth in SEQ ID NO: 123, or a sequence having at least 90%, 95%, 96%, 97%, 98%, or 99% identity to SEQ ID NO: 123, and/or a light chain comprising an amino acid sequence set forth in SEQ ID NO: 124, or a sequence having at least 90%, 95%, 96%, 97%, 98%, or 99% identity to SEQ ID NO: 124.

In one embodiment, an anti-IL1RAP antibody, or antigen binding portion thereof, is the human antibody 33E9_21A5. The 33E9_21A5 antibody comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 26, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69. In further embodiments, disclosed herein is an antibody having a heavy chain variable region comprising the amino acid sequence of SEQ ID NO: 125 and a light chain variable region comprising the amino acid sequence of SEQ ID NO: 126.

In some embodiments, an anti-IL1RAP antibody, or antigen-binding portion thereof, comprises a heavy chain comprising an amino acid sequence set forth in SEQ ID NO: 125, or a sequence having at least 90%, 95%, 96%, 97%, 98%, or 99% identity to SEQ ID NO: 125, and/or a light chain comprising an amino acid sequence set forth in SEQ ID NO: 126, or a sequence having at least 90%, 95%, 96%, 97%, 98%, or 99% identity to SEQ ID NO: 126.

In one embodiment, an anti-IL1RAP antibody, or antigen binding portion thereof, is the human antibody 35D11_22A1. The 35D11_22A1 antibody comprises a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 101, and a light chain variable region comprising a CDR3 domain comprising the amino acid sequence of SEQ ID NO: 129, a CDR2 domain comprising the amino acid sequence of SEQ ID NO: 62, and a CDR1 domain comprising the amino acid sequence of SEQ ID NO: 69. In further embodiments, disclosed herein is an antibody having a heavy chain variable region comprising the amino acid sequence of SEQ ID NO: 127 and a light chain variable region comprising the amino acid sequence of SEQ ID NO: 128.

In some embodiments, an anti-IL1RAP antibody, or antigen-binding portion thereof, comprises a heavy chain comprising an amino acid sequence set forth in SEQ ID NO: 127, or a sequence having at least 90%, 95%, 96%, 97%, 98%, or 99% identity to SEQ ID NO: 127, and/or a light chain comprising an amino acid sequence set forth in SEQ ID NO: 128, or a sequence having at least 90%, 95%, 96%, 97%, 98%, or 99% identity to SEQ ID NO: 128.

In one embodiment, an anti-IL1RAP antibody, or antigen binding portion thereof, is the human antibody 39A9_28A4. The 39A9_28A4 antibody comprises a heavy chain variable region comprising a CDR3 domain comprising the amino acid sequence of SEQ ID NO: 133, a CDR2 domain comprising the amino acid sequence of SEQ ID NO: 132, and a CDR1 domain comprising the amino acid sequence of SEQ ID NO: 131, and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 135. In further embodiments, disclosed herein is an antibody having a heavy chain variable region comprising the amino acid sequence of SEQ ID NO: 130 and a light chain variable region comprising the amino acid sequence of SEQ ID NO: 134.

In some embodiments, an anti-IL1RAP antibody, or antigen-binding portion thereof, comprises a heavy chain comprising an amino acid sequence set forth in SEQ ID NO: 130, or a sequence having at least 90%, 95%, 96%, 97%, 98%, or 99% identity to SEQ ID NO: 130, and/or a light chain comprising an amino acid sequence set forth in SEQ ID NO: 134, or a sequence having at least 90%, 95%, 96%, 97%, 98%, or 99% identity to SEQ ID NO: 134.

In one embodiment, an anti-IL1RAP antibody, or antigen binding portion thereof, is the human antibody 34D1_21B3. The 34D1_21B3 antibody comprises a heavy chain variable region comprising a CDR3 domain comprising the amino acid sequence of SEQ ID NO: 51, a CDR2 domain comprising the amino acid sequence of SEQ ID NO: 50, and a CDR1 domain comprising the amino acid sequence of SEQ ID NO: 49, and a light chain variable region comprising a CDR3 domain comprising the amino acid sequence of SEQ ID NO: 55, a CDR2 domain comprising the amino acid sequence of SEQ ID NO: 139, and a CDR1 domain comprising the amino acid sequence of SEQ ID NO: 138. In further embodiments, disclosed herein is an antibody having a heavy chain variable region comprising the amino acid sequence of SEQ ID NO: 136 and a light chain variable region comprising the amino acid sequence of SEQ ID NO: 137.

In some embodiments, an anti-IL1RAP antibody, or antigen-binding portion thereof, comprises a heavy chain comprising an amino acid sequence set forth in SEQ ID NO: 136, or a sequence having at least 90%, 95%, 96%, 97%, 98%, or 99% identity to SEQ ID NO: 136, and/or a light chain comprising an amino acid sequence set forth in SEQ ID NO: 137, or a sequence having at least 90%, 95%, 96%, 97%, 98%, or 99% identity to SEQ ID NO: 137.

In one embodiment, an anti-IL1RAP antibody, or antigen binding portion thereof, is the human antibody 33H2_21B1. The 33H2_21B1 antibody comprises a heavy chain variable region comprising a CDR3 domain comprising the amino acid sequence of SEQ ID NO: 142, a CDR2 domain comprising the amino acid sequence of SEQ ID NO: 42, and a CDR1 domain comprising the amino acid sequence of SEQ ID NO: 141, and a light chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45. In further embodiments, disclosed herein is an antibody having a heavy chain variable region comprising the amino acid sequence of SEQ ID NO: 140 and a light chain variable region comprising the amino acid sequence of SEQ ID NO: 143.

In some embodiments, an anti-IL1RAP antibody, or antigen-binding portion thereof, comprises a heavy chain comprising an amino acid sequence set forth in SEQ ID NO: 140, or a sequence having at least 90%, 95%, 96%, 97%, 98%, or 99% identity to SEQ ID NO: 140, and/or a light chain comprising an amino acid sequence set forth in SEQ ID NO: 143, or a sequence having at least 90%, 95%, 96%, 97%, 98%, or 99% identity to SEQ ID NO: 143.

In one embodiment, an anti-IL1RAP antibody, or antigen binding portion thereof, is the human antibody 36A12_21C1. The 36A12_21C1 antibody comprises a heavy chain variable region comprising a CDR3 domain comprising the amino acid sequence of SEQ ID NO: 43, a CDR2 domain comprising the amino acid sequence of SEQ ID NO: 146, and a CDR1 domain comprising the amino acid sequence of SEQ ID NO: 145, and a light chain variable region comprising a CDR3 domain comprising the amino acid sequence of SEQ ID NO: 150, a CDR2 domain comprising the amino acid sequence of SEQ ID NO: 149, and a CDR1 domain comprising the amino acid sequence of SEQ ID NO: 148. In further embodiments, disclosed herein is an antibody having a heavy chain variable region comprising the amino acid sequence of SEQ ID NO: 144 and a light chain variable region comprising the amino acid sequence of SEQ ID NO: 147.

In some embodiments, an anti-IL1RAP antibody, or antigen-binding portion thereof, comprises a heavy chain comprising an amino acid sequence set forth in SEQ ID NO: 144, or a sequence having at least 90%, 95%, 96%, 97%, 98%, or 99% identity to SEQ ID NO: 144, and/or a light chain comprising an amino acid sequence set forth in SEQ ID NO: 147, or a sequence having at least 90%, 95%, 96%, 97%, 98%, or 99% identity to SEQ ID NO: 147.

In one embodiment, an anti-IL1RAP antibody, or antigen binding portion thereof, is the human antibody 38G11_28A2. The 38G11_28A2 antibody comprises a heavy chain variable region comprising a CDR3 domain comprising the amino acid sequence of SEQ ID NO: 43, a CDR2 domain comprising the amino acid sequence of SEQ ID NO: 153, and a CDR1 domain comprising the amino acid sequence of SEQ ID NO: 152, and a light chain variable region comprising a CDR3 domain comprising the amino acid sequence of SEQ ID NO: 157, a CDR2 domain comprising the amino acid sequence of SEQ ID NO: 156, and a CDR1 domain comprising the amino acid sequence of SEQ ID NO: 155. In further embodiments, disclosed herein is an antibody having a heavy chain variable region comprising the amino acid sequence of SEQ ID NO: 151 and a light chain variable region comprising the amino acid sequence of SEQ ID NO: 154.

In some embodiments, an anti-IL1RAP antibody, or antigen-binding portion thereof, comprises a heavy chain comprising an amino acid sequence set forth in SEQ ID NO: 151, or a sequence having at least 90%, 95%, 96%, 97%, 98%, or 99% identity to SEQ ID NO: 151, and/or a light chain comprising an amino acid sequence set forth in SEQ ID NO: 154, or a sequence having at least 90%, 95%, 96%, 97%, 98%, or 99% identity to SEQ ID NO: 154.

In one embodiment, an anti-IL1RAP antibody, or antigen binding portion thereof, is the human antibody 40C3_22B6. The 40C3_22B6 antibody comprises a heavy chain variable region comprising a CDR3 domain comprising the amino acid sequence of SEQ ID NO: 43, a CDR2 domain comprising the amino acid sequence of SEQ ID NO: 159, and a CDR1 domain comprising the amino acid sequence of SEQ ID NO: 145, and a light chain variable region comprising a CDR3 domain comprising the amino acid sequence of SEQ ID NO: 162, a CDR2 domain comprising the amino acid sequence of SEQ ID NO: 161, and a CDR1 domain comprising the amino acid sequence of SEQ ID NO: 148. In further embodiments, disclosed herein is an antibody having a heavy chain variable region comprising the amino acid sequence of SEQ ID NO: 158 and a light chain variable region comprising the amino acid sequence of SEQ ID NO: 160.

In some embodiments, an anti-IL1RAP antibody, or antigen-binding portion thereof, comprises a heavy chain comprising an amino acid sequence set forth in SEQ ID NO: 158, or a sequence having at least 90%, 95%, 96%, 97%, 98%, or 99% identity to SEQ ID NO: 158, and/or a light chain comprising an amino acid sequence set forth in SEQ ID NO:

160, or a sequence having at least 90%, 95%, 96%, 97%, 98%, or 99% identity to SEQ ID NO: 160.

In one embodiment, an anti-IL1RAP antibody, or antigen binding portion thereof, is the human antibody 5D12_18A4. The 5D12_18A4 antibody comprises a heavy chain variable region comprising a CDR3 domain comprising the amino acid sequence of SEQ ID NO: 166, a CDR2 domain comprising the amino acid sequence of SEQ ID NO: 165, and a CDR1 domain comprising the amino acid sequence of SEQ ID NO: 164, and a light chain variable region comprising a CDR3 domain comprising the amino acid sequence of SEQ ID NO: 169, a CDR2 domain comprising the amino acid sequence of SEQ ID NO: 168, and a CDR1 domain comprising the amino acid sequence of SEQ ID NO: 155. In further embodiments, disclosed herein is an antibody having a heavy chain variable region comprising the amino acid sequence of SEQ ID NO: 163 and a light chain variable region comprising the amino acid sequence of SEQ ID NO: 167.

In some embodiments, an anti-IL1RAP antibody, or antigen-binding portion thereof, comprises a heavy chain comprising an amino acid sequence set forth in SEQ ID NO: 163, or a sequence having at least 90%, 95%, 96%, 97%, 98%, or 99% identity to SEQ ID NO: 163, and/or a light chain comprising an amino acid sequence set forth in SEQ ID NO: 167, or a sequence having at least 90%, 95%, 96%, 97%, 98%, or 99% identity to SEQ ID NO: 167.

In one embodiment, an anti-IL1RAP antibody, or antigen binding portion thereof, is the human antibody 5D12_C108Y. The 5D12_C108Y antibody comprises a heavy chain variable region comprising a CDR3 domain comprising the amino acid sequence of SEQ ID NO: 171, a CDR2 domain comprising the amino acid sequence of SEQ ID NO: 165, and a CDR1 domain comprising the amino acid sequence of SEQ ID NO: 164, and a light chain variable region comprising a CDR3 domain comprising the amino acid sequence of SEQ ID NO: 169, a CDR2 domain comprising the amino acid sequence of SEQ ID NO: 168, and a CDR1 domain comprising the amino acid sequence of SEQ ID NO: 155. In further embodiments, disclosed herein is an antibody having a heavy chain variable region comprising the amino acid sequence of SEQ ID NO: 170 and a light chain variable region comprising the amino acid sequence of SEQ ID NO: 172.

In some embodiments, an anti-IL1RAP antibody, or antigen-binding portion thereof, comprises a heavy chain comprising an amino acid sequence set forth in SEQ ID NO: 170, or a sequence having at least 90%, 95%, 96%, 97%, 98%, or 99% identity to SEQ ID NO: 170, and/or a light chain comprising an amino acid sequence set forth in SEQ ID NO: 172, or a sequence having at least 90%, 95%, 96%, 97%, 98%, or 99% identity to SEQ ID NO: 172.

In one embodiment, an anti-IL1RAP antibody, or antigen binding portion thereof, is the human antibody 37D11_21C2. The 37D11_21C2 antibody comprises a heavy chain variable region comprising a CDR3 domain comprising the amino acid sequence of SEQ ID NO: 176, a CDR2 domain comprising the amino acid sequence of SEQ ID NO: 175, and a CDR1 domain comprising the amino acid sequence of SEQ ID NO: 174, and a light chain variable region comprising a CDR3 domain comprising the amino acid sequence of SEQ ID NO: 179, a CDR2 domain comprising the amino acid sequence of SEQ ID NO: 178, and a CDR1 domain comprising the amino acid sequence of SEQ ID NO: 79. In further embodiments, disclosed herein is an antibody having a heavy chain variable region comprising the amino acid sequence of SEQ ID NO: 173 and a light chain variable region comprising the amino acid sequence of SEQ ID NO: 177.

In some embodiments, an anti-IL1RAP antibody, or antigen-binding portion thereof, comprises a heavy chain comprising an amino acid sequence set forth in SEQ ID NO: 173, or a sequence having at least 90%, 95%, 96%, 97%, 98%, or 99% identity to SEQ ID NO: 173, and/or a light chain comprising an amino acid sequence set forth in SEQ ID NO: 177, or a sequence having at least 90%, 95%, 96%, 97%, 98%, or 99% identity to SEQ ID NO: 177.

In one embodiment, an anti-IL1RAP antibody, or antigen binding portion thereof, is the human antibody 42D10_28A5. The 42D10_28A5 antibody comprises a heavy chain variable region comprising a CDR3 domain comprising the amino acid sequence of SEQ ID NO: 183, a CDR2 domain comprising the amino acid sequence of SEQ ID NO: 182, and a CDR1 domain comprising the amino acid sequence of SEQ ID NO: 181, and a light chain variable region comprising a CDR3 domain comprising the amino acid sequence of SEQ ID NO: 179, a CDR2 domain comprising the amino acid sequence of SEQ ID NO: 80, and a CDR1 domain comprising the amino acid sequence of SEQ ID NO: 79. In further embodiments, disclosed herein is an antibody having a heavy chain variable region comprising the amino acid sequence of SEQ ID NO: 180 and a light chain variable region comprising the amino acid sequence of SEQ ID NO: 184.

In some embodiments, an anti-IL1RAP antibody, or antigen-binding portion thereof, comprises a heavy chain comprising an amino acid sequence set forth in SEQ ID NO: 180, or a sequence having at least 90%, 95%, 96%, 97%, 98%, or 99% identity to SEQ ID NO: 180, and/or a light chain comprising an amino acid sequence set forth in SEQ ID NO: 184, or a sequence having at least 90%, 95%, 96%, 97%, 98%, or 99% identity to SEQ ID NO: 184.

In one embodiment, an anti-IL1RAP antibody, or antigen binding portion thereof, is the human antibody 34H8_21B4. The 34H8_21B4 antibody comprises a heavy chain variable region comprising a CDR3 domain comprising the amino acid sequence of SEQ ID NO: 188, a CDR2 domain comprising the amino acid sequence of SEQ ID NO: 187, and a CDR1 domain comprising the amino acid sequence of SEQ ID NO: 186, and a light chain variable region comprising a CDR3 domain comprising the amino acid sequence of SEQ ID NO: 63, a CDR2 domain comprising the amino acid sequence of SEQ ID NO: 62, and a CDR1 domain comprising the amino acid sequence of SEQ ID NO: 190. In further embodiments, disclosed herein is an antibody having a heavy chain variable region comprising the amino acid sequence of SEQ ID NO: 185 and a light chain variable region comprising the amino acid sequence of SEQ ID NO: 189.

In some embodiments, an anti-IL1RAP antibody, or antigen-binding portion thereof, comprises a heavy chain comprising an amino acid sequence set forth in SEQ ID NO: 71, or a sequence having at least 90%, 95%, 96%, 97%, 98%, or 99% identity to SEQ ID NO: 71, and/or a light chain comprising an amino acid sequence set forth in SEQ ID NO: 73, or a sequence having at least 90%, 95%, 96%, 97%, 98%, or 99% identity to SEQ ID NO: 73.

The foregoing anti-IL1RAP antibody CDR sequences establish a novel family of IL1RAP binding proteins, isolated in accordance with this disclosure, and comprising antigen binding polypeptides that include the CDR sequences listed in Table 5, as well as the Sequence Summary.

To generate and to select CDRs having preferred IL1RAP binding and/or neutralizing activity with respect to hIL1RAP, standard methods known in the art for generating antibodies, or antigen binding portions thereof, and assessing the IL1RAP binding and/or neutralizing characteristics of those antibodies, or antigen binding portions thereof, may be used, including but not limited to those specifically described herein.

In certain embodiments, the antibody comprises a heavy chain constant region, such as an IgG1, IgG2, IgG3, IgG4, IgA, IgE, IgM, or IgD constant region. In certain embodiments, the anti-IL1RAP antibody, or antigen binding portion thereof, comprises a heavy chain immunoglobulin constant domain selected from the group consisting of a human IgG constant domain, a human IgM constant domain, a human IgE constant domain, and a human IgA constant domain. In further embodiments, the antibody, or antigen binding portion thereof, has an IgG1 heavy chain constant region, an IgG2 heavy chain constant region, an IgG3 constant region, or an IgG4 heavy chain constant region. Preferably, the heavy chain constant region is an IgG1 heavy chain constant region or an IgG4 heavy chain constant region. In one embodiment, the antibody, or antigen binding portion thereof, is an IgG4 isotype.

Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-IL1RAP antibody binding portion is a Fab, a Fab', a F(ab')2, a Fv, a disulfide linked Fv, an scFv, a single domain antibody, or a diabody.

In certain embodiments, the anti-IL1RAP antibody, or antigen binding portion thereof, is a multispecific antibody, e.g. a bispecific antibody.

In certain embodiments, the anti-IL1RAP antibody, or antigen binding portion thereof, comprises a heavy chain constant region comprising the amino acid sequence set forth in SEQ ID NO: 1 and/or a light chain constant region comprising the amino acid sequence set forth in SEQ ID NO: 5.

In certain embodiments, the anti-IL1RAP antibody, or antigen binding portion thereof, comprises a heavy chain constant region comprising the amino acid sequence set forth in SEQ ID NO: 9 and/or a light chain constant region comprising the amino acid sequence set forth in SEQ ID NO: 13.

In certain embodiments, the anti-IL1RAP antibody, or antigen binding portion thereof, comprises a heavy chain constant region comprising the amino acid sequence set forth in SEQ ID NO: 17 and/or a light chain constant region comprising the amino acid sequence set forth in SEQ ID NO: 21.

In certain embodiments, the anti-IL1RAP antibody, or antigen binding portion thereof, comprises a heavy chain constant region comprising the amino acid sequence set forth in SEQ ID NO: 25 and/or a light chain constant region comprising the amino acid sequence set forth in SEQ ID NO: 29.

In certain embodiments, the anti-IL1RAP antibody, or antigen binding portion thereof, comprises a heavy chain constant region comprising the amino acid sequence set forth in SEQ ID NO: 32 and/or a light chain constant region comprising the amino acid sequence set forth in SEQ ID NO: 36.

In certain embodiments, the anti-IL1RAP antibody, or antigen binding portion thereof, comprises a heavy chain constant region comprising the amino acid sequence set forth in SEQ ID NO: 40 and/or a light chain constant region comprising the amino acid sequence set forth in SEQ ID NO: 44.

In certain embodiments, the anti-IL1RAP antibody, or antigen binding portion thereof, comprises a heavy chain constant region comprising the amino acid sequence set forth in SEQ ID NO: 48 and/or a light chain constant region comprising the amino acid sequence set forth in SEQ ID NO: 52.

In certain embodiments, the anti-IL1RAP antibody, or antigen binding portion thereof, comprises a heavy chain constant region comprising the amino acid sequence set forth in SEQ ID NO: 56 and/or a light chain constant region comprising the amino acid sequence set forth in SEQ ID NO: 60.

In certain embodiments, the anti-IL1RAP antibody, or antigen binding portion thereof, comprises a heavy chain constant region comprising the amino acid sequence set forth in SEQ ID NO: 64 and/or a light chain constant region comprising the amino acid sequence set forth in SEQ ID NO: 68.

In certain embodiments, the anti-IL1RAP antibody, or antigen binding portion thereof, comprises a heavy chain constant region comprising the amino acid sequence set forth in SEQ ID NO: 71 and/or a light chain constant region comprising the amino acid sequence set forth in SEQ ID NO: 73.

In certain embodiments, the anti-IL1RAP antibody, or antigen binding portion thereof, comprises a heavy chain constant region comprising the amino acid sequence set forth in SEQ ID NO: 74 and/or a light chain constant region comprising the amino acid sequence set forth in SEQ ID NO: 78.

In certain embodiments, the anti-IL1RAP antibody, or antigen binding portion thereof, comprises a heavy chain constant region comprising the amino acid sequence set forth in SEQ ID NO: 9 and/or a light chain constant region comprising the amino acid sequence set forth in SEQ ID NO: 82.

In certain embodiments, the anti-IL1RAP antibody, or antigen binding portion thereof, comprises a heavy chain constant region comprising the amino acid sequence set forth in SEQ ID NO: 83 and/or a light chain constant region comprising the amino acid sequence set forth in SEQ ID NO: 87.

In certain embodiments, the anti-IL1RAP antibody, or antigen binding portion thereof, comprises a heavy chain constant region comprising the amino acid sequence set forth in SEQ ID NO: 90 and/or a light chain constant region comprising the amino acid sequence set forth in SEQ ID NO: 93.

In certain embodiments, the anti-IL1RAP antibody, or antigen binding portion thereof, comprises a heavy chain constant region comprising the amino acid sequence set forth in SEQ ID NO: 96 and/or a light chain constant region comprising the amino acid sequence set forth in SEQ ID NO: 98.

In certain embodiments, the anti-IL1RAP antibody, or antigen binding portion thereof, comprises a heavy chain constant region comprising the amino acid sequence set forth in SEQ ID NO: 100 and/or a light chain constant region comprising the amino acid sequence set forth in SEQ ID NO: 103.

In certain embodiments, the anti-IL1RAP antibody, or antigen binding portion thereof, comprises a heavy chain constant region comprising the amino acid sequence set forth in SEQ ID NO: 106 and/or a light chain constant region comprising the amino acid sequence set forth in SEQ ID NO: 108.

In certain embodiments, the anti-IL1RAP antibody, or antigen binding portion thereof, comprises a heavy chain constant region comprising the amino acid sequence set forth in SEQ ID NO: 109 and/or a light chain constant region comprising the amino acid sequence set forth in SEQ ID NO: 113.

In certain embodiments, the anti-IL1RAP antibody, or antigen binding portion thereof, comprises a heavy chain constant region comprising the amino acid sequence set forth in SEQ ID NO: 32 and/or a light chain constant region comprising the amino acid sequence set forth in SEQ ID NO: 114.

In certain embodiments, the anti-IL1RAP antibody, or antigen binding portion thereof, comprises a heavy chain constant region comprising the amino acid sequence set forth in SEQ ID NO: 116 and/or a light chain constant region comprising the amino acid sequence set forth in SEQ ID NO: 36.

In certain embodiments, the anti-IL1RAP antibody, or antigen binding portion thereof, comprises a heavy chain constant region comprising the amino acid sequence set forth in SEQ ID NO: 118 and/or a light chain constant region comprising the amino acid sequence set forth in SEQ ID NO: 120.

In certain embodiments, the anti-IL1RAP antibody, or antigen binding portion thereof, comprises a heavy chain constant region comprising the amino acid sequence set forth in SEQ ID NO: 121 and/or a light chain constant region comprising the amino acid sequence set forth in SEQ ID NO: 122.

In certain embodiments, the anti-IL1RAP antibody, or antigen binding portion thereof, comprises a heavy chain constant region comprising the amino acid sequence set forth in SEQ ID NO: 123 and/or a light chain constant region comprising the amino acid sequence set forth in SEQ ID NO: 124.

In certain embodiments, the anti-IL1RAP antibody, or antigen binding portion thereof, comprises a heavy chain constant region comprising the amino acid sequence set forth in SEQ ID NO: 125 and/or a light chain constant region comprising the amino acid sequence set forth in SEQ ID NO: 126.

In certain embodiments, the anti-IL1RAP antibody, or antigen binding portion thereof, comprises a heavy chain constant region comprising the amino acid sequence set forth in SEQ ID NO: 127 and/or a light chain constant region comprising the amino acid sequence set forth in SEQ ID NO: 128.

In certain embodiments, the anti-IL1RAP antibody, or antigen binding portion thereof, comprises a heavy chain constant region comprising the amino acid sequence set forth in SEQ ID NO: 130 and/or a light chain constant region comprising the amino acid sequence set forth in SEQ ID NO: 134.

In certain embodiments, the anti-IL1RAP antibody, or antigen binding portion thereof, comprises a heavy chain constant region comprising the amino acid sequence set forth in SEQ ID NO: 136 and/or a light chain constant region comprising the amino acid sequence set forth in SEQ ID NO: 137.

In certain embodiments, the anti-IL1RAP antibody, or antigen binding portion thereof, comprises a heavy chain constant region comprising the amino acid sequence set forth in SEQ ID NO: 140 and/or a light chain constant region comprising the amino acid sequence set forth in SEQ ID NO: 143.

In certain embodiments, the anti-IL1RAP antibody, or antigen binding portion thereof, comprises a heavy chain constant region comprising the amino acid sequence set forth in SEQ ID NO: 144 and/or a light chain constant region comprising the amino acid sequence set forth in SEQ ID NO: 147.

In certain embodiments, the anti-IL1RAP antibody, or antigen binding portion thereof, comprises a heavy chain constant region comprising the amino acid sequence set forth in SEQ ID NO: 151 and/or a light chain constant region comprising the amino acid sequence set forth in SEQ ID NO: 154.

In certain embodiments, the anti-IL1RAP antibody, or antigen binding portion thereof, comprises a heavy chain constant region comprising the amino acid sequence set forth in SEQ ID NO: 158 and/or a light chain constant region comprising the amino acid sequence set forth in SEQ ID NO: 160.

In certain embodiments, the anti-IL1RAP antibody, or antigen binding portion thereof, comprises a heavy chain constant region comprising the amino acid sequence set forth in SEQ ID NO: 163 and/or a light chain constant region comprising the amino acid sequence set forth in SEQ ID NO: 167.

In certain embodiments, the anti-IL1RAP antibody, or antigen binding portion thereof, comprises a heavy chain constant region comprising the amino acid sequence set forth in SEQ ID NO: 170 and/or a light chain constant region comprising the amino acid sequence set forth in SEQ ID NO: 172.

In certain embodiments, the anti-IL1RAP antibody, or antigen binding portion thereof, comprises a heavy chain constant region comprising the amino acid sequence set forth in SEQ ID NO: 173 and/or a light chain constant region comprising the amino acid sequence set forth in SEQ ID NO: 177.

In certain embodiments, the anti-IL1RAP antibody, or antigen binding portion thereof, comprises a heavy chain constant region comprising the amino acid sequence set forth in SEQ ID NO: 180 and/or a light chain constant region comprising the amino acid sequence set forth in SEQ ID NO: 184.

In certain embodiments, the anti-IL1RAP antibody, or antigen binding portion thereof, comprises a heavy chain constant region comprising the amino acid sequence set forth in SEQ ID NO: 185 and/or a light chain constant region comprising the amino acid sequence set forth in SEQ ID NO: 189.

Replacements of amino acid residues in the Fc portion to alter antibody effector function are have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment includes a labeled anti-IL1RAP antibody, or antibody portion thereof, where the antibody is derivatized or linked to one or more functional molecule(s) (e.g., another peptide or protein). For example, a labeled antibody can be derived by functionally linking an antibody or antibody portion of the disclosure (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying IL1RAP positive tumors. In a certain embodiment, anti-IL1RAP antibodies (or ADCs) described herein are labeled with $^{111}$I via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the disclosure provides a glycosylated binding protein wherein the anti-IL1RAP antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the disclosure is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the disclosure.

In still another embodiment, the glycosylation of the anti-IL1RAP antibody or antigen binding portion is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-IL1RAP antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies disclosed herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the disclosure. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure and the other heavy and light chain are specific for an antigen other than the antigens of interest by cross-linking an antibody of the disclosure to a second antibody by standard chemical crosslinking methods.

In a preferred system for recombinant expression of an antibody, or antigen binding portion thereof, a recombinant expression vector encoding both the antibody heavy chain and the antibody light chain is introduced into CHO cells comprising a glutamine synthase expression system, commercially available from Lonza (hereafter GS-CHO) (Bebbington, C. R. et al. (1992), Biotechnology, 10, pages 169-175).

In another system for recombinant expression of an antibody, or antigen binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the disclosure provides a method of synthesizing a recombinant antibody by culturing a host cell in a suitable culture medium until a recombinant antibody is synthesized. Recombinant antibodies may be produced using nucleic acid molecules corresponding to the amino acid sequences disclosed herein. In one embodiment, the nucleic acid molecules set forth in SEQ ID NOs: 191-259 are used in the production of a recombinant antibody. The method can further comprise isolating the recombinant antibody from the culture medium.

III. Anti-IL1RAP Antibody Drug Conjugates (ADCs)

Anti-IL1RAP antibodies described herein may be conjugated to a drug moiety to form an anti-IL1RAP Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues or cells, e.g., IL1RAP expressing tumors or IL1RAP expressing cells. Thus, in certain embodiments, the disclosure provides anti-IL1RAP ADCs for therapeutic use, e.g., treatment of cancer.

Anti-IL1RAP ADCs comprise an anti-IL1RAP antibody, i.e., an antibody that specifically binds to IL1RAP, linked to one or more drug moieties. The specificity of the ADC is defined by the specificity of the antibody, i.e., anti-IL1RAP. In one embodiment, an anti-IL1RAP antibody is linked to one or more cytotoxic drug(s) which is delivered internally to a cancer cell expressing IL1RAP.

Examples of drugs that may be used in the anti-IL1RAP ADCs are provided below, as are linkers that may be used to conjugate the antibody and the one or more drug(s). The terms "drug," "agent," and "drug moiety" are used interchangeably herein. The terms "linked" and "conjugated" are also used interchangeably herein and indicate that the antibody and moiety are covalently linked.

In some embodiments, the ADC has the following formula (formula I):

$$Ab\text{-}(L\text{-}D)_n \quad (I)$$

wherein Ab an anti-IL1RAP antibody described herein, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing IL1RAP; and n is an integer from 1 to 20. In some embodiments, n ranges from 1 to 8, 1 to 7, 1 to 6, 1 to 5, 1 to 4, 1 to 3, 1 to 2, or is 1. The DAR of an ADC is equivalent to the "n" referred to in Formula I.

Additional details regarding drugs (D of Formula I) and linkers (L of Formula I) that may be used in the ADCs, as well as alternative ADC structures, are described below.

A. Anti-IL1RAP ADCs: Exemplary Drugs for Conjugation

Anti-IL1RAP antibodies may be used in ADCs to target one or more drug(s) to a cell of interest, e.g., a cell expressing IL1RAP. The anti-IL1RAP ADCs disclosed herein provide a targeted therapy that may, for example, reduce the side effects often seen with anti-cancer therapies, as the one or more drug(s) is delivered to a specific cell. In one embodiment, the drug used in an ADC is saporin. In another embodiment, the drug used in an ADC is dacarbazine. In another embodiment, the drug used in an ADC is carboplatin.

Examples of drugs that may be used in ADCs, i.e., drugs that may be conjugated to the anti-IL1RAP antibodies, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Mitotic Inhibitors

In one aspect, anti-IL1RAP antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by effecting microtubule polymerization (e.g., inhibiting microtubule polymerization) or microtubule depolymerization (e.g., stabilizing the microtubule cytoskeleton against depolymrization). Thus, in one embodiment, an anti-IL1RAP antibody of the invention is conjugated to one or more mitotic inhibitor(s) that disrupts microtubule formation by inhibiting tubulin polymerization. In another embodiment, an anti-IL1RAP antibody of the invention is conjugated to one or more mitotic inhibitor(s) that stabilizes the microtubule cytoskeleton from deploymerization. In one embodiment, the mitotic inhibitor used in the ADCs of the invention is Ixempra (ixabepilone). Examples of mitotic inhibitors that may be used in the anti-IL1RAP ADCs of the invention are provided below. Included in the genus of mitotic inhibitors are auristatins, described below.

a. Dolastatins

The anti-IL1RAP antibodies of the invention may be conjugated to at least one dolastatin to form an ADC. Dolastatins are short peptidic compounds isolated from the Indian Ocean sea hare *Dolabella auricularia* (see Pettit et al., J. Am. Chem. Soc., 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-IL1RAP ADC of the invention comprises an anti-IL1RAP antibody, as described herein, and at least one dolastatin. Auristatins are synthetic derivatives of dolastatin 10.

b. Auristatins

Anti-IL1RAP antibodies may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein.

In one embodiment, anti-IL1RAP antibodies are conjugated to at least one MMAE (monomethyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-IL1RAP antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent antimitotic mechanism.

The structure of MMAE is provided below.

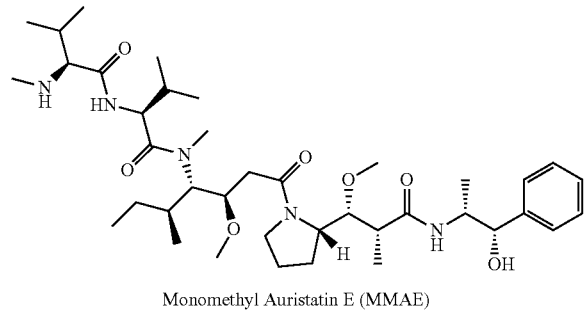 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

Monomethyl Auristatin E (MMAE)

In one embodiment, the antibody is coupled to a single drug and, therefore, has a DAR of 1. In certain embodiments, the ADC will have a DAR of 2 to 8, or, alternatively, 2 to 4.

c. Maytansinoids

The anti-IL1RAP antibodies of the invention may be conjugated to at least one maytansinoid to form an ADC. Maytansinoids are potent antitumor agents that were originally isolated from members of the higher plant families Celastraceae, Rhamnaceae, and Euphorbiaceae, as well as some species of mosses (Kupchan et al, J. Am. Chem. Soc. 94:1354-1356 [1972]; Wani et al, J. Chem. Soc. Chem. Commun. 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate, and is described in more detail in the linker section below. The structure of an exemplary maytansinoid, mertansine (DM1), is provided below.

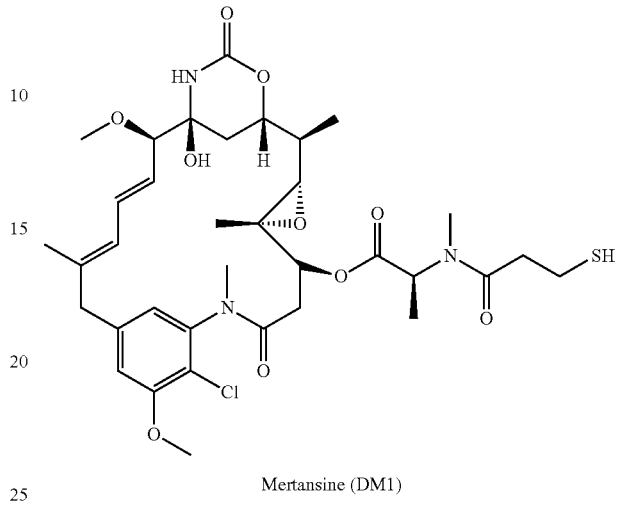

Mertansine (DM1)

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) Cancer Res 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine), and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

In one embodiment of the invention, an anti-IL1RAP antibody is conjugated to at least one DM1. In one embodiment, an anti-IL1RAP antibody is conjugated to at least one DM2. In one embodiment, an anti-IL1RAP antibody is conjugated to at least one DM3. In one embodiment, an anti-IL1RAP antibody is conjugated to at least one DM4.

2. Antitumor Antibiotics

Anti-IL1RAP antibodies may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-IL1RAP ADCs include, but are not limited to, actinomycines (e.g., pyrrolo[2,1-c][1,4]benzodiazepines), anthracyclines, calicheamicins, and duocarmycins. In addition to the foregoing, additional antitumor antibiotics that may be used in the anti-IL1RAP ADCs include bleomycin (Blenoxane, Bristol-Myers Squibb), mitomycin, and plicamycin (also known as mithramycin).

3. Immunomodulating Agents

In one aspect, anti-IL1RAP antibodies may be conjugated to at least one immunomodulating agent. As used herein, the term "immunomodulating agent" refers to an agent that can stimulate or modify an immune response. In one embodiment, an immunomodulating agent is an immunostimuator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, bacillus calmette-guerin (BCG) and levamisole (Ergamisol). Other examples of immunomodulating agents that may be used in the ADCs include, but are not limited to, cancer vaccines, and cytokines.

As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant disclosure, administering an ADC comprising an anti-IL1RAP antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-IL1RAP ADCs include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in one embodiment, the anti-IL1RAP antibody is conjugated to at least one cancer vaccine that is either an immunostimulator or is an immunosuppressant.

The anti-IL1RAP antibodies may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) *Cancers* 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the disclosure provides an ADC comprising an anti-IL1RAP antibody described herein and a cytokine.

The anti-IL1RAP antibodies may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-IL1RAP ADCs include, but are not limited to erythropoietin (Epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, an ADC may comprise an anti-IL1RAP antibody described herein and a CSF.

4. Alkylating Agents

The anti-IL1RAP antibodies may be conjugated to one or more alkylating agent(s).

Alkylating agents are a class of antineoplastic compounds that attaches an alkyl group to DNA. Examples of alkylating agents that may be used in the ADCs include, but are not limited to, alkyl sulfonates, ethylenimimes, methylamine derivatives, epoxides, nitrogen mustards, nitrosoureas, triazines and hydrazines.

4. DNA Damaging Agents

In one embodiment, the antibodies and antigen-binding portions thereof described herein may be conjugated to one or more DNA damaging agents. The term "DNA damaging agent", as used herein, refers to an agent which is capable of damaging DNA and are well known to those of ordinary skill in the art (see, for example, Cheung-Ong et al., *Cell Chemical Biology,* 20(5): 648-659, 2013).

DNA damaging agents include DNA alkylating agents. DNA alkylating agents are a class of antineoplastic compounds that attaches an alkyl group ($C_nH_{2n+1}$) to DNA at a guanine base of DNA. Examples of DNA alkylating agents that may be used in the ADCs include, but are not limited to, alkyl sulfonates (e.g., busulfan), ethylenimimes (e.g., altretamine and thiotepa), methylamine derivatives, epoxides, nitrogen mustards (e.g., bendamustine, chlorambucil, cyclophosphamide, ifosfamide, mechlorethamine, melphalan), nitrosoureas (e.g., carmustine, lomustine, and streptozocin), triazines (e.g., dacarbazine and temozolomide), and hydrazines.

DNA damaging agents also include indolino-benzodiazepines (IGNs). IGNs represent a chemical class of cytotoxic molecules with high in vitro potency ($IC_{50}$ values in the low pmol/L range) toward cancer cells. Examples of IGN DNA alkylating agents that can be used as a cytotoxic payload in an ADC are described in Miller et al. (2016) *Molecular Cancer Therapeutics,* 15(8)). The IGN compounds described in Miller et al. bind to the minor groove of DNA followed by covalent reaction of guanine residues with the two imine functionalities in the molecule resulting in cross-linking of DNA. The structure of an exemplary IGN is provided below.

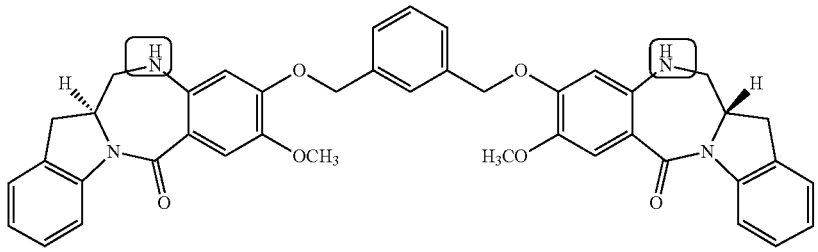

2

In one embodiment, a DNA damaging agent may also include a pyrrolobenzodiazepine (PBD) or pyridinobenzodiazepine (PDD) (see, e.g., N. Veillard et al. "Pyridinobenzodiazepines (PDDs): A new class of sequence-selective DNA mono-alkylating ADC payloads with low hydrophobicity" [abstract]. In: Proceedings of the 109th Annual Meeting of the American Association for Cancer Research; 2018 Apr. 14-18; Chicago, Ill. Philadelphia (Pa.): AACR; 2018. Abstract no 736/3 and Stefano J. E., et al. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.)).

In another embodiment, the DNA damaging agent is a PARP inhibitor, e.g., olaparib, rucaparib, niraparib, or iniparib. In one embodiment, the PARP inhibitor is olaparib. In one embodiment, the PARP inhibitor is rucaparib. In one embodiment, the PARP inhibitor is niraparib. In one embodiment, the PARP inhibitor is iniparib. In one embodiment, the agent is a saporin toxin.

5. Antiangiogenic Agents

In one aspect, the anti-IL1RAP antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

6. Antimetabolites

The anti-IL1RAP antibodies may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolies that may be used in the ADCs include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

7. Boron-Containing Agents

The anti-IL1RAP antibody may be conjugated to at least one boron containing agent. Boron-containing agents comprise a class of cancer therapeutic compounds which interfere with cell proliferation. Representative examples of boron containing agents include, but are not limited to, borophycin and bortezomib (Velcade, Millenium Pharmaceuticals).

8. Chemoprotective Agents

The anti-IL1RAP antibodies may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

9. Photoactive Therapeutic Agents

The anti-IL1RAP antibodies may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

10. Radionuclide Agents (Radioactive Isotopes)

The anti-IL1RAP antibodies may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111 1, Sb-119, I-125, Ho-161, Os-189m and Ir-192. Decay energies of useful beta-particle-emitting nuclides are preferably Dy-152, At-211, Bi-212, Ra-223, Rn-219, Po-215, Bi-21 1, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

11. Radiosensitizers

The anti-IL1RAP antibodies may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin®, benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

12. Topoisomerase Inhibitors

The anti-IL1RAP antibodies may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

13. Tyrosine Kinase Inhibitors

The anti-IL1RAP antibodies may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

14. Other Agents

Examples of other agents that may be used in the ADCs include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the anti-IL1RAP ADCs are not exclusive, in that certain examples of drugs may be found in more than one category, e.g., ansamitocins are both mitotic inhibitors and antitumor antibiotics.

All stereoisomers of the above drug moieties are contemplated for use herein, i.e. any combination of R and S configurations at the chiral carbons of D.

The above agents (i.e., naked agents not conjugated to an antibody) may also be used in combination therapies with the anti-IL1RAP antibodies described herein. In one embodiment, anti-IL1RAP antibodies or ADCs are used with any of the foregoing agents in a combination therapy to treat cancer, where the agent is administered prior to, at the same time as, or following administration of the anti-IL1RAP antibody or ADC to the subject.

B. Anti-IL1RAP ADCs: Exemplary Linkers

An anti-IL1RAP ADC comprises an anti-IL1RAP antibody and at least one drug(s), whereby the antibody and the at least one drug are conjugated by a linker. The term "linker," as used herein, refers to a chemical moiety that may be bifunctional or multifunctional, and is used to attach an antibody to a drug moiety. A linker may include one conjugating component or may include multiple components.

For example, the linker may include a spacer, which is a moiety that extends the drug linkage to avoid, for example, shielding the active site of the antibody or improving the solubility of the ADC. Other examples of components of linkers include a stretcher unit and an amino acid unit.

Two methods are commonly used for conjugating drugs to antibodies: alkylation of reduced interchain cysteine disulfides through an enzymatically non-cleavable maleimido or simple and cleavable disulfide linker, and acylation of lysines by cleavable linear amino acids.

In one aspect, a linker covalently attaches an antibody to a drug moiety. An ADC is prepared using a linker having reactive functionality for binding to the antibody and the drug. For example, a cysteine thiol, or an amine, e.g., N-terminus or amino acid side chain such as lysine, of the antibody may form a bond with a functional group of the linker.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

Suitable linkers include, for example, cleavable and non-cleavable linkers. A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker.

Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in IL1RAP-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-IL1RAP ADCs described herein is a non-cleavable linker that promotes cellular internalization.

In some embodiments, the ADC has the following formula (formula I):

$$Ab\text{-}(L\text{-}D)_n \quad (I)$$

or a pharmaceutically acceptable salt or solvate thereof; wherein Ab is the antibody, e.g., anti-IL1RAP antibody, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing IL1RAP; and n is an integer from 1 to 20.

In some embodiments, n ranges from 1 to 8, 1 to 7, 1 to 6, 1 to 5, 1 to 4, 1 to 3, 1 to 2, or is 1.

In some embodiments, the -D moieties are the same. In yet another embodiment, the -D moieties are different.

In some embodiments, a linker component comprises an "amino acid unit." In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In one embodiment, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

Another approach for the generation of ADCs involves the use of heterobifunctional cross-linkers which link the anti-IL1RAP antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio)

butyrate (SPDB), N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio) butyrate (SCPB) or N-sulfosuccinimidyl4-(5-N,N-dimethylcarboxamido-2-pyridyldithio) butyrate (SSCPB)). The antibodies may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC (see also U.S. Pat. No. 6,913,748, incorporated by reference herein).

In one embodiment, charged linkers (also referred to as pro-charged linkers) are used to conjugate anti-IL1RAP antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers that may be used include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly(lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfosuccinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the disclosure.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-IL1RAP antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

IV. Uses of Anti-IL1RAP Antibodies and Anti-IL1RAP ADCs

The antibodies and antibody portions (and ADCs) preferably are capable of neutralizing human IL1RAP activity both in vivo and in vitro. Accordingly, such antibodies and antibody portions can be used to inhibit hIL1RAP activity, e.g., in a cell culture containing hIL1RAP, in human subjects or in other mammalian subjects having IL1RAP with which an antibody disclosed herein cross-reacts. In one embodiment, the disclosure provides a method for inhibiting hIL1RAP activity comprising contacting hIL1RAP with an antibody or antibody portion such that hIL1RAP activity is inhibited. For example, in a cell culture containing, or suspected of containing hIL1RAP, an antibody or antibody portion can be added to the culture medium to inhibit hIL1RAP activity in the culture.

In another embodiment, disclosed herein is a method for reducing hIL1RAP activity in a subject, advantageously from a subject suffering from a IL1RAP associated disorder, e.g., cancer such as acute myeloid leukemia (AML), myelodysplastic syndrome (MDS), NSCLC, or ovarian cancer, or a disorder in which IL1RAP activity is detrimental. The disclosure provides methods for reducing IL1RAP activity in a subject suffering from such a disease or disorder, which method comprises administering to the subject an antibody or antibody portion of the disclosure such that IL1RAP activity in the subject is reduced.

Preferably, the IL1RAP is human IL1RAP, and the subject is a human subject. Alternatively, the subject can be a mammal expressing a IL1RAP to which antibodies of the disclosure are capable of binding. Still further the subject can be a mammal into which IL1RAP has been introduced (e.g., by administration of IL1RAP or by expression of a IL1RAP transgene). Antibodies of the disclosure can be administered to a human subject for therapeutic purposes. Moreover, antibodies of the disclosure can be administered to a non-human mammal expressing a IL1RAP with which the antibody is capable of binding for veterinary purposes or as an animal model of human disease. Regarding the latter, such animal models may be useful for evaluating the therapeutic efficacy of antibodies and ADCs of the disclosure (e.g., testing of efficacy, dosages and time courses of administration).

As used herein, the term "a disorder in which IL1RAP activity is detrimental" is intended to include diseases and other disorders in which the presence of IL1RAP in a subject suffering from the disorder has been shown to be or is suspected of being either responsible for the pathophysiology of the disorder or a factor that contributes to a worsening of the disorder. Accordingly, a disorder in which IL1RAP activity is detrimental is a disorder in which reduction of IL1RAP activity is expected to alleviate the symptoms and/or progression of the disorder. Such disorders may be evidenced, for example, by an increase in the concentration of IL1RAP in a biological cell, fluid or tissue of a subject suffering from the disorder (e.g., an increase in the concentration of IL1RAP in a tumor, serum, plasma, synovial fluid, etc. of the subject), which can be detected, for example, using an anti-IL1RAP antibody as described above.

Non-limiting examples of disorders that can be treated with the antibodies, or antigen binding fragments thereof, include those disorders discussed below. For example, suitable disorders include, but are not limited to, a variety of cancers including, but not limited to, acute myeloid leukemia (AML), myelodysplastic syndrome (MDS), NSCLC, or ovarian cancer.

Other examples of cancers that may be treated using the compositions and methods disclosed herein include, but are not limited to carcinoma, lymphoma, blastoma, sarcoma, and leukemia or lymphoid malignancies. More particular examples of such cancers include but are not limited to breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lymphoma/ primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. PVNS, acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, the antibodies and ADCs disclosed herein are used to treat a solid tumor, e.g., inhibit growth of or decrease size of a solid tumor, e.g., a primary tumor, overexpressing IL1RAP or which is IL1RAP positive. In another embodiment, the antibodies and ADCs disclosed herein are used to treat leukemia, e.g., acute myeloid leukemia (AML), myelodysplastic syndrome (MDS), NSCLC, or ovarian cancer. Diseases and disorders described herein may be treated by anti-IL1RAP antibodies or ADCs, as well as pharmaceutical compositions comprising such anti-IL1RAP antibodies or ADCs.

In certain embodiments, the antibodies and ADCs disclosed herein are administered to a subject in need thereof in order to treat advanced cancers, including solid tumor types, likely to exhibit elevated levels of IL1RAP.

In certain embodiments, the disclosure includes a method for inhibiting or decreasing solid tumor growth in a subject having a solid tumor, said method comprising administering an anti-IL1RAP antibody or ADC described herein, to the subject having the solid tumor, such that the solid tumor growth is inhibited or decreased.

In further embodiments, the solid tumor is an IL1RAP expressing solid tumor. In further embodiments, the solid tumor is a primary tumor. In certain embodiments the anti-IL1RAP antibodies or ADCs described herein are administered to a subject having cancer, alone or in combination with an additional agent, e.g., radiation and/or chemotherapy, or an immune checkpoint inhibitor.

In certain embodiments, the disclosure includes a method for inhibiting or decreasing solid tumor growth in a subject having a solid tumor which was identified as a IL1RAP expressing or IL1RAP positive tumor, said method comprising administering an anti-IL1RAP antibody or ADC described herein, to the subject having the solid tumor, such that the solid tumor growth is inhibited or decreased. In further embodiments, the solid tumor is a primary tumor.

In certain embodiments, the disclosure includes a method for inhibiting or decreasing solid tumor growth in a subject having a solid tumor which was identified as not expressing IL1RAP or IL1RAP negative tumor, said method comprising administering an anti-IL1RAP antibody or ADC described herein, to the subject having the solid tumor, such that the solid tumor growth is inhibited or decreased. In further embodiments, the solid tumor is a primary tumor.

Methods for identifying IL1RAP expressing tumors are known in the art, and include FDA-approved tests and validation assays. For example, these assays may use primers that are specific for the IL1RAP gene and/or cDNA and result in the amplification of the IL1RAP gene/cDNA, or a portion thereof. The amplified PCR products may be subsequently analyzed, for example, by gel electrophoresis using standard methods known in the art to determine the size of the PCR products. Such tests may be used to identify tumors that may be treated with the methods and compositions described herein.

In another aspect, this application features a method of treating (e.g., curing, suppressing, ameliorating, delaying or preventing the onset of, or preventing recurrence or relapse of) or preventing a IL1RAP-associated disorder, in a subject. The method includes: administering to the subject a IL1RAP binding agent (particularly an antagonist), e.g., an anti-IL1RAP antibody or fragment thereof as described herein, in an amount sufficient to treat or prevent the IL1RAP-associated disorder. The IL1RAP antagonist, e.g., the anti-IL1RAP antibody or fragment thereof, can be administered to the subject, alone or in combination with other therapeutic modalities as described herein.

In some embodiments, the anti-IL1RAP antibody or fragment thereof used in the methods of the invention is a human or humanized anti-IL1RAP antibody or fragment thereof.

In another embodiment, antibody-dependent cell-mediated cytotoxicity (ADCC) activity is not necessary for anti-IL1RAP antibodies to inhibit tumor growth or reduce tumor size. Accordingly, in one embodiment, an antibody, or antigen binding portion thereof, of the invention comprises an isotype lacking effector function (e.g., human $IgG_4$).

Antibodies or ADCs, or antigen binding portions thereof, can be used alone or in combination to treat such diseases. It should be understood that the antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody. The additional agent also can be an agent that imparts a beneficial attribute to the therapeutic composition, e.g., an agent which affects the viscosity of the composition.

It should be further understood that the combinations which are to be included within this disclosure are those combinations useful for their intended purpose. The agents set forth below are illustrative for purposes and not intended to be limited. The combinations, which are part of this disclosure, can be the antibodies of the disclosure and at least one additional agent selected from the lists below. The combination can also include more than one additional agent, e.g., two or three additional agents if the combination is such that the formed composition can perform its intended function.

The combination therapy can include one or more IL1RAP antagonists, e.g., anti-IL1RAP antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In a particular embodiment, the anti-IL1RAP antibodies disclosed herein are used in combination with an anti-cancer agent or an antineoplastic agent. The terms "anti-cancer agent" and "antineoplastic agent" refer to drugs used to treat malignancies, such as cancerous growths. In one embodiment, the anti-IL1RAP antibodies or ADCs of the invention are administered in combination with one or more immune checkpoint inhibitors (e.g., antibody or small molecule immune checkpoint inhibitors) for the treatment of a cancer. In some embodiments, the immune checkpoint inhibitor (ICI) is an inhibitor (e.g., an antibody) of Programmed Death-Ligand 1 (PD-L1, also known as B7-H1, CD274), Programmed Death 1 (PD-1), CTLA-4, PD-L2 (B7-DC, CD273), LAG3, TIM3, 2B4, 4-1BB, A2aR, B7H1, B7H3, BTLA, CD2, CD6, CD27, CD28, CD30, CD38, CD39, CD40, CD47, CD70, CD73, CD80, CD86, CD137, CD160, CD166, CD200, CD200R1, CD226, CD276, DR3, GALS, GITR, HAVCR2, HVEM, IDO1, IDO2, ICOS (inducible T cell costimulator), KIR, LAG3, LAIR1, TREM2, LILRB1, LILRB2, LILRB3, LILRB4, LIGHT, MARCO (macrophage receptor with collageneous structure), PS (phosphatidylserine), OX-40, SLAM, SIRPA, CSF1R, CD47, SIRPA, TIGHT, TGFβ, VISTA, or any combinations thereof.

In some embodiments, the immune checkpoint inhibitor is an anti-CTLA-4, PD-L1, or PD-1 antibody therapy such as, but not limited to Yervoy® (ipilimumab; Bristol-Myers Squibb), Opdivo® (nivolumab; Bristol-Myers Squibb), Keytruda® (pembrolizumab, Merck), and Tecentriq® (atezolizumab; Roche).

In other embodiments, the immune checkpoint inhibitor is an anti-CD38 antibody therapy such as isatuximab (Sanofi), Darzalex® (daratumumab; Genmab A/S and Janssen Biotech), MOR202 (MorphoSys AG), and Tusk Therapeutics Ltd.'s anti-CD38 monoclonal antibody.

In some embodiments, the checkpoint inhibitor is an antibody or small molecule currently undergoing clinical testing, including, for example, an antibody against IDO (Epacadostat and Indoximod and BMS-986205), 4-1BB/

CD137 (Utomilumab and Urelumab), KIR (Lirilulmab), CD40 (CP-870,893), CD27 (Varlilumab), LAG-3 (Relatilimab), MHCII (Eftilagimod Alpha).

In one embodiment, the anti-IL1RAP antibodies or ADCs of the invention are administered in combination with one checkpoint inhibitor, e.g., an anti-CTLA-4, CD38, PD-L1, or PD-1 antibody. In other embodiments, the anti-IL1RAP antibodies or ADCs of the invention are administered in combination with more than one checkpoint inhibitor, e.g., an anti-IL1RAP antibody or ADC of the invention in combination with an anti-CD38 antibody and an anti-PD-L1 antibody, or an anti-IL1RAP antibody or ADC of the invention in combination with an anti-CD38 antibody and an anti-PD-1 antibody.

Drug therapy may be used alone, or in combination with other treatments such as chemotherapy, surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone.

Provided herein are methods for treating cancer, e.g., acute myeloid leukemia (AML), myelodysplastic syndrome (MDS), lung cancer, including non-small cell lung cancer (NSCLC) and ovarian cancer, or a disorder in which IL1RAP activity is detrimental, in a patient comprising administering to the patient an anti-IL1RAP antibody, or fragment thereof, or an ADC of the invention wherein the combination therapy exhibits synergy, e.g., therapeutic synergy, in the subject. As used herein, "synergy" or "therapeutic synergy" refers to a phenomenon where treatment of patients with a combination of therapeutic agents manifests a therapeutically superior outcome to the outcome achieved by each individual constituent of the combination used at its optimum dose (Corbett, T. H. et al., Cancer Treatment Reports, 66:1187 (1982)). For example, a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components.

In particular embodiments, the anti-IL1RAP antibodies or ADCs can be administered alone or with another anti-cancer agent which acts in conjunction with or synergistically with the antibody to treat the disease associated with IL1RAP activity. Such anti-cancer agents include, for example, one or more agents well known in the art (e.g., cytotoxins, chemotherapeutic agents, such as gemcitabine, carboplatin, and 5-Fu, small molecules and radiation) or one or more immune checkpoint inhibitor as set forth above. In one embodiment, the one or more chemotherapeutic agent is pemetrexed (Alimta®) and/or platinum chemotherapy, e.g., cisplatin or carboplatin (see e.g., Gandhi et al. *New England Journal of Medicine* DOI: 10.1056/NEJMoa1801005, Apr. 16, 2018).

Other examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Examples of anti-cancer agents that can be administered in combination with an anti-IL1RAP antibody or ADC of the invention include any one or more of those agents described above in Section III (A) of this disclosure.

In one embodiment, the anti-IL1RAP antibodies or ADCs of the invention are administered in combination with one or more compound which is capable of decreasing T regulatory cells and/or increasing effector T cell:T regulatory cell ratio in a subject (see, e.g., Eriksson et al. (2016) *Journal of Translational Medicine* 14:282). In one embodiment, the compound is, for example, gemcitabine.

In another embodiment, the anti-IL1RAP antibodies or ADCs can be administered in combination with an anti-cancer agent that regulates the tumor micro-environment, including inhibiting the activity or population of MDSCs and macrophages, such as, for example, CSF-1R antibodies, all-trans retinoic acid, gemcitabine, COX2 inhibitor (SC58236), amino-biphosphonate, phosphodiesterase-5 inhibitor (sildenafil and tadalafil), KIT-specific antibody, nitroaspirin, titerpenoid, 25-hydroxyvitamin D3, VEGF-trap, VEGF-specific antibody (e.g., Avastin), doxorubicin-cyclophosphamide, antagonists for CXCR2 (e.g., S-265610) and CXCR4 (e.g., AMD3100), tyrosine kinase inhibitor (e.g., Sunitinib), and PROK2-specific antibody (see V. Bronte and D. Gabrilovich, Myeloid derived suppressor cells, *Nature Rev. Immunology* poster, available through www.Biolegend.com).

In another embodiment, the anti-IL1RAP antibodies or ADCs can be administered in combination with anti-cancer agents that modulate tumor agiogenesis such as, but not limited to angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

In some embodiments, the antibody or antigen binding portion thereof or the ADC is administered in combination with IL-6 and/or interferon-gamma (IFN-γ). For example, IL-6 and/or IFN-γ may be administered prior to the antibody or antigen binding portion thereof or the ADC.

In another embodiment, the antibody or antigen binding portion thereof or the ADC is administered in combination with a DNA alkylator (e.g., cisplatin) and/or a PARP inhibitor.

Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof.

In particular embodiments of the invention, the anti-IL1RAP antibodies or ADCs described herein can be used in a combination therapy with an inhibitor of NAMPT (see examples of inhibitors in US 2013/0303509; AbbVie, Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment, anti-IL1RAP antibodies and ADCs described herein are administered in combination with a NAMPT inhibitor for the treatment of cancer in a subject.

In particular embodiments, the anti-IL1RAP antibodies or ADCs described herein can be used in a combination therapy with SN-38, which is the active metabolite of the topoisomerase inhibitor irinotecan.

The pharmaceutical compositions may include a "therapeutically effective amount" or a "prophylactically effective amount" of an antibody or antibody portion. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another aspect, this application provides a method for detecting the presence of IL1RAP in a sample in vitro (e.g., a biological sample, such as serum, plasma, tissue, biopsy). The subject method can be used to diagnose a disorder, e.g., a cancer. The method includes: (i) contacting the sample or a control sample with the anti-IL1RAP antibody or fragment thereof as described herein; and (ii) detecting formation of a complex between the anti-IL1RAP antibody or fragment thereof, and the sample or the control sample, wherein a statistically significant change in the formation of the complex in the sample relative to the control sample is indicative of the presence of IL1RAP in the sample.

Given their ability to bind to human IL1RAP, the anti-human IL1RAP antibodies, or portions thereof, (as well as ADCs thereof) can be used to detect human IL1RAP (e.g., in a biological sample, such as serum or plasma), using a conventional immunoassay, such as an enzyme linked immunosorbent assays (ELISA), an radioimmunoassay (RIA) or tissue immunohistochemistry. In one aspect, the disclosure provides a method for detecting human IL1RAP in a biological sample comprising contacting a biological sample with an antibody, or antibody portion, and detecting either the antibody (or antibody portion) bound to human IL1RAP or unbound antibody (or antibody portion), to thereby detect human IL1RAP in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$SM.

Alternative to labeling the antibody, human IL1RAP can be assayed in biological fluids by a competition immunoassay utilizing rhIL1RAP standards labeled with a detectable substance and an unlabeled anti-human IL1RAP antibody. In this assay, the biological sample, the labeled rhIL1RAP standards and the anti-human IL1RAP antibody are combined and the amount of labeled rhIL1RAP standard bound to the unlabeled antibody is determined. The amount of human IL1RAP in the biological sample is inversely proportional to the amount of labeled rhIL1RAP standard bound to the anti-IL1RAP antibody. Similarly, human IL1RAP can also be assayed in biological fluids by a competition immunoassay utilizing rhIL1RAP standards labeled with a detectable substance and an unlabeled anti-human IL1RAP antibody.

In yet another aspect, this application provides a method for detecting the presence of IL1RAP in vivo (e.g., in vivo imaging in a subject). The subject method can be used to diagnose a disorder, e.g., a IL1RAP-associated disorder. The method includes: (i) administering the anti-IL1RAP antibody or fragment thereof as described herein to a subject or a control subject under conditions that allow binding of the antibody or fragment to IL1RAP; and (ii) detecting formation of a complex between the antibody or fragment and IL1RAP, wherein a statistically significant change in the formation of the complex in the subject relative to the control subject is indicative of the presence of IL1RAP.

V. Pharmaceutical Compositions

The disclosure also provides pharmaceutical compositions comprising an antibody, or antigen binding portion thereof, or ADC and a pharmaceutically acceptable carrier. The pharmaceutical compositions comprising antibodies or ADCs are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies. In another embodiment, the pharmaceutical composition comprises one or more antibodies or ADCs and one or more prophylactic or therapeutic agents other than antibodies or ADCs for treating a disorder in which IL1RAP activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions or ADCs can be incorporated into pharmaceutical compositions suitable for administration to a subject. Typically, the pharmaceutical composition comprises an antibody or antibody portion and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

Various delivery systems are known and can be used to administer one or more antibodies or ADCs or the combination of one or more antibodies and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290, 540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody, combination therapy, or a composition is administered using Alkermes AIR® pulmonary drug delivery technology (Alkermes, Inc., Cambridge, Mass.). In a specific embodiment, prophylactic or therapeutic agents are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies antagonists is administered locally to the affected area to a subject to prevent, treat, manage, and/or ameliorate a disorder or a symptom thereof. In another embodiment, an effective amount of one or more antibodies is administered locally to the affected area in combination with an effective amount of one or more therapies (e.g., one or more prophylactic or therapeutic agents) other than an antibody of a subject to prevent, treat, manage, and/or ameliorate a disorder or one or more symptoms thereof.

A pharmaceutical composition is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the disclosure comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions is packaged in a hermetically sealed container such as an ampoule or sachette indicating the quantity of the agent. In one embodiment, one or more of the prophylactic or therapeutic agents, or pharmaceutical compositions is supplied as a dry sterilized lyophilized powder or water free concentrate in a hermetically sealed container and can be reconstituted (e.g., with water or saline) to the appropriate concentration for administration to a subject. The antibodies and antibody-portions or ADCs can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

Example 1. IL1RAP is Expressed in Leukemia Cell Lines

The following experiments were performed to determine IL1RAP protein expression in leukemia cell lines.
Methods
Tissue Culture and Cell Lines
Human leukemia cell lines EOL1, Monomac 6, OCI/AML1, KG-1, and Karpas 299 were obtained from DSMZ. Cells were maintained in RPMI-1640 medium (Invitrogen) with 10% fetal bovine serum (FBS) (Sigma).
Flow Cytometry
Staining for flow cytometry was performed in 1× cold PBS with 0.5% BSA. Primary antibodies (1 ug/ml) were incubated with live cells on ice for 30 minutes, after a brief wash, cells were incubated with Alexa Fluro® 488-conjugated anti-mouse IgG secondary antibody @1:1000 (#4408, Cell Signaling Technology). Acquisition of the data was performed on a MACSQuant® Flow Cytometers (Miltenyi Biotec) and analyzed with FlowJo® software.
Results
A panel of leukemia cell lines was examined for their surface expression of IL1RAP using a mouse monoclonal anti-IL1RAP antibody (MAB676, R&D System). Flow cytometry analysis was performed for acute myeloid leukemia cell lines EOL1, Monomac 6, OCI/AML1, and KG-1, as well as a T cell leukemia cell line, Karpas 299. Abundant surface expression of IL1RAP was observed in all cell lines tested (see FIG. 1).

Example 2. Generation of Human Monoclonal Antibodies Against the IL1RAP Extracellular Domain The following experiments were performed to generate fully human antibodies against the extracellular domain of IL1RAP (SEQ ID NO:286) (IL1RAP-ECD).
Methods
Immunizations in Humanized Mice
Monoclonal antibodies were obtained by immunizing with either recombinant human IL1RAP-ECD or 293T cells expressing full-length human IL1RAP tagged with MYC-DDK at the C-terminus. The transgenic mice were engineered with the capacity to produce human immunoglobulins at the variable region. The mice received 5 rounds of either recombinant protein or cells by intraperitoneal injection (IP) and allowed to rest for one month. Then, mice were boosted 4 and 2 days prior to fusion of the spleen with rabbit splenocytes expressing full length IL1RAP or recombinant protein of the extracelluar domain (ECD) of IL1RAP. Human IL1RAP-ECD recombinant protein was expressed by EBNA293 cells and purified.

For each hybridoma, each variable domain was cloned by RT-PCR into an expression vector that provided the appropriate constant regions. Four plasmid isolates of each cloning were subjected to Sanger Sequencing. After analysis, unique recombinant heavy chains were paired with unique recombinant light chains. These plasmid pairs were transfected into CHO cells in 24-well plates. Eight to twelve days later conditioned medium from each pairing was screened by FLOW™ or Octet™ for binding to IL1-RAP.

Recombinant IL1RAP Cloning

Human, rat, mouse IL1RAP cDNA were purchased from Origene (RC211970, RR213032, MR223729, Rockville, Md.). The encoded protein aligns 100% with GenBank IL1RAP_HUMAN. *Macaca fascicularis* IL1RAP cDNA was synthesized from Gen9 (CST-35853, Cambridge, Mass.). Ectodomains of human, *Macaca fascicularis*, rat and mouse were cloned by PCR. The synthetic genes were based on GenBank sequences (see Table 1).

All DNA sequences were cloned into appropriate CMV-based expression vectors with non-native signal peptides and C-terminal histidine tags for purification.

TABLE 1

Source of IL1RAP protein sequences

| Species | GenBank Protein Reference |
|---|---|
| Human | NP_002173.1 |
| Macaca fascicularis | G7NYP7 |
| Rattus norvegicus | NP_037100.1 |
| Mus musculus | NP_032390.1 |

The retroviral MSCV construct was used to express full-length human IL1RAP protein on the surface of HEK-293T, CHO, and rabbit splenocytes (see Table 2). Mouse, rat and *Macaca fascicularis* IL1RAP were also expressed on the surface of HEK-293T.

TABLE 2

IL1RAP cell-surface expression vectors

| Plasmid name | Species | Sequence feature | Comment |
|---|---|---|---|
| CST-30815 | Human | Met1-Val570 (Plus Myc-DDK) | Full construct |
| CST-35853 | Macaca Fascicularis | Met1-Val570 (Plus Myc-DDK) | Full construct |

TABLE 2-continued

IL1RAP cell-surface expression vectors

| Plasmid name | Species | Sequence feature | Comment |
|---|---|---|---|
| RR213032 | Rattus norvegicus | Met1-Val570 (Plus Myc-DDK) | Full construct |
| MR223729 | Mus musculus | Met1-Val570 (Plus Myc-DDK) | Full construct |

A series of plasmid constructs designed to secrete a soluble IL1RAP ectodomain were constructed from the full-length plasmids. Each of the constructs in Table 3 was cloned as a fusion protein with an N-terminal maltose binding protein (MBP) and a C-terminal tag of eight histidines (8xHis). Both human and mouse versions of the constructs were generated.

TABLE 3

Secreted, soluble recombinant IL1RAP vectors

| Plasmid name | Species | Sequence feature | Comment |
|---|---|---|---|
| BBP1554 | Human | MBP-IL1RAP(S21-T367)-8xHis | Full ectodomain |
| BBP2182 | Mus musculus | MBP-IL1RAP(S21-T367)-8xHis | Full ectodomain |

Cloning VH and VL Sequences from Hybridomas

For determination of CDR sequences, total RNA was isolated from hybridoma cells using an RNeasy® kit (Qiagen, Hilden, Germany). First and second-strand cDNA synthesis was performed using a OneTaq® One-Step RT-PCR kit (New England BioLabs, Ipswich, Mass.). Several primer sets were used (see Table 4). PCR products were separated by agarose electrophoresis and fragments were excised and purified by a QIAquick® gel extraction kit (Qiagen, Hilden, Germany). Fragments were cloned directly into expression vectors with BspQI (New England BioLabs, Ipswich, Mass.) by Golden Gate cloning techniques. Four colonies from each reaction were scaled up for miniprep-scale plasmid purification by SequeMid® DNA Purification Kit (Aline Biosciences, Woburn, Mass.).

TABLE 4

Oligonucleotide Sequences

| SEQ ID NO | Oligonucleolide Sequence | Oligonucleotide Purpose |
|---|---|---|
| 260 | ATAGCTCTTCAGGGaccATGAARCAYCTGTGGTTCTTCCT | IGHV4 leader |
| 261 | ATAGCTCTTCAGGGaccATGGACATACTTTGTTCCACGC | IGHV2 leader |
| 262 | ATAGCTCTTCAGGGaccATGGACACACTTTGCTACACAC | IGHV2-26 leader |
| 263 | ATAGCTCTTCAGGGaccATGTCTGTCTCCTTCCTCATCT | IGHV6 leader |
| 264 | ATAGCTCTTCAGGGaccATGGACTGGACCTGGAGVATC | IGHV1 leader |
| 265 | ATAGCTCTTCAGGGaccATGGACTGGATTTGGAGGRTC | IGHV1-58 leader |
| 266 | ATAGCTCTTCAGGGaccATGGACTGCACCTGGAGGATC | IGHV1-24 leader |
| 267 | ATAGCTCTTCAGGGaccATGGACTGGACCTGGAGGKTC | IGHV1-69/1-46/7-4-1 leader |
| 268 | ATAGCTCTTCAGGGaccATGGAGTTKGGRCTGAGCTGG | IGHV3 leader |
| 269 | ATAGCTCTTCAGGGaccATGGAGTTTKGGCTKAGCTGG | IGHV3-53/3-49 leader |

TABLE 4-continued

Oligonucleotide Sequences

| SEQ ID NO | Oligonucleotide Sequence | Oligonucleotide Purpose |
|---|---|---|
| 270 | ATAGCTCTTCAGGGaccATGGAACTGGGGCTCCGCTGG | IGHV3-21 leader |
| 271 | ATAGCTCTTCAGGGaccATGGARTTGGGGCTGWGCTGG | IGHV3-48/3-7 leader |
| 272 | ATAGCTCTTCAGGGaccATGGGGTCAACCGCCATCCTC | IGHV5 leader |
| 273 | ATAGCTCTTCAGGGaccATGGACATGAGGGTSCCYGCTCAGCTC | IgkV1a leader |
| 274 | ATAGCTCTTCAGGGaccATGGACATGAGRGTCCTCGCTCAGCTC | IgkV1b leader |
| 275 | ATAGCTCTTCAGGGaccATGGAAGCCCCAGCDCAGCTTCTC | IgkV3 leader |
| 276 | ATAGCTCTTCAGGGaccATGGAAACCCCAGCGCAGCTTCTC | IgkV3-20 leader |
| 277 | ATAGCTCTTCAGGGaccATGGTGTTGCAGACCCAGGTCTTC | IgkV4 leader |
| 278 | ATAGCTCTTCAGGGaccATGGGGTCCCAGGTTCACCTCCTC | IgkV5 leader |
| 279 | ATAGCTCTTCAGGGaccATGAGGCTCCYTGCTCAGCTCCTG | IgkV2 leader |
| 280 | ATAGCTCTTCTTCGTTTGATCTCCASCTTGGTC | Kappa FW4 |
| 281 | ATAGCTCTTCTTCGTTTAATCTCCAGTCGTGTC | Kappa FW4 |
| 282 | ATAGCTCTTCTGGCTGAGGAGACGGTGACC | Heavy FW4 |
| 283 | ATAGCTCTTCATGTGACGCTGTTGTGACTCAGGA | VL-FOR L1 |
| 284 | ATAGCTCTTCATGTGACCYTGTGCTCACTCAGTC | VL-FOR L2 |
| 285 | GATGCTCTTCTGGGCTGGCCTAGGACAGTCAMCYTGG | VL-REV L |

Transient Expression System of Medium Scale Antibody Production or Recombinant Proteins The IL1-RAP recombinant proteins and anti-IL1-RAP antibodies were expressed in Chinese hamster ovary (CHO) cells in a 1 shake flask (working volume of 100-mL) using recommended transfection and media components of the ExpiCHO™ system (Invitrogen, Carlsbad, Calif.). Cell culture supernatants were harvested 14 days post-transfection, centrifuged, and filtered (0.22 um).

Antibody and Protein Purification

Conditioned medium from CHO cell cultures was clarified, filtered, and purified by loading onto an ÄKTA Pure™ system with a 5mLMabSelect SuRe® column (GE Healthcare). Antibodies were eluted with 100 mM glycine, pH 3.5 and neutralized with 1M Tris-Cl, pH 8.5, and dialyzed against PBS.

Recombinant target proteins were purified from conditioned medium by Ni-NTA chromatography. His-tagged proteins were eluted and dialyzed against PBS.

Recombinant Antibody Analyses

Concentration:

Concentration of recombinant antibodies was determined on a Fortebio Octet Red™ (Pall ForteBio, Fremont, Calif.) instrument using Protein A tips and a human IgG1 antibody for the standard curve.

Purity Testing by SDS-PAGE:

Purity testing was performed by sodium dodecyl sulfate polyacrylamide gel electrophoresis (SDS-PAGE) of reduced and non-reduced samples. Samples (10 ug) were mixed with loading buffer (+/−β-mercaptoethanol), heated, and electrophoresed on a 4-20% gel (Invitrogen, Carlsbad, Calif.). Bands were visualized by Coomassie InstantBlue™ (Expedeon, San Diego, Calif.) staining.

Purity Testing by Endotoxin:

Endotoxin concentrations were measured by the Limulus amoebocyte lysate (LAL) kinetic turbidometric method using the Endosafe-PTS™ system (Charles River Laboratories, Wilmington, Mass.).

Purity Testing by HPLC-SEC:

Samples were screened for aggregation or other forms of antibody on a 1260 Infinity System™ (Agilent, Santa Clara, Calif.) with a TSKgel UltraSW Aggregate Guard™ column and HPLC column (Tosoh Bioscience). Samples and standards were detected by absorbance at 280 nm. Comparison against the standard curve provided the molar mass of sample components.

Affinity:

The affinity of antibodies to various recombinant IL1-RAP protein was determined on an Octet Red™ instrument. After loading reagents into a 96-well plate, the Octet Red™ with Protein A-conjugated biosensors was programmed as follows: 30 seconds for baseline #1; 120 seconds to immobilize the antibody; 30 seconds for baseline #2; 300 seconds for association of antibody to recombinant IL1-RAP; and 300-600 seconds for dissociation of recombinant IL1-RAP from the antibody.

Binding Competition Binning:

Binding competition among different antibodies was determined using a real-time, interferometry assay on an Octet Red™ instrument with Protein A-conjugated biosensors. To assess whether two antibodies competed for binding to a recombinant IL1-RAP protein, the assay was performed as follows. Protein A biosensors were first submerged into wells containing 10 ug/mL of individual monoclonal antibodies for 5 minutes. Following the capture step, the biosensors were dipped briefly (15 seconds) into buffer and then any unoccupied sites on the biosensor were saturated by submerging them for 5 minutes into wells containing 100 ug/mL of an irrelevant monoclonal antibody. The Octet™ biosensors were then dipped briefly (15 seconds) in buffer before immersion for 1 minute into wells containing recombinant IL1-RAP. The biosensors were dipped briefly (15 seconds) in buffer before immersion for 1 minute into wells containing a second recombinant antibody.

For the control case where the second antibody was the same as the first, there was no increase in signal, because there was no additional binding to the recombinant target.

For the control case where buffer was used instead of the first antibody, no recombinant target bound the non-quenching antibody on the biosensor and no second antibody bound the biosensor.

For cases where a boost in signal was seen with the second antibody, the two antibodies were determined not to compete.

For cases where no boost in signal was seen with the second antibody, the two antibodies were determined to compete for binding.

Immunofluorescence (IF) Based High Content Screening (HCS)

High content immunofluorescence was used to identify wells that contain immunoglobulin that preferentially bound cells expressing IL1RAP. Briefly, CHO cells and CHO-hIL1RAP cells seeded 24 hours before the assay were incubated for 60 minutes at 37° C. with hybridoma supernatant diluted 2-fold in DMEM+10% fetal bovine serum (FBS). After incubation, cells were fixed in 4% formaldehyde, washed with PBS, permeabilized with 0.3% Triton-X-100, and labeled with anti-rat Alexa 488 (at hybridoma stage) or anti-human Alexa 488 secondary antibodies (with recombinant IL1RAP antibodies) for 1 hour at room temperature. Unbound secondary antibody was removed with PBS washes, and cells were stained with DNA dye (propidium iodide and Hoechst 33342).

Potential hits were initially identified via low-resolution, high throughput screening using a TTP Labtech Acumen eX3™ (TTP Labtech, Cambridge, Mass.), quantifying the fluorescence differential for each sample on both positive and negative cell lines. Those hits were subsequently verified and the subcellular localization of each sample was characterized using a Thermo ArrayScan VTi™ (Thermo Fisher Scientific, Waltham, Mass.) to obtain high-resolution images of both cell lines.

Flow Cytometry

Staining for flow cytometry was performed in 1× cold PBS with 0.5% BSA. Primary antibodies (1 ug/ml) were incubated with live cells on ice for 30 minutes, after a brief wash, cells were incubated with Alexa Fluro® 488-conjugated anti-human IgG secondary antibody @1:1000 (709-546-149, Jackson ImmunoResearch). Acquisition of the data was performed on a MACSQuant® Flow Cytometers (Miltenyi Biotec) and analyzed with FlowJo software.

Correction of Sequence Liabilities

There are a number of amino acid sequences that are predictors of poor performance in clinical-scale production and stability. These include, for example, non-consensus cysteine residues (Cys), non-consensus N-linked glycoylation sites (Asn-xxx-Ser/Thr), acid-sensitive sequences (Asp-Pro). Some of the antibodies derived from hybridoma cloning contain one or more of these sequence liabilities yet otherwise have properties with desirable biological effects.

Some antibody sequences with these sequence liabilities were engineered to eliminate the sequence liability with the intent of retaining or improving the binding properties. Antibodies with a nonconsensus Cys residue have been mutated by replacing the Cys with a germline sequence (if the Cys is in a framework), a Ser residue, or an Ala residue. Constructs of this type were generated and tested for function after expression in CHO cells.

In one case, antibody 5D12_18A4, with a dissociation constant (KD) value of 19 nM, contains a non-consensus Cys sequence in the VH sequence. This heavy chain sequence was engineered to contain a Cys108Tyr mutation. The new heavy chain plasmid was paired with the original light chain plasmid and transfected into CHO cells. The antibody was screened for expression and affinity for human IL1RAP. The 5D12-C108Y antibody expresses at a comparable level to the 5D12_18A4 parent and has a KD value of 13 nM.

In a second case, antibody 1008_15A1, with a dissociation constant (KD) value of 30 nM, contains a non-consensus Cys sequence in the VH sequence. This heavy chain sequence was engineered to contain a Cys43Ala mutation. The new heavy chain plasmid was paired with the original light chain plasmid and transfected into CHO cells. The antibody was screened for expression and affinity for human IL1RAP. The 1008_C43A antibody expresses at a comparable level to the 1008_15A1 parent and has a KD value of 13 nM.

Some antibody sequences with a non-consensus N-linked glycosylation site have been modified at either the Asn site or the Ser/Thr site. Where possible, the Asn or Ser/Thr codons can be mutated back to the germline sequence. In addition, replacing the Asn with Gln or similar amino acid and the Ser or Thr with a similar or smaller amino acid offer a reasonable chance of success.

In one case, antibody $32C_{12-21}A4$, with a dissociation constant (KD) value of 1 nM, contains a non-consensus N-linked glycosylation site in CDR1 of the VL sequence. This light chain was engineered to contain an Asn26Ser mutation. The new light chain plasmid was paired with the orginal heavy chain sequence and transfected into CHO cells. The antibody was screened for expression and affinity for human IL1RAP. The 32C12-N26S antibody expresses 40% higher than the 32C12 parent. The 32C12-N26S antibody has a KD value of 19 nM.

Complete amino acid sequences of the heavy and light chains from 36 antibodies are set forth in Table 5, below.

TABLE 5

Variable region sequences of human antibodies

| SEQ ID NO: | Clone Name | Protein Domain | Sequence |
|---|---|---|---|
| 1 | 5G8_18A1 | VH | QVELQESGPGLVKPSDTLSLTCTVTGGSISTYYWSWIRQPPGKGLEWI GYIFYTGTTNYNPSLKSRVTISVDASKNQFSLKLNSVTAADTAVYYCA RDGSLDYWGQGALVTVSS |

TABLE 5-continued

Variable region sequences of human antibodies

| SEQ ID NO: | Clone Name | Protein Domain | Sequence |
|---|---|---|---|
| 2 | 5G8_18A1 | CDR-H1 | GGSISTYYWS |
| 3 | 5G8_18A1 | CDR-H2 | YIFYTGTTNYNPSLKS |
| 4 | 5G8_18A1 | CDR-H3 | DGSLDY |
| 5 | 5G8_18A1 | VL | DIQMTQSPSSLSASVGDRVTITCRASQSISNYLNWYQQKPGKAPKLLIF VASLLQSGVPSRFSGSGSGTDFTLTISSLQPEDFATYYCQQSYSTPFTF GPGTKLEIK |
| 6 | 5G8_18A1 | CDR-L1 | RASQSISNYLN |
| 7 | 5G8_18A1 | CDR-L2 | VASLLQS |
| 8 | 5G8_18A1 | CDR-L3 | QQSYSTPFT |
| 9 | 10C8_15A1 | VH | QVQLVESGGGVVQPGRSLRISCAASGFTFRSYGMHWVRQAPGKGLE WVAIIWHDESYKYYVDSVKGRFTISRDNSKNTLYLQMNSLRAEDTA VYYCARGDYYGSGSYYDAFDIWGQGTMVTVSS |
| 10 | 10C8_15A1 | CDR-H1 | GFTFRSYGMH |
| 11 | 10C8_15A1 | CDR-H2 | IIWHDESYKYYVDSVKG |
| 12 | 10C8_15A1 | CDR-H3 | GDYYGSGSYYDAFDI |
| 13 | 10C8_15A1 | VL | DIQMTQSPSSLSASVGDRVIITCRASQGISNYLAWFQQKPGKCPNLLIY AASTLRSGVPSRFSGSGSGTDFTLTISSLQPEDVATYYCQKYNSAPYTF GQGTKVEIK |
| 14 | 10C8_15A1 | CDR-L1 | RASQGISNYLA |
| 15 | 10C8_15A1 | CDR-L2 | AASTLRS |
| 16 | 10C8_15A1 | CDR-L3 | QKYNSAPYT |
| 17 | 12F3_17C2 | VH | QVQLVESGGGVVQPGRSLRLSCAASGFTFSHYGMHWVRQAPGKGLE WVAVIWYDGSKKYYVDSVKGRFTISRDNSKNTLYLQMNSLRGEDTA VYYCARDGGAVADNWIDSWGQGTLVTVSS |
| 18 | 12F3_17C2 | CDR-H1 | GFTFSHYGMH |
| 19 | 12F3_17C2 | CDR-H2 | IWYDGSKKYYVDSVKG |
| 20 | 12F3_17C2 | CDR-H3 | DGGAVADNWIDS |
| 21 | 12F3_17C2 | VL | DIQMTQSPSSLSASVGDRVTITCRASQSIRSYLNWYQQKPGKAPKLLIF AASSLQSGVPSRFSGSGSGTDFTLTVSSLQPEDFATYSCQQSYSTPYTF GQGTKVEIK |
| 22 | 12F3_17C2 | CDR-L1 | RASQSIRSYLN |
| 23 | 12F3_17C2 | CDR-L2 | AASSLQS |
| 24 | 12F3_17C2 | CDR-L3 | QQSYSTPYT |
| 25 | 16H2_17D2 | VH | QVQLVESGGGVVQPGGSLRLSCAASGFTFSSHGMHWVRQAPGKGLE WVAVIWYDGSNKFYTDSVQGRFTISRDNSKNTLNLQMNSLRAEDTA VYYCAREGLRAGYYFDFWGQGTLVTVSS |
| 26 | 16H2_17D2 | CDR-H1 | GFTFSSHGMH |
| 27 | 16H2_17D2 | CDR-H2 | VIWYDGSNKFYTDSVQG |
| 28 | 16H2_17D2 | CDR-H3 | EGLRAGYYFDF |
| 29 | 16H2_17D2 | VL | DIQMTQSPSSLSASVGDRVTITCRASQRISFYSNWYQQKPGKAPKLLI YAASSLQSGVPSRFSGSGSGTDFTLTISSLQPEDFATYFCQQSHSTPLTF GGGTKLEIK |
| 30 | 16H2_17D2 | CDR-L1 | RASQRISFYSN |
| 23 | 16H2_17D2 | CDR-L2 | AASSLQS |
| 31 | 16H2_17D2 | CDR-L3 | QQSHSTPLT |

TABLE 5-continued

Variable region sequences of human antibodies

| SEQ ID NO: | Clone Name | Protein Domain | Sequence |
|---|---|---|---|
| 32 | 32C12_21A4 | VH | QVQLVESGGGVVQPGRSLRLSCAASGFTFRNYGIHWVRQAPGKGLE WVAVIWYDGSNKFYADSVKGRFTISRDNSKNTLYLQMNSLRVEDTA VYYCAREEGIAVAPFDYWGQGTLVTVSS |
| 33 | 32C12_21A4 | CDR-H1 | GFTFRNYGIH |
| 34 | 32C12_21A4 | CDR-H2 | VIWYDGSNKFYADSVKG |
| 35 | 32C12_21A4 | CDR-H3 | EEGIAVAPFDY |
| 36 | 32C12_21A4 | VL | DIQMTQSPSSLSASVGDRVAITCRANQSIASYLNWYQQKPGKAPKLLI YGASSLQNGVPSRFSGSGSRTDFTLTISSLQPEDFATYYCQQSYSTEITF GQGTRLEIK |
| 37 | 32C12_21A4 | CDR-L1 | RANQSIASYLN |
| 38 | 32C12_21A4 | CDR-L2 | GASSLQN |
| 39 | 32C12_21A4 | CDR-L3 | QQSYSTEIT |
| 40 | 34C11_21B2 | VH | EVQVVESGGGLVQPGGSLRLSCAASGFTFRSYWMSWVRQAPGKGLE WVANIKQDGSERHYVDSVKGRFTISRDNAKTSLYLQMSSLRAEDTAV YYCAREGYFGSGYFDYWGQGTLVTVSS |
| 41 | 34C11_21B2 | CDR-H1 | GFTFRSYWMS |
| 42 | 34C11_21B2 | CDR-H2 | NIKQDGSERHYVDSVKG |
| 43 | 34C11_21B2 | CDR-H3 | EGYFGSGYFDY |
| 44 | 34C11_21B2 | VL | DIQMTQSPSTLSASVGDRVIITCRASQSISRGLAWYQQKPGKAPKLLIY KASNLESGVPSRFSGSGSGTEFTLTISSLQPDDFAAYYCQQYSYYSHTF GQGTKLEIK |
| 45 | 34C11_21B2 | CDR-L1 | RASQSISRGLA |
| 46 | 34C11_21B2 | CDR-L2 | KASNLES |
| 47 | 34C11_21B2 | CDR-L3 | QQYSYYSHT |
| 48 | 36A10_21B6 | VH | QGQVVESGGGVVQPGRSLRLSCAASGFTFSSYTLHWVRQAPGKGLE WVAVIWYDGSNKYYVDSVKGRFTISRDNSKNTLYLQMNSLRAEDTA VYYCAREYGSGSYYNVYYGMDVWGQGTTVTLSS |
| 49 | 36A10_21B6 | CDR-H1 | GFTFSSYTLH |
| 50 | 36A10_21B6 | CDR-H2 | VIWYDGSNKYYVDSVKG |
| 51 | 36A10_21B6 | CDR-H3 | EYGSGSYYNVYYGMDV |
| 52 | 36A10_21B6 | VL | DIVMTQSPLSLPVTPGEPASISCRSSQSLLHSNGYNYLDWYLQKPGQS PHLLIYLASNRASGVPDRFSGSGSGTDFTLKISRVEAEDVGFYYCMQT LQIPLTFGGGTKVEIK |
| 53 | 36A10_21B6 | CDR-L1 | RSSQSLLHSNGYNYLD |
| 54 | 36A10_21B6 | CDR-L2 | LASNRAS |
| 55 | 36A10_21B6 | CDR-L3 | MQTLQIPLT |
| 56 | 39G1_21C4 | VH | QVQLQESGPGLVKPSETLSLTCAVSGYSASGVYYWGWIRQPPGKGLE WIGNIYHSGSTYYNPSLERRVSISLDTSKNHFSLRLNFVTAADTAVYY CARDRFDAFDIWGQGTMVTVSS |
| 57 | 39G1_21C4 | CDR-H1 | GYSASGVYYWG |
| 58 | 39G1_21C4 | CDR-H2 | NIYHSGSTYYNPSLER |
| 59 | 39G1_21C4 | CDR-H3 | DRFDAFDI |
| 60 | 39G1_21C4 | VL | EIVMTQSPATLSVSPGERATLSCRASQSINNILAWYQQKPGQAPRLLIY GASTRATGIPARFSGSGSGTEFTLTISSLQSEDFAVYYCQQYNNWPLTF GGGTKVEIK |

TABLE 5-continued

Variable region sequences of human antibodies

| SEQ ID NO: | Clone Name | Protein Domain | Sequence |
|---|---|---|---|
| 61 | 39G1_21C4 | CDR-L1 | RASQSINNILA |
| 62 | 39G1_21C4 | CDR-L2 | GASTRAT |
| 63 | 39G1_21C4 | CDR-L3 | QQYNNWPLT |
| 64 | 37E10_15B5 | VH | QVQLVESGGGVVQPGRSLRLSCAASGFTFRSHGMHWVRQAPGKGLEWVAVIWYDGSSEYYADSVKGRFTISRDNSKNTLYLQMNSLRAEDTAVYYCARENVYGSGWFFDYWGQGTLVTVSS |
| 65 | 37E10_15B5 | CDR-H1 | GFTFRSHGMH |
| 66 | 37E10_15B5 | CDR-H2 | VIWYDGSSEYYADSVKG |
| 67 | 37E10_15B5 | CDR-H3 | ENVYGSGWFFDY |
| 68 | 37E10_15B5 | VL | EIVMTQSPATLSVSPGERASLSCRASQSVGSNLAWYQQRPGQAPRLLIFGASTRATGIPARFSGSRSGTEFTLTISSLQSEDFALYYCQQYNNWPPWTFGQGTKLEIK |
| 69 | 37E10_15B5 | CDR-L1 | RASQSVGSNLA |
| 62 | 37E10_15B5 | CDR-L2 | GASTRAT |
| 70 | 37E10_15B5 | CDR-L3 | QQYNNWPPWT |
| 71 | 44E5_15C5 | VH | QVQLVESGGGVVQPGRSLRLSCAASGFTFRSHGMHWVRQAPGKGLEWVAVIWYDGSSDYYADSVKGRFTISRDNSKNTLFLQMNSLSAEDTAVYYCARENVYGSGWFFDYWGQGTLVTVSS |
| 65 | 44E5_15C5 | CDR-H1 | GFTFRSHGMH |
| 72 | 44E5_15C5 | CDR-H2 | VIWYDGSSDYYADSVKG |
| 67 | 44E5_15C5 | CDR-H3 | ENVYGSGWFFDY |
| 73 | 44E5_15C5 | VL | EIVMTQSPATLSVSPGERASLSCRASQSVGSNLAWYQQKPGQAPRLLIFGASTRATGIPARFSGSRSGTEFTLTISSLQSEDFALYYCQQYNNWPPWTFGQGTKLEIK |
| 69 | 44E5_15C5 | CDR-L1 | RASQSVGSNLA |
| 62 | 44E5_15C5 | CDR-L2 | GASTRAT |
| 70 | 44E5_15C5 | CDR-L3 | QQYNNWPPWT |
| 74 | 38E10_21C3 | VH | EVQLLESGGGLVQPGGSLRLSCAASGFTFSNYAMTWVRQAPGKGLEWVSSISISRAGTYYADSVKGRFTISRDNSKNTLNLQMNSLRAEDTAEYYCAREYYYGMDVWGQGTTVTVSS |
| 75 | 38E10_21C3 | CDR-H1 | GFTFSNYAMT |
| 76 | 38E10_21C3 | CDR-H2 | SISISRAGTYYADSVKG |
| 77 | 38E10_21C3 | CDR-H3 | EYYYGMDV |
| 78 | 38E10_21C3 | VL | EIVLTQSPATLSLSPGERATLSCRASQSVSSYLAWYQQKPGQTPRLLIYDASNRATGIPARFSGSGSGTDFTLTISSLETEDFAVYYCQQLINWPLTFGGGTKLEIK |
| 79 | 38E10_21C3 | CDR-L1 | RASQSVSSYLA |
| 80 | 38E10_21C3 | CDR-L2 | DASNRAT |
| 81 | 38E10_21C3 | CDR-L3 | QQLINWPLT |
| 9 | 10C8_C43A | VH | QVQLVESGGGVVQPGRSLRISCAASGFTFRSYGMHWVRQAPGKGLEWVAIIWHDESYKYYVDSVKGRFTISRDNSKNTLYLQMNSLRAEDTAVYYCARGDYYGSGSYYDAFDIWGQGTMVTVSS |
| 10 | 10C8_C43A | CDR-H1 | GFTFRSYGMH |
| 11 | 10C8_C43A | CDR-H2 | IIWHDESYKYYVDSVKG |
| 12 | 10C8_C43A | CDR-H3 | GDYYGSGSYYDAFDI |

TABLE 5-continued

Variable region sequences of human antibodies

| SEQ ID NO: | Clone Name | Protein Domain | Sequence |
|---|---|---|---|
| 82 | 10C8_C43A | VL | DIQMTQSPSSLSASVGDRVIITCRASQGISNYLAWFQQKPGKAPNLLIY AASTLRSGVPSRFSGSGSGTDFTLTISSLQPEDVATYYCQKYNSAPYTF GQGTKVEIK |
| 14 | 10C8_C43A | CDR-L1 | RASQGISNYLA |
| 15 | 10C8_C43A | CDR-L2 | AASTLRS |
| 16 | 10C8_C43A | CDR-L3 | QKYNSAPYT |
| 83 | 16H2_17D1 | VH | EVQLLESGADLVQPGGSLRLSCAASGFTFSSYAMSWVRQAPGKGLE WVSTIRISGGTTYYADSVKGRFTISRDNSKNTLYLQMNSLRAEDTAV YYCVRDYYNGMDVWGQGTTVTVSS |
| 84 | 16H2_17D1 | CDR-H1 | GFTFSSYAMS |
| 85 | 16H2_17D1 | CDR-H2 | TIRISGGTTYYADSVKG |
| 86 | 16H2_17D1 | CDR-H3 | DYYNGMDV |
| 87 | 16H2_17D1 | VL | EIVLTQSPATLSLSPGERATLSCRASQRVSSYLAWYQQKPGQAPRLLI YDASNRATGIPARFSGSGSGTDFTLTISSLEPEDFAVYYCQQRSYWPP AFGQGTKLEIK |
| 88 | 16H2_17D1 | CDR-L1 | RASQRVSSYLA |
| 80 | 16H2_17D1 | CDR-L2 | DASNRAT |
| 89 | 16H2_17D1 | CDR-L3 | QQRSYWPPA |
| 90 | 24G3_17C5 | VH | EVQLLESGGGLVQRGGSLRLSCAASGFTFSSYAMSWVRQAPGKGLE WVSSISGSGDSTNYADSVKGRFTISRDNSKNTLHLQMNSLRAEDTAV YYCVRDYYYGMDVWGHGTTVTVSS |
| 84 | 24G3_17C5 | CDR-H1 | GFTFSSYAMS |
| 91 | 24G3_17C5 | CDR-H2 | SISGSGDSTNYADSVKG |
| 92 | 24G3_17C5 | CDR-H3 | DYYYGMDV |
| 93 | 24G3_17C5 | VL | EIVLTQSPATLSLSPGERATLSCRASQSVNSYLAWYQQKPGQAPRLLI YDASNRATGIPARFSGSGSGTDFTLTISSLEPEDFAVYYCQQRSYWPIT FGQGTRLEIK |
| 94 | 24G3_17C5 | CDR-L1 | RASQSVNSYLA |
| 80 | 24G3_17C5 | CDR-L2 | DASNRAT |
| 95 | 24G3_17C5 | CDR-L3 | QQRSYWPIT |
| 96 | 26C5_15B4 | VH | EAQLLESGGGLVQPGGSLRLSCAASGFTFSSYAMSWVRQAPGKGLE WVSTISGSGGSTHYADSVKGRFTISRDNSKNTLYLQMNSLRAEDTAV YYCVRDYYYGMDVWGQGTTVTVSS |
| 84 | 26C5_15B4 | CDR-H1 | GFTFSSYAMS |
| 97 | 26C5_15B4 | CDR-H2 | TISGSGGSTHYADSVKG |
| 92 | 26C5_15B4 | CDR-H3 | DYYYGMDV |
| 98 | 26C5_15B4 | VL | EIVLTQSPATLSLSPGERATLSCRASQSVSSYLAWYQQKPGQAPRLLIY DASNRATGIPARFSGSGSGTDFTLTISSLEPEDFAVYYCQQRSYWPPTF GQGTKLEIK |
| 79 | 26C5_15B4 | CDR-L1 | RASQSVSSYLA |
| 80 | 26C5_15B4 | CDR-L2 | DASNRAT |
| 99 | 26C5_15B4 | CDR-L3 | QQRSYWPPT |
| 100 | 17E9_15B1 | VH | QVQLVESGGGVVQPGRSLRLSCAASGFTFSSYGMHWVRQAPGKGLE WVAVIWYDGSKKYYVDSVQGRFTISRDNSKNTLYLQMNSLRGEDTA VYYCARDGGAVADNWIDSWGQGTLVTVSS |

TABLE 5-continued

Variable region sequences of human antibodies

| SEQ ID NO: | Clone Name | Protein Domain | Sequence |
|---|---|---|---|
| 101 | 17E9_15B1 | CDR-H1 | GFTFSSYGMH |
| 102 | 17E9_15B1 | CDR-H2 | VIWYDGSKKYYVDSVQG |
| 20 | 17E9_15B1 | CDR-H3 | DGGAVADNWIDS |
| 103 | 17E9_15B1 | VL | DIQMTQSPSSLSASVGDRVTLTCRASQNIRSYLNWYQQKPGKAPKLLI FAASSLPSGVPSRFSGSGSVTDFTLTVSSLQPEDFATYSCQQSYSTPYT FGQGTKLEIK |
| 104 | 17E9_15B1 | CDR-L1 | RASQNIRSYLN |
| 105 | 17E9_15B1 | CDR-L2 | AASSLPS |
| 24 | 17E9_15B1 | CDR-L3 | QQSYSTPYT |
| 106 | 10C8-15A4 | VH | EEQLLESGADLAQPGGSLRLSCAASGFTFSSYAMSWVRQAPGKGLE WVSTIRISGDTTYYADSVKGRFTISRDNSKNTLFLQMNSLRAEDTAVY YCVRDYYNGMDVWGHGTTVTVSS |
| 84 | 10C8-15A4 | CDR-H1 | GFTFSSYAMS |
| 107 | 10C8-15A4 | CDR-H2 | TIRISGDTTYYADSVKG |
| 86 | 10C8-15A4 | CDR-H3 | DYYNGMDV |
| 108 | 10C8-15A4 | VL | EIVLTQSPATLSLSPGERATLSCRASQRVSSYLAWYQQKPGQAPRLLI YDASNRATGIPARFSGSGSGTDFTLTISSLEPEDFAVYYCQQRSYWPP AFGQGTKLEIK |
| 88 | 10C8-15A4 | CDR-L1 | RASQRVSSYLA |
| 80 | 10C8-15A4 | CDR-L2 | DASNRAT |
| 89 | 10C8-15A4 | CDR-L3 | QQRSYWPPA |
| 109 | 32A2_21A3 | VH | QVQLVQSGAEVKKPGASVKVSCKASGYTFTGYYMHWVRQAPGQGL EWMGWINPNSGGTNYAQKFQGRVTMTRDTSISTAYMELSRLRSDDT AVYYCAREAVAGTSDAFDIWGQGTMVTVSS |
| 110 | 32A2_21A3 | CDR-H1 | GYTFTGYYMH |
| 111 | 32A2_21A3 | CDR-H2 | WINPNSGGTNYAQKFQG |
| 112 | 32A2_21A3 | CDR-H3 | EAVAGTSDAFDI |
| 113 | 32A2_21A3 | VL | DIQMTQSPSSLSASVGDRVTITCRANQSIASYLNWYQQKPGKVPKLLI YGASSLQNGVPSRFSGSGSRTDFTLTISSLQPEDFATYYCQQSYSTEITF GQGTRLEIK |
| 37 | 32A2_21A3 | CDR-L1 | RANQSIASYLN |
| 38 | 32A2_21A3 | CDR-L2 | GASSLQN |
| 39 | 32A2_21A3 | CDR-L3 | QQSYSTEIT |
| 32 | 32C12-N26S | VH | QVQLVESGGGVVQPGRSLRLSCAASGFTFRNYGIHWVRQAPGKGLE WVAVIWYDGSNKFYADSVKGRFTISRDNSKNTLYLQMNSLRVEDTA VYYCAREEGIAVAPFDYWGQGTLVTVSS |
| 33 | 32C12-N26S | CDR-H1 | GFTFRNYGIH |
| 34 | 32C12-N26S | CDR-H2 | VIWYDGSNKFYADSVKG |
| 35 | 32C12-N26S | CDR-H3 | EEGIAVAPFDY |
| 114 | 32C12-N26S | VL | DIQMTQSPSSLSASVGDRVAITCRASQSIASYLNWYQQKPGKAPKLLI YGASSLQNGVPSRFSGSGSRTDFTLTISSLQPEDFATYYCQQSYSTEITF GQGTRLEIK |
| 115 | 32C12-N26S | CDR-L1 | RASQSIASYLN |
| 38 | 32C12-N26S | CDR-L2 | GASSLQN |
| 39 | 32C12-N26S | CDR-L3 | QQSYSTEIT |

TABLE 5-continued

Variable region sequences of human antibodies

| SEQ ID NO: | Clone Name | Protein Domain | Sequence |
| --- | --- | --- | --- |
| 116 | 41G4_15B6 | VH | QVQLVESGGGVVQPGRSLRLSCAASGFTFRNYGMHWVRQAPGKGLE WVAVIWYDGSNKFYADSVKGRFTISRDNSKNTLYLQMNSLRVEDTA VYYCAREEGIAVAPFDYWGQGTLVTVSS |
| 117 | 41G4_15B6 | CDR-H1 | GFTFRNYGMH |
| 34 | 41G4_15B6 | CDR-H2 | VIWYDGSNKFYADSVKG |
| 35 | 41G4_15B6 | CDR-H3 | EEGIAVAPFDY |
| 36 | 41G4_15B6 | VL | DIQMTQSPSSLSASVGDRVAITCRANQSIASYLNWYQQKPGKAPKLLI YGASSLQNGVPSRFSGSGSRTDFTLTISSLQPEDFATYYCQQSYSTEITF GQGTRLEIK |
| 37 | 41G4_15B6 | CDR-L1 | RANQSIASYLN |
| 38 | 41G4_15B6 | CDR-L2 | GASSLQN |
| 39 | 41G4_15B6 | CDR-L3 | QQSYSTEIT |
| 118 | 31F9_21A1 | VH | QVQLVESGGGMVQPGRSLRLSCTASGFTFSSHGMHWVRQAPGKGLE WVAVIWFDGSNEYYVDSVKGRFTISRDNSKNTLYLQMNSLRAEDTA VYYCARENVYGSGWFFDYWGQGTLVTVSS |
| 26 | 31F9_21A1 | CDR-H1 | GFTFSSHGMH |
| 119 | 31F9_21A1 | CDR-H2 | VIWFDGSNEYYVDSVKG |
| 67 | 31F9_21A1 | CDR-H3 | ENVYGSGWFFDY |
| 120 | 31F9_21A1 | VL | EIVMTQSPATLSVSPGERASLSCRASQSVGSNLAWYQQKPGQAPRLLI FGASTRATGIPARFSGSRSGTEFTLTISSLQSEDFALYYCQQYNNWPP WTFGQGTKVEIK |
| 69 | 31F9_21A1 | CDR-L1 | RASQSVGSNLA |
| 62 | 31F9_21A1 | CDR-L2 | GASTRAT |
| 70 | 31F9_21A1 | CDR-L3 | QQYNNWPPWT |
| 121 | 32D4_21D6 | VH | QLQLVESGGGVVQPGRSLRLSCAASGFTFSSYGMHWVRQAPGKGLE WVAVIWYDGSSEYYADSVKGRFTISRDNSKNTLYLQMNSLRAEDTA VYYCARENVYGSGWFFDYWGQGTLVTVSS |
| 101 | 32D4_21D6 | CDR-H1 | GFTFSSYGMH |
| 66 | 32D4_21D6 | CDR-H2 | VIWYDGSSEYYADSVKG |
| 67 | 32D4_21D6 | CDR-H3 | ENVYGSGWFFDY |
| 122 | 32D4_21D6 | VL | EIVMTQSPATLSVSPGERASLSCRASQSVGSNLAWYQQKPGQAPRLLI FGASTRATGIPARFSGSRSGTEFTLTISSLQSEDFALYYCQQYNNWPP WTFGQGTKVEIK |
| 69 | 32D4_21D6 | CDR-L1 | RASQSVGSNLA |
| 62 | 32D4_21D6 | CDR-L2 | GASTRAT |
| 70 | 32D4_21D6 | CDR-L3 | QQYNNWPPWT |
| 123 | 32F9_21A5 | VH | QLQLVESGGGVVQPGRSLRLSCAASGFTFSSHGMHWVRQAPGKGLE WVAVIWYDGSSEYYADSVKGRFTISRDNSKNTLYLQMNSLRAEDTA VYYCARENVYGSGWFFDYWGQGSLVTVSS |
| 26 | 32F9_21A5 | CDR-H1 | GFTFSSHGMH |
| 66 | 32F9_21A5 | CDR-H2 | VIWYDGSSEYYADSVKG |
| 67 | 32F9_21A5 | CDR-H3 | ENVYGSGWFFDY |
| 124 | 32F9_21A5 | VL | EIVMTQSPATLSVSPGERASLSCRASQSVGSNLAWYQQKPGQAPRLLI FGASTRATGIPARFSGSRSGTEFTLTISSLQSEDFALYYCQQYNNWPP WTFGQGTKLEIK |

TABLE 5-continued

Variable region sequences of human antibodies

| SEQ ID NO: | Clone Name | Protein Domain | Sequence |
|---|---|---|---|
| 69 | 32F9_21A5 | CDR-L1 | RASQSVGSNLA |
| 62 | 32F9_21A5 | CDR-L2 | GASTRAT |
| 70 | 32F9_21A5 | CDR-L3 | QQYNNWPPWT |
| 125 | 33E9_21A6 | VH | QLQLVESGGGVVQFGRSLRLSCAASGFTFSSHGMHWVRQAPGKGLEWVAVIWYDGSSEYYADSVKGRFTISRDNSKNTLYLQMNSLRAEDTAVYYCARENVYGSGWFFDYWGQGTLVTVSS |
| 26 | 33E9_21A6 | CDR-H1 | GFTFSSHGMH |
| 66 | 33E9_21A6 | CDR-H2 | VIWYDGSSEYYADSVKG |
| 67 | 33E9_21A6 | CDR-H3 | ENVYGSGWFFDY |
| 126 | 33E9_21A6 | VL | EIVMTQSPATLSVSPGERASLSCRASQSVGSNLAWYQQKPGQAPRLLIFGASTRATGIPARFSGSRSGTEFTLTISSLQSEDFALYYCQQYNNWPPWTFGQGTKLEIK |
| 69 | 33E9_21A6 | CDR-L1 | RASQSVGSNLA |
| 62 | 33E9_21A6 | CDR-L2 | GASTRAT |
| 70 | 33E9_21A6 | CDR-L3 | QQYNNWPPWT |
| 127 | 35D11_22A1 | VH | QLQLVESGGGVVQPGRSLRLSCAASGFTFSSYGMHWVRQAPGKGLEWVAVIWYDGSSEYYADSVKGRFTISRDNSKNTLFLQMNSLRADDTAVYYCARENVYGSGWFFDYWGQGTLVTVSS |
| 101 | 35D11_22A1 | CDR-H1 | GFTFSSYGMH |
| 66 | 35D11_22A1 | CDR-H2 | VIWYDGSSEYYADSVKG |
| 67 | 35D11_22A1 | CDR-H3 | ENVYGSGWFFDY |
| 128 | 35D11_22A1 | VL | EIVMTQSPATLSVSPGERASLSCRASQSVGSNLAWYQQKPGQAPRLLIFGASTRATGIPARFSGSRSGTEFTLTISSLQSEDFALYYCQQYDNWPPWTFGQGTKLEIK |
| 69 | 35D11_22A1 | CDR-L1 | RASQSVGSNLA |
| 62 | 35D11_22A1 | CDR-L2 | GASTRAT |
| 129 | 35D11_22A1 | CDR-L3 | QQYDNWPPWT |
| 130 | 39A9_28A4 | VH | QVQLVESGGGVVQPGRSLRLSCAASGFTLSGYGMHWVRQAPGKGLEWVAVIWYDGSNKYYADSVKGRFTISRDNSKNMLFLQMNSLRAEDTAVYYCVRENGFGSGWFFDYWGQGNLVTVSS |
| 131 | 39A9_28A4 | CDR-H1 | GFTLSGYGMH |
| 132 | 39A9_28A4 | CDR-H2 | VIWYDGSNKYYADSVKG |
| 133 | 39A9_28A4 | CDR-H3 | ENGFGSGWFFDY |
| 134 | 39A9_28A4 | VL | EIVMTQSPATLSVSPGERATLSCRTSQSVSRDLAWYQQKPGQAPRLLIYGASTRATGIPVRFSGSGSGTEFTLTISSLQSEDFAVYYCQQYNNWPPWTFGQGTKLEIK |
| 135 | 39A9_28A4 | CDR-L1 | RTSQSVSRDLA |
| 62 | 39A9_28A4 | CDR-L2 | GASTRAT |
| 70 | 39A9_28A4 | CDR-L3 | QQYNNWPPWT |
| 136 | 34D1_21B3 | VH | QGQLVESGGGVVQPGRSLRLSCAASGFTFSSYTLHWVRQAPGKGLEWVAVIWYDGSNKYVDSVKGRFTISRDNSKNTLYLQMNSLRAEDTAVYYCAREYGSGSYYNVYYGMDVWGQGTTVTVSS |
| 49 | 34D1_21B3 | CDR-H1 | GFTFSSYTLH |
| 50 | 34D1_21B3 | CDR-H2 | VIWYDGSNKYVDSVKG |
| 51 | 34D1_21B3 | CDR-H3 | EYGSGSYYNVYYGMDV |

TABLE 5-continued

Variable region sequences of human antibodies

| SEQ ID NO: | Clone Name | Protein Domain | Sequence |
|---|---|---|---|
| 137 | 34D1_21B3 | VL | DIVMTQSPLSLPVTPGEPASISCRSSQSLLHSNGYKYLDWYLQKAGQS PHLLIYLGSNRASGVPDRFSGSGSGTDFTLKISRVEAEDVGFYYCMQT LQIPLTFGGGTKLEIK |
| 138 | 34D1_21B3 | CDR-L1 | RSSQSLLHSNGYKYLD |
| 139 | 34D1_21B3 | CDR-L2 | LGSNRAS |
| 55 | 34D1_21B3 | CDR-L3 | MQTLQIPLT |
| 140 | 33H2_21B1 | VH | EVQVVESGGGLVQPGGSLRLSCATSGFTFRSYWMTWVRQAPGKGLE WVANIKQDGSERHYVDSVKGRFTISRDNAKTSLYLQMSSLRAEDTA MYYCAREGYYGSGYFDYWGQGTLVTVSS |
| 141 | 33H2_21B1 | CDR-H1 | GFTFRSYWMT |
| 42 | 33H2_21B1 | CDR-H2 | NIKQDGSERHYVDSVKG |
| 142 | 33H2_21B1 | CDR-H3 | EGYYGSGYFDY |
| 143 | 33H2_21B1 | VL | DIQMTQSPSTLSASVGDRVIITCRASQSISRGLAWYQQKPGKAPKLLIY KASNLESGVPSRFSGSGSGTEFTLTISSLQPDDFAAYYCQQYSYYSHTF GQGTKVEIK |
| 45 | 33H2_21B1 | CDR-L1 | RASQSISRGLA |
| 46 | 33H2_21B1 | CDR-L2 | KASNLES |
| 47 | 33H2_21B1 | CDR-L3 | QQYSYYSHT |
| 144 | 36A12_21C1 | VH | EVQLVESGGGLVQPGGSLRLSCAASGFTLSFYWMTWVRQAPGKGLE WVANIKQDGNEKNYVDSVKGRFTISKDNAKKSVFLQMNSLRAEDTA VYYCAREGYFGSGYFDYWGQGTLVTVSS |
| 145 | 36A12_21C1 | CDR-H1 | GFTLSFYWMT |
| 146 | 36A12_21C1 | CDR-H2 | NIKQDGNEKNYVDSVKG |
| 43 | 36A12_21C1 | CDR-H3 | EGYFGSGYFDY |
| 147 | 36A12_21C1 | VL | DIQMTQSPSTLSASVGDRVTITCRASQSINSWLAWYQQKPGKAPKLLI YKASTLESGVPSRFSGSGSGTEFTLTISSLQPDDFAPYYCQHYNSYPHT FGQGTKVEIK |
| 148 | 36A12_21C1 | CDR-L1 | RASQSINSWLA |
| 149 | 36A12_21C1 | CDR-L2 | KASTLES |
| 150 | 36A12_21C1 | CDR-L3 | QHYNSYPHT |
| 151 | 38G11_28A2 | VH | EVQLVESGGGLVQPGGSLRLSCAASGFTFSSYWMSWVRQAPGKGLE WVANIKQDGSEKHYVDSVKGRFTISRDNAKNSLYLQMNSLRAEDTA VYYCAREGYFGSGYFDYWGQGTLVTVSS |
| 152 | 38G11_28A2 | CDR-H1 | GFTFSSYWMS |
| 153 | 38G11_28A2 | CDR-H2 | NIKQDGSEKHYVDSVKG |
| 43 | 38G11_28A2 | CDR-H3 | EGYFGSGYFDY |
| 154 | 38G11_28A2 | VL | DIQLTQSPSFLSASVGDRVTITCRASQGISSYLAWYQQKPGKAPKLLIY AASTLQSGVPSRFSGSGSGTEFTLTISSLQPEDFATYYCQQYSFYSHTF GQGTKLEIK |
| 155 | 38G11_28A2 | CDR-L1 | RASQGISSYLA |
| 156 | 38G11_28A2 | CDR-L2 | AASTLQS |
| 157 | 38G11_28A2 | CDR-L3 | QQYSFYSHT |
| 158 | 40C3_22B6 | VH | EVQLVESGGGLVQPGGSLRLSCAASGFTLSFYWMTWVRQAPGKGLE WVANIKQDGNEKNFVDSVKGRFTISRDNAKKSVFLQMNSLRAEDTA VYYCAREGYFGSGYFDYWGQGTLVTVSS |

TABLE 5-continued

Variable region sequences of human antibodies

| SEQ ID NO: | Clone Name | Protein Domain | Sequence |
|---|---|---|---|
| 145 | 40C3_22B6 | CDR-H1 | GFTLSFYWMT |
| 159 | 40C3_22B6 | CDR-H2 | NIKQDGNEKNFVDSVKG |
| 43 | 40C3_22B6 | CDR-H3 | EGYFGSGYFDY |
| 160 | 40C3_22B6 | VL | DIQMTQSPSTLSASVGDRVTITCRASQSINSWLAWYQQKPGKAPKLLI YKASSLESGVPSRFSGSGSGTEFTLTISSLQPDDFATYYCQQYNSYPHT FGQGTKLEIK |
| 148 | 40C3_22B6 | CDR-L1 | RASQSINSWLA |
| 161 | 40C3_22B6 | CDR-L2 | KASSLES |
| 162 | 40C3_22B6 | CDR-L3 | QQYNSYPHT |
| 163 | 5D12_18A4 | VH | QVQLQESGPGLVKPLGTLSLTCAVSGGSISNSNWWSWVRQPPGKGLE WIGEIYHSGSTNYNPSLKSRVTIALDWSKNQFSLQLRSVTAADTAVY YCARYGSGPFGGDCWGQGTLVTVSS |
| 164 | 5D12_18A4 | CDR-H1 | GGSISNSNWWS |
| 165 | 5D12_18A4 | CDR-H2 | EIYHSGSTNYNPSLKS |
| 166 | 5D12_18A4 | CDR-H3 | YGSGPFGGDC |
| 167 | 5D12_18A4 | VL | DIQLTQSPSFLSASVGDRVTISCRASQGISSYLAWYQQKPGKAPKLLIY AASTLQGGVPSRFSGSGSGTTFTLTISSLQPEDFATYYCQQLNTYPFTF GPGTKLEIK |
| 155 | 5D12_18A4 | CDR-L1 | RASQGISSYLA |
| 168 | 5D12_18A4 | CDR-L2 | AASTLQG |
| 169 | 5D12_18A4 | CDR-L3 | QQLNTYPFT |
| 170 | 5D12_C108Y | VH | QVQLQESGPGLVKPLGTLSLTCAVSGGSISNSNWWSWVRQPPGKGLE WIGEIYHSGSTNYNPSLKSRVTIALDWSKNQFSLQLRSVTAADTAVY YCARYGSGPFGGDYWGQGTLVTVSS |
| 164 | 5D12_C108Y | CDR-H1 | GGSISNSNWWS |
| 165 | 5D12_C108Y | CDR-H2 | EIYHSGSTNYNPSLKS |
| 171 | 5D12_C108Y | CDR-H3 | YGSGPFGGDY |
| 172 | 5D12-C108Y | VL | DIQLTQSPSFLSASVGDRVTISCRASQGISSYLAWYQQKPGKAPKLLIY AASTLQGGVPSRFSGSGSGTTFTLTISSLQPEDFATYYCQQLNTYPFTF GPGTKLEIK |
| 155 | 5D12-C108Y | CDR-L1 | RASQGISSYLA |
| 168 | 5D12-C108Y | CDR-L2 | AASTLQG |
| 169 | 5D12-C108Y | CDR-L3 | QQLNTYPFT |
| 173 | 37D11_21C2 | VH | QVQIKESGPGLVKPSETLSLTCAVSGFSFSSGYYWGWIRQPPGKGLEW LGSFFHNGNTYYNPSLRSRVTISVDTSKNHFSLKLTSVTAADTAVYYC AGFGDLPHYHYYVMDVWGQGTTVTVSS |
| 174 | 37D11_21C2 | CDR-H1 | GFSFSSGYYWG |
| 175 | 37D11_21C2 | CDR-H2 | SFFHNGNTYYNPSLRS |
| 176 | 37D11_21C2 | CDR-H3 | FGDLPHYHYYVMDV |
| 177 | 37D11_21C2 | VL | EIVLTQSPATLSLSPGERATLSCRASQSVSSYLAWYQQKPGQAPRLLIY DASNRAIGIPARFSGSGSGTDFTLTISSLEPEDFAVYYCQQRSNWPPYT FGQGTKLEIK |
| 79 | 37D11_21C2 | CDR-L1 | RASQSVSSYLA |
| 178 | 37D11_21C2 | CDR-L2 | DASNRAI |
| 179 | 37D11_21C2 | CDR-L3 | QQRSNWPPYT |

TABLE 5-continued

Variable region sequences of human antibodies

| SEQ ID NO: | Clone Name | Protein Domain | Sequence |
|---|---|---|---|
| 180 | 42D10_28A5 | VH | QVQPKESGPGVVKPSETLSLTCAVSGFPISRGYYWGWIRQPPGKGLE WIGNIFHSGTTYYNPSLKSRVTISVDTSKNQISLKLTSVTAADTAVYY CVGFGDLPHYQYYVMDIWGQGTTVTSS |
| 181 | 42D10_28A5 | CDR-H1 | GFPISRGYYWG |
| 182 | 42D10_28A5 | CDR-H2 | NIFHSGTTYYNPSLKS |
| 183 | 42D10_28A5 | CDR-H3 | FGDLPHYQYYVMDI |
| 184 | 42D10_28A5 | VL | EIVLTQSPATLSLSPGERATLSCRASQSVSSYLAWYQQKPGQAPRLLIY DASNRATGIPARFSGSGSGTDFTLTISSLEPEDFAVYYCQQRSNWPPYT FGQGTKLEIK |
| 79 | 42D10_28A5 | CDR-L1 | RASQSVSSYLA |
| 80 | 42D10_28A5 | CDR-L2 | DASNRAT |
| 179 | 42D10_28A5 | CDR-L3 | QQRSNWPPYT |
| 185 | 34H8_21B4 | VH | QVQLQESGPGLVKPSETLSLTCAVSGYSASGLYYWAWIRQPPGKGLE WIGNIYHSGRTYYNPSLESRVSISLDTSKHQVSLKLKSVTYADTAVYF CARDRFDGFDIWGQGTMVTVSS |
| 186 | 34H8_21B4 | CDR-H1 | GYSASGLYYWA |
| 187 | 34H8_21B4 | CDR-H2 | NIYHSGRTYYNPSLES |
| 188 | 34H8_21B4 | CDR-H3 | DRFDGFDI |
| 189 | 34H8_21B4 | VL | EIVMTQSPATLSVSPGERATLSCRASQTINNILAWYQQKPGQAPRLLIY GASTRATGIPARFSGSGSGTEFTLTISSLQSEDFAVYYCQQYNNWPLTF GGGTKLEIK |
| 190 | 34H8_21B4 | CDR-L1 | RASQTINNILA |
| 62 | 34H8_21B4 | CDR-L2 | GASTRAT |
| 63 | 34H8_21B4 | CDR-L3 | QQYNNWPLT |

Complete nucleic acid sequences encoding the heavy and light chains from these 36 antibodies are set forth in Table 6, below.

TABLE 6

Variable region DNA sequences of human antibodies

| 191 | 5G8_18A1 | VH | CAGGTGGAGCTGCAGGAGTCGGGCCCAGGACTGGTGAAGCCTTCGGACACC CTGTCCCTCACCTGCACTGTCACTGGTGGCTCCATCAGTACTTACTACTGGA GCTGGATCCGGCAGCCCCCAGGGAAGGGACTGGAGTGGATTGGGTATATCT TTTACACTGGGACCACCAACTACAACCCCTCCCTCAAGAGTCGAGTCACCAT ATCAGTAGACGCGTCCAAGAACCAGTTCTCCCTGAAGTTGAACTCTGTGAC CGCTGCGGACACGGCCGTGTATTACTGTGCGAGAGATGGGAGCCTGGACTA CTGGGGCCAGGGAGCCCTGGTCACCGTCTCCTCA |
| 192 | 5G8_18A1 | VL | GACATCCAGATGACCCAGTCTCCATCCTCCCTGTCTGCATCTGTAGGAGACA GAGTCACCATCACTTGCCGGGCAAGTCAGAGCATTAGCAACTATTTAAATT GGTATCAGCAGAAACCAGGGAAAGCCCCTAAGCTCCTGATCTTTGTTGCAT CCCTTTTGCAAAGTGGGGTCCCATCAAGGTTCAGTGGCAGTGGATCTGGGA CAGATTTCACTCTCACCATCAGCAGTCTGCAACCTGAAGATTTTGCAACTTA CTACTGTCAACAGAGTTACAGTACCCCATTCACTTTCGGCCCTGGGACCAAG CTGGAGATCAAA |
| 193 | 10C8_15A1 | VH | CAGGTGCAGCTGGTGGAGTCTGGGGGAGGCGTGGTCCAGCCTGGGAGGTCC CTGAGAATCTCCTGTGCAGCGTCTGGATTCACCTTCAGGAGCTATGGCATGC ACTGGGTCCGCCAGGCTCCAGGCAAGGGACTGGAGTGGGTGGCAATTATCT GGCATGATGGAAGTTATAAATATTATGTAGACTCCGTGAAGGGCCGATTCA CCATCTCCAGAGACAATTCCAAGAACACGCTGTATCTGCAAATGAACAGCC |

TABLE 6-continued

Variable region DNA sequences of human antibodies

|   |   |   |   |
|---|---|---|---|
| | | | TGAGAGCCGAGGACACGGCTGTGTATTATTGTGCGAGAGGCGATTACTATG<br>GTTCGGGGAGTTATTATGATGCTTTTGATATCTGGGGCCAAGGGACAATGGT<br>CACCGTCTCCTCA |
| 194 | 10C8_15A1 | VL | GACATCCAGATGACCCAGTCTCCATCCTCCCTGTCTGCATCTGTAGGAGACA<br>GAGTCATCATCACTTGCCGGGCGAGTCAAGGCATTAGCAATTATTTAGCCTG<br>GTTTCAGCAGAAACCAGGGAAATGTCCTAACCTCCTGATCTATGCTGCATCC<br>ACTTTGCGATCAGGGGTCCCATCTCGGTTCAGTGGCAGTGGATCTGGGACA<br>GATTTCACTCTCACCATCAGCAGCCTGCAGCCTGAAGATGTTGCAACTTATT<br>ACTGTCAAAAGTATAACAGTGCCCCGTACACTTTTGGCCAGGGGACCAAGG<br>TGGAGATCAAA |
| 195 | 12F3_17C2 | VH | CAGGTGCAGCTGGTGGAGTCTGGGGGAGGCGTGGTCCAGCCTGGGAGGTCC<br>CTGAGACTCTCCTGTGCAGCGTCTGGATTCACCTTCAGTCACTATGGCATGC<br>ACTGGGTCCGCCAGGCTCCAGGCAAGGGGCTGGAGTGGGTGGCAGTTATAT<br>GGTATGATGGAAGTAAAAAATACTATGTAGACTCCGTGAAGGGCCGATTCA<br>CCATCTCCAGAGACAATTCCAAGAACACGCTGTATCTGCAAATGAACAGCC<br>TGAGAGGCGAGGACACGGCTGTGTATTACTGTGCGAGAGATGGGGGAGCA<br>GTGGCTGACAACTGGATCGACTCCTGGGGCCAGGGAACCCTGGTCACCGTC<br>TCCTCA |
| 196 | 12F3_17C2 | VL | GACATCCAGATGACCCAGTCTCCATCCTCCCTGTCTGCATCTGTAGGAGACA<br>GAGTCACTATCACTTGCCGGGCAAGTCAGAGCATTAGAAGCTATTTAAATT<br>GGTATCAGCAGAAACCCGGGAAAGCCCCTAAGCTCCTGATCTTTGCTGCAT<br>CCAGTTTGCAAAGTGGGGTCCCATCCAGGTTCAGTGGCAGTGGATCTGGGA<br>CAGATTTCACTCTCACCGTCAGCAGTCTGCAACCTGAAGATTTTGCAACTTA<br>CTCCTGTCAACAAAGTTACAGTACCCCGTACACTTTTGGCCAGGGGACCAA<br>GGTGGAGATCAAA |
| 197 | 16H2_17D2 | VH | CAGGTGCAGTTGGTGGAGTCTGGGGGAGGCGTGGTCCAGCCTGGGGGGTCC<br>CTGAGACTCTCCTGTGCAGCGTCTGGATTCACCTTCAGTAGCCATGGCATGC<br>ACTGGGTCCGCCAGGCTCCAGGCAAGGGGCTGGAGTGGGTGGCAGTTATAT<br>GGTATGATGGAAGTAATAAAATTCTATACAGACTCCGTGCAGGGCCGATTCA<br>CCATTTCCAGAGACAATTCCAAGAACACGCTGAATCTGCAAATGAACAGTC<br>TGAGAGCCGAGGACACGGCTGTATATTACTGTGCGAGAGAGGGTTTGAGGG<br>CCGGGTACTACTTTGACTTCTGGGGCCAGGGAACCCTGGTCACCGTCTCCTC<br>A |
| 198 | 16H2_17D2 | VL | GACATCCAGATGACCCAGTCTCCATCCTCCCTGTCTGCATCTGTAGGAGACA<br>GAGTCACCATCACTTGCCGGGCAAGTCAGAGGATTAGCTTCTATTCAAATTG<br>GTATCAGCAGAAACCAGGGAAAGCCCCTAAGCTCCTGATCTATGCTGCATC<br>CAGTTTGCAAAGTGGGGTCCCATCAAGGTTCAGTGGCAGTGGCTCTGGGAC<br>AGATTTCACTCTCACCATCAGCAGTCTGCAACCTGAAGATTTTGCAACTTAC<br>TTCTGTCAACAGAGTCACAGTACCCCGCTCACTTTCGGCGGAGGGACCAAG<br>CTGGAGATCAAA |
| 199 | 32C12_21A4 | VH | CAGGTGCAGCTGGTGGAGTCTGGGGGAGGCGTGGTCCAGCCTGGGAGGTCC<br>CTGCGACTCTCCTGTGCAGCGTCTGGATTCACCTTCAGGAACTATGGCATTC<br>ACTGGGTCCGCCAGGCTCCAGGCAAGGGGCTGGAGTGGGTGGCAGTTATAT<br>GGTATGATGGAAGTAATAAAATTCTATGCAGACTCCGTGAAGGGCCGATTCA<br>CCATCTCCAGAGACAATTCCAAGAACACGCTGTATCTGCAAATGAACAGCC<br>TGAGAGTCGAGGACACGGCTGTATATTACTGTGCGAGAGAGGAGGGGATA<br>GCAGTGGCCCCCTTTGACTACTGGGGCCAGGGAACCCTGGTCACCGTCTCCT<br>CA |
| 200 | 32C12_21A4 | VL | GACATCCAGATGACCCAGTCTCCATCCTCCCTGTCTGCATCTGTAGGAGACA<br>GAGTCGCCATCACTTGCCGGGCAAATCAGAGTATTGCCAGTTATTTAAATTG<br>GTATCAGCAGAAACCAGGGAAAGCCCCTAAACTCCTGATCTATGGTGCATC<br>CAGTTTGCAAAATGGGGTCCCATCAAGGTTCAGTGGCAGTGGATCTAGGAC<br>AGATTTCACTCTCACCATCAGCAGTCTGCAACCTGAAGATTTTGCAACTTAC<br>TACTGTCAACAGAGTTACAGCACCGAGATCACCTTCGGCCAAGGGACACGA<br>CTGGAGATTAAA |
| 201 | 34C11_21B2 | VH | GAGGTGCAGGTGGTGGAGTCTGGGGGAGGCTTGGTCCAGCCTGGGGGGTCC<br>CTGAGACTCTCCTGTGCAGCCTCTGGATTCACCTTTAGAAGCTATTGGATGA<br>GCTGGGTCCGCCAGGCTCCAGGGAAGGGGCTGGAGTGGGTGGCCAACATA<br>AAGCAGGATGGAAGTGAGAGACACTATGTGGACTCTGTGAAGGGCCGATTC<br>ACCATCTCCAGAGACAACGCCAAGAACATCACTGTATCTGCAAATGAGCAGC<br>CTGAGAGCCGAGGACACGGCTGTGTATTACTGTGCGAGAGAGGGGTACTTT<br>GGTTCGGGCTACTTTGACTACTGGGGCCAGGGAACCCTGGTCACCGTCTCCT<br>CA |
| 202 | 34C11_21B2 | VL | GACATCCAGATGACCCAGTCTCCCTCCACCCTGTCTGCATCTGTAGGAGACA<br>GAGTCATCATCACTTGCCGGGCCAGTCAGAGATTAGTAGGGGGTTGGCCT |

TABLE 6-continued

Variable region DNA sequences of human antibodies

|     |     |    |     |
| --- | --- | -- | --- |
|     |     |    | GGTATCAGCAGAAACCAGGGAAAGCCCCTAAACTCTTGATCTATAAGGCGT<br>CTAATTTAGAAAGTGGGGTCCCATCAAGGTTCAGCGGCAGTGGATCTGGGA<br>CAGAATTCACTCTCACCATCAGCAGCCTGCAGCCTGATGATTTTGCAGCTTA<br>TTACTGCCAACAGTATAGTTATTATTCTCACACTTTTGGCCAGGGGACCAAG<br>CTGGAGATCAAA |
| 203 | 36A10_21B6 | VH | CAGGGGCAGGTGGTGGAGTCTGGGGGAGGCGTGGTCCAGCCTGGGAGGTC<br>CCTGAGACTCTCCTGTGCAGCGTCTGGATTCACCTTCAGTAGTTATACCTTG<br>CACTGGGTCCGCCAGGCTCCAGGCAAGGGGCTGGAGTGGGTGGCAGTCATA<br>TGGTATGATGGAAGTAATAAGTATTATGTAGACTCCGTGAAGGGCCGATTC<br>ACCATCTCCAGAGACAATTCCAAGAACACGCTGTATCTGCAAATGAACAGC<br>CTGAGAGCCGAGGACACGGCTGTGTATTACTGTGCGAGAGAGTATGGTTCG<br>GGGGAGTTATTATAACGTCTACTACGGTATGGACGTCTGGGGCCAGGGGACC<br>ACGGTCACCCTCTCCTCA |
| 204 | 36A10_21B6 | VL | GATATTGTGATGACTCAGTCTCCACTCTCCCTGCCCGTCACCCCTGGAGAGC<br>CGGCCTCCATCTCCTGCAGGTCTAGTCAGAGCCTCCTTCATAGTAATGGATA<br>CAACTATTTGGATTGGTATCTGCAGAAGCCAGGCCAGTCTCCACACCTCTTG<br>ATCTATTTGGCTTCTAATCGGGCCTCCGGGGTCCCTGACAGGTTCAGTGGCA<br>GTGGATCAGGCACAGATTTTACACTGAAAATCAGCAGAGTGGAGGCTGAGG<br>ATGTTGGGTTTTATTACTGCATGCAAACTCTACAAATTCCGCTCACTTTCGG<br>CGGAGGGACCAAGGTGGAGATCAAA |
| 205 | 39G1_21C4 | VH | CAGGTGCAGCTGCAGGAGTCGGGCCCAGGACTGGTGAAGCCTTCGGAGACC<br>CTGTCCCTCACCTGCGCTGTCTCTGGTTACTCCGCCAGCGGTGTTTACTACTG<br>GGGCTGGATCCGGCAGCCCCCAGGGAAGGGGCTGGAGTGGATTGGAAATA<br>TCTATCATAGTGGGAGCACCTATTACAACCCGTCCCTCGAGAGGCGAGTTA<br>GTATATCACTAGACACGTCCAAGAACCACTTCTCCCTGAGGCTGAATTTTGT<br>GACCGCCGCAGACACGGCCGTGTATTACTGTGCGAGAGATAGGTTTGATGC<br>TTTTGATATCTGGGGCCAAGGGACAATGGTCACCGTCTCCTCA |
| 206 | 39G1_21C4 | VL | GAAATAGTGATGACGCAGTCTCCAGCCACCCTGTCTGTGTCTCCAGGGGAA<br>AGAGCCACCCTCTCCTGCAGGGCCAGTCAGAGTATTAACAACATCTTAGCC<br>TGGTACCAGCAGAAACCTGGCCAGGCTCCCAGGCTCCTCATCTATGGTGCA<br>TCCACCAGGGCCACTGGTATCCCAGCCAGGTTCAGTGGCAGTGGGTCTGGG<br>ACAGAGTTCACTCTCACCATCAGCAGCCTGCAGTCTGAAGATTTTGCAGTTT<br>ATTACTGTCAGCAGTATAATAACTGGCCTCTCACTTTCGGCGGAGGGACCA<br>AGGTGGAGATCAAA |
| 207 | 37E10_15B5 | VH | CAGGTGCAGCTGGTGGAGTCTGGGGGAGGCGTGGTCCAGCCTGGGAGGTCC<br>CTGAGACTCTCCTGTGCAGCGTCTGGATTCACCTTTAGGAGTCATGGCATGC<br>ACTGGGTCCGCCAGGCTCCAGGCAAGGGACTGGAGTGGGTGGCAGTTATAT<br>GGTATGATGGAAGTAGTGAGTACTATGCAGACTCCGTGAAGGGCCGATTCA<br>CCATCTCCAGAGACAATTCCAAGAACACGCTGTATCTGCAAATGAACAGCC<br>TGAGAGCCGAGGACACGGCTGTGTATTATTGTGCGAGAGAAAACGTGTATG<br>GCAGTGGCTGGTTTTTTGACTACTGGGGCCAGGGAACCCTGGTCACCGTCTC<br>CTCA |
| 208 | 37E10_15B5 | VL | GAAATAGTGATGACGCAGTCTCCAGCCACCCTGTCTGTGTCTCCAGGGGAA<br>AGAGCCTCCCTCTCCTGCAGGGCCAGTCAGAGTGTTGGCAGCAACTTAGCC<br>TGGTACCAGCAGAGACCTGGCCAGGCTCCCAGGCTCCTCATCTTTGGTGCAT<br>CCACCAGGGCCACTGGTATCCCAGCCAGGTTCAGTGGCAGTAGGTCTGGGA<br>CAGAGTTCACTCTCACCATCAGCAGCCTGCAGTCTGAAGATTTTGCACTTTA<br>TTACTGTCAGCAGTATAATAACTGGCCTCCGTGGACGTTCGGCCAAGGGAC<br>CAAGCTGGAGATCAAA |
| 209 | 44E5_15C5 | VH | CAGGTGCAGCTGGTGGAGTCTGGGGGAGGCGTGGTCCAGCCTGGGAGGTCC<br>CTGAGACTCTCCTGTGCAGCGTCTGGATTCACCTTCAGGAGTCATGGCATGC<br>ACTGGGTCCGCCAGGCACCAGGCAAGGGACTGGAGTGGGTGGCAGTTATAT<br>GGTATGATGGAAGTAGTGACTACTATGCAGACTCCGTGAAGGGCCGATTCA<br>CCATCTCCAGAGACAATTCCAAGAACACACTATTTCTGCAAATGAACAGCC<br>TGAGCGCCGAGGACACGGCTGTGTATTATTGTGCGAGAGAAAACGTGTATG<br>GCAGTGGCTGGTTTTTTGACTACTGGGGCCAGGGAACCCTGGTCACCGTCTC<br>CTCA |
| 210 | 44E5_15C5 | VL | GAAATAGTGATGACGCAGTCTCCAGCCACCCTGTCTGTGTCTCCAGGGGAA<br>AGAGCCTCCCTCTCCTGCAGGGCCAGTCAGAGTGTTGGCAGCAACTTAGCC<br>TGGTACCAGCAGAAACCTGGCCAGGCTCCCAGGCTCCTCATCTTTGGTGCAT<br>CCACCAGGGCCACTGGTATCCCAGCCAGGTTCAGTGGCAGTAGGTCTGGGA<br>CAGAGTTCACTCTCACCATCAGCAGCCTGCAGTCTGAAGATTTTGCACTTTA<br>TTACTGTCAGCAGTATAATAACTGGCCTCCGTGGACGTTCGGCCAAGGGAC<br>CAAGCTGGAGATCAAA |
| 211 | 38E10_21C3 | VH | GAGGTGCAGCTGTTGGAGTCTGGGGGAGGCTTGGTACAGCCTGGGGGGTCC<br>CTGAGACTCTCCTGTGCAGCCTCTGGATTCACCTTTAGCAACTATGCCATGA<br>CCTGGGTCCGCCAGGCTCCAGGGAAGGGGCTGGAGTGGGTCTCAAGTATTA<br>GTATTAGTCGTGCTGGCACATACTACGCAGACTCCGTGAAGGGCCGGTTCA<br>CCATCTCCAGAGACAATTCCAAGAACACGCTGAATCTGCAAATGAACAGCC |

TABLE 6-continued

Variable region DNA sequences of human antibodies

|  |  |  |  |
|---|---|---|---|
|  |  |  | TGAGAGCCGAGGACACGGCCGAATATTACTGTGCGAGAGTACTACTACG<br>GCATGGACGTCTGGGGCCAAGGGACCACGGTCACCGTCTCCTCA |
| 212 | 38E10_21C3 | VL | GAAATTGTGTTGACACAGTCTCCAGCCACCCTGTCTTTGTCTCCAGGGGAAA<br>GAGCCACCCTCTCCTGCAGGGCCAGTCAGAGTGTTAGCAGCTACTTAGCCT<br>GGTACCAACAGAAACCTGGCCAGACTCCCAGGCTCCTCATCTATGATGCAT<br>CCAACAGGGCCACTGGCATCCCAGCCAGGTTCAGTGGCAGTGGGTCTGGGA<br>CAGACTTCACGCTCACCATCAGCAGCCTAGAGACTGAAGATTTTGCAGTTTA<br>TTACTGTCAGCAGCTTATCAACTGGCCGCTCACTTTCGGCGGAGGGACCAA<br>GCTGGAGATCAAA |
| 193 | 10C8_C43A | VH | CAGGTGCAGCTGGTGGAGTCTGGGGGAGGCGTGGTCCAGCCTGGGAGGTCC<br>CTGAGAATCTCCTGTGCAGCGTCTGGATTCACCTTCAGGAGCTATGGCATGC<br>ACTGGGTCCGCCAGGCTCCAGGCAAGGGACTGGAGTGGGTGGCAATTATCT<br>GGCATGATGAAAGTTATAAATATTATGTAGACTCCGTGAAGGGCCGATTCA<br>CCATCTCCAGAGACAATTCCAAGAACACGCTGTATCTGCAAATGAACAGCC<br>TGAGAGCCGAGGACACGGCTGTGTATTATTGTGCGAGAGGCGATTACTATG<br>GTTCGGGGAGTTATTATGATGCTTTTGATATCTGGGGCCAAGGGACAATGGT<br>CACCGTCTCCTCA |
| 213 | 10C8_C43A | VL | GACATCCAGATGACCCAGTCTCCATCCTCCCTGTCTGCATCTGTAGGAGACA<br>GAGTCATCATCACTTGCCGGGCGAGTCAAGGCATTAGCAATTATTTAGCCTG<br>GTTTCAGCAGAAACCAGGGAAAGcTCCTAACCTCCTGATCTATGCTGCATCC<br>ACTTTGCGATCAGGGGTCCCATCTCGGTTCAGTGGCAGTGGATCTGGGACA<br>GATTTCACTCTCACCATCAGCAGCCTGCAGCCTGAAGATGTTGCAACTTATT<br>ACTGTCAAAAGTATAACAGTGCCCCGTACACTTTTGGCCAGGGGACCAAGG<br>TGGAGATCAAA |
| 214 | 16H2_17D1 | VH | GAGGTGCAGTTGTTGGAATCTGGGGCAGACTTGGTACAGCCTGGGGGGTCC<br>CTGAGACTCTCCTGTGCAGCCTCTGGATTCACCTTTAGCAGCTATGCCATGA<br>GTTGGGTCCGCCAGGCTCCAGGAAAGGGGCTGGAGTGGGTCTCAACTATTC<br>GTATTAGTGGTGGCACCACATACTACGCAGACTCCGTGAAGGGCCGGTTCA<br>CCATCTCCAGAGACAATTCCAAGAACACGCTGTATCTGCAAATGAACAGCC<br>TGAGAGCCGAAGACACGGCCGTATATTACTGCGTAAGGGACTACTATAACG<br>GTATGGACGTCTGGGGCCAAGGGACCACGGTCACCGTCTCCTCA |
| 215 | 16H2_17D1 | VL | GAAATTGTGTTGACACAGTCTCCAGCCACCCTGTCTTTGTCTCCAGGGGAAA<br>GAGCCACCCTCTCCTGCAGGGCCAGTCAGCGTGTTAGCAGCTACTTAGCCTG<br>GTACCAACAGAAACCTGGCCAGGCTCCCAGGCTCCTCATCTATGATGCATC<br>CAACAGGGCCACTGGCATCCCAGCCAGGTTCAGTGGCAGTGGGTCTGGGAC<br>AGACTTCACTCTCACCATCAGCAGCCTAGAGCCTGAAGATTTTGCAGTTTAT<br>TACTGTCAGCAGCGTAGCTACTGGCCTCCCGCTTTTGGCCAGGGGACCAAG<br>CTGGAGATCAAA |
| 216 | 24G3_17C5 | VH | AGCTATGCCATGAGCTGGGTCCGCCAGGCTCCAGGGAAGGGGCTGGAGTGG<br>GTCTCAAGTATTAGTGGTAGTGGTGATAGCACAAACTACGCAGACTCCGTG<br>AAGGGCCGGTTCACCATCTCCAGAGACAATTCCAAGAACACGCTGCATCTG<br>CAAATGAACAGCCTGAGAGCCGAGGACACGGCCGTATATTACTGCGTAAGG<br>GACTACTACTACGGTATGGACGTCTGGGGCCACGGGACCACGGTCACCGTC<br>TCCTCA |
| 217 | 24G3_17C5 | VL | GAAATTGTGTTGACACAGTCTCCAGCCACCCTGTCTTTGTCTCCAGGGGAAA<br>GAGCCACCCTCTCCTGCAGGGCCAGTCAGAGTGTTAACAGCTACTTAGCCT<br>GGTACCAACAGAAACCTGGCCAGGCTCCCAGGCTCCTCATCTATGATGCAT<br>CCAACAGGGCCACTGGCATCCCAGCCAGGTTCAGTGGCAGTGGGTCTGGGA<br>CAGACTTCACTCTCACCATCAGCAGCCTAGAGCCTGAAGATTTTGCAGTTTA<br>TTACTGTCAGCAGCGTAGCTACTGGCCGATCACCTTCGGCCAAGGGACACG<br>ACTGGAGATTAAA |
| 218 | 26C5_15B4 | VH | GAGGCGCAGCTGTTGGAGTCTGGGGGAGGCTTGGTACAGCCTGGGGGGTCC<br>CTGAGACTCTCCTGTGCAGCCTCTGGATTCACCTTTAGCAGCTATGCCATGA<br>GCTGGGTCCGCCAGGCTCCAGGGAAGGGGCTGGAGTGGGTCTCAACTATTA<br>GTGGTAGTGGTGGTAGTACACACTACGCAGACTCCGTGAAGGGCCGGTTCA<br>CCATCTCCAGAGACAATTCCAAGAATACGTTGTATCTGCAAATGAACAGCC<br>TGAGAGCCGAGGACACGGCCGTATATTACTGCGTAAGGGACTACTACTACG<br>GTATGGACGTCTGGGGCCAAGGGACCACGGTCACCGTCTCCTCA |
| 219 | 26C5_15B4 | VL | GAAATTGTGTTGACACAGTCTCCAGCCACCCTGTCTTTGTCTCCAGGGGAAA<br>GAGCCACCCTCTCCTGCAGGGCCAGTCAGAGTGTTAGCAGCTACTTAGCCT<br>GGTACCAACAGAAACCTGGCCAGGCTCCCAGGCTCCTCATCTATGATGCAT<br>CCAACAGGGCCACTGGCATCCCAGCCAGGTTCAGTGGCAGTGGGTCTGGGA<br>CAGACTTCACTCTCACCATCAGCAGCCTAGAGCCTGAAGATTTTGCAGTTTA<br>TTACTGTCAGCAGCGTAGCTACTGGCCTCCCACTTTTGGCCAGGGGACCAAG<br>CTGGAGATCAAA |
| 220 | 17E9_15B1 | VH | CAGGTGCAGCTGGTGGAGTCTGGGGGAGGCGTGGTCCAGCCTGGGAGGTCC<br>CTGAGACTCTCCTGTGCAGCGTCTGGATTCACCTTCAGTAGCTATGGAATGC<br>ACTGGGTCCGCCAGGCTCCAGGCAAGGGGCTGGAGTGGGTGGCAGTTATAT |

TABLE 6-continued

Variable region DNA sequences of human antibodies

|     |             |    |                                                                                                                                                                                                                                                                                                                                                             |
| --- | ----------- | -- | ----------------------------------------------------------------------------------------------------------------------------------------------------------------------------------------------------------------------------------------------------------------------------------------------------------------------------------------------------------- |
|     |             |    | GGTATGATGGAAGTAAAAAATACTATGTAGACTCCGTGCAGGGCCGATTCA CCATCTCCAGAGACAATTCCAAGAATACGCTGTATCTGCAAATGAACAGCC TGAGAGGCGAGGACACGGCTGTGTATTACTGTGCGAGAGATGGGGGAGCA GTGGCTGACAATTGGATCGACTCCTGGGGCCAGGGAACCCTGGTCACCGTC TCCTCA |
| 221 | 17E9_15B1   | VL | GACATCCAGATGACCCAGTCTCCATCCTCCCTGTCTGCGTCTGTAGGAGACA GAGTCACTCTCACTTGCCGGGCAAGTCAGAACATTAGAAGCTATTTAAATT GGTATCAGCAGAAACCAGGGAAAGCCCCTAAGCTCCTGATCTTTGCTGCAT CCAGTTTGCCAAGTGGGGTCCCATCAAGGTTCAGTGGCAGTGGATCTGTGA CAGATTTCACTCTCACCGTCAGCAGTCTGCAACCTGAAGATTTTGCAACTTA CTCCTGTCAACAGAGTTACAGTACCCCGTACACTTTTGGCCAGGGGACCAA GCTGGAGATCAAA |
| 222 | 10C8_15A4   | VH | GAGGAACAGCTGTTGGAATCTGGGGCAGACTTGGCACAGCCGGGGGGGTCC CTGAGACTCTCCTGTGCAGCCTCTGGATTCACCTTTAGCAGCTATGCCATGA GTTGGGTCCGCCAGGCTCCAGGAAAGGGACTGGAGTGGGTCTCAACTATTC GTATTAGTGGTGATACCACTTACTACGCAGACTCCGTGAAGGGCCGGTTCA CCATCTCCAGAGACAATTCCAAGAACACGCTGTTTCTGCAAATGAACAGCC TGAGAGCCGAAGACACGGCCGTGTATTACTGCGTAAGGGACTACTATAACG GTATGGACGTCTGGGGCCATGGGACCACGGTCACCGTCTCCTCA |
| 223 | 10C8-15A4   | VL | GAAATTGTGTTGACACAGTCTCCAGCCACCCTGTCTTTGTCTCCAGGGGAAA GAGCCACCCTCTCCTGCAGGGCCAGTCAGCGTGTTAGCAGCTATTTAGCCTG GTACCAACAGAAACCTGGCCAGGCTCCCAGGCTCCTCATCTATGATGCATC CAACAGGGCCACTGGCATCCCAGCCAGGTTCAGTGGCAGTGGGTCTGGGAC AGACTTCACTCTCACCATCAGCAGCCTAGAGCCTGAAGATTTTGCAGTTTAT TACTGTCAGCAGCGTAGCTACTGGCCTCCCGCTTTTGGCCAGGGGACCAAG CTGGAGATCAAA |
| 224 | 32A2_21A3   | VH | CAGGTGCAGCTGGTGCAGTCTGGGGCTGAGGTGAAGAAGCCTGGGGCCTCA GTGAAGGTCTCCTGCAAGGCTTCTGGATACACCTTCACCGGCTACTATATGC ACTGGGTGCGACAGGCCCCTGGACAAGGGCTTGAGTGGATGGGATGGATCA ACCCTAACAGTGGTGGCACAAACTATGCACAGAAGTTTCAGGGCAGGGTCA CCATGACCAGGGACACGTCCATCAGCACAGCCTACATGGAGCTGAGCAGGC TGAGATCTGACGACACGGCCGTGTATTACTGTGCGAGAGAAGCAGTGGCTG GTACCTCTGATGCTTTTGATATCTGGGGCCAAGGGACAATGGTCACCGTCTC CTCA |
| 225 | 32A2_21A3   | VL | GACATCCAGATGACCCAGTCTCCATCCTCCCTGTCTGCATCTGTTGGAGACA GAGTCACCATCACTTGCCGGGCAAATCAGAGTATTGCCAGTTATTTAAATTG GTATCAGCAGAAACCAGGAAAAGTCCCTAAACTCCTGATCTATGGTGCATC CAGTTTGCAAAATGGGGTCCCATCAAGGTTCAGTGGCAGTGGATCTAGGAC AGATTTCACTCTCACCATCAGCAGTCTGCAACCTGAAGATTTTGCAACTTAC TACTGTCAACAAAGTTACAGCACCGAAATCACCTTCGGCCAAGGGACACGA CTGGAGATTAAA |
| 199 | 32C12-N26S  | VH | CAGGTGCAGCTGGTGGAGTCTGGGGGAGGCGTGGTCCAGCCTGGGAGGTCC CTGCGACTCTCCTGTGCAGCGTCTGGATTCACCTTCAGGAACTATGGCATTC ACTGGGTCCGCCAGGCTCCAGGCAAGGGGCTGGAGTGGGTGGCAGTTATAT GGTATGATGGAAGTAATAAATTCTATGCAGACTCCGTGAAGGGCCGATTCA CCATCTCCAGAGACAATTCCAAGAACACGCTGTATCTGCAAATGAACAGCC TGAGAGTCGAGGACACGGCTGTATATTACTGTGCGAGAGAGGAGGGGATA GCAGTGGCCCCCTTTGACTACTGGGGCCAGGGAACCCTGGTCACCGTCTCCT CA |
| 226 | 32C12_N26S  | VL | GACATCCAGATGACCCAGTCTCCATCCTCCCTGTCTGCATCTGTAGGAGACA GAGTCGCCATCACTTGCCGGGCAAgTCAGAGTATTGCCAGTTATTTAAATTG GTATCAGCAGAAACCAGGGAAAGCCCCTAAACTCCTGATCTATGGTGCATC CAGTTTGCAAAATGGGGTCCCATCAAGGTTCAGTGGCAGTGGATCTAGGAC AGATTTCACTCTCACCATCAGCAGTCTGCAACCTGAAGATTTTGCAACTTAC TACTGTCAACAGAGTTACAGCACCGAGATCACCTTCGGCCAAGGGACACGA CTGGAGATTAAA |
| 227 | 41G4_15B6   | VH | CAGGTGCAGCTGGTGGAGTCTGGGGGAGGCGTGGTCCAGCCTGGGAGGTCC CTGCGACTCTCCTGTGCAGCGTCTGGATTCACCTTTAGGAACTATGGCATGC ACTGGGTCCGCCAGGCTCCAGGCAAGGGGCTGGAGTGGGTGGCAGTTATAT GGTATGATGGAAGTAATAAATTCTATGCAGACTCCGTGAAGGGCCGATTCA CCATCTCCAGAGACAATTCCAAGAACACGCTGTATCTGCAAATGAACAGCC TGAGAGTCGAGGACACGGCTGTATATTACTGTGCGAGAGAGGAGGGGATA GCAGTGGCCCCCTTTGACTACTGGGGCCAGGGAACCCTGGTCACCGTCTCCT CA |
| 228 | 41G4_15B6   | VL | GACATCCAGATGACCCAGTCTCCATCCTCCCTGTCTGCATCTGTAGGAGACA GAGTCGCCATCACTTGCCGGGCAAATCAGAGTATTGCCAGTTATTTAAATTG GTATCAGCAGAAACCAGGGAAAGCCCCTAAACTCCTGATCTATGGTGCATC CAGTTTGCAAAATGGGGTCCCATCAAGGTTCAGTGGCAGTGGATCTAGGAC AGATTTCACTCTCACCATCAGCAGTCTGCAACCTGAAGATTTTGCAACTTAC |

TABLE 6-continued

| | | | Variable region DNA sequences of human antibodies |
|---|---|---|---|
| | | | TACTGTCAACAGAGTTACAGCACCGAGATCACCTTCGGCCAAGGGACACGA<br>CTGGAGATTAAA |
| 229 | 31F9_21A1 | VH | CAGGTGCAGCTGGTGGAATCTGGGGGAGGCATGGTCCAGCCTGGGAGGTCC<br>CTGAGACTCTCCTGTACAGCGTCTGGATTCACCTTCAGTAGTCATGGCATGC<br>ACTGGGTCCGCCAGGCTCCAGGCAAGGGACTGGAGTGGGTGGCAGTTATTT<br>GGTTTGATGGAAGTAATGAATATTATGTAGACTCCGTGAAGGGCCGATTCA<br>CCATCTCCAGAGACAATTCCAAGAACACACTGTATCTGCAAATGAACAGCC<br>TGAGAGCCGAGGACACGGCTGTGTATTATTGTGCGAGAGAAAACGTTTATG<br>GCAGTGGCTGGTTTTTTGACTACTGGGGCCAGGGAACCCTGGTCACCGTCTC<br>CTCA |
| 230 | 31F9_21A1 | VL | GAAATAGTGATGACGCAGTCTCCAGCCACCCTGTCTGTGTCTCCAGGGGAA<br>AGAGCCTCCCTCTCCTGCAGGGCCAGTCAGAGTGTTGGCAGCAACTTAGCC<br>TGGTACCAGCAGAAACCTGGCCAGGCTCCCAGGCTCCTCATCTTTGGTGCAT<br>CCACCAGGGCCACTGGTATCCCAGCCAGGTTCAGTGGCAGTAGGTCTGGGA<br>CAGAGTTCACTCTCACCATCAGCAGCCTGCAGTCTGAAGATTTTGCACTTTA<br>TTACTGTCAGCAGTATAATAACTGGCCTCCGTGGACGTTCGGCCAAGGGAC<br>CAAGGTGGAGATCAAA |
| 231 | 32D4_21D6 | VH | CAGTTGCAGCTGGTGGAGTCTGGGGGAGGCGTGGTCCAGCCTGGCAGGTCC<br>CTGAGACTCTCCTGTGCAGCGTCTGGATTCACCTTCAGTAGTTATGGCATGC<br>ACTGGGTCCGCCAGGCTCCAGGCAAGGGACTGGAGTGGGTGGCAGTTATAT<br>GGTATGATGGAAGTAGTGAGTACTATGCAGACTCCGTGAAGGGCCGATTCA<br>CCATCTCCAGAGACAATTCCAAGAACACGCTGTATCTGCAAATGAACAGCC<br>TGAGAGCCGAGGACACGGCTGTGTATTATTGTGCGAGAGAAAACGTGTATG<br>GCAGTGGCTGGTTTTTTGACTACTGGGGCCAGGGAACCCTGGTCACCGTCTC<br>CTCA |
| 232 | 32D4_21D6 | VL | GAAATAGTGATGACGCAGTCTCCAGCCACCCTGTCTGTGTCTCCAGGGGAA<br>AGAGCCTCCCTCTCCTGCAGGGCCAGTCAGAGTGTTGGCAGCAACTTAGCC<br>TGGTACCAGCAGAAACCTGGCCAGGCTCCCAGGCTCCTCATCTTTGGTGCAT<br>CCACCAGGGCCACTGGTATCCCAGCCAGGTTCAGTGGCAGTAGGTCTGGGA<br>CAGAGTTCACTCTCACCATCAGCAGCCTGCAGTCTGAAGATTTTGCACTTTA<br>TTACTGTCAGCAGTATAATAACTGGCCTCCGTGGACGTTCGGCCAAGGGAC<br>CAAGGTGGAGATCAAA |
| 233 | 32F9_21A5 | VH | GTCATGGCATGCACTGGGTCCGCCAGGCTCCAGGCAAGGGACTGGAGTGGG<br>TGGCAGTTATATGGTATGATGGAAGTAGTGAGTACTATGCAGACTCCGTGA<br>AGGGCCGATTCACCATCTCCAGAGACAATTCCAAGAACACGCTGTATCTGC<br>AAATGAACAGCCTGAGAGCCGAGGACACGGCTGTGTATTATTGTGCGAGAG<br>AAAACGTATATGGCAGTGGCTGGTTTTTTGACTACTGGGGCCAGGGAAGCC<br>TGGTCACCGTCTCCTCA |
| 234 | 32F9_21A5 | VL | GAAATAGTGATGACGCAGTCTCCAGCCACCCTGTCTGTGTCTCCAGGGGAA<br>AGAGCCTCCCTCTCCTGCAGGGCCAGTCAGAGTGTTGGCAGCAACTTAGCC<br>TGGTACCAGCAGAAACCTGGCCAGGCTCCCAGGCTCCTCATCTTTGGTGCAT<br>CCACCAGGGCCACTGGTATCCCAGCCAGGTTCAGTGGCAGTAGGTCTGGGA<br>CAGAGTTCACTCTCACCATCAGCAGCCTGCAGTCTGAAGATTTTGCACTTTA<br>TTACTGTCAGCAGTATAATAACTGGCCTCCGTGGACGTTCGGCCAAGGGAC<br>CAAGCTGGAGATCAAA |
| 235 | 33E9_21A6 | VH | CAGTTGCAGTTGGTGGAGTCTGGGGGAGGCGTGGTCCAGTTTGGCAGGTCC<br>CTGAGACTCTCCTGTGCAGCGTCTGGATTCACCTTCAGTAGTCATGGCATGC<br>ACTGGGTCCGCCAGGCTCCAGGCAAGGGACTGGAGTGGGTGGCAGTTATAT<br>GGTATGATGGAAGTAGTGAGTACTATGCAGACTCCGTGAAGGGCCGATTCA<br>CCATCTCCAGAGACAATTCCAAGAACACGCTGTATCTGCAAATGAACAGCC<br>TGAGAGCCGAGGACACGGCTGTGTATTATTGTGCGAGAGAAAACGTGTATG<br>GCAGTGGCTGGTTTTTTGACTACTGGGGCCAGGGAACCCTGGTCACCGTCTC<br>CTCA |
| 236 | 33E9_21A6 | VL | GAAATAGTGATGACGCAGTCTCCAGCCACCCTGTCTGTGTCTCCAGGGGAA<br>AGAGCCTCCCTCTCCTGCAGGGCCAGTCAGAGTGTTGGCAGCAACTTAGCC<br>TGGTACCAGCAGAAACCTGGCCAGGCTCCCAGGCTCCTCATCTTTGGTGCAT<br>CCACCAGGGCCACTGGTATCCCAGCCAGGTTCAGTGGCAGTAGGTCTGGGA<br>CAGAGTTCACTCTCACCATCAGCAGCCTGCAGTCTGAAGATTTTGCACTTTA<br>TTACTGTCAGCAGTATAATAACTGGCCTCCGTGGACGTTCGGCCAAGGGAC<br>CAAGCTGGAGATCAAA |
| 237 | 35D11_22A1 | VH | CAGTTGCAGCTGGTGGAGTCTGGGGGAGGCGTGGTCCAGCCTGGCAGGTCC<br>CTAAGACTCTCCTGTGCAGCGTCTGGATTCACCTTCAGTAGTTATGGCATGC<br>ACTGGGTCCGCCAGGCTCCAGGCAAGGGACTGGAGTGGGTGGCAGTTATAT<br>GGTATGATGGAAGTAGTGAGTATTATGCAGACTCCGTGAAGGGCCGATTCA<br>CCATCTCCAGAGACAATTCCAAGAACACGCTGTTTCTGCAAATGAACAGCC<br>TGAGAGCCGATGACACGGCTGTGTATTATTGTGCGAGAGAAAACGTGTATG<br>GCAGTGGCTGGTTTTTTGACTACTGGGGCCAGGGAACCCTGGTCACCGTCTC<br>CTCA |

TABLE 6-continued

Variable region DNA sequences of human antibodies

| 238 | 35D11_22A1 | VL | GAAATAGTGATGACGCAGTCTCCAGCCACCCTGTCTGTGTCTCCAGGGGAA
AGAGCCTCCCTCTCCTGCAGGGCCAGTCAGAGTGTTGGCAGCAACTTAGCC
TGGTACCAGCAGAAACCTGGCCAGGCTCCCAGGCTCCTCATCTTTGGTGCAT
CCACCAGGGCCACTGGTATCCCAGCCAGGTTCAGTGGCAGTAGGTCTGGGA
CAGAGTTCACTCTCACCATCAGCAGCCTGCAGTCTGAAGATTTTGCACTTTA
TTACTGTCAGCAGTATGATAACTGGCCTCCGTGGACGTTCGGCCAAGGGAC
CAAGCTGGAGATCAAA |
|---|---|---|---|
| 239 | 39A9_28A4 | VH | CAGGTGCAGCTGGTGGAGTCTGGGGGAGGCGTGGTCCAGCCTGGGAGGTCT
CTGAGACTCTCCTGTGCAGCGTCTGGATTCACCTTAAGTGGCTATGGCATGC
ACTGGGTCCGCCAGGCTCCAGGCAAGGGACTGGAGTGGGTGGCAGTTATAT
GGTATGATGGAAGTAATAAATACTATGCAGACTCCGTGAAGGGCCGATTCA
CCATCTCCAGAGACAATTCCAAGAACATGCTGTTTCTGCAAATGAACAGCC
TGAGAGCCGAGGACACGGCTGTGTATTACTGTGTGAGAGAAAACGGGTTTG
GCAGTGGCTGGTTTTTTGACTACTGGGGCCAGGGAAACCTGGTCACCGTCTC
CTCA |
| 240 | 39A9_28A4 | VL | GAAATAGTGATGACGCAGTCTCCAGCCACCCTGTCTGTGTCTCCAGGGGAA
AGAGCCACCCTCTCCTGCAGGACCAGTCAGAGTGTAAGTAGAGACTTAGCC
TGGTACCAGCAGAAACCTGGCCAGGCTCCCAGGCTCCTCATCTATGGTGCA
TCCACCAGGGCCACTGGTATTCCAGTCAGGTTCAGTGGCAGTGGGTCTGGG
ACAGAGTTCACTCTCACCATCAGCAGCCTGCAGTCTGAAGATTTTGCAGTTT
ATTACTGTCAGCAGTATAATAACTGGCCTCCGTGGACGTTCGGCCAAGGGA
CCAAGCTGGAGATCAAA |
| 241 | 34D1_21B3 | VH | CAGGGGCAGCTGGTGGAGTCTGGGGGAGGCGTGGTCCAGCCTGGGAGGTCC
CTGAGACTCTCCTGTGCAGCGTCTGGATTCACCTTCAGTAGTTATACCTTGC
ACTGGGTCCGCCAGGCTCCAGGCAAGGGGCTGGAGTGGGTGGCAGTCATAT
GGTATGATGGAAGTAATAAGTATTATGTAGACTCCGTGAAGGGCCGATTCA
CCATCTCCAGAGACAATTCCAAGAACACGCTGTATCTGCAAATGAACAGCC
TGAGAGCCGAGGACACGGCTGTGTATTACTGTGCGAGAGAGTATGGTTCGG
GGAGTTATTATAACGTCTACTACGGTATGGACGTCTGGGGCCAGGGGACCA
CGGTCACCGTCTCCTCA |
| 242 | 34D1_21B3 | VL | GATATTGTGATGACTCAGTCTCCACTCTCCCTGCCCGTCACCCCTGGAGAGC
CGGCCTCCATCTCCTGCAGGTCTAGTCAGAGCCTCCTGCATAGCAATGGATA
CAAGTATTTGGATTGGTATCTGCAGAAAGCAGGGCAGTCTCCACACCTCTTG
ATCTATTTGGGTTCTAATCGGGCCTCCGGGGTCCCTGACAGGTTCAGTGGCA
GTGGATCAGGCACAGATTTTACACTGAAAATCAGCAGAGTGGAGGCTGAGG
ATGTTGGATTTTATTACTGCATGCAAACTCTACAAATTCCGCTCACTTTCGG
CGGAGGGACCAAGCTGGAGATCAAA |
| 243 | 33H2_21B1 | VH | GAGGTGCAGGTGGTGGAGTCTGGGGGAGGCTTGGTCCAGCCTGGGGGGTCC
CTGAGACTCTCCTGTGCAACCTCTGGATTCACCTTTAGAAGCTATTGGATGA
CCTGGGTCCGCCAGGCTCCAGGGAAGGGGCTGGAGTGGGTGGCCAATATAA
AGCAGGATGAAGTGAGAGACACTATGTGGACTCTGTGAAGGGCCGATTCA
CCATCTCCAGAGACAACGCCAAGACATCACTGTATCTGCAAATGAGCAGCC
TGAGAGCCGAGGACACGGCTATGTATTACTGTGCGAGAGAGGGGTACTATG
GTTCGGGCTACTTTGACTACTGGGGCCAGGGAACCCTGGTCACCGTCTCCTC
A |
| 244 | 33H2_21B1 | VL | GACATCCAGATGACCCAGTCTCCCTCCACCCTGTCTGCATCTGTAGGAGACA
GAGTCATCATCACTTGCCGGGCCAGTCAGAGTATTAGTAGGGGGTTGGCCT
GGTATCAGCAGAAACAGGGAAAGCCCCTAAACTCTTGATCTATAAGGCGT
CTAATTTAGAAAGTGGGGTCCCATCAAGGTTCAGCGGCAGTGGATCTGGGA
CAGAATTCACTCTCACCATCAGCAGCCTGCAGCCTGATGATTTTGCAGCTTA
TTACTGCCAACAGTATAGTTATTATTCTCACACTTTTGGCCAGGGGACCAAG
GTGGAGATCAAA |
| 245 | 36A12_21C1 | VH | GAGGTGCAACTGGTGGAGTCTGGGGGAGGCTTGGTCCAGCCTGGGGGGTCC
CTGAGACTCTCCTGTGCAGCCTCTGGATTCACCTTAAGTTTCTATTGGATGA
CCTGGGTCCGCCAGGCTCCAGGGAAGGGGCTGGAGTGGGTGGCCAACATAA
AGCAAGATGGAAATGAGAAAAACTATGTGGACTCTGTGAAGGGCCGATTCA
CCATCTCCAAAGACAACGCCAAGAAATCAGTGTTTCTGCAAATGAACAGCC
TGAGAGCCGAGGACACGGCTGTGTATTACTGTGCGAGAGAGGGGTACTTTG
GTTCGGGCTACTTTGACTACTGGGGCCAGGGAACCCTGGTCACCGTCTCCTC
A |
| 246 | 36A12_21C1 | VL | GACATCCAGATGACCCAGTCTCCTTCCACCCTGTCTGCATCTGTGGGAGACA
GAGTCACCATCACTTGTCGGGCCAGTCAGAGTATTAATAGCTGGTTGGCCTG
GTATCAGCAGAAACCAGGGAAAGCCCCTAAGCTCCTGATCTATAAGGCGTC
TACTTTAGAAAGTGGGGTCCCATCAAGGTTCAGCGGCAGTGGATCTGGGAC
AGAATTCACTCTCACCATCAGCAGCCTGCAGCCTGATGATTTTGCACCTTAT
TACTGCCAGCATTATAATAGTTATCCTCACACTTTTGGCCAGGGGACCAAGG
TGGAGATCAAA |
| 247 | 38G11_28A2 | VH | GAGGTGCAGCTGGTGGAGTCTGGGGGAGGCTTGGTCCAGCCTGGGGGGTCC
CTGAGACTCTCCTGTGCAGCCTCTGGATTCACTTTTAGTAGTTATTGGATGA |

TABLE 6-continued

Variable region DNA sequences of human antibodies

| | | | |
|---|---|---|---|
| | | | GCTGGGTCCGCCAGGCTCCAGGGAAGGGGCTGGAGTGGGTGGCCAACATA<br>AAGCAAGATGGAAGTGAGAAACACTATGTGGACTCTGTGAAGGGCCGATTC<br>ACCATCTCCAGAGACAACGCCAAGAACTCACTGTATCTGCAAATGAACAGC<br>CTGAGAGCCGAGGACACGGCTGTGTATTACTGTGCGAGAGAGGGGTACTTT<br>GGTTCGGGCTACTTTGACTACTGGGGCCAGGGAACCCTGGTCACCGTCTCCT<br>CA |
| 248 | 38G11_28A2 | VL | GACATCCAGTTGACCCAGTCTCCATCCTTCCTGTCTGCATCTGTAGGAGACA<br>GAGTCACCATCACTTGCCGGGCCAGTCAGGGCATTAGCAGTTATTTAGCCTG<br>GTATCAGCAAAAACCAGGGAAAGCCCCTAAGCTCCTGATCTATGCTGCATC<br>CACTTTGCAAAGTGGGGTCCCATCAAGGTTCAGCGGCAGTGGATCTGGGAC<br>AGAATTCACTCTCACAATCAGCAGCCTGCAGCCTGAAGATTTTGCAACTTAT<br>TACTGCCAACAGTATAGTTTTTATTCTCACACTTTTGGCCAGGGGACCAAGC<br>TGGAGATCAAA |
| 249 | 40C3_22B6 | VH | GAGGTGCAACTGGTGGAGTCTGGGGGAGGCTTGGTCCAGCCTGGGGGGTCC<br>CTGAGACTCTCCTGTGCAGCCTCTGGATTCACCTTAAGTTTCTATTGGATGA<br>CCTGGGTCCGCCAGGCTCCAGGGAAGGGGCTGGAGTGGGTGGCCAATATAA<br>AGCAAGATGGAAATGAGAAAAACTTTGTGGACTCTGTGAAGGGCCGATTCA<br>CCATCTCCAGAGACAACGCCAAGAAATCAGTGTTTCTGCAAATGAACAGCC<br>TGAGAGCCGAGGACACGGCTGTGTATTACTGTGCGAGAGAGGGGTACTTTG<br>GTTCGGGCTACTTTGACTACTGGGGCCAGGGAACCCTGGTCACCGTCTCCTC<br>A |
| 250 | 40C3_22B6 | VL | GACATCCAGATGACCCAGTCTCCTTCCACCCTGTCTGCATCTGTAGGAGACA<br>GAGTCACCATCACTTGCCGGGCCAGTCAGAGTATTAATAGCTGGTTGGCCT<br>GGTATCAGCAGAAACCAGGGAAAGCCCCTAAGCTCCTGATCTATAAGGCGT<br>CTAGTTTAGAAAGTGGGGTCCCATCAAGGTTCAGCGGCAGTGGATCTGGGA<br>CAGAATTCACTCTCACCATCAGCAGCCTGCAGCCTGATGATTTTGCAACTTA<br>TTACTGCCAGCAGTATAATAGTTATCCTCACACTTTTGGCCAGGGGACCAAG<br>CTGGAGATCAAA |
| 251 | 5D12_18A4 & | VH | GACATCCAGTTGACCCAGTCTCCATCCTTCCTGTCTGCATCTGTAGGAGACA<br>GAGTCACCATCTCTTGCCGGGCCAGTCAGGGCATTAGCAGTTATTTGGCCTG<br>GTATCAGCAAAAACCAGGGAAAGCCCCTAAGCTCCTGATCTATGCTGCATC<br>CACTTTGCAAGGTGGGGTCCCATCAAGGTTCAGCGGCAGTGGATCTGGGAC<br>AACATTCACTCTCACAATCAGCAGCCTGCAGCCTGAAGATTTTGCAACTTAT<br>TACTGTCAACAGCTTAATACTTACCCATTCACTTTCGGCCCTGGGACCAAGC<br>TGGAGATCAAA |
| 252 | 5D12_18A4 | VL | GACATCCAGTTGACCCAGTCTCCATCCTTCCTGTCTGCATCTGTAGGAGACA<br>GAGTCACCATCTCTTGCCGGGCCAGTCAGGGCATTAGCAGTTATTTGGCCTG<br>GTATCAGCAAAAACCAGGGAAAGCCCCTAAGCTCCTGATCTATGCTGCATC<br>CACTTTGCAAGGTGGGGTCCCATCAAGGTTCAGCGGCAGTGGATCTGGGAC<br>AACATTCACTCTCACAATCAGCAGCCTGCAGCCTGAAGATTTTGCAACTTAT<br>TACTGTCAACAGCTTAATACTTACCCATTCACTTTCGGCCCTGGGACCAAGC<br>TGGAGATCAAA |
| 253 | 5D12_ C108Y | VH | CAGGTGCAGCTGCAGGAGTCGGGCCCAGGACTGGTGAAGCCTTTGGGGACC<br>CTGTCCCTCACCTGCGCTGTCTCTGGTGGCTCCATCAGCAATAGTAACTGGT<br>GGAGTTGGGTCCGCCAGCCCCCAGGAAGGGGCTGGAGTGGATTGGAGAA<br>ATCTATCATAGTGGGAGCACCAACTACAACCCGTCCCTCAAGAGTCGAGTC<br>ACCATAGCACTAGACTGGTCCAAGAACCAGTTCTCCCTGCAGCTGAGGTCT<br>GTGACCGCCGCGGACACGGCCGTGTATTACTGTGCGCGGTATGGTTCGGGT<br>CCTTTTGGCGGTGACTaCTGGGGCCAGGGAACCCTGGTCACCGTCTCCTCA |
| 252 | 5D12-C108Y | VL | GACATCCAGTTGACCCAGTCTCCATCCTTCCTGTCTGCATCTGTAGGAGACA<br>GAGTCACCATCTCTTGCCGGGCCAGTCAGGGCATTAGCAGTTATTTGGCCTG<br>GTATCAGCAAAAACCAGGGAAAGCCCCTAAGCTCCTGATCTATGCTGCATC<br>CACTTTGCAAGGTGGGGTCCCATCAAGGTTCAGCGGCAGTGGATCTGGGAC<br>AACATTCACTCTCACAATCAGCAGCCTGCAGCCTGAAGATTTTGCAACTTAT<br>TACTGTCAACAGCTTAATACTTACCCATTCACTTTCGGCCCTGGGACCAAGC<br>TGGAGATCAAA |
| 254 | 37D11_21C2 | VH | CAGGTGCAGATAAAGGAGTCGGGCCCAGGACTGGTGAAGCCTTCGGAGAC<br>CCTGTCCCTCACCTGCGCTGTCTCTGGTTTCTCCTTCAGCAGTGGTTATTACT<br>GGGGCTGGATCCGGCAGCCCCCAGGGAAGGGTCTGGAGTGGCTTGGGAGTT<br>TCTTTCATAATGGGAATACCTACTACAACCCGTCCCTCAGGAGTCGAGTCAC<br>CATCTCAGTAGACACGTCCAAGAACCACTTCTCCCTGAAGCTGACCTCTGTG<br>ACCGCCGCAGACACGGCCGTGTATTACTGTGCGGGATTCGGGGACTTACCC<br>CATTATCATTATTACGTTATGGACGTCTGGGGCCAAGGGACCACGGTCACC<br>GTCTCCTCA |
| 255 | 37D11_21C2 | VL | GAAATTGTGTTGACACAGTCTCCAGCCACCCTGTCTTTGTCTCCAGGGGAAA<br>GAGCCACCCTCTCCTGCAGGGCCAGTCAGAGTGTTAGCAGCTACTTAGCCT<br>GGTACCAACAGAAACCTGGCCAGGCTCCCAGGCTCCTCATCTATGATGCAT<br>CCAACAGGGCCATTGGCATCCCAGCCAGGTTCAGTGGCAGTGGGTCTGGGA<br>CAGACTTCACTCTCACCATCAGCAGCCTAGAGCCTGAAGATTTTGCAGTTTA |

TABLE 6-continued

Variable region DNA sequences of human antibodies

| | | | |
|---|---|---|---|
| | | | TTACTGTCAGCAGCGTAGCAACTGGCCTCCGTACACTTTTGGCCAGGGGACC<br>AAGCTGGAGATCAAA |
| 256 | 42D10_28A5 | VH | CAGGTGCAGCCAAAGGAGTCGGGCCCAGGAGTGGTGAAGCCTTCGGAGAC<br>CCTGTCCCTCACCTGCGCTGTCTCTGGTTTCCCCATCAGCCGTGGTTATTACT<br>GGGGCTGGATCCGGCAGCCCCCAGGGAAGGGTCTGGAGTGGATTGGGAAT<br>ATCTTTCATAGTGGGACCACCTACTACAATCCGTCCCTCAAGAGTCGAGTCA<br>CCATCTCAGTAGACACGTCCAAGAACCAGATCTCCCTGAAGCTGACCTCTGT<br>GACCGCCGCAGACACGGCCGTATATTATTGTGTGGGATTCGGGGACTTGCC<br>CCACTACCAATATTACGTTATGGACATCTGGGGCCAAGGGACCACGGTCAC<br>CGTCTCCTCA |
| 257 | 42D10_28A5 | VL | GAAATTGTGTTGACACAGTCTCCAGCCACCCTGTCTTTGTCTCCAGGGGAAA<br>GAGCCACCCTCTCCTGCAGGGCCAGTCAGAGTGTTAGCAGCTACTTAGCCT<br>GGTACCAACAGAAACCTGGCCAGGCTCCCAGGCTCCTCATCTATGATGCAT<br>CCAACAGGGCCACTGGCATCCCAGCCAGGTTCAGTGGCAGTGGGTCTGGGA<br>CAGACTTCACTCTCACCATCAGCAGCCTAGAGCCTGAAGATTTTGCAGTTTA<br>TTACTGTCAGCAGCGTAGCAACTGGCCTCCGTACACTTTTGGCCAGGGGACC<br>AAGCTGGAGATCAAA |
| 258 | 34H8_21B4 | VH | CAGGTGCAGCTGCAGGAGTCGGGCCCAGGACTGGTGAAGCCTTCGGAGACC<br>CTGTCCCTCACCTGCGCTGTCTCTGGTTACTCCGCCAGCGGTCTTTACTACTG<br>GGCCTGGATCCGGCAGCCCCCAGGGAAGGGACTGGAGTGGATTGGAAATAT<br>CTATCATAGTGGGAGAACCTACTACAATCCGTCCCTCGAGAGTCGAGTCAG<br>CATATCACTAGACACGTCCAAGCACCAGGTCTCCCTGAAACTGAAATCTGT<br>GACCTACGCAGACACGGCCGTGTATTTCTGTGCGAGAGATAGGTTTGATGG<br>TTTTGATATTTGGGGCCAAGGGACAATGGTCACCGTCTCCTCA |
| 259 | 34H8_21B4 | VL | GAAATAGTGATGACGCAGTCTCCAGCCACCCTGTCTGTGTCTCCAGGGGAA<br>AGAGCCACCCTCTCCTGCAGGGCCAGTCAGACTATTAACAACATCTTAGCCT<br>GGTACCAGCAGAAACCTGGCCAGGCTCCCAGGCTCCTCATCTATGGTGCAT<br>CCACCAGGGCCACTGGTATCCCAGCCAGGTTCAGTGGCAGTGGGTCTGGGA<br>CAGAGTTCACTCTCACCATCAGCAGCCTGCAGTCTGAAGATTTTGCAGTTTA<br>TTACTGTCAGCAGTATAATAACTGGCCTCTCACTTTCGGCGGAGGGACCAA<br>GCTGGAGATCAAA |

The affinity of the thirty six antibodies was calculated using huIL1-RAP ECD recombinant protein by Octet™. Values ranged from 0.2 nM to 127 nM (see Table 7, below).

TABLE 7

$K_D$ values for anti-IL1-RAP Antibodies

| Sample | KD (human) |
|---|---|
| 5G8_18A1 | 0.4 nM |
| 10C8_15A1 | 30 nM |
| 10C8_C43A | 13 nM |
| 10C8_15A4 | 1 nM |
| 12F3_17C2 | 12 nM |
| 16H2_17D2 | 0.2 nM |
| 32C12_21A4 | 1.4 nM |
| 32C12-N26S | 19 nM |
| 34C11_21B2 | 0.2 nM |
| 36A10_21B6 | 0.4 nM |
| 39G1_21C4 | 1.6 nM |
| 37E10_15B5 | 0.3 nM |
| 44E5_15C5 | 0.4 nM |
| 38E10_21C3 | 2 nM |
| 16H2_17D1 | 50 nM |
| 24G3_17C5 | 37 nM |
| 26C5_15B4 | 127 nM |
| 17E9_15B1 | 21 nM |
| 32A2_21A3 | 2 nM |
| 41G4_15B6 | 5 nM |
| 31F9_21A1 | 2 nM |
| 32D4_21D6 | 3 nM |
| 32F9_21A5 | 2 nM |
| 33E9_21A6 | 2 nM |
| 35D11_22A1 | 3 nM |
| 39A9_28A4 | 3 nM |
| 34D1_21B3 | 3 nM |
| 33H2_21B1 | 7 nM |

TABLE 7-continued $K_D$ values for anti-IL1-RAP Antibodies

| Sample | KD (human) |
|---|---|
| 36A12_21C1 | 24 nM |
| 38G11_28A2 | 29 nM |
| 40C3_22B6 | 23 nM |
| 5D12_18A4 | 19 nM |
| 5D12-C108Y | 13 nM |
| 37D11_21C2 | 13 nM |
| 42D10_28A5 | 7 nM |
| 34H8_21B4 | 5 nM |

Results

Fully human antibodies against IL1RAP were generated by hybridoma procedures. Briefly, transgenic mice were immunized with either recombinant human IL1RAP-ECD or 293T cells overexpressing IL1RAP and boosted with rabbit splenocytes expressing full length human IL1RAP or with ECD of IL1RAP recombinant protein. Splenocytes were fused with the mouse myeloma cell line X63-Ag8.653. Clones from the transgenic mice were identified by immunofluorescence (IF) based high content screening (HCS) on CHO cells overexpressing hIL1RAP, and parental CHO cells not expressing IL1RAP.

Over 1,000 hits were identified that bind strongly to CHO-human IL1RAP, but not parental CHO cells. 68 clones were selected for molecular cloning. Based on unique CDR3 sequences from the heavy chain variable domain, 35 antibodies from 13 families were confirmed by binding in RAP positive cell lines EMI and Karpas 299 (see Table 8) by flow cytometry (MACSQuant® www.miltenybiotec.com). Binding properties of representative antibody clone 44E5_15C5 is shown in FIG. 2.

TABLE 8

Anti-IL1RAP antibodies binding to endogenous cell lines by flow cytometry.

| Ab families | Clone ID | EOL-1 | Karpas 299 | MOLT3 | DMS79 | H69 |
|---|---|---|---|---|---|---|
| 1 | 38E10_21C3 | (+++) | (++/+++) | (+) | | |
| 2 | 10C8_15A4 | (+++) | (+++) | | (−) | |
|   | 16H2_17D1 | (+++) | (+++) | | (−) | |
|   | 26C5_15B4 | (+++) | (+++) | | (−) | |
|   | 24G3_1705 | (++) | (++) | | ND | |
| 3 | 16H2_17D2 | (+++) | (++++) | | (+/−) | |
| 4 | 17E9_15B1 | (+++) | (+++) | | (+/−) | |
|   | 12F3_17C2 | (+++) | (+++) | | ND | |
| 5 | 10C8_15A1 | (+++) | (++++) | (−) | ND | |
| 6 | 32A2_21A3 | (+++) | (++++) | (+) | | |
|   | 41G4_15B6 | (+++) | ND | | ND | |
|   | 32C12_21A4 | (+++) | (++++) | (+) | | |
| 7 | 31F9_21A1 | (+++) | (++++) | (+) | | |
|   | 32F9_21A5 | (+++) | (++++) | (+) | | |
|   | 33E9_21A6 | (+++) | (++++) | (+) | | |
|   | 32D4_21D6 | (+++) | (++++) | (+) | | |
|   | 35D11_22A1 | (+++) | (++++) | (+) | | |
|   | 37E10_15B5 | (+++) | (++++) | | (−) | |
|   | 44E5_15C5 | (+++) | (++++) | | (−) | |
|   | 39A9_28A4 | (+++) | (++++) | (−) | | |
| 8 | 34D1_21B3 | (+++) | (++) | (+) | | |
|   | 36A10_21B6 | (+++) | (++) | (+) | | |
| 9 | 36A12_21C1 | (+++) | (+++) | (+) | | |
|   | 40C3_22B6 | (+++) | (+++) | | | |
|   | 33H2_21B1 | (+++) | (+++) | (+) | | |
|   | 34C11_21B2 | (+++) | (+++) | (+) | | |
|   | 38G11_28A2 | (++) | (++) | | (−) | |
| 10 | 5D12_18A4 | (+++) | (++) | | ND | |
| 11 | 5G8_18A1 | (+++) | (+/++) | | (−) | |
|   | 9G4_22B3 | (++/+++) | (+) | | | |
| 12 | 37D11_21C2 | (++/+++) | (++) | (+/−) | | |
|   | 42D10_28A5 | (++) | (++) | | (−) | |
| 13 | 34H8_21134 | (+++) | (++++) | (+) | | |
|   | 39G1_21C4 | (+++) | (++++) | (+) | | |

(−) No binding
(+) Weak binding
(++) Moderate binding
(+++) Strong binding
ND Not determined Selected antibodies were evaluated in pairs for their ability to simulataneously bind recombinant human IL1-RAP. The analysis was performed by Octet™ loaded with Protein A Biosensors. A total of five different bins were determined as follows. Some of the bins overlapped with each other such that a given antibody may be in more than one bin.

(1) The following five antibodies competed with each other for binding: 5D12_18A4, 24G3_17C5, 34C$_{11-21}$B2, 38E10_21C3, 39G1_21C4.

(2) The following six antibodies competed with each other: 1008_15A1, 16H2_17D2, 32C12_21A4, 37E10_15B5, 44E5_15C5, 5G8_18A1.

(3) Two antibodies competed with each other in a unique arrangement—5G8_18A1, 36A10_21B6.

(4) Two antibodies competed with each other in a unique arrangement—36A10_21B6, 37D11_21C2.

(5) Two antibodies competed with each other in a unique arrangement—37D11_21C2, 12F3_17C2.

A diagram representing the arrangement of these competing bins shown in FIG. 3.

Example 3. Antigen Density of IL1RAP in Leukemia Cell Lines

Experiments were performed to determine IL1RAP antigen density in leukemia cell lines. The following methods were used.
Methods
Tissue Culture and Cell Lines
Human leukemia cell lines EOL1, MV (4;11), MOLM 13, MOLM 14, OCI/AML1, KG-1, Karpas 299, and SUDHL4 were obtained from either ATCC or DSMZ. Cells were maintained in RPMI-1640 medium (Invitrogen) with 10% fetal bovine serum (FBS) (Sigma).
Antigen Density Measurement
The antigen density of IL1RAP on the cell surface of cancer cell lines was quantified using BD Quantibrite™ Beads PE fluorescence Quantitation kit (BD Bioscience, Cat. #340495) and a human IL1RAP antibody (44E5_15C5) conjugated to the fluorochrome PE.
Results
PE conjugated anti-IL1RAP antibody (44E5_15C5) was chosen to evaluate antigen density. Cell surface IL1RAP density in these cell lines is summarized in Table 9.

TABLE 9

Antigen density of IL1RAP in leukemia cell lines.

| Cell lines | Cell Surface Ag density |
|---|---|
| EOL1 | 9670 |
| MV (4; 11) | 24036 |
| OCI/AML1 | 3012 |
| MOLM13 | 10969 |
| MOLM14 | 10243 |
| KG-1 | 1194 |
| Karpas 299 | 42824 |
| SUDHL4 | 184 |

Example 4. Binding of Anti-IL1RAP Monoclonal Antibodies to IL1RAP Orthologs

Figure 4C:
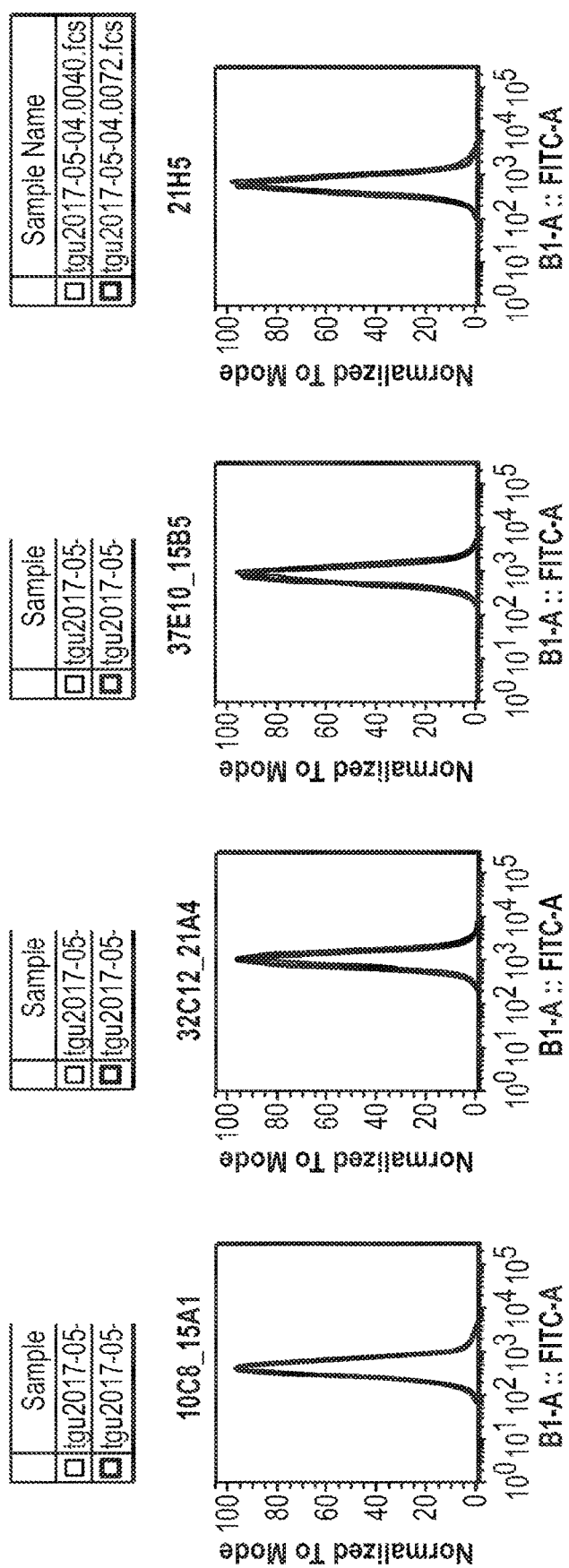
Figure 4C:
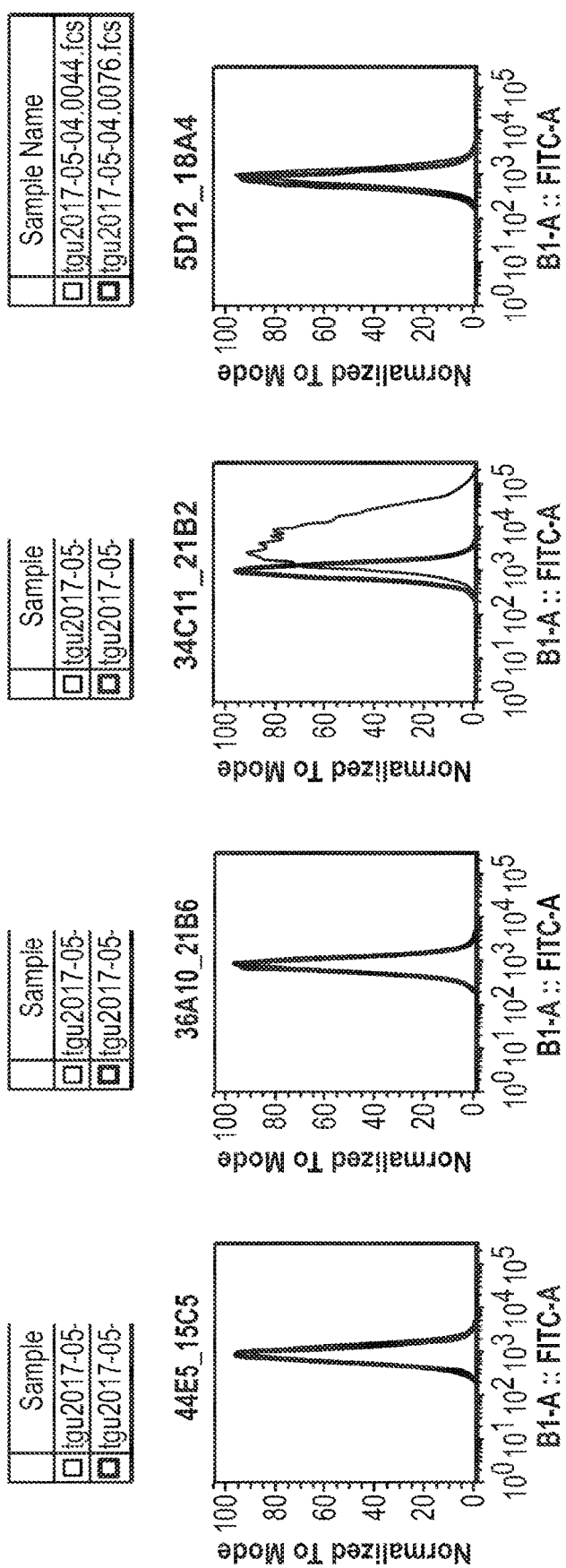
Figure 4C:
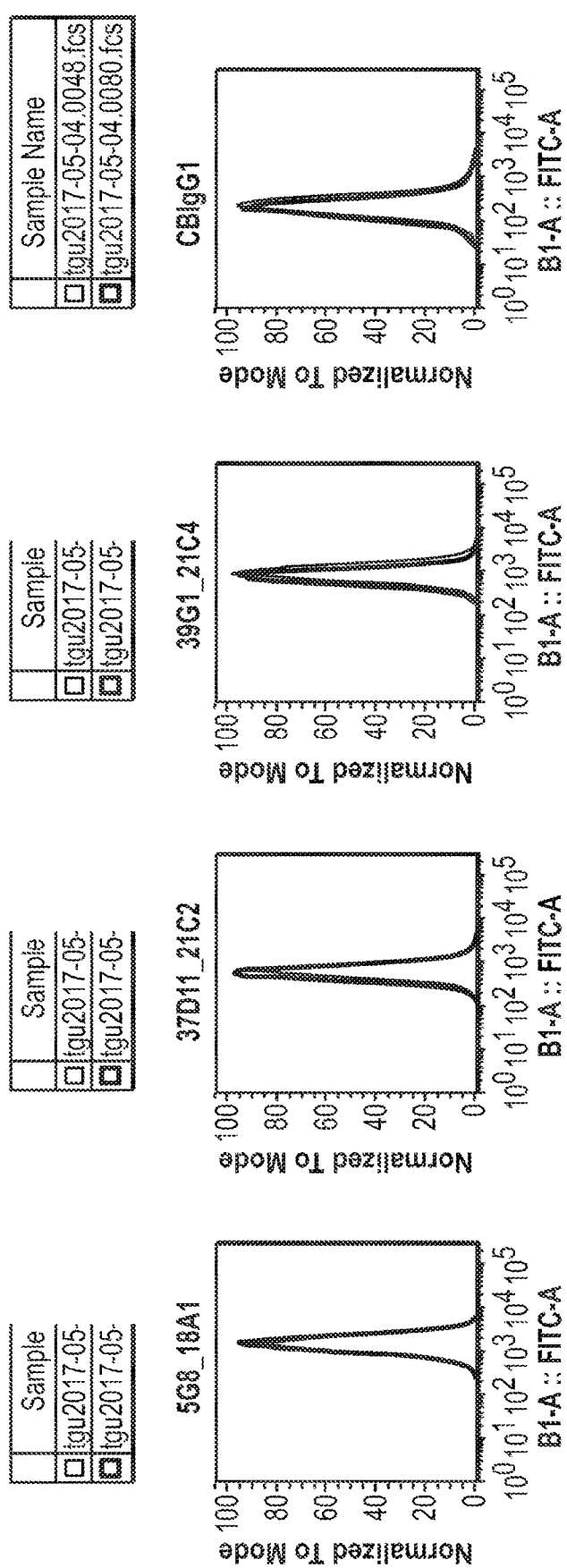
Figure 4D:
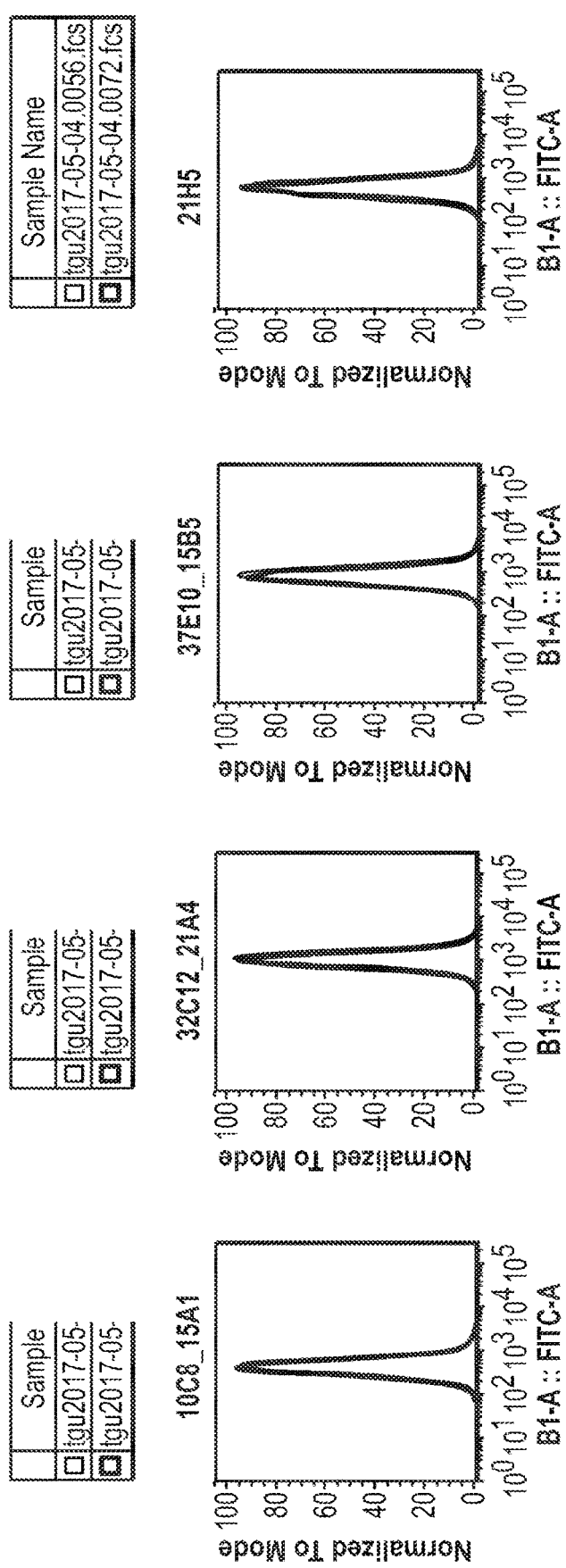
Figure 4D:
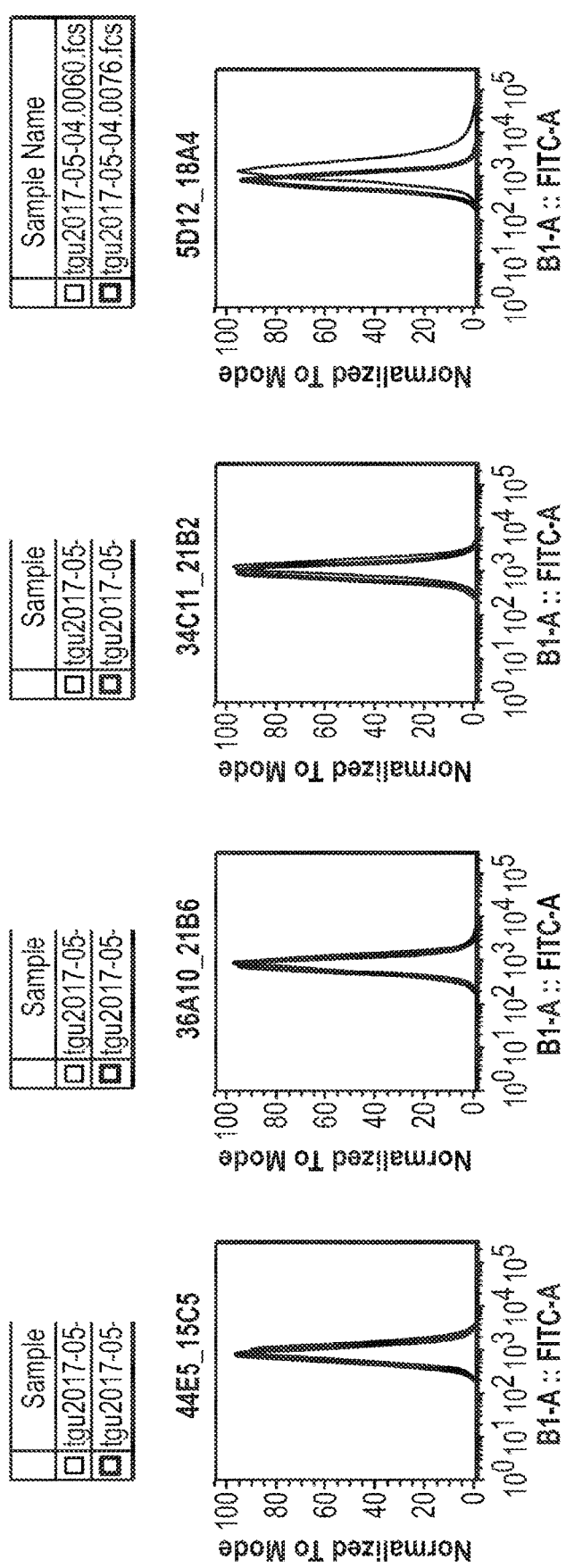
Figure 4D:
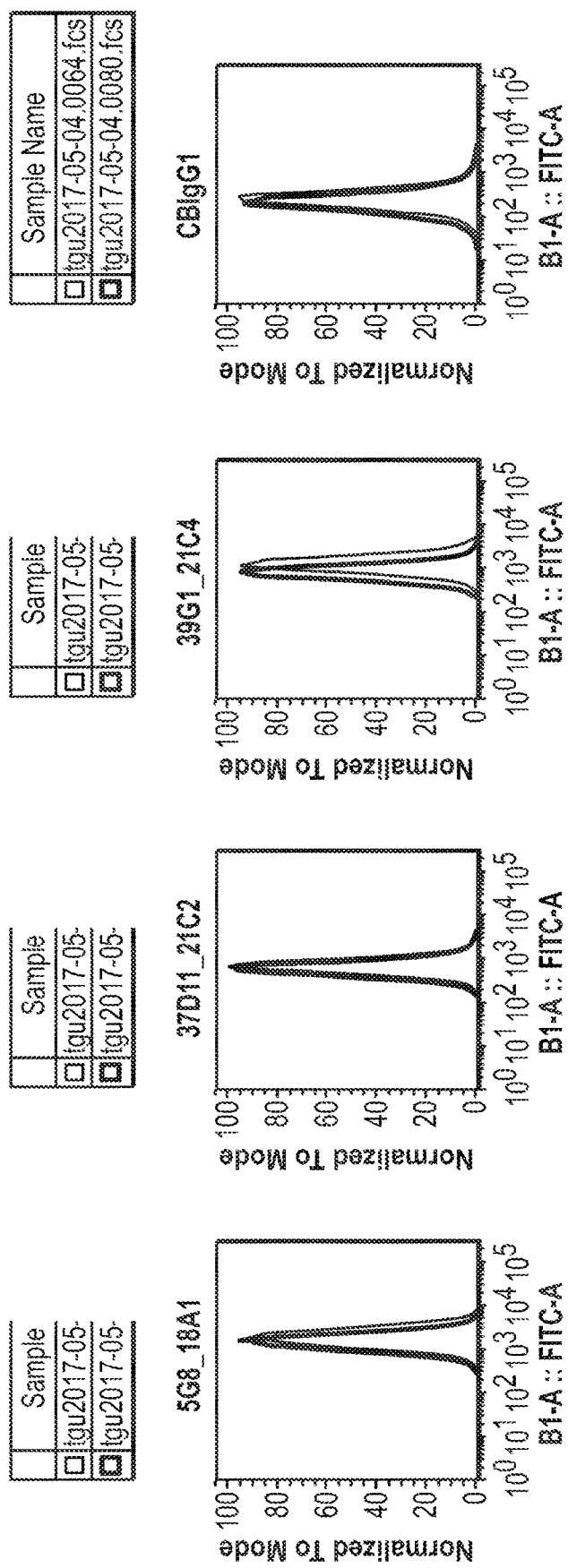

Experiments were performed to determine the binding of anti-IL1RAP human monoclonal antibodies to IL1RAP in different species. The following methods were used.
Methods
Tissue Culture and Cell Lines
293T cell line was purchased from American Type Culture Collection (ATCC). 293T cells expressing human, Macaca fascicularis, rat, and mouse IL1RAP were maintained in DMEM medium (Invitrogen) with 10% fetal bovine serum (FBS) (Sigma) in the presence of 2 ug/ml puromycin (Invitrogen).
Flow Cytometry
Staining for flow cytometry was performed in 1× cold PBS with 0.5% BSA. Primary antibodies (1 ug/ml) were incubated with live cells on ice for 30 minutes, after a brief wash, cells were incubated with Alexa Fluro® 488-conjugated anti-human IgG secondary antibody @1:1000 (709-546-149, Jackson ImmunoResearch). Acquisition of the data was performed on a MACSQuant® Flow Cytometers (Miltenyi Biotec) and analyzed with FlowJo software.
Results
To evaluate the binding of anti-IL1RAP human monoclonal antibodies to IL1RAP in different species, 293 cells overexpressing human, Macaca fascicularis, rat, and mouse IL1RAP were generated. While all antibodies bind human and Macaca fascicularis IL1RAP (FIGS. 4A-4B), 24G3_17C5 and 34C11_21B2 bind 293 cells expressing rat IL1RAP and 24G3_17C5, 5D12_18A4, and 39G1_21C4 bind weakly to 293 cells expressing mouse IL1RAP (FIGS. 4C-4D).

Example 5. Internalization of Anti-IL1RAP Antibody in AML Cell Line

Experiments were performed to characterize anti-IL1RAP antibody internalization in EOL-1 cells. The following methods were used.
Methods
Tissue Culture and Cell Lines
Human leukemia cell lines EOL1 was obtained from DSMZ. They were maintained in RPMI-1640 medium (Invitrogen) with 10% fetal bovine serum (FBS) (Sigma).
Internalization Assay
Live EOL1 cells were incubated with 44E5_15C5 antibody for 30 minutes at 37° C. After cytospin, cells were fixed with 4% PFA and permeablized with 100% methanol, and stained with LAMP1 antibody (#9091, Cell Signaling Technology, Inc.).
Results
Live EOL1 cells were incubated with 44E5_15C5 for 0.5 hours at 37° C. Cells were then fixed, permeablized, and co-stained with LAMP1 antibody. 44E5_15C5 is co-localized to lysozyme, marked by LAMP1 antibody (see FIG. 5).

Example 6. Antibody Internalization and In Vitro Cytotoxicity by Secondary ADC

Figure 6B:
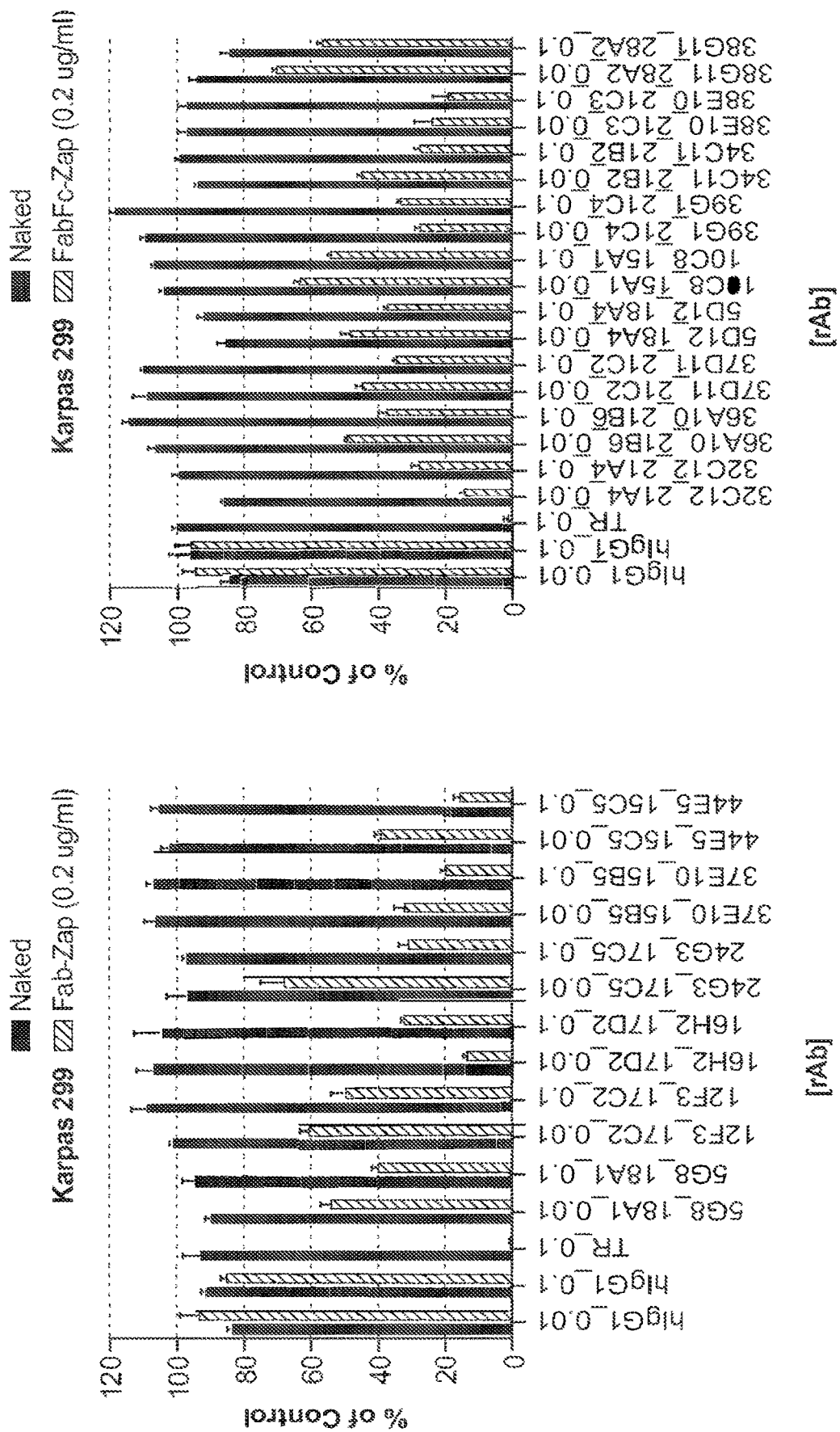
Figure 7A:
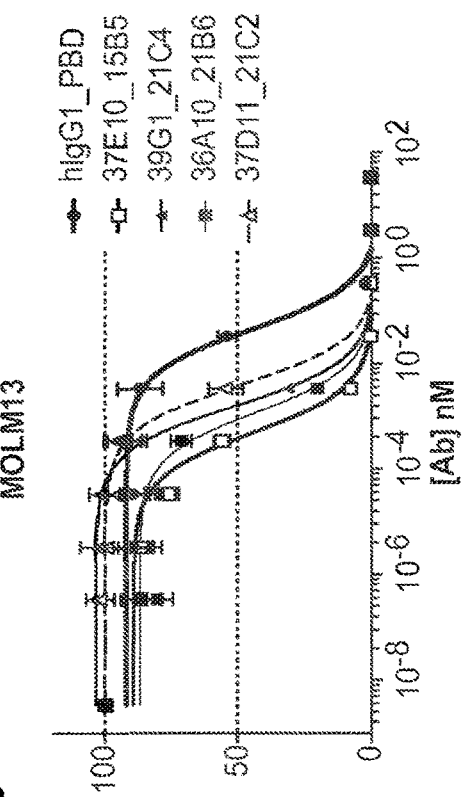
FIGS. 7A, 7B, 7C, 7D, 7E and 7F show in vitro efficacy of anti-IL1RAP ADC in AML cell lines EOL1 (FIG. 7A), MOLM13 (FIG. 7B), MOLM14 (FIG. 7C), MV (4;11) (FIG. 7D), OCI/AML1 (FIG. 7E), and KG-1 (FIG. 7F). 3,000 cells were seeded in 96 well plates, and treated with Tesirine PBD conjugated antibodies for 5 days. Then cells were lysed by CellTiter Glo™ 2.0 (Promega), results were recorded by luminometer. hIgG1 (anti-HBV surface Ag antibody, in house) conjugated antibody was included as a negative control. IC50 values are listed at the bottom of each graph.
Figure 7B:
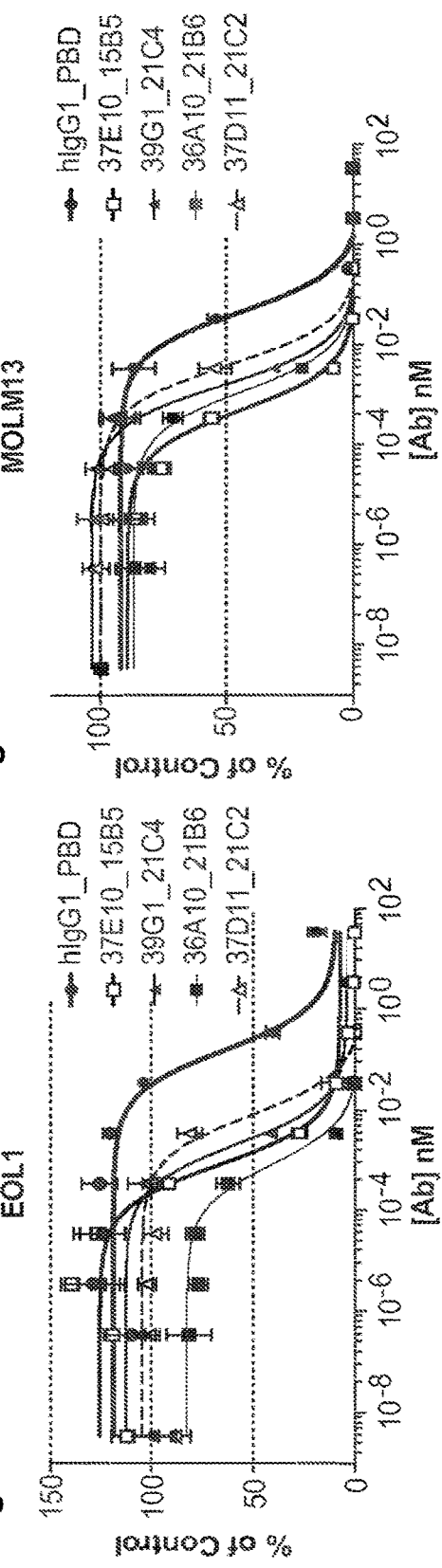
Figure 7C:
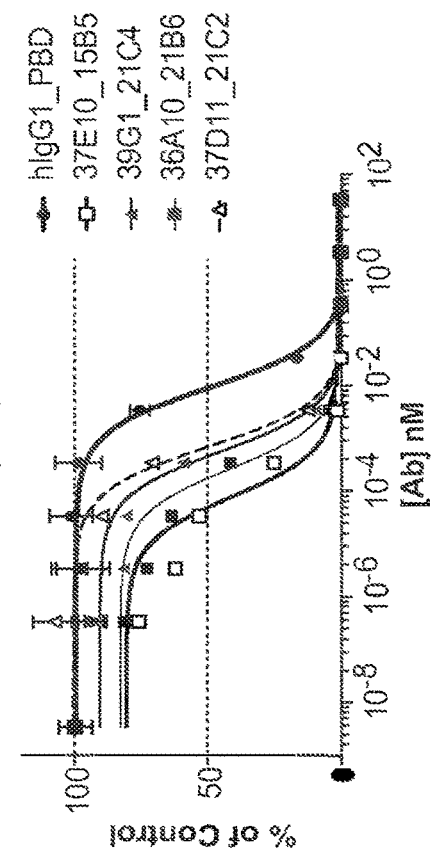
Figure 7D:
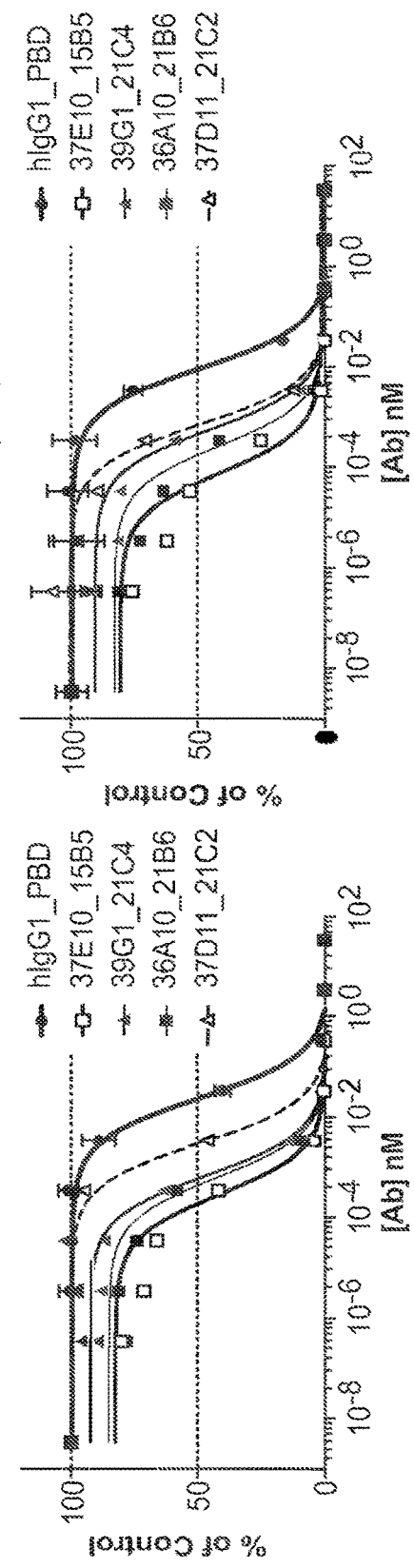
Figures 7E, 7F:
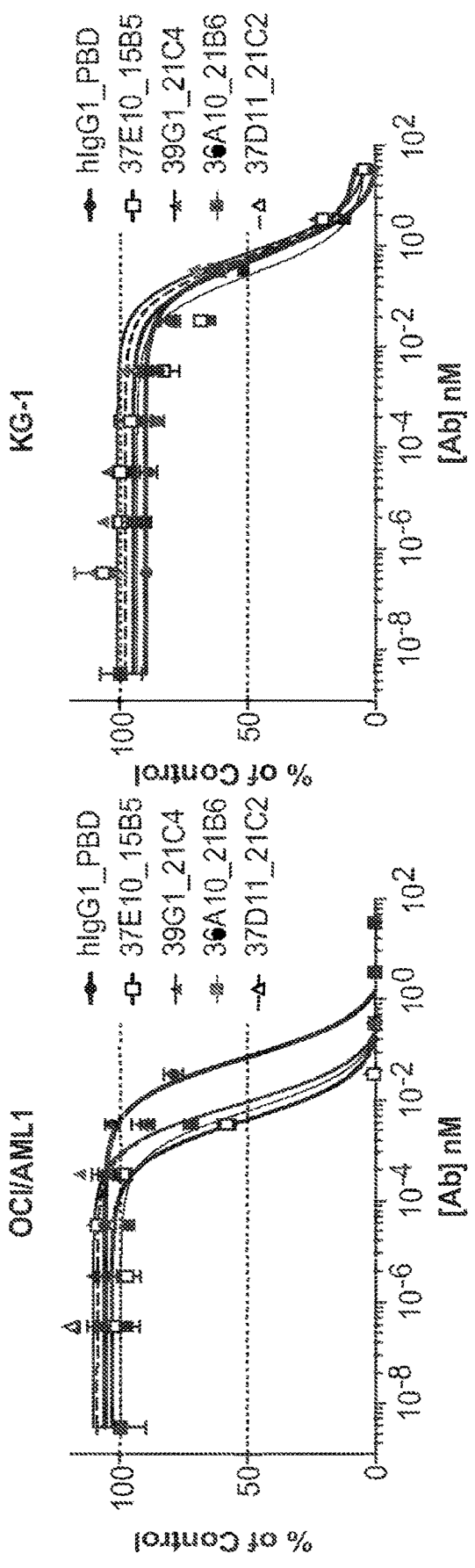

The following experiments were performed to characterize anti-IL1RAP antibody internalization and in vitro cytotoxicity.
Methods
Internalization and In Vitro Cytotoxicity
5000 cells/50 ul/well of different cell lines were plated in 96-well microplates. Primary antibodies (0.01 ug/ml, or 0.1 ug/ml final concentration) and Fab-Zap™ or FabFc-Zap™ at 0.2 ug/ml final concentration (Advanced targeting systems) were added in a volume of 50 ul. The plates were incubated for 72 hours at 37° C. in the presence of 5% CO2. For each plate, 100 ul/well of Cell Titer-Glo™ reagent (#G7573 and #G9243, Promega) was added and allowed to shake for 2 minutes and incubate at room temperature for 30 minutes prior to reading on a luminescent plate reader. Data was analyzed using GraphPad™ Prism. Transferrin receptor (TR) and hIgG1 antibodies were included as positive and negative controls.
Results
Antibody internalization and secondary ADC efficacy was evaluated with Fab-Zap™ (or FabFc-Zap) as a conjugated secondary reagent. Fab-ZAP™ uses a human primary antibody to target and eliminate cells. This secondary conjugate is used to evaluate the potential of a primary antibody to internalize. Clearly, most antibodies showed good efficacy in both EOL1 and Karpas 299 cell lines, indicating that these antibodies underwent internalization and released saporin toxin inside cells, and these two cell lines were sensitive to saporin (FIGS. 6A and 6B). On the other hand, there was no cytotoxicity in IL1RAP negative DMS79 cell line (FIG. 6C).

Example 7. In Vitro Cytotoxicity by Primary Antibody Drug Conjugates

Experiments were performed to characterize the in vitro efficacy of anti-IL1RAP PBD conjugated antibody. The following methods were used.
Methods
Tissue Culture and Cell Lines
Human leukemia cell lines (EOL1, MOLM 13, MOLM 14, MV (4;11), OCI/AML1, and KG-1) were obtained either from ATCC or DSMZ. They were maintained in RPMI-1640 medium (Invitrogen) with 10% fetal bovine serum (FBS) (Sigma).
Antibody Drug Conjugation
Human monoclonal antibodies were conjugated to the valine-alanine-pyrrolobenzodiazepine, MA-PEG8-VA-PAB-SG3199 (PBD as previously described in, for example, Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.).

Briefly, each antibody was partially reduced with an appropriate molar amount of TCEP for 2 hours at 37° C. After incubation, the antibodies were cooled to room temperature and a 6-fold molar excess of PBD was added to the partially reduced antibody for 1 hour. After this incubation, the entire mixture was run over a gel filtration column to remove free drug. A fraction of the eluate was then used for concentration and DAR determination using A280 and HIC respectively. The drug to antibody ratio for 37E10_15B5-PBD, 39G1_21C4-PBD, 36A10_21B6-PBD, and 37D11_21C2-PBD was 3.1, 2.5, 2.7, and 2.4, respectively. The drug to antibody ratio for control human IgG1-PBD (control) was 3.0.
In Vitro Efficacy
Cells were seeded onto 96 well plate at 3000 cells/well. ADCs were added to the wells in complete culture medium in a serial dilution. Each treatment was replicated in 2 wells. 5 days later, cell viability was measured by CellTiter™ Glo Luminescent Cell viability assay (Promega) according to manufacturer's instructions. Cell viability was graphed by Prism™ using ratio of cell viability of test conditions to that of control wells that are treated with growth medium only.
Results
Anti-IL1RAP antibodies were conjugated to Tesirine PBD, a DNA damage agent. Primary conjugated antibodies were evaluated for in vitro efficacy against a series of AML cell lines. PBD conjugated antibodies showed great efficacy in AML cell lines in an antigen density dependent manner (see FIGS. 7A-7F and Table 9).

Example 8. Blockage of IL1 Signaling by Anti-IL1RAP Antibody

The following experiments were performed to characterize the ability of anti-IL1RAP antibody to block IL1 signaling.
Methods
IL-1 Signaling Reporter Cell Assay
HEK-Blue IL-1β cells (Invivogen, CA) were harvested and plated in technical duplicates at a density of 50,000 cells per well in a 96-well plate. IL1RAP antibodies, or a corresponding human IgG1 control antibody was added to the wells in a concentration range of 1-10 µg/ml. After incubating cells with antibodies for 30 minutes, IL-1β was added to a final concentration of 0.5 ng/ml, and the plate was incubated overnight. To examine whether any of the antibodies were able to induce IL-1R activation in the absence of IL-1β, samples were incubated with 10 µg/mL antibody without addition of the ligand. The following day, substrate was added to the supernatants, and samples were analyzed for absorbance at 620 nm.

Results

Figure 8A:
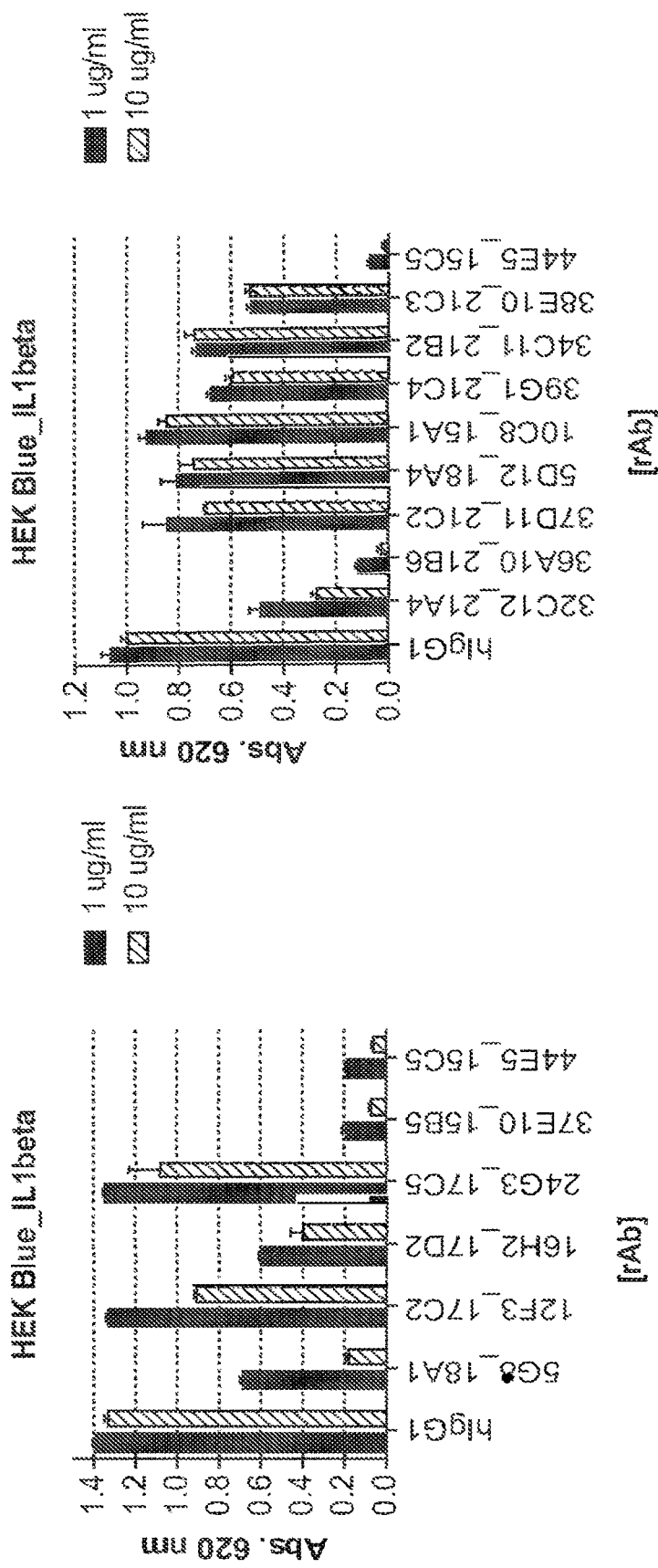
FIGS. 8A, 8B, and 8C show blockage of IL1α/β signaling by anti-IL1RAP antibodies. IL1RAP antibodies 37E10_15B5, 44E5_15C5, 16H2_17D2, and 36A10_21B6 displayed potent inhibition of IL1R1 signaling in a dose dependent manner (FIG. 8A). Antibodies 37E10_15B5 and 44E5_15C5 block IL-1β and IL-1α signaling with subnanomolar EC$_{50}$ (FIGS. 8B and 8C).

Since IL1RAP is essential for IL1 signaling, the ability of the IL1RAP antibodies described herein to inhibit IL-1 signaling was investigated. Whereas antibodies showed various degrees of inhibitory effect in an IL-1 reporter assay, IL1RAP antibodies 37E10_15B5, 44E5_15C5, 16H2_17D2, 5G8_18A1 and 36A10_21B6 displayed potent inhibition of IL1R1 signaling in a dose dependent manner (FIG. 8A).

None of the IL1RAP antibodies tested affected IL1R1 signaling in the absence of IL-1, thereby excluding agonistic functions on IL1 induced signaling.

Figure 8B:
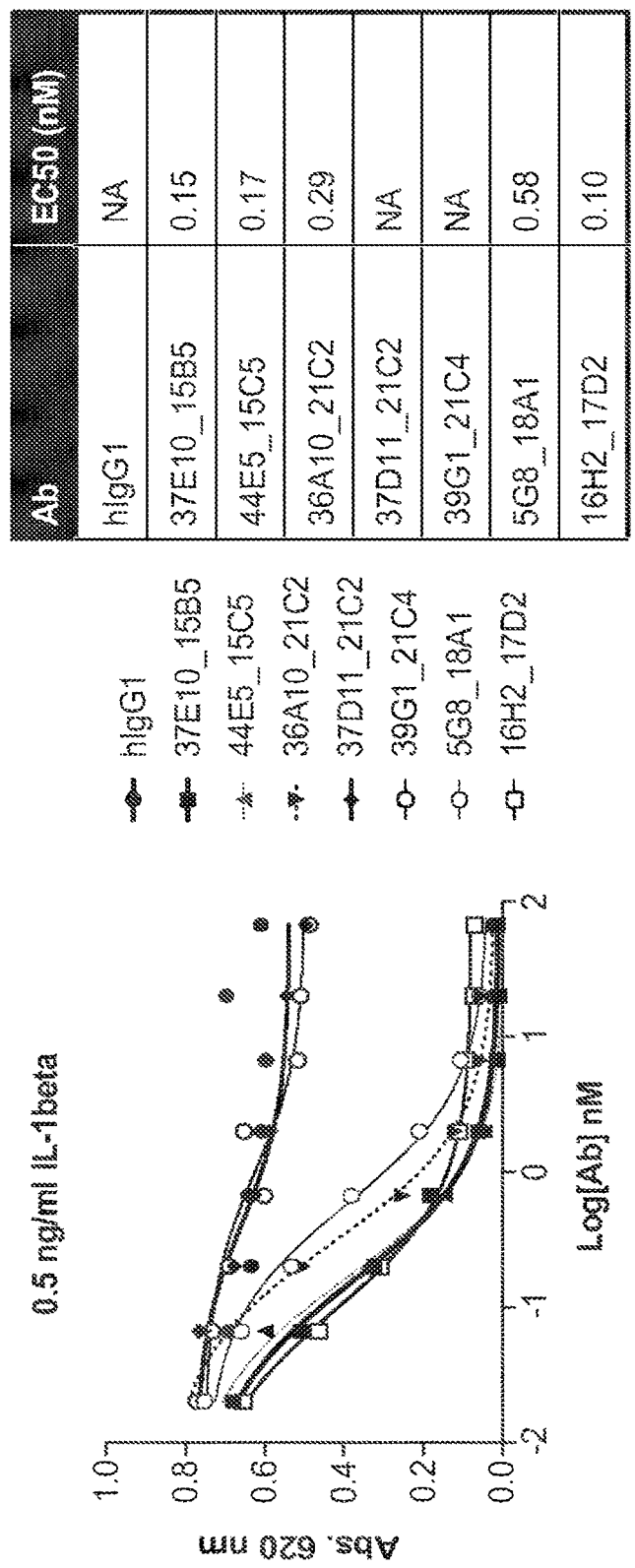
Figure 8C:
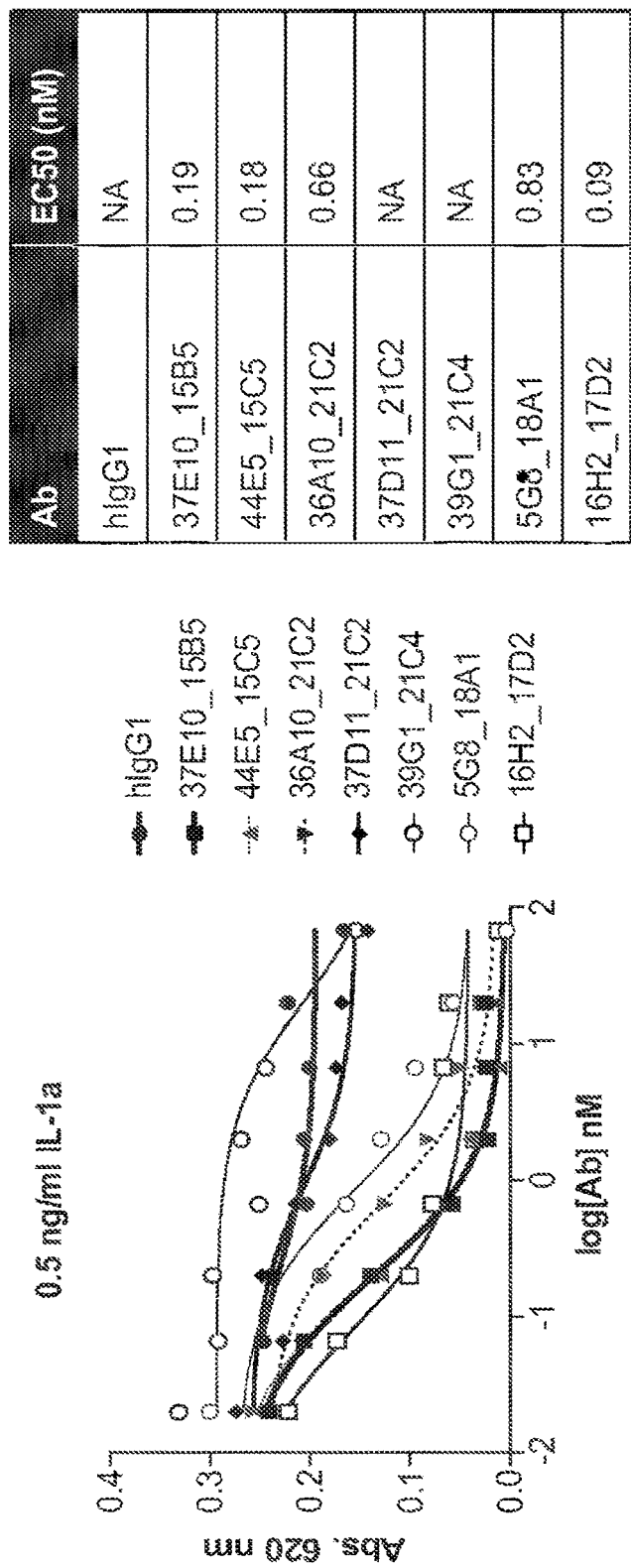

In addition, serial dilution of IL1RAP antibodies was performed to determine $EC_{50}$ against IL-1β and IL-1α (FIGS. 8B and 8C). Many of these antibodies, including 37E10_15B5 and 44E5_15C5 can block IL-1β and IL-1α signaling with subnanomolar $EC_{50}$. On the other hand, 37D11_21C2 and 39G1_21C4 do not inhibit IL-1 signaling.

Example 9. Blockage of IL-33 Signaling by Anti-IL1RAP Ab

Experiments were performed to characterize the ability of anti-IL1RAP antibody to block IL-33 signaling. The following methods were used.

Methods

IL-33 Signaling Reporter Cell Assay

HEK-Blue IL-33 cells (Invivogen, CA) were harvested and plated in technical duplicates at a density of 50,000 cells per well in a 96-well plate. antibodies, or a corresponding human IgG1 control antibody was added to the wells in a concentration range of 1-10 µg/ml. After incubating cells with antibodies for 30 minutes, IL-33 was added to a final concentration of 0.5 ng/ml, and the plate was incubated overnight. To examine whether any of the antibodies were able to induce ST2 activation in the absence of IL-33, samples were incubated with 10 µg/mL antibody without addition of the ligand. The following day, substrate was added to the supernatants, and samples were analyzed for absorbance at 620 nm.

Results

Since IL1RAP plays an important role in IL-33 signaling, the ability of the developed antibodies to inhibit IL-33 signaling was investigated. Whereas antibodies showed various degree of inhibitory effect in an IL-33 reporter assay, 37E10_15B5, 44E5_15C5, and 36A10_21B6 can partially inhibit IL-33 signaling in a dose dependent manner (see FIGS. 9A and 9B). Neither of the antibodies affected IL-33 signaling in the absence of IL-33, thereby excluding agonistic functions on IL-33 induced signaling (data not shown). On the other hand, 37D11_21C2 and 39G1_21C4 do not inhibit IL-33 signaling.

Sequence Summary

| SEQ ID NO: | Clone Name | Protein Domain |
|---|---|---|
| 1 | 5G8_18A1 | VH amino acid sequence |
| 2 | 5G8_18A1 | CDR-H1 amino acid sequence |
| 3 | 5G8_18A1 | CDR-H2 amino acid sequence |
| 4 | 5G8_18A1 | CDR-H3 amino acid sequence |
| 5 | 5G8_18A1 | VL amino acid sequence |
| 6 | 5G8_18A1 | CDR-L1 amino acid sequence |
| 7 | 5G8_18A1 | CDR-L2 amino acid sequence |
| 8 | 5G8_18A1 | CDR-L3 amino acid sequence |
| 9 | 10C8_15A1, 10C8_C43A | VH amino acid sequence |
| 10 | 10C8_15A1, 10C8_C43A | CDR-H1 amino acid sequence |
| 11 | 10C8_15A1, 10C8_C43A | CDR-H2 amino acid sequence |
| 12 | 10C8_15A1, 10C8_C43A | CDR-H3 amino acid sequence |
| 13 | 10C8_15A1 | VL amino acid sequence |
| 14 | 10C8_15A1, 10C8_C43A | CDR-L1 amino acid sequence |
| 15 | 10C8_15A1, 10C8_C43A | CDR-L2 amino acid sequence |
| 16 | 10C8_15A1, 10C8_C43A | CDR-L3 amino acid sequence |
| 17 | 12F3_17C2 | VH amino acid sequence |
| 18 | 12F3_17C2 | CDR-H1 amino acid sequence |
| 19 | 12F3_17C2 | CDR-H2 amino acid sequence |
| 20 | 12F3_17C2, 17E9_15B1 | CDR-H3 amino acid sequence |
| 21 | 12F3_17C2 | VL amino acid sequence |
| 22 | 12F3_17C2 | CDR-L1 amino acid sequence |
| 23 | 12F3_17C2, 16H2_17D2 | CDR-L2 amino acid sequence |
| 24 | 12F3_17C2, 17E9_15B1 | CDR-L3 amino acid sequence |
| 25 | 16H2_17D2 | VH amino acid sequence |
| 26 | 16H2_17D2, 31F9_21A1, 32F9_21A5, 33E9_21A6 | CDR-H1 amino acid sequence |
| 27 | 16H2_17D2 | CDR-H2 amino acid sequence |
| 28 | 16H2_17D2 | CDR-H3 amino acid sequence |
| 29 | 16H2_17D2 | VL amino acid sequence |
| 30 | 16H2_17D2 | CDR-L1 amino acid sequence |
| 31 | 16H2_17D2 | CDR-L3 amino acid sequence |
| 32 | 32C12_21A4, 32C12-N26S | VH amino acid sequence |
| 33 | 32C12_21A4, 32C12-N26S | CDR-H1 amino acid sequence |
| 34 | 32C12_21A4, 32C12-N26S, 41G4_15B6 | CDR-H2 amino acid sequence |
| 35 | 32C12_21A4, 32C12-N26S, 41G4_15B6 | CDR-H3 amino acid sequence |
| 36 | 32C12_21A4, 41G4_15B6 | VL amino acid sequence |
| 37 | 32C12_21A4, 32A2_21A3, 41G4_15B6 | CDR-L1 amino acid sequence |
| 38 | 32C12_21A4, 32A2_21A3, 32C12-N26S, 41G4_15B6 | CDR-L2 amino acid sequence |
| 39 | 32C12_21A4, 32A2_21A3, 32C12-N26S, 41G4_15B6 | CDR-L3 amino acid sequence |
| 40 | 34C11_21B2 | VH amino acid sequence |
| 41 | 34C11_21B2 | CDR-H1 amino acid sequence |
| 42 | 34C11_21B2, 33H2_21B1 | CDR-H2 amino acid sequence |
| 43 | 34C11_21B2, 36A12_21C1, 38G11_28A2, 40C3_22B6 | CDR-H3 amino acid sequence |
| 44 | 34C11_21B2 | VL amino acid sequence |
| 45 | 34C11_21B2, 33H2_21B1 | CDR-L1 amino acid sequence |
| 46 | 34C11_21B2, 33H2_21B1 | CDR-L2 amino acid sequence |

-continued

Sequence Summary

| SEQ ID NO: | Clone Name | Protein Domain |
|---|---|---|
| 47 | 34C11_21B2, 33H2_21B1 | CDR-L3 amino acid sequence |
| 48 | 36A10_21B6 | VH amino acid sequence |
| 49 | 36A10_21B6, 34D1_21B3 | CDR-H1 amino acid sequence |
| 50 | 36A10_21B6, 34D1_21B3 | CDR-H2 amino acid sequence |
| 51 | 36A10_21B6, 34D1_21B3 | CDR-H3 amino acid sequence |
| 52 | 36A10_21B6 | VL amino acid sequence |
| 53 | 36A10_21B6 | CDR-L1 amino acid sequence |
| 54 | 36A10_21B6 | CDR-L2 amino acid sequence |
| 55 | 36A10_21B6, 34D1_21B3 | CDR-L3 amino acid sequence |
| 56 | 39G1_21C4 | VH amino acid sequence |
| 57 | 39G1_21C4 | CDR-H1 amino acid sequence |
| 58 | 39G1_21C4 | CDR-H2 amino acid sequence |
| 59 | 39G1_21C4 | CDR-H3 amino acid sequence |
| 60 | 39G1_21C4 | VL amino acid sequence |
| 61 | 39G1_21C4 | CDR-L1 amino acid sequence |
| 62 | 39G1_21C4, 37E10_15B5, 44E5_15C5, 31F9_21A1, 32D4_21D6, 32F9_21A5, 33E9_21A6, 35D11_22A1, 39A9_28A4, 34H8_21B4 | CDR-L2 amino acid sequence |
| 63 | 39G1_21C4, 34H8_21B4 | CDR-L3 amino acid sequence |
| 64 | 37E10_15B5 | VH amino acid sequence |
| 65 | 37E10_15B5, 44E5_15C5 | CDR-H1 amino acid sequence |
| 66 | 37E10_15B5, 32D4_21D6, 32F9_21A5, 33E9_21A6, 35D11_22A1 | CDR-H2 amino acid sequence |
| 67 | 37E10_15B5, 44E5_15C5, 31F9_21A1, 32D4_21D6, 32F9_21A5, 33E9_21A6, 35D11_22A1 | CDR-H3 amino acid sequence |
| 68 | 37E10_15B5 | VL amino acid sequence |
| 69 | 37E10_15B5, 44E5_15C5, 31F9_21A1, 32D4_21D6, 32F9_21A5, 33E9_21A6, 35D11_22A1 | CDR-L1 amino acid sequence |
| 70 | 37E10_15B5, 44E5_15C5, 31F9_21A1, 32D4_21D6, 32F9_21A5, 33E9_21A6, 39A9_28A4 | CDR-L3 amino acid sequence |
| 71 | 44E5_15C5 | VH amino acid sequence |
| 72 | 44E5_15C5 | CDR-H2 amino acid sequence |
| 73 | 44E5_15C5 | VL amino acid sequence |
| 74 | 38E10_21C3, | VH amino acid sequence |
| 75 | 38E10_21C3 | CDR-H1 amino acid sequence |
| 76 | 38E10_21C3 | CDR-H2 amino acid sequence |
| 77 | 38E10_21C3 | CDR-H3 amino acid sequence |
| 78 | 38E10_21C3 | VL amino acid sequence |
| 79 | 38E10_21C3, 26C5_15B4, 37D11_21C2, 42D10_28A5 | CDR-L1 amino acid sequence |
| 80 | 38E10_21C3, 16H2_17D1, 24G3_17C5, 26C5_15B4, 10C8-15A4, , 42D10_28A5 | CDR-L2 amino acid sequence |
| 81 | 38E10_21C3, 42D10_28A5 | CDR-L3 amino acid sequence |
| 82 | 10C8_C43A | VL amino acid sequence |
| 83 | 16H2_17D1 | VH amino acid sequence |
| 84 | 16H2_17D1, 24G3_17C5, 26C5_15B4, 1008-15A4 | CDR-H1 amino acid sequence |
| 85 | 16H2_17D1 | CDR-H2 amino acid sequence |
| 86 | 16H2_17D1, 10C8-15A4 | CDR-H3 amino acid sequence |
| 87 | 16H2_17D1 | VL amino acid sequence |
| 88 | 16H2_17D1, 10C8-15A4 | CDR-L1 amino acid sequence |
| 89 | 16H2_17D1, 10C8-15A4 | CDR-L3 amino acid sequence |
| 90 | 24G3_17C5 | VH amino acid sequence |
| 91 | 24G3_17C5 | CDR-H2 amino acid sequence |
| 92 | 24G3_17C5, 26C5_15B4 | CDR-H3 amino acid sequence |
| 93 | 24G3_17C5 | VL amino acid sequence |
| 94 | 24G3_17C5 | CDR-L1 amino acid sequence |
| 95 | 24G3_17C5 | CDR-L3 amino acid sequence |
| 96 | 26C5_15B4 | VH amino acid sequence |
| 97 | 26C5_15B4 | CDR-H2 amino acid sequence |
| 98 | 26C5_15B4 | VL amino acid sequence |
| 99 | 26C5_15B4 | CDR-L3 amino acid sequence |
| 100 | 17E9_15B1 | VH amino acid sequence |
| 101 | 17E9_15B1, 32D4_21D6, 35D11_22A1 | CDR-H1 amino acid sequence |
| 102 | 17E9_15B1 | CDR-H2 amino acid sequence |
| 103 | 17E9_15B1 | VL amino acid sequence |
| 104 | 17E9_15B1 | CDR-L1 amino acid sequence |
| 105 | 17E9_15B1 | CDR-L2 amino acid sequence |
| 106 | 10C8-15A4 | VH amino acid sequence |
| 107 | 10C8-15A4 | CDR-H2 amino acid sequence |
| 108 | 10C8-15A4 | VL amino acid sequence |
| 109 | 32A2_21A3 | VH amino acid sequence |
| 110 | 32A2_21A3 | CDR-H1 amino acid sequence |
| 111 | 32A2_21A3 | CDR-H2 amino acid sequence |
| 112 | 32A2_21A3 | CDR-H3 amino acid sequence |
| 113 | 32A2_21A3 | VL amino acid sequence |
| 114 | 32C12-N26S | VL amino acid sequence |
| 115 | 32C12-N26S | CDR-L1 amino acid sequence |
| 116 | 41G4_15B6 | VH amino acid sequence |
| 117 | 41G4_15B6 | CDR-H1 amino acid sequence |
| 118 | 31F9_21A1 | VH amino acid sequence |
| 119 | 31F9_21A1 | CDR-H2 amino acid sequence |
| 120 | 31F9_21A1 | VL amino acid sequence |
| 121 | 32D4_21D6 | VH amino acid sequence |
| 122 | 32D4_21D6 | VL amino acid sequence |
| 123 | 32F9_21A5 | VH amino acid sequence |
| 124 | 32F9_21A5 | VL amino acid sequence |
| 125 | 33E9_21A6 | VH amino acid sequence |
| 126 | 33E9_21A6 | VL amino acid sequence |
| 127 | 35D11_22A1 | VH amino acid sequence |
| 128 | 35D11_22A1 | VL amino acid sequence |
| 129 | 35D11_22A1 | CDR-L3 amino acid sequence |
| 130 | 39A9_28A4 | VH amino acid sequence |
| 131 | 39A9_28A4 | CDR-H1 amino acid sequence |
| 132 | 39A9_28A4 | CDR-H2 amino acid sequence |

Sequence Summary

| SEQ ID NO: | Clone Name | Protein Domain |
|---|---|---|
| 133 | 39A9_28A4 | CDR-H3 amino acid sequence |
| 134 | 39A9_28A4 | VL amino acid sequence |
| 135 | 39A9_28A4 | CDR-L1 amino acid sequence |
| 136 | 34D1_21B3 | VH amino acid sequence |
| 137 | 34D1_21B3 | VL amino acid sequence |
| 138 | 34D1_21B3 | CDR-L1 amino acid sequence |
| 139 | 34D1_21B3 | CDR-L2 amino acid sequence |
| 140 | 33H2_21B1 | VH amino acid sequence |
| 141 | 33H2_21B1 | CDR-H1 amino acid sequence |
| 142 | 33H2_21B1 | CDR-H3 amino acid sequence |
| 143 | 33H2_21B1 | VL amino acid sequence |
| 144 | 36A12_21C1 | VH amino acid sequence |
| 145 | 36A12_21C1, 40C3_22B6 | CDR-H1 amino acid sequence |
| 146 | 36A12_21C1 | CDR-H2 amino acid sequence |
| 147 | 36A12_21C1 | VL amino acid sequence |
| 148 | 36A12_21C1, 40C3_22B6 | CDR-L1 amino acid sequence |
| 149 | 36A12_21C1 | CDR-L2 amino acid sequence |
| 150 | 36A12_21C1 | CDR-L3 amino acid sequence |
| 151 | 38G11_28A2 | VH amino acid sequence |
| 152 | 38G11_28A2 | CDR-H1 amino acid sequence |
| 153 | 38G11_28A2 | CDR-H2 amino acid sequence |
| 154 | 38G11_28A2 | VL amino acid sequence |
| 155 | 38G11_28A2, 5D12_18A4, 5D12-C108Y | CDR-L1 amino acid sequence |
| 156 | 38G11_28A2 | CDR-L2 amino acid sequence |
| 157 | 38G11_28A2 | CDR-L3 amino acid sequence |
| 158 | 40C3_22B6 | VH amino acid sequence |
| 159 | 40C3_22B6 | CDR-H2 amino acid sequence |
| 160 | 40C3_22B6 | VL amino acid sequence |
| 161 | 40C3_22B6 | CDR-L2 amino acid sequence |
| 162 | 40C3_22B6 | CDR-L3 amino acid sequence |
| 163 | 5D12_18A4 | VH amino acid sequence |
| 164 | 5D12_18A4, 5D12_C108Y | CDR-H1 amino acid sequence |
| 165 | 5D12_18A4, 5D12_C108Y | CDR-H2 amino acid sequence |
| 166 | 5D12_18A4 | CDR-H3 amino acid sequence |
| 167 | 5D12_18A4 | VL amino acid sequence |
| 168 | 5D12_18A4, 5D12-C108Y | CDR-L2 amino acid sequence |
| 169 | 5D12_18A4, 5D12-C108Y | CDR-L3 amino acid sequence |
| 170 | 5D12_C108Y | VH amino acid sequence |
| 171 | 5D12_C108Y | CDR-H3 amino acid sequence |
| 172 | 5D12-C108Y | VL amino acid sequence |
| 173 | 37D11_21C2 | VH amino acid sequence |
| 174 | 37D11_21C2 | CDR-H1 amino acid sequence |
| 175 | 37D11_21C2 | CDR-H2 amino acid sequence |
| 176 | 37D11_21C2 | CDR-H3 amino acid sequence |
| 177 | 37D11_21C2 | VL amino acid sequence |
| 178 | 37D11_21C2 | CDR-L2 amino acid sequence |
| 179 | 37D11_21C2, 42D10_28A5 | CDR-L3 amino acid sequence |
| 180 | 42D10_28A5 | VH amino acid sequence |
| 181 | 42D10_28A5 | CDR-H1 amino acid sequence |
| 182 | 42D10_28A5 | CDR-H2 amino acid sequence |
| 183 | 42D10_28A5 | CDR-H3 amino acid sequence |
| 184 | 42D10_28A5 | VL amino acid sequence |
| 185 | 34H8_21B4 | VH amino acid sequence |
| 186 | 34H8_21B4 | CDR-H1 amino acid sequence |
| 187 | 34H8_21B4 | CDR-H2 amino acid sequence |
| 188 | 34H8_21B4 | CDR-H3 amino acid sequence |
| 189 | 34H8_21B4 | VL amino acid sequence |
| 190 | 34H8_21B4 | CDR-L1 amino acid sequence |
| 191 | 5G8_18A1 | VH nucleotide sequence |
| 192 | 5G8_18A1 | VL nucleotide sequence |
| 193 | 10C8_15A1, 10C8_C43A | VH nucleotide sequence |
| 194 | 10C8_15A1 | VL nucleotide sequence |
| 195 | 12F3_17C2 | VH nucleotide sequence |
| 196 | 12F3_17C2 | VL nucleotide sequence |
| 197 | 16H2_17D2 | VH nucleotide sequence |
| 198 | 16H2_17D2 | VL nucleotide sequence |
| 199 | 32C12_21A4, 32C12_N26S | VH nucleotide sequence |
| 200 | 32C12_21A4 | VL nucleotide sequence |
| 201 | 34C11_21B2 | VH nucleotide sequence |
| 202 | 34C11_21B2 | VL nucleotide sequence |
| 203 | 36A10_21B6 | VH nucleotide sequence |
| 204 | 36A10_21B6 | VL nucleotide sequence |
| 205 | 39G1_21C4 | VH nucleotide sequence |
| 206 | 39G1_21C4 | VL nucleotide sequence |
| 207 | 37E10_15B5 | VH nucleotide sequence |
| 208 | 37E10_15B5 | VL nucleotide sequence |
| 209 | 44E5_15C5 | VH nucleotide sequence |
| 210 | 44E5_15C5 | VL nucleotide sequence |
| 211 | 38E10_21C3 | VH nucleotide sequence |
| 212 | 38E10_21C3 | VL nucleotide sequence |
| 213 | 10C8_C43A | VL nucleotide sequence |
| 214 | 16H2_17D1 | VH nucleotide sequence |
| 215 | 16H2_17D1 | VL nucleotide sequence |
| 216 | 24G3_17C5 | VH nucleotide sequence |
| 217 | 24G3_17C5 | VL nucleotide sequence |
| 218 | 26C5_15B4 | VH nucleotide sequence |
| 219 | 26C5_15B4 | VL nucleotide sequence |
| 220 | 17E9_15B1 | VH nucleotide sequence |
| 221 | 17E9_15B1 | VL nucleotide sequence |
| 222 | 10C8_15A4 | VH nucleotide sequence |
| 223 | 10C8-15A4 | VL nucleotide sequence |
| 224 | 32A2_21A3 | VH nucleotide sequence |
| 225 | 32A2_21A3 | VL nucleotide sequence |
| 226 | 32C12_N26S | VL nucleotide sequence |
| 227 | 41G4_15B6 | VH nucleotide sequence |
| 228 | 41G4_15B6 | VL nucleotide sequence |
| 229 | 31F9_21A1 | VH nucleotide sequence |
| 230 | 31F9_21A1 | VL nucleotide sequence |
| 231 | 32D4_21D6 | VH nucleotide sequence |
| 232 | 32D4_21D6 | VL nucleotide sequence |
| 233 | 32F9_21A5 | VH nucleotide sequence |
| 234 | 32F9_21A5 | VL nucleotide sequence |
| 235 | 33E9_21A6 | VH nucleotide sequence |
| 236 | 33E9_21A6 | VL nucleotide sequence |
| 237 | 35D11_22A1 | VH nucleotide sequence |
| 238 | 35D11_22A1 | VL nucleotide sequence |
| 239 | 39A9_28A4 | VH nucleotide sequence |
| 240 | 39A9_28A4 | VL nucleotide sequence |
| 241 | 34D1_21B3 | VH nucleotide sequence |
| 242 | 34D1_21B3 | VL nucleotide sequence |
| 243 | 33H2_21B1 | VH nucleotide sequence |
| 244 | 33H2_21B1 | VL nucleotide sequence |
| 245 | 36A12_21C1 | VH nucleotide sequence |
| 246 | 36A12_21C1 | VL nucleotide sequence |
| 247 | 38G11_28A2 | VH nucleotide sequence |
| 248 | 38G11_28A2 | VL nucleotide sequence |
| 249 | 40C3_22B6 | VH nucleotide sequence |
| 250 | 40C3_22B6 | VL nucleotide sequence |
| 251 | 5D12_18A4 | VH nucleotide sequence |
| 252 | 5D12_18A4, 5D12-C108Y | VL nucleotide sequence |
| 253 | 5D12_ C108Y | VH nucleotide sequence |
| 254 | 37D11_21C2 | VH nucleotide sequence |
| 255 | 37D11_21C2 | VL nucleotide sequence |
| 256 | 42D10_28A5 | VH nucleotide sequence |
| 257 | 42D10_28A5 | VL nucleotide sequence |
| 258 | 34H8_21B4 | VH nucleotide sequence |
| 259 | 34H8_21B4 | VL nucleotide sequence |
| 260 | IGHV4 leader | |
| 261 | IGHV2 leader | |
| 262 | IGHV2-26 leader | |
| 263 | IGHV6 leader | |
| 264 | IGHV1 leader | |
| 265 | IGHV1-58 leader | |
| 266 | IGHV1-24 leader | |
| 267 | IGHV1-69/1-46/7-4-1 leader | |
| 268 | IGHV3 leader | |

Sequence Summary

| SEQ ID NO: | Clone Name | Protein Domain |
|---|---|---|
| 269 | IGHV3-53/3-49 | leader |
| 270 | IGHV3-21 | leader |
| 271 | IGHV3-48/3-7 | leader |
| 272 | IGHV5 | leader |
| 273 | IgkV1a | leader |
| 274 | IgkV1b | leader |
| 275 | IgkV3 | leader |
| 276 | IgkV3-20 | leader |
| 277 | IgkV4 | leader |
| 278 | IgkV5 | leader |
| 279 | IgkV2 | leader |
| 280 | Kappa FW4 | |
| 281 | Kappa FW4 | |
| 282 | Heavy FW4 | |
| 283 | VL-FOR L1 | |
| 284 | VL-FOR L2 | |
| 285 | VL-REV L | |
| 286 | Human IL1RAP protein | |

INCORPORATION BY REFERENCE

The contents of all references, patents, pending patent applications and published patents, Sequence Listing, and Accession Numbers, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

The invention claimed is:

1. An anti-IL1RAP antibody, or antigen-binding portion thereof, comprising
a heavy chain variable region comprising a CDR3 domain comprising the amino acid sequence of SEQ ID NO: 67, a CDR2 domain comprising the amino acid sequence of SEQ ID NO: 66, and a CDR1 domain comprising the amino acid sequence of SEQ ID NO: 65; and a light chain variable region comprising a CDR3 domain comprising the amino acid sequence of SEQ ID NO: 70, a CDR2 domain comprising the amino acid sequence of SEQ ID NO: 62, and a CDR1 domain comprising the amino acid sequence of SEQ ID NO: 69;
a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10; and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14;
a heavy chain variable region comprising a CDR3 domain comprising the amino acid sequence of SEQ ID NO: 51, a CDR2 domain comprising the amino acid sequence of SEQ ID NO: 50, and a CDR1 domain comprising the amino acid sequence of SEQ ID NO: 49; and a light chain variable region comprising a CDR3 domain comprising the amino acid sequence of SEQ ID NO: 55, a CDR2 domain comprising the amino acid sequence of SEQ ID NO: 54, and a CDR1 domain comprising the amino acid sequence of SEQ ID NO: 53;
a heavy chain variable region comprising a CDR3 domain comprising the amino acid sequence of SEQ ID NO:

59, a CDR2 domain comprising the amino acid sequence of SEQ ID NO: 58, and a CDR1 domain comprising the amino acid sequence of SEQ ID NO: 57; and a light chain variable region comprising a CDR3 domain comprising the amino acid sequence of SEQ ID NO: 63, a CDR2 domain comprising the amino acid sequence of SEQ ID NO: 62, and a CDR1 domain comprising the amino acid sequence of SEQ ID NO: 61; or a heavy chain variable region comprising a CDR3 domain comprising the amino acid sequence of SEQ ID NO: 176, a CDR2 domain comprising the amino acid sequence of SEQ ID NO: 175, and a CDR1 domain comprising the amino acid sequence of SEQ ID NO: 174; and a light chain variable region comprising a CDR3 domain comprising the amino acid sequence of SEQ ID NO: 179, a CDR2 domain comprising the amino acid sequence of SEQ ID NO: 178, and a CDR1 domain comprising the amino acid sequence of SEQ ID NO: 79.

2. An anti-IL1RAP antibody, or antigen-binding portion thereof, comprising a heavy chain variable region comprising the amino acid sequence of SEQ ID NO: 64 and a light chain variable region comprising the amino acid sequence of SEQ ID NO: 68;

a heavy chain variable region comprising the amino acid sequence of SEQ ID NO: 9 and a light chain variable region comprising the amino acid sequence of SEQ ID NO: 82;

a heavy chain variable region comprising the amino acid sequence of SEQ ID NO: 48 and a light chain variable region comprising the amino acid sequence of SEQ ID NO: 52;

a heavy chain variable region comprising the amino acid sequence of SEQ ID NO: 56 and a light chain variable region comprising the amino acid sequence of SEQ ID NO: 60; or a heavy chain variable region comprising the amino acid sequence of SEQ ID NO: 173 and a light chain variable region comprising the amino acid sequence of SEQ ID NO: 177.

3. A pharmaceutical composition comprising the antibody, or antigen binding portion thereof, of claim 1, and a pharmaceutically acceptable carrier.

4. The antibody, or antigen binding portion thereof, of claim 1, conjugated to at least one drug.

5. The antibody, or antigen binding portion thereof, of claim 1, wherein the antibody, or antigen binding portion thereof, is an $IgG_1$ isotype, $IgG_2$ isotype, $IgG_3$ isotype, or $IgG_4$ isotype.

6. A pharmaceutical composition comprising the antibody, or antigen binding portion thereof, of claim 2, and a pharmaceutically acceptable carrier.

7. The antibody, or antigen binding portion thereof, of claim 2, conjugated to at least one drug.

8. The antibody, or antigen binding portion thereof, of claim 2, wherein the antibody, or antigen binding portion thereof, is an $IgG_1$ isotype, $IgG_2$ isotype, $IgG_3$ isotype, or $IgG_4$ isotype.

* * * * *

SEQUENCE LISTING

```
<160> NUMBER OF SEQ ID NOS: 286

<210> SEQ ID NO 1
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Glu Leu Gln Glu Ser Gly Pro Gly Leu Val Lys Pro Ser Asp
1               5                   10                  15

Thr Leu Ser Leu Thr Cys Thr Val Thr Gly Gly Ser Ile Ser Thr Tyr
                20                  25                  30

Tyr Trp Ser Trp Ile Arg Gln Pro Pro Gly Lys Gly Leu Glu Trp Ile
            35                  40                  45

Gly Tyr Ile Phe Tyr Thr Gly Thr Thr Asn Tyr Asn Pro Ser Leu Lys
        50                  55                  60

Ser Arg Val Thr Ile Ser Val Asp Ala Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Asp Gly Ser Leu Asp Tyr Trp Gly Gln Gly Ala Leu Val Thr Val
            100                 105                 110

Ser Ser

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Ser Ile Ser Thr Tyr Tyr Trp Ser
1               5                   10
```

```
<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ile Phe Tyr Thr Gly Thr Thr Asn Tyr Asn Pro Ser Leu Lys Ser
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Gly Ser Leu Asp Tyr
1               5

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Phe Val Ala Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Leu Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Ser Ile Ser Asn Tyr Leu Asn
1               5                   10

<210> SEQ ID NO 7
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 7

Val Ala Ser Leu Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Ser Tyr Ser Thr Pro Phe Thr
1               5

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Glu Ser Gly Gly Val Val Gln Pro Gly Arg
1               5                   10                  15

Ser Leu Arg Ile Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Ile Ile Trp His Asp Glu Ser Tyr Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Ser Gly Ser Tyr Tyr Asp Ala Phe Asp
            100                 105                 110

Ile Trp Gly Gln Gly Thr Met Val Thr Val Ser Ser
        115                 120

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Thr Phe Arg Ser Tyr Gly Met His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Ile Ile Trp His Asp Glu Ser Tyr Lys Tyr Tyr Val Asp Ser Val Lys
1               5                   10                  15

Gly

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Asp Tyr Tyr Gly Ser Gly Ser Tyr Tyr Asp Ala Phe Asp Ile
1               5                   10                  15

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Gly Ile Ser Asn Tyr
            20                  25                  30

Leu Ala Trp Phe Gln Gln Lys Pro Gly Lys Cys Pro Asn Leu Leu Ile
        35                  40                  45

Tyr Ala Ala Ser Thr Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Val Glu Ile Lys
            100                 105

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Gly Ile Ser Asn Tyr Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Ala Ala Ser Thr Leu Arg Ser
1               5
```

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gln Lys Tyr Asn Ser Ala Pro Tyr Thr
1               5
```

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Asp Gly Gly Ala Val Ala Asn Trp Ile Asp Ser Trp Gly
            100                 105                 110

Gln Gly Thr Leu Val Thr Val Ser Ser
        115                 120
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Gly Phe Thr Phe Ser His Tyr Gly Met His
1               5                   10
```

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Ile Trp Tyr Asp Gly Ser Lys Lys Tyr Tyr Val Asp Ser Val Lys Gly
1               5                   10                  15
```

```
<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Gly Gly Ala Val Ala Asp Asn Trp Ile Asp Ser
1               5                   10

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Glu Asp Phe Ala Thr Tyr Ser Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Gln Ser Ile Arg Ser Tyr Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ser Ser Leu Gln Ser
1               5

<210> SEQ ID NO 24
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 24

Gln Gln Ser Tyr Ser Thr Pro Tyr Thr
1               5

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Phe Tyr Thr Asp Ser Val
    50                  55                  60

Gln Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Glu Gly Leu Arg Ala Gly Tyr Tyr Phe Asp Phe Trp Gly Gln
            100                 105                 110

Gly Thr Leu Val Thr Val Ser Ser
        115                 120

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Thr Phe Ser Ser His Gly Met His
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Ile Trp Tyr Asp Gly Ser Asn Lys Phe Tyr Thr Asp Ser Val Gln
1               5                   10                  15

Gly

<210> SEQ ID NO 28
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 28

Glu Gly Leu Arg Ala Gly Tyr Tyr Phe Asp Phe
1               5                   10

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Phe Tyr
            20                  25                  30

Ser Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser His Ser Thr Pro Leu
                85                  90                  95

Thr Phe Gly Gly Gly Thr Lys Leu Glu Ile Lys
            100                 105

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Gln Arg Ile Ser Phe Tyr Ser Asn
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Ser His Ser Thr Pro Leu Thr
1               5

<210> SEQ ID NO 32
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 32

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Asn Tyr
                20                  25                  30

Gly Ile His Trp Val Arg Gln Ala Pro Gly Lys Gly Leu Glu Trp Val
            35                  40                  45

Ala Val Ile Trp Tyr Asp Gly Ser Asn Lys Phe Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Glu Glu Gly Ile Ala Val Ala Pro Phe Asp Tyr Trp Gly Gln
            100                 105                 110

Gly Thr Leu Val Thr Val Ser Ser
        115                 120

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Phe Thr Phe Arg Asn Tyr Gly Ile His
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Ile Trp Tyr Asp Gly Ser Asn Lys Phe Tyr Ala Asp Ser Val Lys
1               5                   10                  15

Gly

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Glu Gly Ile Ala Val Ala Pro Phe Asp Tyr
1               5                   10

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 36

Asp Ile Gln Met Thr Gln Ser Pro Ser Ser Leu Ser Ala Ser Val Gly
1               5                   10                  15

Asp Arg Val Ala Ile Thr Cys Arg Ala Asn Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Asn Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Glu Ile
                85                  90                  95

Thr Phe Gly Gln Gly Thr Arg Leu Glu Ile Lys
            100                 105

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ala Asn Gln Ser Ile Ala Ser Tyr Leu Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ala Ser Ser Leu Gln Asn
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gln Ser Tyr Ser Thr Glu Ile Thr
1               5

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Val Val Glu Ser Gly Gly Gly Leu Val Gln Pro Gly Gly
1               5                   10                  15
```

```
Ser Leu Arg Leu Ser Cys Ala Ala Ser Gly Phe Thr Phe Arg Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Arg His Tyr Val Asp Ser Val
 50                  55                  60

Lys Gly Arg Phe Thr Ile Ser Arg Asp Asn Ala Lys Thr Ser Leu Tyr
 65                  70                  75                  80

Leu Gln Met Ser Ser Leu Arg Ala Glu Asp Thr Ala Val Tyr Tyr Cys
                85                  90                  95

Ala Arg Glu Gly Tyr Phe Gly Ser Gly Tyr Phe Asp Tyr Trp Gly Gln
            100                 105                 110

Gly Thr Leu Val Thr Val Ser Ser
        115                 120

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Phe Thr Phe Arg Ser Tyr Trp Met Ser
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Ile Lys Gln Asp Gly Ser Glu Arg His Tyr Val Asp Ser Val Lys
1               5                   10                  15

Gly

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Gly Tyr Phe Gly Ser Gly Tyr Phe Asp Tyr
1               5                   10

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Thr Leu Ser Ala Ser Val Gly
1               5                   10                  15
```

```
Asp Arg Val Ile Ile Thr Cys Arg Ala Ser Gln Ser Ile Ser Arg Gly
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ala Tyr Tyr Cys Gln Gln Tyr Ser Tyr Tyr Ser His
                85                  90                  95

Thr Phe Gly Gln Gly Thr Lys Leu Glu Ile Lys
            100                 105

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ala Ser Gln Ser Ile Ser Arg Gly Leu Ala
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Ala Ser Asn Leu Glu Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Tyr Ser Tyr Tyr Ser His Thr
1               5

<210> SEQ ID NO 48
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Gly Gln Val Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Leu His Trp Val Arg Gln Ala Pro Gly Lys Gly Leu Glu Trp Val
        35                  40                  45
```

```
Ala Val Ile Trp Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Tyr Gly Ser Gly Ser Tyr Tyr Asn Val Tyr Tyr Gly Met
            100                 105                 110

Asp Val Trp Gly Gln Gly Thr Thr Val Thr Leu Ser Ser
        115                 120                 125

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Phe Ser Ser Tyr Thr Leu His
 1               5                  10

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Ile Trp Tyr Asp Gly Ser Asn Lys Tyr Tyr Val Asp Ser Val Lys
 1               5                  10                  15

Gly

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Tyr Gly Ser Gly Ser Tyr Tyr Asn Val Tyr Tyr Gly Met Asp Val
 1               5                  10                  15

<210> SEQ ID NO 52
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45
```

```
Pro His Leu Leu Ile Tyr Leu Ala Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Phe Tyr Tyr Cys Met Gln Thr
                 85                  90                  95

Leu Gln Ile Pro Leu Thr Phe Gly Gly Gly Thr Lys Val Glu Ile Lys
            100                 105                 110
```

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Arg Ser Ser Gln Ser Leu Leu His Ser Asn Gly Tyr Asn Tyr Leu Asp
 1               5                  10                  15
```

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Leu Ala Ser Asn Arg Ala Ser
 1               5
```

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Met Gln Thr Leu Gln Ile Pro Leu Thr
 1               5
```

<210> SEQ ID NO 56
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ala Ser Gly Val
                 20                  25                  30

Tyr Tyr Trp Gly Trp Ile Arg Gln Pro Pro Gly Lys Gly Leu Glu Trp
             35                  40                  45

Ile Gly Asn Ile Tyr His Ser Gly Ser Thr Tyr Tyr Asn Pro Ser Leu
 50                  55                  60

Glu Arg Arg Val Ser Ile Ser Leu Asp Thr Ser Lys Asn His Phe Ser
```

```
                65                   70                  75                  80
Leu Arg Leu Asn Phe Val Thr Ala Ala Asp Thr Ala Val Tyr Tyr Cys
                    85                  90                  95
Ala Arg Asp Arg Phe Asp Ala Phe Asp Ile Trp Gly Gln Gly Thr Met
            100                 105                 110
Val Thr Val Ser Ser
        115

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Tyr Ser Ala Ser Gly Val Tyr Tyr Trp Gly
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Ile Tyr His Ser Gly Ser Thr Tyr Tyr Asn Pro Ser Leu Glu Arg
1               5                   10                  15

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Arg Phe Asp Ala Phe Asp Ile
1               5

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Asn Asn Ile
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80
```

```
Glu Asp Phe Ala Val Tyr Tyr Cys Gln Gln Tyr Asn Asn Trp Pro Leu
                85                  90                  95
Thr Phe Gly Gly Gly Thr Lys Val Glu Ile Lys
            100                 105

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ala Ser Gln Ser Ile Asn Asn Ile Leu Ala
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Ala Ser Thr Arg Ala Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Tyr Asn Asn Trp Pro Leu Thr
1               5

<210> SEQ ID NO 64
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Glu Ser Gly Gly Val Val Gln Pro Gly Arg
1               5                   10                  15
Ser Leu Arg Leu Ser Cys Ala Ala Ser Gly Phe Thr Phe Arg Ser His
                20                  25                  30
Gly Met His Trp Val Arg Gln Ala Pro Gly Lys Gly Leu Glu Trp Val
            35                  40                  45
Ala Val Ile Trp Tyr Asp Gly Ser Glu Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Asn Val Tyr Gly Ser Gly Trp Phe Phe Asp Tyr Trp Gly
            100                 105                 110
```

```
Gln Gly Thr Leu Val Thr Val Ser Ser
        115                 120
```

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gly Phe Thr Phe Arg Ser His Gly Met His
1               5                   10
```

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Val Ile Trp Tyr Asp Gly Ser Ser Glu Tyr Tyr Ala Asp Ser Val Lys
1               5                   10                  15
Gly
```

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Glu Asn Val Tyr Gly Ser Gly Trp Phe Phe Asp Tyr
1               5                   10
```

<210> SEQ ID NO 68
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Glu Ile Val Met Thr Gln Ser Pro Ala Thr Leu Ser Val Ser Pro Gly
1               5                   10                  15

Glu Arg Ala Ser Leu Ser Cys Arg Ala Ser Gln Ser Val Gly Ser Asn
            20                  25                  30

Leu Ala Trp Tyr Gln Gln Arg Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Arg Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Asn Trp Pro Pro
                85                  90                  95

Trp Thr Phe Gly Gln Gly Thr Lys Leu Glu Ile Lys
            100                 105
```

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

```
Arg Ala Ser Gln Ser Val Gly Ser Asn Leu Ala
1               5                   10
```

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

```
Gln Gln Tyr Asn Asn Trp Pro Pro Trp Thr
1               5                   10
```

<210> SEQ ID NO 71
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 71

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser His
            20                  25                  30

Gly Met His Trp Val Arg Gln Ala Pro Gly Lys Gly Leu Glu Trp Val
        35                  40                  45

Ala Val Ile Trp Tyr Asp Gly Ser Ser Asp Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Ser Ala Glu Asp Thr Ala Val Tyr Tyr Cys
                85                  90                  95

Ala Arg Glu Asn Val Tyr Gly Ser Gly Trp Phe Phe Asp Tyr Trp Gly
            100                 105                 110

Gln Gly Thr Leu Val Thr Val Ser Ser
        115                 120
```

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

```
Val Ile Trp Tyr Asp Gly Ser Ser Asp Tyr Tyr Ala Asp Ser Val Lys
1               5                   10                  15

Gly
```

<210> SEQ ID NO 73
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Ile Val Met Thr Gln Ser Pro Ala Thr Leu Ser Val Ser Pro Gly
1               5                   10                  15

Glu Arg Ala Ser Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Arg Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Asn Trp Pro Pro
                85                  90                  95

Trp Thr Phe Gly Gln Gly Thr Lys Leu Glu Ile Lys
            100                 105
```

<210> SEQ ID NO 74
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ser Ile Ser Ile Ser Arg Ala Gly Thr Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Glu Tyr Tyr Cys
                85                  90                  95

Ala Arg Glu Tyr Tyr Tyr Gly Met Asp Val Trp Gly Gln Gly Thr Thr
            100                 105                 110

Val Thr Val Ser Ser
        115
```

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

```
Gly Phe Thr Phe Ser Asn Tyr Ala Met Thr
1               5                   10
```

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Ser Ile Ser Ile Ser Arg Ala Gly Thr Tyr Tyr Ala Asp Ser Val Lys
1               5                   10                  15

Gly
```

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Glu Tyr Tyr Tyr Gly Met Asp Val
1               5
```

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Thr Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Thr
65                  70                  75                  80

Glu Asp Phe Ala Val Tyr Tyr Cys Gln Gln Leu Ile Asn Trp Pro Leu
                85                  90                  95

Thr Phe Gly Gly Gly Thr Lys Leu Glu Ile Lys
            100                 105
```

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Arg Ala Ser Gln Ser Val Ser Ser Tyr Leu Ala
1               5                   10
```

-continued

```
<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Ala Ser Asn Arg Ala Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Gln Leu Ile Asn Trp Pro Leu Thr
1               5

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Gly Ile Ser Asn Tyr
            20                  25                  30

Leu Ala Trp Phe Gln Gln Lys Pro Gly Lys Ala Pro Asn Leu Leu Ile
        35                  40                  45

Tyr Ala Ala Ser Thr Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Val Glu Ile Lys
            100                 105

<210> SEQ ID NO 83
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Leu Glu Ser Gly Ala Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

-continued

```
Ser Thr Ile Arg Ile Ser Gly Gly Thr Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Val Arg Asp Tyr Tyr Asn Gly Met Asp Val Trp Gly Gln Gly Thr Thr
            100                 105                 110
Val Thr Val Ser Ser
        115

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Phe Thr Phe Ser Ser Tyr Ala Met Ser
1               5                   10

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Ile Arg Ile Ser Gly Gly Thr Thr Tyr Tyr Ala Asp Ser Val Lys
1               5                   10                  15
Gly

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Tyr Tyr Asn Gly Met Asp Val
1               5

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Arg Val Ser Ser Tyr
            20                  25                  30
Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Tyr Trp Pro Pro
                85                  90                  95

Ala Phe Gly Gln Gly Thr Lys Leu Glu Ile Lys
            100                 105
```

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Arg Ala Ser Gln Arg Val Ser Ser Tyr Leu Ala
1               5                   10
```

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Gln Gln Arg Ser Tyr Trp Pro Pro Ala
1               5
```

<210> SEQ ID NO 90
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Glu Val Gln Leu Leu Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ser Ile Ser Gly Ser Gly Asp Ser Thr Asn Tyr Ala Asp Ser Val
        50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Val Arg Asp Tyr Tyr Tyr Gly Met Asp Val Trp Gly His Gly Thr Thr
                100                 105                 110

Val Thr Val Ser Ser
            115
```

<210> SEQ ID NO 91
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Ile Ser Gly Ser Gly Asp Ser Thr Asn Tyr Ala Asp Ser Val Lys
1               5                   10                  15

Gly

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Tyr Tyr Tyr Gly Met Asp Val
1               5

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Tyr Trp Pro Ile
                85                  90                  95

Thr Phe Gly Gln Gly Thr Arg Leu Glu Ile Lys
            100                 105

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ala Ser Gln Ser Val Asn Ser Tyr Leu Ala
1               5                   10

<210> SEQ ID NO 95
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 95

Gln Gln Arg Ser Tyr Trp Pro Ile Thr
1               5

<210> SEQ ID NO 96
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Ala Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Tyr Tyr Tyr Gly Met Asp Val Trp Gly Gln Gly Thr Thr
            100                 105                 110

Val Thr Val Ser Ser
        115

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Ile Ser Gly Ser Gly Gly Ser Thr His Tyr Ala Asp Ser Val Lys
1               5                   10                  15

Gly

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

```
Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Tyr Trp Pro Pro
                85                  90                  95

Thr Phe Gly Gln Gly Thr Lys Leu Glu Ile Lys
            100                 105

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Gln Arg Ser Tyr Trp Pro Pro Thr
1               5

<210> SEQ ID NO 100
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Asp Gly Gly Ala Val Ala Asp Asn Trp Ile Asp Ser Trp Gly
            100                 105                 110

Gln Gly Thr Leu Val Thr Val Ser Ser
        115                 120

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Thr Phe Ser Ser Tyr Gly Met His
1               5                   10

<210> SEQ ID NO 102
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 102

Val Ile Trp Tyr Asp Gly Ser Lys Lys Tyr Tyr Val Asp Ser Val Gln
1               5                   10                  15

Gly

<210> SEQ ID NO 103
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asn Ile Arg Ser Tyr
            20                  25                  30

Leu Asn Trp Tyr Gln Gln Lys Pro Gly Lys Ala Pro Lys Leu Leu Ile
        35                  40                  45

Phe Ala Ala Ser Ser Leu Pro Ser Gly Val Pro Ser Arg Phe Ser Gly
    50                  55                  60

Ser Gly Ser Val Thr Asp Phe Thr Leu Thr Val Ser Ser Leu Gln Pro
65                  70                  75                  80

Glu Asp Phe Ala Thr Tyr Ser Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ala Ser Gln Asn Ile Arg Ser Tyr Leu Asn
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Ala Ser Ser Leu Pro Ser
1               5

<210> SEQ ID NO 106
<211> LENGTH: 117
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 106

Glu Glu Gln Leu Leu Glu Ser Gly Ala Asp Leu Ala Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Arg Ile Ser Gly Asp Thr Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Val Arg Asp Tyr Tyr Asn Gly Met Asp Val Trp Gly His Gly Thr Thr
            100                 105                 110

Val Thr Val Ser Ser
        115

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Ile Arg Ile Ser Gly Asp Thr Thr Tyr Tyr Ala Asp Ser Val Lys
1               5                   10                  15

Gly

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Tyr Trp Pro Pro
                85                  90                  95

Ala Phe Gly Gln Gly Thr Lys Leu Glu Ile Lys
            100                 105

<210> SEQ ID NO 109
<211> LENGTH: 121

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ala Val Ala Gly Thr Ser Asp Ala Phe Asp Ile Trp Gly
            100                 105                 110

Gln Gly Thr Met Val Thr Val Ser Ser
        115                 120

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Tyr Thr Phe Thr Gly Tyr Tyr Met His
1               5                   10

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Trp Ile Asn Pro Asn Ser Gly Gly Thr Asn Tyr Ala Gln Lys Phe Gln
1               5                   10                  15

Gly

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Glu Ala Val Ala Gly Thr Ser Asp Ala Phe Asp Ile
1               5                   10

<210> SEQ ID NO 113
<211> LENGTH: 107
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Ser Ile Ala Ser Tyr
            20                  25                  30

Leu Asn Trp Tyr Gln Gln Lys Pro Gly Lys Val Pro Lys Leu Leu Ile
        35                  40                  45

Tyr Gly Ala Ser Ser Leu Gln Asn Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Glu Ile
                85                  90                  95

Thr Phe Gly Gln Gly Thr Arg Leu Glu Ile Lys
            100                 105

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Asn Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Glu Ile
                85                  90                  95

Thr Phe Gly Gln Gly Thr Arg Leu Glu Ile Lys
            100                 105

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Ala Ser Gln Ser Ile Ala Ser Tyr Leu Asn
1               5                   10

<210> SEQ ID NO 116
<211> LENGTH: 120
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Glu Glu Gly Ile Ala Val Ala Pro Phe Asp Tyr Trp Gly Gln
            100                 105                 110

Gly Thr Leu Val Thr Val Ser Ser
        115                 120

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Phe Thr Phe Arg Asn Tyr Gly Met His
1               5                   10

<210> SEQ ID NO 118
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Val Glu Ser Gly Gly Met Val Gln Pro Gly Arg
1               5                   10                  15

Ser Leu Arg Leu Ser Cys Thr Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Glu Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Val Tyr Gly Ser Gly Trp Phe Phe Asp Tyr Trp Gly
            100                 105                 110

Gln Gly Thr Leu Val Thr Val Ser Ser
        115                 120
```

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Val Ile Trp Phe Asp Gly Ser Asn Glu Tyr Tyr Val Asp Ser Val Lys
1               5                   10                  15

Gly

<210> SEQ ID NO 120
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Glu Ile Val Met Thr Gln Ser Pro Ala Thr Leu Ser Val Ser Pro Gly
1               5                   10                  15

Glu Arg Ala Ser Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Arg Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Asn Trp Pro Pro
                85                  90                  95

Trp Thr Phe Gly Gln Gly Thr Lys Val Glu Ile Lys
            100                 105

<210> SEQ ID NO 121
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

Gln Leu Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ser Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Val Tyr Gly Ser Gly Trp Phe Phe Asp Tyr Trp Gly

```
                    100                 105                 110

Gln Gly Thr Leu Val Thr Val Ser Ser
            115                 120

<210> SEQ ID NO 122
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Ile Val Met Thr Gln Ser Pro Ala Thr Leu Ser Val Ser Pro Gly
1               5                   10                  15

Glu Arg Ala Ser Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Arg Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Asn Trp Pro Pro
                85                  90                  95

Trp Thr Phe Gly Gln Gly Thr Lys Val Glu Ile Lys
            100                 105

<210> SEQ ID NO 123
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Leu Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Val Ile Trp Tyr Asp Gly Ser Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Val Tyr Gly Ser Gly Trp Phe Phe Asp Tyr Trp Gly
            100                 105                 110

Gln Gly Ser Leu Val Thr Val Ser Ser
            115                 120

<210> SEQ ID NO 124
<211> LENGTH: 108
<212> TYPE: PRT
<213> ORGANISM: Artificial Sequence
<220> FEATURE:
<223> OTHER INFORMATION: Description of Artificial Sequence: Synthetic
```

```
                polypeptide

<400> SEQUENCE: 124

Glu Ile Val Met Thr Gln Ser Pro Ala Thr Leu Ser Val Ser Pro Gly
1               5                   10                  15

Glu Arg Ala Ser Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
50                  55                  60

Ser Arg Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Asn Trp Pro Pro
                85                  90                  95

Trp Thr Phe Gly Gln Gly Thr Lys Leu Glu Ile Lys
            100                 105

<210> SEQ ID NO 125
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Leu Gln Leu Val Glu Ser Gly Gly Gly Val Val Gln Phe Gly Arg
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Val Ile Trp Tyr Asp Gly Ser Ser Glu Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Val Tyr Gly Ser Gly Trp Phe Phe Asp Tyr Trp Gly
            100                 105                 110

Gln Gly Thr Leu Val Thr Val Ser Ser
        115                 120

<210> SEQ ID NO 126
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Ile Val Met Thr Gln Ser Pro Ala Thr Leu Ser Val Ser Pro Gly
1               5                   10                  15

Glu Arg Ala Ser Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45
```

```
Phe Gly Ala Ser Thr Arg Ala Thr Gly Ile Pro Ala Arg Phe Ser Gly
            50                  55                  60

Ser Arg Ser Gly Thr Glu Phe Thr Leu Thr Ile Ser Ser Leu Gln Ser
 65                  70                  75                  80

Glu Asp Phe Ala Leu Tyr Tyr Cys Gln Gln Tyr Asn Asn Trp Pro Pro
                 85                  90                  95

Trp Thr Phe Gly Gln Gly Thr Lys Leu Glu Ile Lys
            100                 105

<210> SEQ ID NO 127
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Leu Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Glu Tyr Tyr Ala Asp Ser Val
    50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Asp Asp Thr Ala Val Tyr Tyr Cys
                 85                  90                  95

Ala Arg Glu Asn Val Tyr Gly Ser Gly Trp Phe Phe Asp Tyr Trp Gly
            100                 105                 110

Gln Gly Thr Leu Val Thr Val Ser Ser
        115                 120

<210> SEQ ID NO 128
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Ile Val Met Thr Gln Ser Pro Ala Thr Leu Ser Val Ser Pro Gly
 1               5                  10                  15

Glu Arg Ala Ser Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Arg Ser Gly Thr Glu Phe Thr Leu Thr Ile Ser Ser Leu Gln Ser
 65                  70                  75                  80

Glu Asp Phe Ala Leu Tyr Tyr Cys Gln Gln Tyr Asp Asn Trp Pro Pro
                 85                  90                  95

Trp Thr Phe Gly Gln Gly Thr Lys Leu Glu Ile Lys
            100                 105
```

-continued

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln Tyr Asp Asn Trp Pro Pro Trp Thr
1               5                   10

<210> SEQ ID NO 130
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Phe
65                  70                  75                  80

Leu Gln Met Asn Ser Leu Arg Ala Glu Asp Thr Ala Val Tyr Tyr Cys
                85                  90                  95

Val Arg Glu Asn Gly Phe Gly Ser Gly Trp Phe Phe Asp Tyr Trp Gly
            100                 105                 110

Gln Gly Asn Leu Val Thr Val Ser Ser
        115                 120

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Phe Thr Leu Ser Gly Tyr Gly Met His
1               5                   10

<210> SEQ ID NO 132
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Val Ile Trp Tyr Asp Gly Ser Asn Lys Tyr Tyr Ala Asp Ser Val Lys
1               5                   10                  15

Gly

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Asn Gly Phe Gly Ser Gly Trp Phe Phe Asp Tyr
1               5                   10

<210> SEQ ID NO 134
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Ile Val Met Thr Gln Ser Pro Ala Thr Leu Ser Val Ser Pro Gly
1               5                   10                  15

Glu Arg Ala Thr Leu Ser Cys Arg Thr Ser Gln Ser Val Ser Arg Asp
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Val Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Leu Glu Ile Lys
            100                 105

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Thr Ser Gln Ser Val Ser Arg Asp Leu Ala
1               5                   10

<210> SEQ ID NO 136
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Gly Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Leu His Trp Val Arg Gln Ala Pro Gly Lys Gly Leu Glu Trp Val

```
                35                  40                  45
Ala Val Ile Trp Tyr Asp Gly Ser Asn Lys Tyr Tyr Val Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Tyr Gly Ser Gly Ser Tyr Tyr Asn Val Tyr Gly Met
            100                 105                 110

Asp Val Trp Gly Gln Gly Thr Thr Val Thr Val Ser Ser
            115                 120                 125

<210> SEQ ID NO 137
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Lys Tyr Leu Asp Trp Tyr Leu Gln Lys Ala Gly Gln Ser
         35                  40                  45

Pro His Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Phe Tyr Tyr Cys Met Gln Thr
                 85                  90                  95

Leu Gln Ile Pro Leu Thr Phe Gly Gly Gly Thr Lys Leu Glu Ile Lys
            100                 105                 110

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Ser Ser Gln Ser Leu Leu His Ser Asn Gly Tyr Lys Tyr Leu Asp
 1               5                  10                  15

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Leu Gly Ser Asn Arg Ala Ser
 1               5

<210> SEQ ID NO 140
```

<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 140

Glu Val Gln Val Val Glu Ser Gly Gly Gly Leu Val Gln Pro Gly Gly
1               5                   10                  15

Ser Leu Arg Leu Ser Cys Ala Thr Ser Gly Phe Thr Phe Arg Ser Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Arg His Tyr Val Asp Ser Val
    50                  55                  60

Lys Gly Arg Phe Thr Ile Ser Arg Asp Asn Ala Lys Thr Ser Leu Tyr
65                  70                  75                  80

Leu Gln Met Ser Ser Leu Arg Ala Glu Asp Thr Ala Met Tyr Tyr Cys
                85                  90                  95

Ala Arg Glu Gly Tyr Tyr Gly Ser Gly Tyr Phe Asp Tyr Trp Gly Gln
            100                 105                 110

Gly Thr Leu Val Thr Val Ser Ser
        115                 120

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 141

Gly Phe Thr Phe Arg Ser Tyr Trp Met Thr
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 142

Glu Gly Tyr Tyr Gly Ser Gly Tyr Phe Asp Tyr
1               5                   10

<210> SEQ ID NO 143
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 143

Asp Ile Gln Met Thr Gln Ser Pro Ser Thr Leu Ser Ala Ser Val Gly
1               5                   10                  15

Asp Arg Val Ile Ile Thr Cys Arg Ala Ser Gln Ser Ile Ser Arg Gly
            20                  25                  30

Leu Ala Trp Tyr Gln Gln Lys Pro Gly Lys Ala Pro Lys Leu Leu Ile

```
                35                  40                  45
Tyr Lys Ala Ser Asn Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Ala Tyr Tyr Cys Gln Gln Tyr Ser Tyr Tyr Ser His
                85                  90                  95

Thr Phe Gly Gln Gly Thr Lys Val Glu Ile Lys
            100                 105

<210> SEQ ID NO 144
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Phe Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Asn Glu Lys Asn Tyr Val Asp Ser Val
    50                  55                  60

Lys Gly Arg Phe Thr Ile Ser Lys Asp Asn Ala Lys Ser Val Phe
65                  70                  75                  80

Leu Gln Met Asn Ser Leu Arg Ala Glu Asp Thr Ala Val Tyr Tyr Cys
                85                  90                  95

Ala Arg Glu Gly Tyr Phe Gly Ser Gly Tyr Phe Asp Tyr Trp Gly Gln
            100                 105                 110

Gly Thr Leu Val Thr Val Ser Ser
        115                 120

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Phe Thr Leu Ser Phe Tyr Trp Met Thr
1               5                   10

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asn Ile Lys Gln Asp Gly Asn Glu Lys Asn Tyr Val Asp Ser Val Lys
1               5                   10                  15

Gly
```

<210> SEQ ID NO 147
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Pro Tyr Tyr Cys Gln His Tyr Asn Ser Tyr Pro His
                85                  90                  95

Thr Phe Gly Gln Gly Thr Lys Val Glu Ile Lys
            100                 105

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ala Ser Gln Ser Ile Asn Ser Trp Leu Ala
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Lys Ala Ser Thr Leu Glu Ser
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln His Tyr Asn Ser Tyr Pro His Thr
1               5

<210> SEQ ID NO 151
<211> LENGTH: 120
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys His Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Phe Gly Ser Gly Tyr Phe Asp Tyr Trp Gly Gln
            100                 105                 110

Gly Thr Leu Val Thr Val Ser Ser
        115                 120

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Phe Thr Phe Ser Ser Tyr Trp Met Ser
1               5                   10

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asn Ile Lys Gln Asp Gly Ser Glu Lys His Tyr Val Asp Ser Val Lys
1               5                   10                  15

Gly

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Ser Tyr Ser His
                 85                  90                  95

Thr Phe Gly Gln Gly Thr Lys Leu Glu Ile Lys
            100                 105

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Ala Ser Gln Gly Ile Ser Ser Tyr Leu Ala
 1               5                  10

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Ala Ser Thr Leu Gln Ser
 1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gln Gln Tyr Ser Phe Tyr Ser His Thr
 1               5

<210> SEQ ID NO 158
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Phe Tyr
                 20                  25                  30

Trp Met Thr Trp Val Arg Gln Ala Pro Gly Lys Gly Leu Glu Trp Val
                 35                  40                  45

Ala Asn Ile Lys Gln Asp Gly Asn Glu Lys Asn Phe Val Asp Ser Val
         50                  55                  60

Lys Gly Arg Phe Thr Ile Ser Arg Asp Asn Ala Lys Lys Ser Val Phe
```

```
                65                  70                  75                  80
Leu Gln Met Asn Ser Leu Arg Ala Glu Asp Thr Ala Val Tyr Tyr Cys
                    85                  90                  95
Ala Arg Glu Gly Tyr Phe Gly Ser Gly Tyr Phe Asp Tyr Trp Gly Gln
                100                 105                 110
Gly Thr Leu Val Thr Val Ser Ser
            115                 120

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asn Ile Lys Gln Asp Gly Asn Glu Lys Asn Phe Val Asp Ser Val Lys
1               5                   10                  15
Gly

<210> SEQ ID NO 160
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Asn Ser Trp
            20                  25                  30
Leu Ala Trp Tyr Gln Gln Lys Pro Gly Lys Ala Pro Lys Leu Leu Ile
        35                  40                  45
Tyr Lys Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asn Ser Tyr Pro His
                85                  90                  95
Thr Phe Gly Gln Gly Thr Lys Leu Glu Ile Lys
            100                 105

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Lys Ala Ser Ser Leu Glu Ser
1               5

<210> SEQ ID NO 162
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 162

Gln Gln Tyr Asn Ser Tyr Pro His Thr
1               5

<210> SEQ ID NO 163
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Gln Leu Gln Glu Ser Gly Pro Gly Leu Val Lys Pro Leu Gly
1               5                   10                  15

Thr Leu Ser Leu Thr Cys Ala Val Ser Gly Gly Ser Ile Ser Asn Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ala Leu Asp Trp Ser Lys Asn Gln Phe Ser
65                  70                  75                  80

Leu Gln Leu Arg Ser Val Thr Ala Ala Asp Thr Ala Val Tyr Tyr Cys
                85                  90                  95

Ala Arg Tyr Gly Ser Gly Pro Phe Gly Gly Asp Cys Trp Gly Gln Gly
            100                 105                 110

Thr Leu Val Thr Val Ser Ser
        115

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Gly Ser Ile Ser Asn Ser Asn Trp Trp Ser
1               5                   10

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Glu Ile Tyr His Ser Gly Ser Thr Asn Tyr Asn Pro Ser Leu Lys Ser
1               5                   10                  15

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Tyr Gly Ser Gly Pro Phe Gly Gly Asp Cys
1               5                   10

<210> SEQ ID NO 167
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Leu Thr Gln Ser Pro Ser Phe Leu Ser Ala Ser Val Gly
1               5                   10                  15

Asp Arg Val Thr Ile Ser Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Gly Gly Val Pro Ser Arg Phe Ser Gly
    50                  55                  60

Ser Gly Ser Gly Thr Thr Phe Thr Leu Thr Ile Ser Ser Leu Gln Pro
65                  70                  75                  80

Glu Asp Phe Ala Thr Tyr Tyr Cys Gln Gln Leu Asn Thr Tyr Pro Phe
                85                  90                  95

Thr Phe Gly Pro Gly Thr Lys Leu Glu Ile Lys
            100                 105

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Ala Ser Thr Leu Gln Gly
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Gln Leu Asn Thr Tyr Pro Phe Thr
1               5

<210> SEQ ID NO 170
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Leu Gln Glu Ser Gly Pro Gly Leu Val Lys Pro Leu Gly
1               5                   10                  15

```
Thr Leu Ser Leu Thr Cys Ala Val Ser Gly Gly Ser Ile Ser Asn Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
 50                  55                  60

Lys Ser Arg Val Thr Ile Ala Leu Asp Trp Ser Lys Asn Gln Phe Ser
65                  70                  75                  80

Leu Gln Leu Arg Ser Val Thr Ala Ala Asp Thr Ala Val Tyr Tyr Cys
                85                  90                  95

Ala Arg Tyr Gly Ser Gly Pro Phe Gly Gly Asp Tyr Trp Gly Gln Gly
            100                 105                 110

Thr Leu Val Thr Val Ser Ser
        115
```

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

```
Tyr Gly Ser Gly Pro Phe Gly Gly Asp Tyr
1               5                   10
```

<210> SEQ ID NO 172
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Asp Ile Gln Leu Thr Gln Ser Pro Ser Phe Leu Ser Ala Ser Val Gly
1               5                   10                  15

Asp Arg Val Thr Ile Ser Cys Arg Ala Ser Gln Gly Ile Ser Ser Tyr
            20                  25                  30

Leu Ala Trp Tyr Gln Lys Pro Gly Lys Ala Pro Lys Leu Leu Ile
        35                  40                  45

Tyr Ala Ala Ser Thr Leu Gln Gly Gly Val Pro Ser Arg Phe Ser Gly
 50                  55                  60

Ser Gly Ser Gly Thr Thr Phe Thr Leu Thr Ile Ser Ser Leu Gln Pro
65                  70                  75                  80

Glu Asp Phe Ala Thr Tyr Tyr Cys Gln Gln Leu Asn Thr Tyr Pro Phe
                85                  90                  95

Thr Phe Gly Pro Gly Thr Lys Leu Glu Ile Lys
            100                 105
```

<210> SEQ ID NO 173
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

-continued

```
Gln Val Gln Ile Lys Glu Ser Gly Pro Gly Leu Val Lys Pro Ser Glu
1               5                   10                  15

Thr Leu Ser Leu Thr Cys Ala Val Ser Gly Phe Ser Phe Ser Ser Gly
            20                  25                  30

Tyr Tyr Trp Gly Trp Ile Arg Gln Pro Pro Gly Lys Gly Leu Glu Trp
        35                  40                  45

Leu Gly Ser Phe Phe His Asn Gly Asn Thr Tyr Tyr Asn Pro Ser Leu
    50                  55                  60

Arg Ser Arg Val Thr Ile Ser Val Asp Thr Ser Lys Asn His Phe Ser
65                  70                  75                  80

Leu Lys Leu Thr Ser Val Thr Ala Ala Asp Thr Ala Val Tyr Tyr Cys
                85                  90                  95

Ala Gly Phe Gly Asp Leu Pro His Tyr His Tyr Tyr Val Met Asp Val
            100                 105                 110

Trp Gly Gln Gly Thr Thr Val Thr Val Ser Ser
        115                 120
```

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

```
Gly Phe Ser Phe Ser Ser Gly Tyr Tyr Trp Gly
1               5                   10
```

<210> SEQ ID NO 175
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

```
Ser Phe Phe His Asn Gly Asn Thr Tyr Tyr Asn Pro Ser Leu Arg Ser
1               5                   10                  15
```

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Phe Gly Asp Leu Pro His Tyr His Tyr Tyr Val Met Asp Val
1               5                   10
```

<210> SEQ ID NO 177
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ile Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys
            100                 105

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Ala Ser Asn Arg Ala Ile
1               5

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gln Gln Arg Ser Asn Trp Pro Pro Tyr Thr
1               5                   10

<210> SEQ ID NO 180
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gln Val Gln Pro Lys Glu Ser Gly Pro Gly Val Val Lys Pro Ser Glu
1               5                   10                  15

Thr Leu Ser Leu Thr Cys Ala Val Ser Gly Phe Pro Ile Ser Arg Gly
            20                  25                  30

Tyr Tyr Trp Gly Trp Ile Arg Gln Pro Pro Gly Lys Gly Leu Glu Trp
        35                  40                  45

Ile Gly Asn Ile Phe His Ser Gly Thr Thr Tyr Tyr Asn Pro Ser Leu
    50                  55                  60

Lys Ser Arg Val Thr Ile Ser Val Asp Thr Ser Lys Asn Gln Ile Ser
65                  70                  75                  80

Leu Lys Leu Thr Ser Val Thr Ala Ala Asp Thr Ala Val Tyr Tyr Cys
                85                  90                  95

Val Gly Phe Gly Asp Leu Pro His Tyr Gln Tyr Tyr Val Met Asp Ile
            100                 105                 110
```

Trp Gly Gln Gly Thr Thr Val Thr Val Ser Ser
        115                 120

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Phe Pro Ile Ser Arg Gly Tyr Tyr Trp Gly
1               5                   10

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asn Ile Phe His Ser Gly Thr Thr Tyr Tyr Asn Pro Ser Leu Lys Ser
1               5                   10                  15

<210> SEQ ID NO 183
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Phe Gly Asp Leu Pro His Tyr Gln Tyr Tyr Val Met Asp Ile
1               5                   10

<210> SEQ ID NO 184
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys
            100                 105

<210> SEQ ID NO 185

```
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gln Val Gln Leu Gln Glu Ser Gly Pro Gly Leu Val Lys Pro Ser Glu
1               5                  10                  15

Thr Leu Ser Leu Thr Cys Ala Val Ser Gly Tyr Ser Ala Ser Gly Leu
            20                  25                  30

Tyr Tyr Trp Ala Trp Ile Arg Gln Pro Pro Gly Lys Gly Leu Glu Trp
        35                  40                  45

Ile Gly Asn Ile Tyr His Ser Gly Arg Thr Tyr Tyr Asn Pro Ser Leu
    50                  55                  60

Glu Ser Arg Val Ser Ile Ser Leu Asp Thr Ser Lys His Gln Val Ser
65                  70                  75                  80

Leu Lys Leu Lys Ser Val Thr Tyr Ala Asp Thr Ala Val Tyr Phe Cys
                85                  90                  95

Ala Arg Asp Arg Phe Asp Gly Phe Asp Ile Trp Gly Gln Gly Thr Met
            100                 105                 110

Val Thr Val Ser Ser
        115

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Tyr Ser Ala Ser Gly Leu Tyr Tyr Trp Ala
1               5                  10

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asn Ile Tyr His Ser Gly Arg Thr Tyr Tyr Asn Pro Ser Leu Glu Ser
1               5                  10                  15

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asp Arg Phe Asp Gly Phe Asp Ile
1               5

<210> SEQ ID NO 189
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 189

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Ile Asn Asn Ile
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Leu Glu Ile Lys
            100                 105

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Ala Ser Gln Thr Ile Asn Asn Ile Leu Ala
1               5                   10

<210> SEQ ID NO 191
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
caggtggagc tgcaggagtc gggcccagga ctggtgaagc cttcggacac cctgtccctc      60
acctgcactg tcactggtgg ctccatcagt acttactact ggagctggat ccggcagccc     120
ccagggaagg gactggagtg gattgggtat atctttttaca ctgggaccac caactacaac    180
ccctccctca agagtcgagt caccatatca gtagacgcgt ccaagaacca gttctccctg     240
aagttgaact ctgtgaccgc tgcggacacg gccgtgtatt actgtgcgag agatgggagc     300
ctggactact ggggccaggg agccctggtc accgtctcct ca                        342

<210> SEQ ID NO 192
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
gacatccaga tgacccagtc tccatcctcc ctgtctgcat ctgtaggaga cagagtcacc      60
atcacttgcc gggcaagtca gagcattagc aactatttaa attggtatca gcagaaacca    120

```
gggaaagccc ctaagctcct gatctttgtt gcatccctttt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccattcac tttcggccct    300
gggaccaagc tggagatcaa a                                              321
```

<210> SEQ ID NO 193
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193

```
caggtgcagc tggtggagtc tgggggaggc gtggtccagc ctgggaggtc cctgagaatc    60
tcctgtgcag cgtctggatt caccttcagg agctatggca tgcactgggt ccgccaggct    120
ccaggcaagg gactggagtg ggtggcaatt atctggcatg atgaaagtta taaatattat    180
gtagactccg tgaagggccg attcaccatc tccagagaca attccaagaa cacgctgtat    240
ctgcaaatga acagcctgag agccgaggac acggctgtgt attattgtgc gagaggcgat    300
tactatggtt cggggagtta ttatgatgct tttgatatct ggggccaagg gacaatggtc    360
accgtctcct ca                                                        372
```

<210> SEQ ID NO 194
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194

```
gacatccaga tgacccagtc tccatcctcc ctgtctgcat ctgtaggaga cagagtcatc    60
atcacttgcc gggcgagtca aggcattagc aattatttag cctggtttca gcagaaacca    120
gggaaatgtc ctaacctcct gatctatgct gcatccactt tgcgatcagg ggtcccatct    180
cggttcagtg gcagtggatc tgggacagat ttcactctca ccatcagcag cctgcagcct    240
gaagatgttg caacttatta ctgtcaaaag tataacagtg ccccgtacac ttttggccag    300
gggaccaagg tggagatcaa a                                              321
```

<210> SEQ ID NO 195
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195

```
caggtgcagc tggtggagtc tgggggaggc gtggtccagc ctgggaggtc cctgagactc    60
tcctgtgcag cgtctggatt caccttcagt cactatggca tgcactgggt ccgccaggct    120
ccaggcaagg ggctggagtg ggtggcagtt atatggtatg atggaagtaa aaaatactat    180
gtagactccg tgaagggccg attcaccatc tccagagaca attccaagaa cacgctgtat    240
ctgcaaatga acagcctgag aggcgaggac acggctgtgt attactgtgc gagagatggg    300
ggagcagtgg ctgacaactg gatcgactcc tggggccagg gaaccctggt caccgtctcc    360
``` tca                                                               363

<210> SEQ ID NO 196
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
gacatccaga tgacccagtc tccatcctcc ctgtctgcat ctgtaggaga cagagtcact      60
atcacttgcc gggcaagtca gagcattaga agctatttaa attggtatca gcagaaaccc     120
gggaaagccc ctaagctcct gatctttgct gcatccagtt tgcaaagtgg ggtcccatcc     180
aggttcagtg gcagtggatc tgggacagat ttcactctca ccgtcagcag tctgcaacct     240
gaagattttg caacttactc ctgtcaacaa agttacagta ccccgtacac ttttggccag     300
gggaccaagg tggagatcaa a                                                321

<210> SEQ ID NO 197
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
caggtgcagt tggtggagtc tgggggaggc gtggtccagc ctgggggtc cctgagactc       60 tcctgtgcag cgtctggatt caccttcagt agccatggca tgcactgggt ccgccaggct    120
ccaggcaagg ggctggagtg ggtggcagtt atatggtatg atggaagtaa taaattctat    180
acagactccg tgcagggccg attcaccatt tccagagaca attccaagaa cacgctgaat    240
ctgcaaatga acagtctgag agccgaggac acggctgtat attactgtgc gagagagggt    300
ttgagggccg ggtactactt tgacttctgg ggccagggaa ccctggtcac cgtctcctca    360

<210> SEQ ID NO 198
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
gacatccaga tgacccagtc tccatcctcc ctgtctgcat ctgtaggaga cagagtcacc      60
atcacttgcc gggcaagtca gaggattagc ttctattcaa attggtatca gcagaaacca    120
gggaaagccc ctaagctcct gatctatgct gcatccagtt tgcaaagtgg ggtcccatca    180
aggttcagtg gcagtggctc tgggacagat ttcactctca ccatcagcag tctgcaacct    240
gaagattttg caacttactt ctgtcaacag agtcacagta ccccgctcac tttcggcgga    300
gggaccaagc tggagatcaa a                                                321

<210> SEQ ID NO 199
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199

```
caggtgcagc tggtggagtc tgggggaggc gtggtccagc ctggaggtc cctgcgactc      60
tcctgtgcag cgtctggatt caccttcagg aactatggca ttcactgggt ccgccaggct    120
ccaggcaagg ggctggagtg ggtggcagtt atatggtatg atggaagtaa taaattctat    180
gcagactccg tgaagggccg attcaccatc tccagagaca attccaagaa cacgctgtat    240
ctgcaaatga acagcctgag agtcgaggac acggctgtat attactgtgc gagagaggag    300
gggatagcag tggccccctt tgactactgg ggccagggaa ccctggtcac cgtctcctca    360
```

<210> SEQ ID NO 200
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 200

```
gacatccaga tgacccagtc tccatcctcc ctgtctgcat ctgtaggaga cagagtcgcc      60
atcacttgcc gggcaaatca gagtattgcc agttatttaa attggtatca gcagaaacca    120
gggaaagccc ctaaactcct gatctatggt gcatccagtt tgcaaaatgg gtcccatca     180
aggttcagtg gcagtggatc taggacagat ttcactctca ccatcagcag tctgcaacct    240
gaagattttg caacttacta ctgtcaacag agttacagca ccgagatcac cttcggccaa    300
gggacacgac tggagattaa a                                              321
```

<210> SEQ ID NO 201
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 201

```
gaggtgcagg tggtggagtc tgggggaggc ttggtccagc ctgggggtc cctgagactc      60
tcctgtgcag cctctggatt caccttaga agctattgga tgagctgggt ccgccaggct    120
ccagggaagg ggctggagtg ggtggccaac ataaagcagg atggaagtga gagacactat    180
gtggactctg tgaagggccg attcaccatc tccagagaca acgccaagac atcactgtat    240
ctgcaaatga gcagcctgag agccgaggac acggctgtgt attactgtgc gagagagggg    300
tactttggtt cgggctactt tgactactgg ggccagggaa ccctggtcac cgtctcctca    360
```

<210> SEQ ID NO 202
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 202

```
gacatccaga tgacccagtc tccctccacc ctgtctgcat ctgtaggaga cagagtcatc      60
atcacttgcc gggccagtca gagtattagt agggggttgg cctggtatca gcagaaacca    120
gggaaagccc ctaaactctt gatctataag gcgtctaatt tagaaagtgg ggtcccatca    180
```

```
aggttcagcg gcagtggatc tgggacagaa ttcactctca ccatcagcag cctgcagcct      240
gatgattttg cagcttatta ctgccaacag tatagttatt attctcacac ttttggccag      300
gggaccaagc tggagatcaa a                                                321

<210> SEQ ID NO 203
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
caggggcagg tggtggagtc tgggggaggc gtggtccagc ctggagggtc cctgagactc       60
tcctgtgcag cgtctggatt caccttcagt agttatacct tgcactgggt ccgccaggct      120
ccaggcaagg ggctggagtg ggtggcagtc atatggtatg atggaagtaa taagtattat      180
gtagactccg tgaagggccg attcaccatc tccagagaca attccaagaa cacgctgtat      240
ctgcaaatga acagcctgag agccgaggac acggctgtgt attactgtgc gagagagtat      300
ggttcgggga gttattataa cgtctactac ggtatggacg tctggggcca ggggaccacg      360
gtcaccctct cctca                                                      375

<210> SEQ ID NO 204
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
gatattgtga tgactcagtc tccactctcc ctgcccgtca cccctggaga gccggcctcc       60
atctcctgca ggtctagtca gagcctcctt catagtaatg gatacaacta tttggattgg      120
tatctgcaga agccaggcca gtctccacac ctcttgatct atttggcttc taatcgggcc      180
tccggggtcc ctgacaggtt cagtggcagt ggatcaggca cagattttac actgaaaatc      240
agcagagtgg aggctgagga tgttggggttt tattactgca tgcaaactct acaaattccg      300
ctcactttcg gcggagggac caaggtggag atcaaa                               336

<210> SEQ ID NO 205
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
caggtgcagc tgcaggagtc gggcccagga ctggtgaagc cttcggagac cctgtccctc       60
acctgcgctg tctctggtta ctccgccagc ggtgtttact actgggctg gatccggcag       120 cccccaggga aggggctgga gtggattgga aatatctatc atagtgggag cacctattac      180
aacccgtccc tcgagaggcg agttagtata tcactagaca cgtccaagaa ccacttctcc      240
ctgaggctga attttgtgac cgccgcagac acggccgtgt attactgtgc gagagatagg      300
tttgatgctt ttgatatctg ggggccaaggg acaatggtca ccgtctcctc a              351

<210> SEQ ID NO 206
```

<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206

```
gaaatagtga tgacgcagtc tccagccacc ctgtctgtgt ctccagggga aagagccacc    60
ctctcctgca gggccagtca gagtattaac aacatcttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctctcac tttcggcgga   300
gggaccaagg tggagatcaa a                                             321
```

<210> SEQ ID NO 207
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207

```
caggtgcagc tggtggagtc tgggggaggc gtggtccagc ctggggggtc cctgagactc    60
tcctgtgcag cgtctggatt cacctttagg agtcatggca tgcactgggt ccgccaggct   120
ccaggcaagg gactggagtg ggtggcagtt atatggtatg atggaagtag tgagtactat   180
gcagactccg tgaagggccg attcaccatc tccagagaca attccaagaa cacgctgtat   240
ctgcaaatga acagcctgag agccgaggac acggctgtgt attattgtgc gagagaaaac   300
gtgtatggca gtggctggtt ttttgactac tggggccagg gaaccctggt caccgtctcc   360
tca                                                                 363
```

<210> SEQ ID NO 208
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208

```
gaaatagtga tgacgcagtc tccagccacc ctgtctgtgt ctccagggga aagagcctcc    60
ctctcctgca gggccagtca gagtgttggc agcaacttag cctggtacca gcagagacct   120
ggccaggctc ccaggctcct catctttggt gcatccacca gggccactgg tatcccagcc   180
aggttcagtg gcagtaggtc tgggacagag ttcactctca ccatcagcag cctgcagtct   240
gaagattttg cactttatta ctgtcagcag tataataact ggcctccgtg gacgttcggc   300
caagggacca gctggagat caaa                                           324
```

<210> SEQ ID NO 209
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
caggtgcagc tggtggagtc tggggggaggc gtggtccagc ctgggaggtc cctgagactc     60
tcctgtgcag cgtctggatt caccttcagg agtcatggca tgcactgggt ccgccaggca    120
ccaggcaagg gactggagtg ggtggcagtt atatggtatg atggaagtag tgactactat    180
gcagactccg tgaagggccg attcaccatc tccagagaca attccaagaa cacactattt    240
ctgcaaatga acagcctgag cgccgaggac acggctgtgt attattgtgc gagagaaaac    300
gtgtatggca gtggctggtt ttttgactac tggggccagg gaaccctggt caccgtctcc    360
tca                                                                  363
```

<210> SEQ ID NO 210
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
gaaatagtga tgacgcagtc tccagccacc ctgtctgtgt ctccagggga aagagccacc     60
ctctcctgca gggccagtca gagtgttggc agcaacttag cctggtacca gcagaaacct    120
ggccaggctc ccaggctcct catctttggt gcatccacca gggccactgg tatcccagcc    180
aggttcagtg gcagtaggtc tgggacagag ttcactctca ccatcagcag cctgcagtct    240
gaagattttg cactttatta ctgtcagcag tataataact ggcctccgtg gacgttcggc    300
caagggacca gctggagat caaa                                            324
```

<210> SEQ ID NO 211
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

```
gaggtgcagc tgttggagtc tggggggaggc ttggtacagc ctgggggggtc cctgagactc    60 tcctgtgcag cctctggatt cacctttagc aactatgcca tgacctgggt ccgccaggct   120
ccagggaagg ggctggagtg ggtctcaagt attagtatta gtcgtgctgg cacatactac   180
gcagactccg tgaagggccg gttcaccatc tccagagaca attccaagaa cacgctgaat   240
ctgcaaatga acagcctgag agccgaggac acggccgaat attactgtgc gagagagtac   300
tactacggca tggacgtctg gggccaaggg accacggtca ccgtctcctc a             351
```

<210> SEQ ID NO 212
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212

```
gaaattgtgt tgacacagtc tccagccacc ctgtctttgt ctccagggga aagagccacc     60
ctctcctgca gggccagtca gagtgttagc agctacttag cctggtacca acagaaacct    120
ggccagactc ccaggctcct catctatgat gcatccaaca gggccactgg catcccagcc    180
aggttcagtg gcagtgggtc tgggacagac ttcacgctca ccatcagcag cctagagact    240
```

```
gaagattttg cagtttatta ctgtcagcag cttatcaact ggccgctcac tttcggcgga    300
gggaccaagc tggagatcaa a                                              321

<210> SEQ ID NO 213
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213
gacatccaga tgacccagtc tccatcctcc ctgtctgcat ctgtaggaga cagagtcatc    60
atcacttgcc gggcgagtca aggcattagc aattatttag cctggtttca gcagaaacca    120
gggaaagctc ctaacctcct gatctatgct gcatccactt tgcgatcagg ggtcccatct    180
cggttcagtg gcagtggatc tgggacagat ttcactctca ccatcagcag cctgcagcct    240
gaagatgttg caacttatta ctgtcaaaag tataacagtg ccccgtacac ttttggccag    300
gggaccaagg tggagatcaa a                                              321

<210> SEQ ID NO 214
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
gaggtgcagt tgttggaatc tgggcagac ttggtacagc ctgggggtc cctgagactc      60 tcctgtgcag cctctggatt caccttagc agctatgcca tgagttgggt ccgccaggct    120
ccaggaaagg ggctggagtg ggtctcaact attcgtatta gtggtggcac cacatactac    180
gcagactccg tgaagggccg gttcaccatc tccagagaca attccaagaa cacgctgtat    240
ctgcaaatga acagcctgag agccgaagac acggccgtat attactgcgt aagggactac    300
tataacggta tggacgtctg ggggccaaggg accacggtca ccgtctcctc a            351

<210> SEQ ID NO 215
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
gaaattgtgt tgacacagtc tccagccacc ctgtctttgt ctccagggga aagagccacc    60
ctctcctgca gggccagtca gcgtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagctact ggcctcccgc ttttggccag    300
gggaccaagc tggagatcaa a                                              321

<210> SEQ ID NO 216
<211> LENGTH: 261
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 216
agctatgcca tgagctgggt ccgccaggct ccagggaagg ggctggagtg ggtctcaagt      60
attagtggta gtggtgatag cacaaaactac gcagactccg tgaagggccg gttcaccatc   120
tccagagaca attccaagaa cacgctgcat ctgcaaatga acagcctgag agccgaggac   180
acggccgtat attactgcgt aagggactac tactacggta tggacgtctg gggccacggg   240
accacggtca ccgtctcctc a                                              261

<210> SEQ ID NO 217
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217
gaaattgtgt tgacacagtc tccagccacc ctgtctttgt ctccagggga aagagccacc      60
ctctcctgca gggccagtca gagtgttaac agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagctact ggccgatcac cttcggccaa   300
gggacacgac tggagattaa a                                              321

<210> SEQ ID NO 218
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218
gaggcgcagc tgttggagtc tgggggaggc ttggtacagc ctggggggtc cctgagactc      60
tcctgtgcag cctctggatt cacctttagc agctatgcca tgagctgggt ccgccaggct   120
ccagggaagg ggctggagtg ggtctcaact attagtggta gtggtggtag tacacactac   180
gcagactccg tgaagggccg gttcaccatc tccagagaca attccaagaa tacgttgtat   240
ctgcaaatga acagcctgag agccgaggac acggccgtat attactgcgt aagggactac   300
tactacggta tggacgtctg gggccaaggg accacggtca ccgtctcctc a             351

<210> SEQ ID NO 219
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 219
gaaattgtgt tgacacagtc tccagccacc ctgtctttgt ctccagggga aagagccacc      60
ctctcctgca gggccagtca gagtgttagc agctacttag cctggtacca acagaaacct   120
ggccaggctc ccaggctcct catctatgat gcatccaaca gggccactgg catcccagcc   180
```

```
aggttcagtg gcagtgggtc tgggacagac ttcactctca ccatcagcag cctagagcct      240
gaagattttg cagtttatta ctgtcagcag cgtagctact ggcctcccac ttttggccag      300
gggaccaagc tggagatcaa a                                                321

<210> SEQ ID NO 220
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220
caggtgcagc tggtggagtc tgggggaggc gtggtccagc ctgggaggtc cctgagactc       60
tcctgtgcag cgtctggatt caccttcagt agctatggaa tgcactgggt ccgccaggct      120
ccaggcaagg gctggagtg gtggcagtt atatggtatg atggaagtaa aaaatactat       180
gtagactccg tgcagggccg attcaccatc tccagagaca attccaagaa tacgctgtat      240
ctgcaaatga acagcctgag aggcgaggac acggctgtgt attactgtgc gagagatggg      300
ggagcagtgg ctgacaattg gatcgactcc tggggccagg gaaccctggt caccgtctcc      360
tca                                                                    363

<210> SEQ ID NO 221
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
gacatccaga tgacccagtc tccatcctcc ctgtctgcgt ctgtaggaga cagagtcact       60
ctcacttgcc gggcaagtca gaacattaga agctatttaa attggtatca gcagaaacca      120
gggaaagccc ctaagctcct gatctttgct gcatccagtt tgccaagtgg ggtcccatca      180
aggttcagtg gcagtggatc tgtgacagat ttcactctca ccgtcagcag tctgcaacct      240
gaagattttg caacttactc ctgtcaacag agttacagta ccccgtacac ttttggccag      300
gggaccaagc tggagatcaa a                                                321

<210> SEQ ID NO 222
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
gaggaacagc tgttggaatc tgggcagac ttggcacagc cggggggtc cctgagactc        60 tcctgtgcag cctctggatt cacctttagc agctatgcca tgagttgggt ccgccaggct      120
ccaggaaagg gactggagtg gtctcaact attcgtatta gtggtgatac cacttactac      180
gcagactccg tgaagggccg gttcaccatc tccagagaca attccaagaa cacgctgttt      240
ctgcaaatga acagcctgag agccgaagac acggccgtgt attactgcgt aagggactac      300
tataacggta tggacgtctg ggggccatggg accacggtca ccgtctcctc a              351

<210> SEQ ID NO 223
```

```
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
gaaattgtgt tgacacagtc tccagccacc ctgtctttgt ctccagggga aagagccacc      60
ctctcctgca gggccagtca gcgtgttagc agctatttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagctact ggcctcccgc ttttggccag     300
gggaccaagc tggagatcaa a                                                321

<210> SEQ ID NO 224
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctaa acagtggtgg cacaaactat     180
gcacagaagt tcagggcag gtcaccatg accagggaca cgtccatcag cacagcctac     240
atggagctga gcaggctgag atctgacgac acggccgtgt attactgtgc gagagaagca     300
gtggctggta cctctgatgc ttttgatatc tggggccaag ggacaatggt caccgtctcc     360
tca                                                                    363

<210> SEQ ID NO 225
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225
gacatccaga tgacccagtc tccatcctcc ctgtctgcat ctgttggaga cagagtcacc      60
atcacttgcc gggcaaatca gagtattgcc agttatttaa attggtatca gcagaaacca     120
ggaaaagtcc ctaaactcct gatctatggt gcatccagtt tgcaaaatgg ggtcccatca     180
aggttcagtg gcagtggatc taggacagat ttcactctca ccatcagcag tctgcaacct     240
gaagattttg caacttacta ctgtcaacaa agttacagca ccgaaatcac cttcggccaa     300
gggacacgac tggagattaa a                                                321

<210> SEQ ID NO 226
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
```

```
gacatccaga tgacccagtc tccatcctcc ctgtctgcat ctgtaggaga cagagtcgcc    60
atcacttgcc gggcaagtca gagtattgcc agttatttaa attggtatca gcagaaacca   120
gggaaagccc ctaaactcct gatctatggt gcatccagtt tgcaaaatgg gtcccatca    180 aggttcagtg gcagtggatc taggacagat ttcactctca ccatcagcag tctgcaacct   240
gaagattttg caacttacta ctgtcaacag agttacagca ccgagatcac cttcggccaa   300
gggacacgac tggagattaa a                                             321

<210> SEQ ID NO 227
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
caggtgcagc tggtggagtc tgggggaggc gtggtccagc ctggggaggtc cctgcgactc    60 tcctgtgcag cgtctggatt cacctttagg aactatggca tgcactgggt ccgccaggct   120
ccaggcaagg ggctggagtg ggtggcagtt atatggtatg atggaagtaa taaattctat   180
gcagactccg tgaagggccg attcaccatc tccagagaca attccaagaa cacgctgtat   240
ctgcaaatga acagcctgag agtcgaggac acggctgtat attactgtgc gagagaggag   300
gggatagcag tggcccccttt tgactactgg ggccagggaa ccctggtcac cgtctcctca   360

<210> SEQ ID NO 228
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
gacatccaga tgacccagtc tccatcctcc ctgtctgcat ctgtaggaga cagagtcgcc    60
atcacttgcc gggcaaatca gagtattgcc agttatttaa attggtatca gcagaaacca   120
gggaaagccc ctaaactcct gatctatggt gcatccagtt tgcaaaatgg gtcccatca    180 aggttcagtg gcagtggatc taggacagat ttcactctca ccatcagcag tctgcaacct   240
gaagattttg caacttacta ctgtcaacag agttacagca ccgagatcac cttcggccaa   300
gggacacgac tggagattaa a                                             321

<210> SEQ ID NO 229
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
caggtgcagc tggtggaatc tgggggaggc atggtccagc ctggggaggtc cctgagactc    60 tcctgtacag cgtctggatt caccttcagt agtcatggca tgcactgggt ccgccaggct   120
ccaggcaagg gactggagtg ggtggcagtt atttggtttg atggaagtaa tgaatattat   180
gtagactccg tgaagggccg attcaccatc tccagagaca attccaagaa cacactgtat   240
ctgcaaatga acagcctgag agccgaggac acggctgtgt attattgtgc gagagaaaac   300
```

```
gtttatggca gtggctggtt ttttgactac tggggccagg gaaccctggt caccgtctcc    360
tca                                                                  363

<210> SEQ ID NO 230
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
gaaatagtga tgacgcagtc tccagccacc ctgtctgtgt ctccagggga aagagcctcc     60
ctctcctgca gggccagtca gagtgttggc agcaacttag cctggtacca gcagaaacct    120
ggccaggctc ccaggctcct catctttggt gcatccacca gggccactgg tatcccagcc    180
aggttcagtg gcagtaggtc tgggacagag ttcactctca ccatcagcag cctgcagtct    240
gaagattttg cactttatta ctgtcagcag tataataact ggcctccgtg gacgttcggc    300
caagggacca aggtggagat caaa                                           324

<210> SEQ ID NO 231
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
cagttgcagc tggtggagtc tggggggaggc gtggtccagc ctggcaggtc cctgagactc     60
tcctgtgcag cgtctggatt caccttcagt agttatggca tgcactgggt ccgccaggct    120
ccaggcaagg gactggagtg ggtggcagtt atatggtatg atggaagtag tgagtactat    180
gcagactccg tgaagggccg attcaccatc tccagagaca attccaagaa cacgctgtat    240
ctgcaaatga acagcctgag agccgaggac acggctgtgt attattgtgc gagagaaaac    300
gtgtatggca gtggctggtt ttttgactac tggggccagg gaaccctggt caccgtctcc    360
tca                                                                  363

<210> SEQ ID NO 232
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
gaaatagtga tgacgcagtc tccagccacc ctgtctgtgt ctccagggga aagagcctcc     60
ctctcctgca gggccagtca gagtgttggc agcaacttag cctggtacca gcagaaacct    120
ggccaggctc ccaggctcct catctttggt gcatccacca gggccactgg tatcccagcc    180
aggttcagtg gcagtaggtc tgggacagag ttcactctca ccatcagcag cctgcagtct    240
gaagattttg cactttatta ctgtcagcag tataataact ggcctccgtg gacgttcggc    300
caagggacca aggtggagat caaa                                           324

<210> SEQ ID NO 233
<211> LENGTH: 272
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
gtcatggcat gcactgggtc cgccaggctc caggcaaggg actggagtgg gtggcagtta    60
tatggtatga tggaagtagt gagtactatg cagactccgt gaagggccga ttcaccatct   120
ccagagacaa ttccaagaac acgctgtatc tgcaaatgaa cagcctgaga gccgaggaca   180
cggctgtgta ttattgtgcg agagaaaacg tatatggcag tggctggttt tttgactact   240
ggggccaggg aagcctggtc accgtctcct ca                                  272

<210> SEQ ID NO 234
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 234
gaaatagtga tgacgcagtc tccagccacc ctgtctgtgt ctccagggga aagagcctcc    60
ctctcctgca gggccagtca gagtgttggc agcaacttag cctggtacca gcagaaacct   120
ggccaggctc ccaggctcct catctttggt gcatccacca gggccactgg tatcccagcc   180
aggttcagtg gcagtaggtc tgggacagag ttcactctca ccatcagcag cctgcagtct   240
gaagattttg cactttatta ctgtcagcag tataataact ggcctccgtg gacgttcggc   300
caagggacca agctggagat caaa                                          324

<210> SEQ ID NO 235
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 235
cagttgcagt tggtggagtc tgggggaggc gtggtccagt ttggcaggtc cctgagactc    60
tcctgtgcag cgtctggatt caccttcagt agtcatggca tgcactgggt ccgccaggct   120
ccaggcaagg gactggagtg ggtggcagtt atatggtatg atggaagtag tgagtactat   180
gcagactccg tgaagggccg attcaccatc tccagagaca attccaagaa cacgctgtat   240
ctgcaaatga acagcctgag agccgaggac acggctgtgt attattgtgc gagagaaaac   300
gtgtatggca gtggctggtt ttttgactac tggggccagg gaaccctggt caccgtctcc   360
tca                                                                 363

<210> SEQ ID NO 236
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 236
gaaatagtga tgacgcagtc tccagccacc ctgtctgtgt ctccagggga aagagcctcc    60
```

```
ctctcctgca gggccagtca gagtgttggc agcaacttag cctggtacca gcagaaacct    120
ggccaggctc ccaggctcct catctttggt gcatccacca gggccactgg tatcccagcc    180
aggttcagtg gcagtaggtc tgggacagag ttcactctca ccatcagcag cctgcagtct    240
gaagattttg cactttatta ctgtcagcag tataataact ggcctccgtg gacgttcggc    300
caagggacca agctggagat caaa                                            324
```

<210> SEQ ID NO 237
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237

```
cagttgcagc tggtggagtc tggggaggc gtggtccagc ctggcaggtc cctaagactc     60
tcctgtgcag cgtctggatt caccttcagt agttatggca tgcactgggt ccgccaggct    120
ccaggcaagg gactggagtg ggtggcagtt atatggtatg atggaagtag tgagtattat    180
gcagactccg tgaagggccg attcaccatc tccagagaca attccaagaa cacgctgttt    240
ctgcaaatga acagcctgag agccgatgac acggctgtgt attattgtgc gagagaaaac    300
gtgtatggca gtggctggtt ttttgactac tggggccagg gaaccctggt caccgtctcc    360
tca                                                                  363
```

<210> SEQ ID NO 238
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238

```
gaaatagtga tgacgcagtc tccagccacc ctgtctgtgt ctccagggga aagagcctcc     60
ctctcctgca gggccagtca gagtgttggc agcaacttag cctggtacca gcagaaacct    120
ggccaggctc ccaggctcct catctttggt gcatccacca gggccactgg tatcccagcc    180
aggttcagtg gcagtaggtc tgggacagag ttcactctca ccatcagcag cctgcagtct    240
gaagattttg cactttatta ctgtcagcag tatgataact ggcctccgtg gacgttcggc    300
caagggacca agctggagat caaa                                            324
```

<210> SEQ ID NO 239
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239

```
caggtgcagc tggtggagtc tgggggaggc gtggtccagc ctggggaggtc tctgagactc    60 tcctgtgcag cgtctggatt cacccttaagt ggctatggca tgcactgggt ccgccaggct   120
ccaggcaagg gactggagtg ggtggcagtt atatggtatg atggaagtaa taaatactat    180
gcagactccg tgaagggccg attcaccatc tccagagaca attccaagaa catgctgttt    240
ctgcaaatga acagcctgag agccgaggac acggctgtgt attactgtgt gagagaaaac    300
```

```
gggtttggca gtggctggtt ttttgactac tggggccagg gaaacctggt caccgtctcc    360
tca                                                                  363
```

<210> SEQ ID NO 240
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 240

```
gaaatagtga tgacgcagtc tccagccacc ctgtctgtgt ctccagggga aagagccacc    60
ctctcctgca ggaccagtca gagtgtaagt agagacttag cctggtacca gcagaaacct   120
ggccaggctc ccaggctcct catctatggt gcatccacca gggccactgg tattccagtc   180
aggttcagtg gcagtgggtc tgggacagag ttcactctca ccatcagcag cctgcagtct   240
gaagattttg cagtttatta ctgtcagcag tataataact ggcctccgtg gacgttcggc   300
caagggacca agctggagat caaa                                          324
```

<210> SEQ ID NO 241
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241

```
caggggcagc tggtggagtc tgggggaggc gtggtccagc ctgggaggtc cctgagactc    60
tcctgtgcag cgtctggatt caccttcagt agttatacct gcactgggt ccgccaggct   120 ccaggcaagg ggctggagtg ggtggcagtc atatggtatg atggaagtaa taagtattat   180
gtagactccg tgaagggccg attccaccatc tccagagaca attccaagaa cacgctgtat   240
ctgcaaatga acagcctgag agccgaggac acggctgtgt attactgtgc gagagagtat   300
ggttcgggga gttattataa cgtctactac ggtatggacg tctggggcca ggggaccacg   360
gtcaccgtct cctca                                                    375
```

<210> SEQ ID NO 242
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 242

```
gatattgtga tgactcagtc tccactctcc ctgcccgtca cccctggaga gccggcctcc    60
atctcctgca ggtctagtca gagcctcctg catagcaatg gatacaagta tttggattgg   120
tatctgcaga aagcagggca gtctccacac ctcttgatct atttgggttc taatcgggcc   180
tccggggtcc ctgacaggtt cagtggcagt ggatcaggca cagatttac actgaaaatc   240 agcagagtgg aggctgagga tgttggattt tattactgca tgcaaactct acaaattccg   300
ctcactttcg gcggagggac caagctggag atcaaa                             336
```

<210> SEQ ID NO 243
<211> LENGTH: 360
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 243

```
gaggtgcagg tggtggagtc tgggggaggc ttggtccagc ctggggggtc cctgagactc    60
tcctgtgcaa cctctggatt caccttaga agctattgga tgacctgggt ccgccaggct   120
ccagggaagg ggctggagtg ggtggccaat ataaagcagg atggaagtga gagacactat   180
gtggactctg tgaagggccg attcaccatc tccagagaca acgccaagac atcactgtat   240
ctgcaaatga gcagcctgag agccgaggac acggctatgt attactgtgc gagagagggg   300
tactatggtt cgggctactt tgactactgg ggccagggaa ccctggtcac cgtctcctca   360
```

<210> SEQ ID NO 244
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244

```
gacatccaga tgacccagtc tcctccacc ctgtctgcat ctgtaggaga cagagtcatc    60
atcacttgcc gggccagtca gagtattagt aggggttgg cctggtatca gcagaaacca   120
gggaaagccc ctaaactctt gatctataag gcgtctaatt tagaaagtgg ggtcccatca   180
aggttcagcg gcagtggatc tgggacagaa ttcactctca ccatcagcag cctgcagcct   240
gatgattttg cagcttatta ctgccaacag tatagttatt attctcacac ttttggccag   300
gggaccaagg tggagatcaa a                                             321
```

<210> SEQ ID NO 245
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245

```
gaggtgcaac tggtggagtc tgggggaggc ttggtccagc ctggggggtc cctgagactc    60
tcctgtgcag cctctggatt caccttaagt ttctattgga tgacctgggt ccgccaggct   120
ccagggaagg ggctggagtg ggtggccaac ataaagcaag atggaaatga gaaaaactat   180
gtggactctg tgaagggccg attcaccatc tccaaagaca acgccaagaa atcagtgttt   240
ctgcaaatga acagcctgag agccgaggac acggctgtgt attactgtgc gagagagggg   300
tactttggtt cgggctactt tgactactgg ggccagggaa ccctggtcac cgtctcctca   360
```

<210> SEQ ID NO 246
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246

```
gacatccaga tgacccagtc tccttccacc ctgtctgcat ctgtgggaga cagagtcacc    60
atcacttgtc gggccagtca gagtattaat agctggttgg cctggtatca gcagaaacca   120
```

```
gggaaagccc ctaagctcct gatctataag gcgtctactt tagaaagtgg ggtcccatca      180
aggttcagcg gcagtggatc tgggacagaa ttcactctca ccatcagcag cctgcagcct      240
gatgattttg caccttatta ctgccagcat tataatagtt atcctcacac ttttggccag      300
gggaccaagg tggagatcaa a                                                321
```

<210> SEQ ID NO 247
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247

```
gaggtgcagc tggtggagtc tgggggaggc ttggtccagc ctggggggtc cctgagactc      60
tcctgtgcag cctctggatt cactttagt agttattgga tgagctgggt ccgccaggct       120
ccagggaagg gctggagtg gtggccaac ataaagcaag atggaagtga aaacactat         180 gtggactctg tgaagggccg attcaccatc tccagagaca acgccaagaa ctcactgtat      240
ctgcaaatga acagcctgag agccgaggac acggctgtgt attactgtgc gagagagggg     300
tactttggtt cgggctactt tgactactgg ggccagggaa ccctggtcac cgtctcctca     360
```

<210> SEQ ID NO 248
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248

```
gacatccagt tgacccagtc tccatccttc ctgtctgcat ctgtaggaga cagagtcacc      60
atcacttgcc gggccagtca gggcattagc agttatttag cctggtatca gcaaaaacca     120
gggaaagccc ctaagctcct gatctatgct gcatccactt tgcaaagtgg ggtcccatca     180
aggttcagcg gcagtggatc tgggacagaa ttcactctca caatcagcag cctgcagcct     240
gaagattttg caacttatta ctgccaacag tatagttttt attctcacac ttttggccag     300
gggaccaagc tggagatcaa a                                               321
```

<210> SEQ ID NO 249
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249

```
gaggtgcaac tggtggagtc tgggggaggc ttggtccagc ctggggggtc cctgagactc      60
tcctgtgcag cctctggatt caccttaagt ttctattgga tgacctgggt ccgccaggct     120
ccagggaagg gctggagtg gtggccaat ataaagcaag atggaaatga aaaactttg       180 gtggactctg tgaagggccg attcaccatc tccagagaca acgccaagaa atcagtgttt     240
ctgcaaatga acagcctgag agccgaggac acggctgtgt attactgtgc gagagagggg     300
tactttggtt cgggctactt tgactactgg ggccagggaa ccctggtcac cgtctcctca     360
```

```
<210> SEQ ID NO 250
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250
gacatccaga tgacccagtc tccttccacc ctgtctgcat ctgtaggaga cagagtcacc    60
atcacttgcc gggccagtca gagtattaat agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccagcag tataatagtt atcctcacac ttttggccag   300
gggaccaagc tggagatcaa a                                             321

<210> SEQ ID NO 251
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
gacatccagt tgacccagtc tccatccttc ctgtctgcat ctgtaggaga cagagtcacc    60
atctcttgcc gggccagtca gggcattagc agttatttgg cctggtatca gcaaaaacca   120
gggaaagccc ctaagctcct gatctatgct gcatccactt tgcaaggtgg ggtcccatca   180
aggttcagcg gcagtggatc tgggacaaca ttcactctca caatcagcag cctgcagcct   240
gaagattttg caacttatta ctgtcaacag cttaatactt acccattcac tttcggccct   300
gggaccaagc tggagatcaa a                                             321

<210> SEQ ID NO 252
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
gacatccagt tgacccagtc tccatccttc ctgtctgcat ctgtaggaga cagagtcacc    60
atctcttgcc gggccagtca gggcattagc agttatttgg cctggtatca gcaaaaacca   120
gggaaagccc ctaagctcct gatctatgct gcatccactt tgcaaggtgg ggtcccatca   180
aggttcagcg gcagtggatc tgggacaaca ttcactctca caatcagcag cctgcagcct   240
gaagattttg caacttatta ctgtcaacag cttaatactt acccattcac tttcggccct   300
gggaccaagc tggagatcaa a                                             321

<210> SEQ ID NO 253
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253
```

-continued

```
caggtgcagc tgcaggagtc gggcccagga ctggtgaagc ctttggggac cctgtccctc        60
acctgcgctg tctctggtgg ctccatcagc aatagtaact ggtggagttg ggtccgccag       120
cccccaggaa aggggctgga gtggattgga gaaatctatc atagtgggag caccaactac       180
aacccgtccc tcaagagtcg agtcaccata gcactagact ggtccaagaa ccagttctcc       240
ctgcagctga ggtctgtgac cgccgcggac acggccgtgt attactgtgc gcggtatggt       300
tcgggtcctt ttggcggtga ctactggggc cagggaaccc tggtcaccgt ctcctca         357
```

<210> SEQ ID NO 254
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 254

```
caggtgcaga taaaggagtc gggcccagga ctggtgaagc cttcggagac cctgtccctc        60
acctgcgctg tctctggttt ctccttcagc agtggttatt actggggctg gatccggcag       120
cccccaggga agggtctgga gtggcttggg agtttctttc ataatgggaa tacctactac       180
aacccgtccc tcaggagtcg agtcaccatc tcagtagaca cgtccaagaa ccacttctcc       240
ctgaagctga cctctgtgac cgccgcagac acggccgtgt attactgtgc gggattcggg       300
gacttacccc attatcatta ttacgttatg gacgtctggg gccaagggac cacggtcacc       360
gtctcctca                                                               369
```

<210> SEQ ID NO 255
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 255

```
gaaattgtgt tgacacagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccaaca gggccattgg catcccagcc       180
aggttcagtg gcagtgggtc tgggacagac ttcactctca ccatcagcag cctagagcct       240
gaagattttg cagtttatta ctgtcagcag cgtagcaact ggcctccgta cacttttggc       300 cagggggacca agctggagat caaa                                             324
```

<210> SEQ ID NO 256
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 256

```
caggtgcagc aaaggagtc gggcccagga gtggtgaagc cttcggagac cctgtccctc        60
acctgcgctg tctctggttt ccccatcagc cgtggttatt actggggctg gatccggcag       120
cccccaggga agggtctgga gtggattggg aatatctttc atagtgggac cacctactac       180
aatccgtccc tcaagagtcg agtcaccatc tcagtagaca cgtccaagaa ccagatctcc       240
```

```
ctgaagctga cctctgtgac cgccgcagac acggccgtat attattgtgt gggattcggg    300
gacttgcccc actaccaata ttacgttatg acatctggg gccaagggac cacggtcacc     360
gtctcctca                                                            369
```

<210> SEQ ID NO 257
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 257

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgta cactttggc    300 caggggacca agctggagat caaa                                           324
```

<210> SEQ ID NO 258
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 258

```
caggtgcagc tgcaggagtc gggcccagga ctggtgaagc cttcggagac cctgtccctc    60
acctgcgctg tctctggtta ctccgccagc ggtctttact actgggcctg gatccggcag   120
cccccaggga agggactgga gtggattgga aatatctatc atagtgggag aacctactac   180
aatccgtccc tcgagagtcg agtcagcata tcactagaca cgtccaagca ccaggtctcc   240
ctgaaactga atctgtgac ctacgcagac acggccgtgt atttctgtgc gagagatagg    300
tttgatggtt ttgatatttg gggccaaggg acaatggtca ccgtctcctc a             351
```

<210> SEQ ID NO 259
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 259

```
gaaatagtga tgacgcagtc tccagccacc ctgtctgtgt ctccagggga aagagccacc    60
ctctcctgca gggccagtca gactattaac aacatcttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctctcac tttcggcgga    300
gggaccaagc tggagatcaa a                                              321
```

<210> SEQ ID NO 260
<211> LENGTH: 40
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 260
atagctcttc agggaccatg aarcayctgt ggttcttcct                40

<210> SEQ ID NO 261
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 261
atagctcttc agggaccatg gacatacttt gttccacgc                39

<210> SEQ ID NO 262
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 262
atagctcttc agggaccatg gacacacttt gctacacac                39

<210> SEQ ID NO 263
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 263
atagctcttc agggaccatg tctgtctcct tcctcatct                39

<210> SEQ ID NO 264
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 264
atagctcttc agggaccatg gactggacct ggagvatc                 38

<210> SEQ ID NO 265
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 265
atagctcttc agggaccatg gactggattt ggaggrtc                 38

<210> SEQ ID NO 266
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
atagctcttc agggaccatg gactgcacct ggaggatc                    38

<210> SEQ ID NO 267
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
atagctcttc agggaccatg gactggacct ggaggktc                    38

<210> SEQ ID NO 268
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
atagctcttc agggaccatg gagttkggrc tgagctgg                    38

<210> SEQ ID NO 269
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
atagctcttc agggaccatg gagtttkggc tkagctgg                    38

<210> SEQ ID NO 270
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
atagctcttc agggaccatg gaactggggc tccgctgg                    38

<210> SEQ ID NO 271
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
atagctcttc agggaccatg garttggggc tgwgctgg                    38

<210> SEQ ID NO 272
<211> LENGTH: 38
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 272
atagctcttc agggaccatg gggtcaaccg ccatcctc                              38

<210> SEQ ID NO 273
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
atagctcttc agggaccatg gacatgaggg tsccygctca gctc                       44

<210> SEQ ID NO 274
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
atagctcttc agggaccatg gacatgagrg tcctcgctca gctc                       44

<210> SEQ ID NO 275
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
atagctcttc agggaccatg gaagccccag cdcagcttct c                          41

<210> SEQ ID NO 276
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
atagctcttc agggaccatg gaaacccag cgcagcttct c                           41

<210> SEQ ID NO 277
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
atagctcttc agggaccatg gtgttgcaga cccaggtctt c                          41

<210> SEQ ID NO 278
<211> LENGTH: 41
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 278
atagctcttc agggaccatg gggtcccagg ttcacctcct c        41

<210> SEQ ID NO 279
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
atagctcttc agggaccatg aggctccytg ctcagctcct g        41

<210> SEQ ID NO 280
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
atagctcttc ttcgtttgat ctccascttg gtc        33

<210> SEQ ID NO 281
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
atagctcttc ttcgtttaat ctccagtcgt gtc        33

<210> SEQ ID NO 282
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
atagctcttc tggctgagga gacggtgacc        30

<210> SEQ ID NO 283
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
atagctcttc atgtgacgct gttgtgactc agga        34

<210> SEQ ID NO 284
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
atagctcttc atgtgaccyt gtgctcactc agtc                                34

<210> SEQ ID NO 285
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gatgctcttc tgggctggcc taggacagtc amcytgg                             37

<210> SEQ ID NO 286
<211> LENGTH: 570
<212> TYPE: PRT
<213> ORGANISM: Homo sapiens

<400> SEQUENCE: 286

```
Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285
```

```
Pro Asp Asp Ile Thr Ile Asp Val Thr Ile Asn Glu Ser Ile Ser His
    290             295                 300
Ser Arg Thr Glu Asp Glu Thr Arg Thr Gln Ile Leu Ser Ile Lys Lys
305             310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
            340                 345                 350
Ala Pro Arg Tyr Thr Val Glu Leu Ala Cys Gly Phe Gly Ala Thr Val
            355                 360                 365
Leu Leu Val Val Ile Leu Ile Val Val Tyr His Val Tyr Trp Leu Glu
    370                 375                 380
Met Val Leu Phe Tyr Arg Ala His Phe Gly Thr Asp Glu Thr Ile Leu
385             390                 395                 400
Asp Gly Lys Glu Tyr Asp Ile Tyr Val Ser Tyr Ala Arg Asn Ala Glu
                405                 410                 415
Glu Glu Glu Phe Val Leu Leu Thr Leu Arg Gly Val Leu Glu Asn Glu
                420                 425                 430
Phe Gly Tyr Lys Leu Cys Ile Phe Asp Arg Asp Ser Leu Pro Gly Gly
            435                 440                 445
Ile Val Thr Asp Glu Thr Leu Ser Phe Ile Gln Lys Ser Arg Arg Leu
            450                 455                 460
Leu Val Val Leu Ser Pro Asn Tyr Val Leu Gln Gly Thr Gln Ala Leu
465             470                 475                 480
Leu Glu Leu Lys Ala Gly Leu Glu Asn Met Ala Ser Arg Gly Asn Ile
                485                 490                 495
Asn Val Ile Leu Val Gln Tyr Lys Ala Val Lys Glu Thr Lys Val Lys
            500                 505                 510
Glu Leu Lys Arg Ala Lys Thr Val Leu Thr Val Ile Lys Trp Lys Gly
            515                 520                 525
Glu Lys Ser Lys Tyr Pro Gln Gly Arg Phe Trp Lys Gln Leu Gln Val
    530                 535                 540
Ala Met Pro Val Lys Lys Ser Pro Arg Arg Ser Ser Ser Asp Glu Gln
545                 550                 555                 560
Gly Leu Ser Tyr Ser Ser Leu Lys Asn Val
                565                 570
```